United States Patent
Bonadio et al.

(10) Patent No.: US 10,499,889 B2
(45) Date of Patent: Dec. 10, 2019

(54) INFLATABLE PNEUMOPERITONEUM DEVICE

(71) Applicant: ATROPOS LIMITED, County Wicklow (IE)

(72) Inventors: Frank Bonadio, Bray (IE); Stephen Williams, Blackrock (IE); Lucy Dolores Halpin, Dublin (IE); Kirk Anthony Shibley, Wayzata, MN (US); Trevor Vaugh, County Offaly (IE); Shane J. MacNally, County Wicklow (IE)

(73) Assignee: ATROPOS LIMITED, Bray, County Wicklow (IE)

( * ) Notice: Subject to any disclaimer, the term of this patent is extended or adjusted under 35 U.S.C. 154(b) by 969 days.

(21) Appl. No.: 14/962,868

(22) Filed: Dec. 8, 2015

(65) Prior Publication Data

US 2016/0242751 A1 Aug. 25, 2016

Related U.S. Application Data

(63) Continuation-in-part of application No. PCT/EP2014/063458, filed on Jun. 25, 2014, and a
(Continued)

(51) Int. Cl.
*A61B 1/32* (2006.01)
*A61B 17/00* (2006.01)
(Continued)

(52) U.S. Cl.
CPC .... *A61B 17/00234* (2013.01); *A61B 17/0218* (2013.01); *A61B 17/3423* (2013.01); *A61B 17/3474* (2013.01); *A61B 2017/00287* (2013.01); *A61B 2017/00557* (2013.01); *A61B 2017/00659* (2013.01);
(Continued)

(58) Field of Classification Search
CPC combination set(s) only.
See application file for complete search history.

(56) References Cited

U.S. PATENT DOCUMENTS

| 30,471 A | 10/1860 | Dudley |
| 4,346,699 A | 8/1982 | Little et al. |

(Continued)

FOREIGN PATENT DOCUMENTS

| CN | 100477968 C | 4/2009 |
| CN | 202397525 U | 8/2012 |

(Continued)

OTHER PUBLICATIONS

Final Office Action dated Nov. 4, 2016, in U.S. Appl. No. 13/725,148 (12 pages).
Non-Final Office Action dated Jan. 9, 2017, in U.S. Appl. No. 14/996,610 (12 pages).
(Continued)

*Primary Examiner* — Sameh R Boles
(74) *Attorney, Agent, or Firm* — Bookoff McAndrews, PLLC

(57) ABSTRACT

An artificial pneumoperitoneum bag device may include an inflatable bag having an opening at an end of the bag. The bag device may also include an indicator including at least one repeating pattern on a wall of the bag. The pattern may extend across at least one side of the bag.

20 Claims, 126 Drawing Sheets

Related U.S. Application Data continuation-in-part of application No. 14/251,362, filed on Apr. 11, 2014, now Pat. No. 8,920,431, application No. 14/962,868, which is a continuation-in-part of application No. 14/584,865, filed on Dec. 29, 2014, now Pat. No. 9,265,492, which is a continuation of application No. 14/251,362, filed on Apr. 11, 2014, now Pat. No. 8,920,431, and a continuation-in-part of application No. 13/725,148, filed on Dec. 21, 2012, now abandoned, application No. 14/962,868, which is a continuation-in-part of application No. 13/725,148, filed on Dec. 21, 2012, now abandoned.

(60) Provisional application No. 62/089,722, filed on Dec. 9, 2014, provisional application No. 61/839,461, filed on Jun. 26, 2013, provisional application No. 61/940,681, filed on Feb. 17, 2014, provisional application No. 61/968,770, filed on Mar. 21, 2014, provisional application No. 61/580,088, filed on Dec. 23, 2011, provisional application No. 61/742,125, filed on Aug. 3, 2012.

(51) Int. Cl.

| | | |
|---|---|---|
| *A61B 17/34* | (2006.01) | |
| *A61B 17/02* | (2006.01) | |
| *A61B 90/00* | (2016.01) | |
| *A61B 17/32* | (2006.01) | |
| *A61B 17/42* | (2006.01) | |
| *A61M 13/00* | (2006.01) | |

(52) U.S. Cl.
CPC .............. *A61B 2017/00951* (2013.01); *A61B 2017/0225* (2013.01); *A61B 2017/320024* (2013.01); *A61B 2017/3466* (2013.01); *A61B 2017/4216* (2013.01); *A61B 2090/061* (2016.02); *A61B 2090/0807* (2016.02); *A61B 2090/3937* (2016.02); *A61M 13/003* (2013.01)

(56) References Cited

U.S. PATENT DOCUMENTS

| | | |
|---|---|---|
| 5,037,379 A | 8/1991 | Clayman et al. |
| 5,074,867 A | 12/1991 | Wilk |
| 5,147,371 A | 9/1992 | Washington et al. |
| 5,190,555 A | 3/1993 | Wetter et al. |
| 5,192,284 A | 3/1993 | Pleatman |
| 5,215,521 A | 6/1993 | Cochran et al. |
| 5,224,930 A | 7/1993 | Spaeth et al. |
| 5,312,416 A | 5/1994 | Spaeth et al. |
| 5,320,627 A | 6/1994 | Sorensen et al. |
| 5,330,483 A | 7/1994 | Heaven et al. |
| 5,337,754 A | 8/1994 | Heaven et al. |
| 5,341,815 A | 8/1994 | Cofone et al. |
| 5,350,387 A | 9/1994 | Semm |
| 5,352,184 A | 10/1994 | Goldberg et al. |
| 5,353,784 A | 10/1994 | Nady-Mohamed |
| 5,354,303 A * | 10/1994 | Spaeth ............ A61B 17/00234 604/171 |
| 5,368,545 A | 11/1994 | Schaller et al. |
| 5,465,731 A | 11/1995 | Bell et al. |
| 5,480,404 A | 1/1996 | Kammerer et al. |
| 5,522,790 A | 6/1996 | Moll et al. |
| 5,562,603 A | 10/1996 | Moll et al. |
| 5,611,803 A | 3/1997 | Heaven et al. |
| 5,618,296 A | 4/1997 | Sorensen et al. |
| 5,640,977 A | 6/1997 | Leahy et al. |
| 5,645,083 A | 7/1997 | Essig et al. |
| 5,735,289 A | 4/1998 | Pfeffer et al. |
| 5,755,724 A | 5/1998 | Yoon |
| 5,769,794 A | 6/1998 | Conlan et al. |
| 5,785,677 A | 7/1998 | Auweiler |
| 5,788,709 A | 8/1998 | Riek et al. |
| 5,813,409 A | 9/1998 | Leahy et al. |
| 5,836,936 A | 11/1998 | Cuschieri |
| 5,895,392 A | 4/1999 | Riek et al. |
| 5,980,544 A | 11/1999 | Vaitekunas |
| 5,997,547 A | 12/1999 | Nakao et al. |
| 6,004,330 A | 12/1999 | Middleman et al. |
| 6,036,681 A | 3/2000 | Hooven |
| 6,162,235 A | 12/2000 | Vaitekunas |
| 6,206,889 B1 | 3/2001 | Bennardo |
| 6,228,095 B1 | 5/2001 | Dennis |
| 6,270,505 B1 | 8/2001 | Yoshida et al. |
| 6,344,026 B1 | 2/2002 | Burbank et al. |
| 6,350,267 B1 | 2/2002 | Stefanchik |
| 6,383,197 B1 | 5/2002 | Conlon et al. |
| 6,409,733 B1 | 6/2002 | Conlon et al. |
| 6,450,983 B1 | 9/2002 | Rambo |
| 6,508,773 B2 | 1/2003 | Burbank et al. |
| 6,613,952 B2 | 9/2003 | Rambo |
| 6,659,105 B2 | 12/2003 | Burbank et al. |
| 6,685,628 B2 | 2/2004 | Vu |
| 6,887,255 B2 | 5/2005 | Shimm |
| 7,163,510 B2 | 1/2007 | Kahle et al. |
| 7,670,338 B2 | 3/2010 | Albrecht et al. |
| 7,670,346 B2 | 3/2010 | Whitfield |
| 7,955,292 B2 | 6/2011 | Leroy et al. |
| 8,152,820 B2 | 4/2012 | Mohamed et al. |
| 8,187,178 B2 | 5/2012 | Bonadio et al. |
| 8,282,572 B2 | 10/2012 | Bilsbury |
| 8,409,217 B2 | 4/2013 | Parihar et al. |
| 8,486,087 B2 | 7/2013 | Fleming |
| 8,827,968 B2 | 9/2014 | Taylor et al. |
| 8,920,431 B2 | 12/2014 | Shibley et al. |
| 8,956,286 B2 | 2/2015 | Shibley et al. |
| 9,044,210 B1 | 6/2015 | Hoyte et al. |
| 9,265,492 B2 | 2/2016 | Shibley et al. |
| 9,655,644 B2 | 5/2017 | Collins |
| 2004/0097960 A1 | 5/2004 | Terachi et al. |
| 2004/0138587 A1 | 7/2004 | Lyons, IV |
| 2004/0158261 A1 | 8/2004 | Vu |
| 2004/0215063 A1 | 10/2004 | Bonadio et al. |
| 2005/0090717 A1 | 4/2005 | Bonadio et al. |
| 2006/0200169 A1 | 9/2006 | Sniffin |
| 2006/0241586 A1 | 10/2006 | Wilk |
| 2007/0135780 A1 | 6/2007 | Pagedas |
| 2007/0135781 A1 | 6/2007 | Hart |
| 2008/0033451 A1 | 2/2008 | Rieber et al. |
| 2009/0326546 A1 | 12/2009 | Mohamed et al. |
| 2010/0219091 A1 | 9/2010 | Turner |
| 2011/0071359 A1 | 3/2011 | Bonadio et al. |
| 2011/0071361 A1 | 3/2011 | Mollenauer et al. |
| 2011/0087235 A1 | 4/2011 | Taylor et al. |
| 2011/0299799 A1 | 12/2011 | Towe |
| 2012/0277758 A1 | 11/2012 | Davis et al. |
| 2013/0131457 A1 | 5/2013 | Seckin |
| 2013/0131689 A1 | 5/2013 | Farascioni |
| 2013/0184536 A1 | 7/2013 | Shibley et al. |
| 2013/0218170 A1 | 8/2013 | Uznanski et al. |
| 2013/0253267 A1 | 9/2013 | Collins |
| 2014/0236168 A1 | 8/2014 | Shibley et al. |
| 2015/0305772 A1 | 10/2015 | McCauley |
| 2016/0100857 A1 | 4/2016 | Wachli et al. |
| 2016/0135798 A1 | 5/2016 | Macleod et al. |
| 2016/0199051 A1 | 7/2016 | Shibley et al. |
| 2017/0049427 A1 | 2/2017 | Do et al. |
| 2017/0056065 A1 | 3/2017 | Do et al. |
| 2017/0231611 A1 | 8/2017 | Holsten et al. |

FOREIGN PATENT DOCUMENTS

| | | |
|---|---|---|
| CN | 205683099 U | 11/2016 |
| EP | 0 578 997 A1 | 1/1994 |
| EP | 0 465 051 B1 | 8/1995 |
| EP | 2 265 186 B1 | 11/2011 |
| GB | 2460099 A | 11/2009 |
| IN | 5813/CHE/2014 | 12/2014 |
| JP | H06-319795 A | 11/1994 |
| JP | H08-294493 A | 11/1996 |

(56) References Cited

FOREIGN PATENT DOCUMENTS

| WO | WO 95/09666 | | 4/1995 |
|---|---|---|---|
| WO | WO 98/09569 | | 3/1998 |
| WO | WO 2005/025427 | A1 | 3/2005 |
| WO | WO 2006/044797 | A2 | 4/2006 |
| WO | WO 2009/158301 | A1 | 12/2009 |
| WO | WO 2010/099541 | A1 | 9/2010 |
| WO | WO 2011/090866 | A2 | 7/2011 |
| WO | WO 2011/110836 | A2 | 9/2011 |
| WO | WO 2013/054093 | A1 | 4/2013 |
| WO | WO 2013/075103 | A1 | 5/2013 |
| WO | WO 2013/093030 | | 6/2013 |
| WO | WO 2014/207077 | A1 | 12/2014 |
| WO | WO 2015/151117 | A1 | 10/2015 |
| WO | WO 2015/151117 | A2 | 10/2015 |
| WO | WO 2016/028429 | | 2/2016 |
| WO | WO 2016/028429 | A1 | 2/2016 |

OTHER PUBLICATIONS

International Preliminary Report on Patentability for International No. PCT/EP2012/076703, dated Jun. 24, 2014 (9 pages).
Requirement for Restriction/Election of Species from U.S. Appl. No. 13/725,148, dated Jun. 5, 2014 (8 pages).
Reply to Requirement for Restriction/Election of Species from U.S. Appl. No. 13/725,148, filed Aug. 5, 2014 (8 pages).
Non-Final Office Action from U.S. Appl. No. 13/725,148, dated Aug. 27, 2014 (13 pages).
Final Office Action dated Mar. 18, 2015, in U.S. Appl. No. 13/725,148 (18 pages).
Reply to Office Action filed on Sep. 17, 2015, in U.S. Appl. No. 13/725,148 (16 pages).
Restriction Requirement in U.S. Appl. No. 14/996,610, dated Jul. 29, 2016 (6 pages).
International Search Report and Written Opinion for corresponding Application No. PCT/EP2015/079163, dated Mar. 23, 2016, (11 pages).
International Search Report dated Nov. 14, 2014, in PCT/EP2014/063458 (8 pages).

* cited by examiner

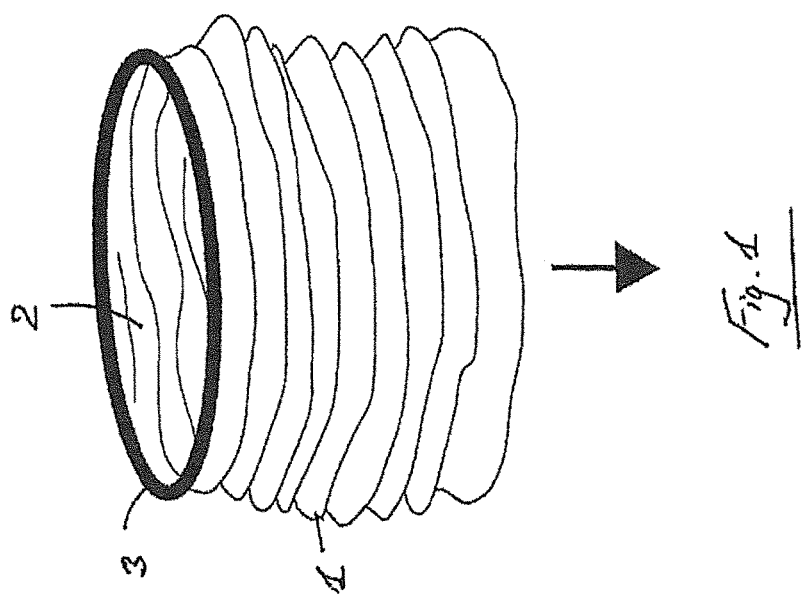
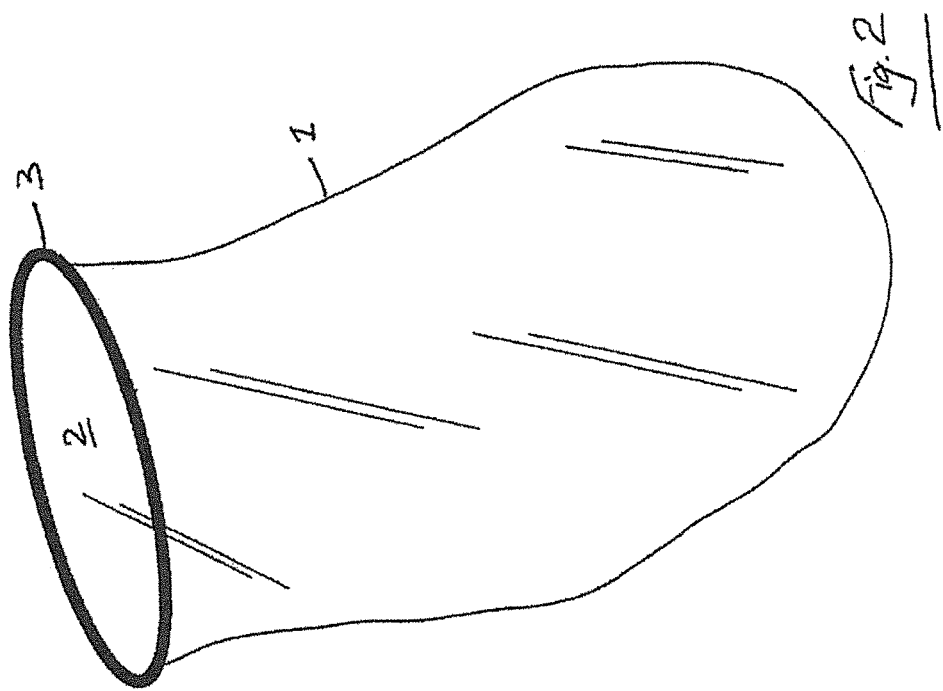

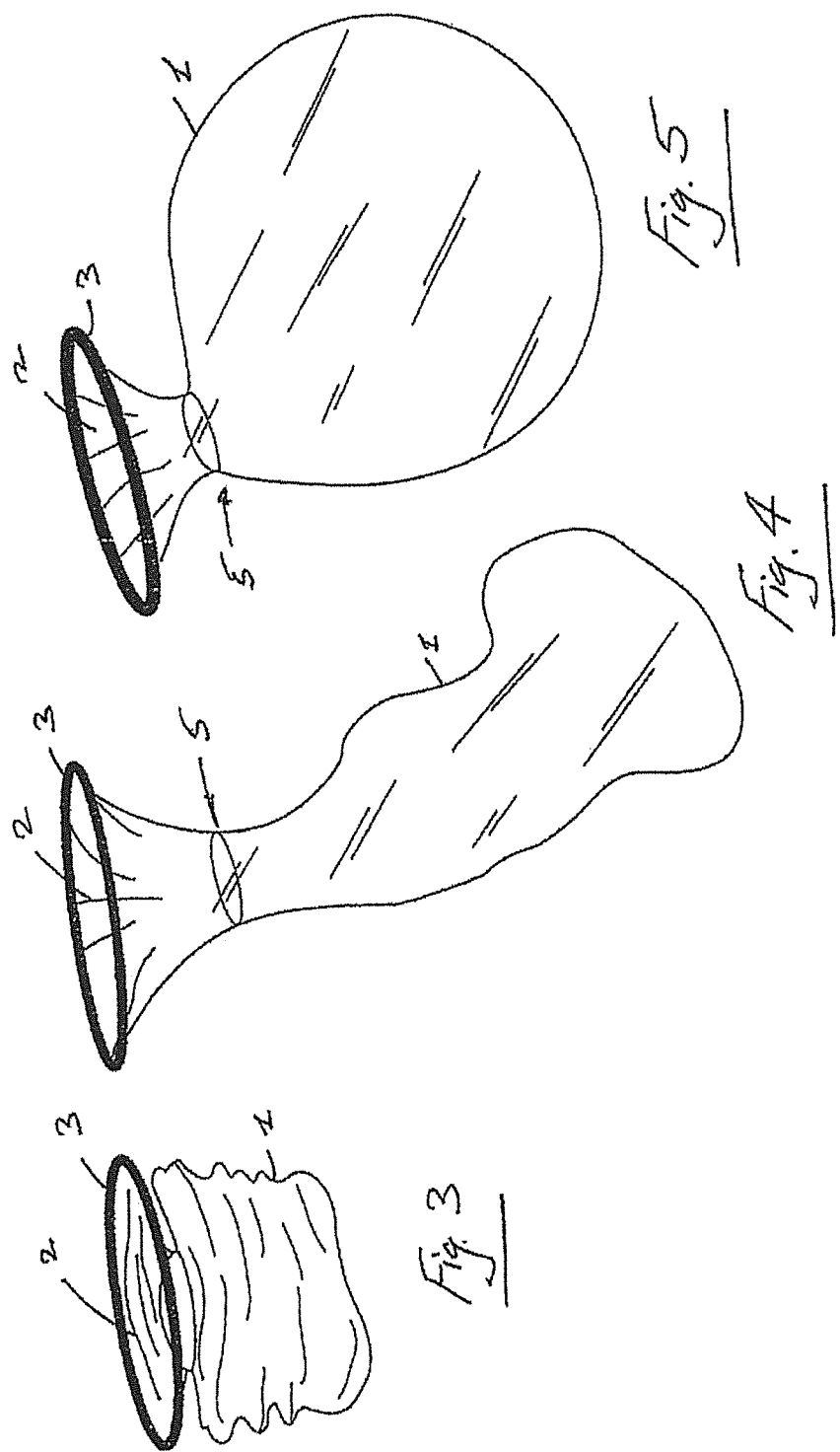

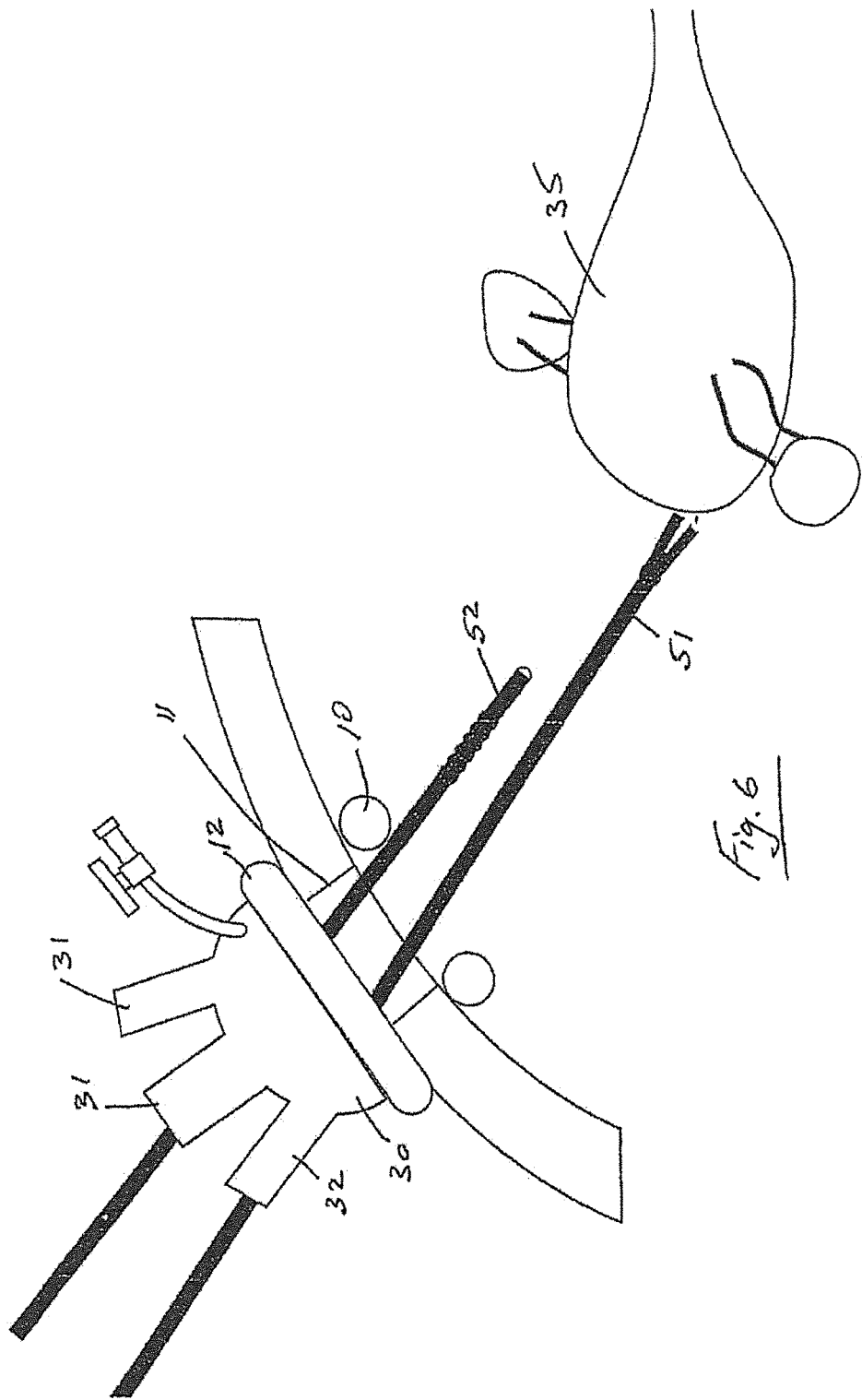

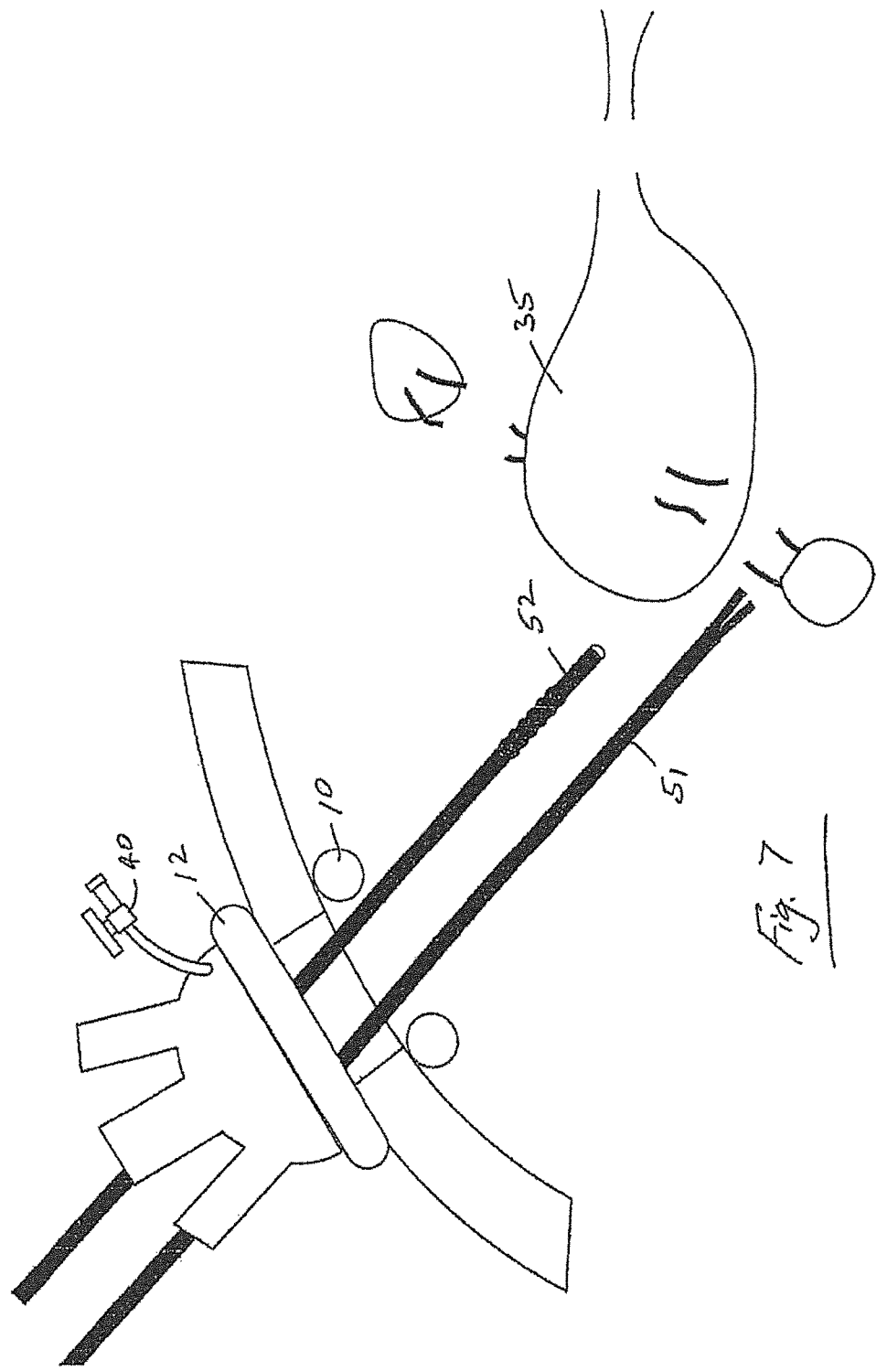

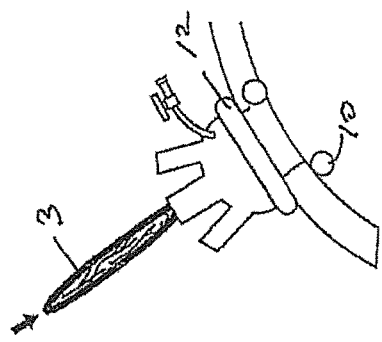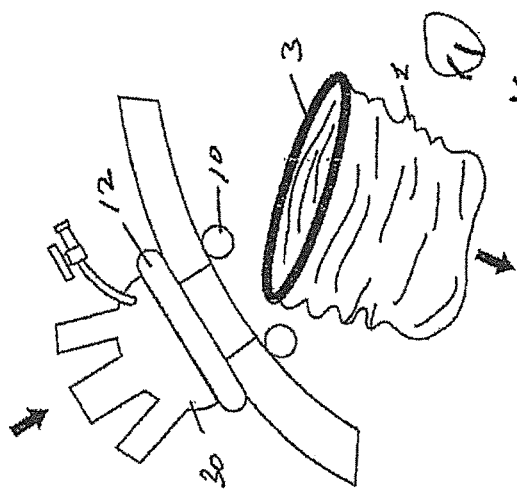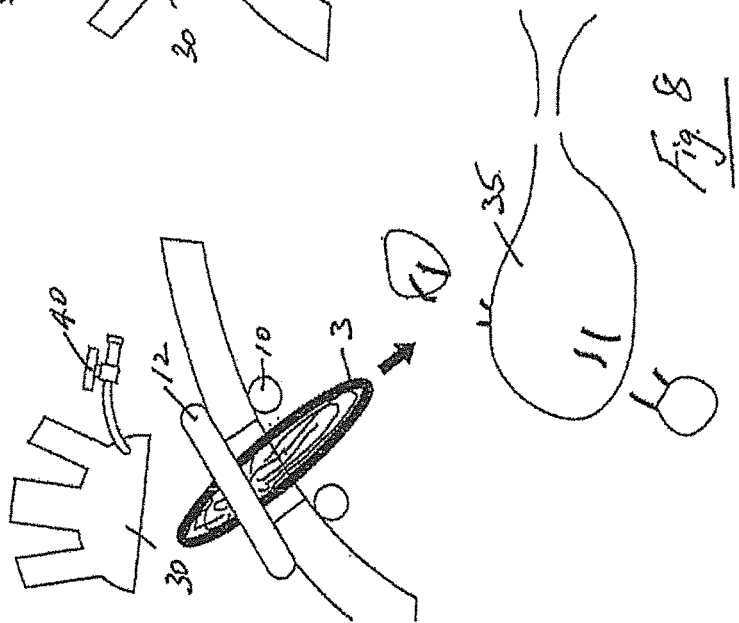

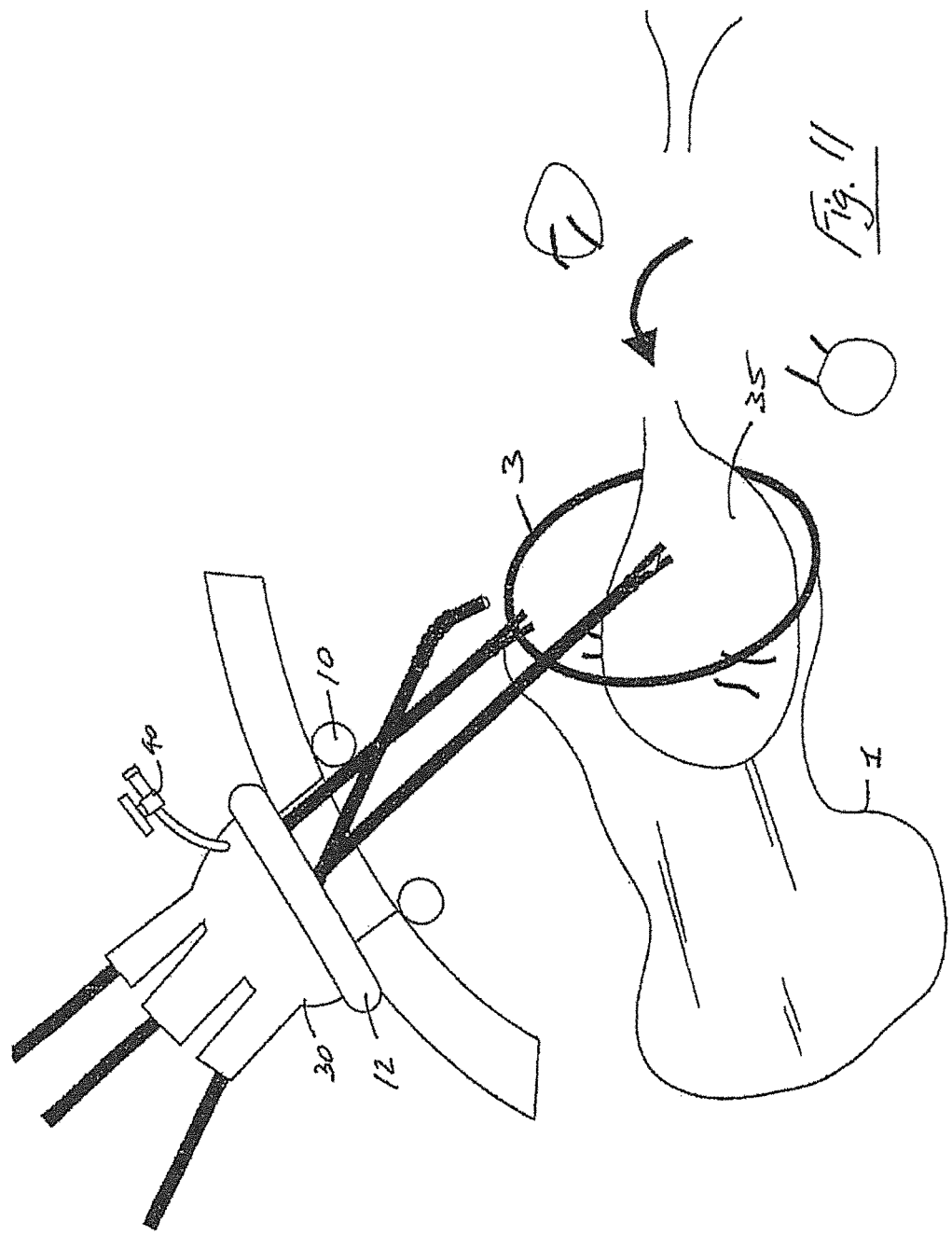

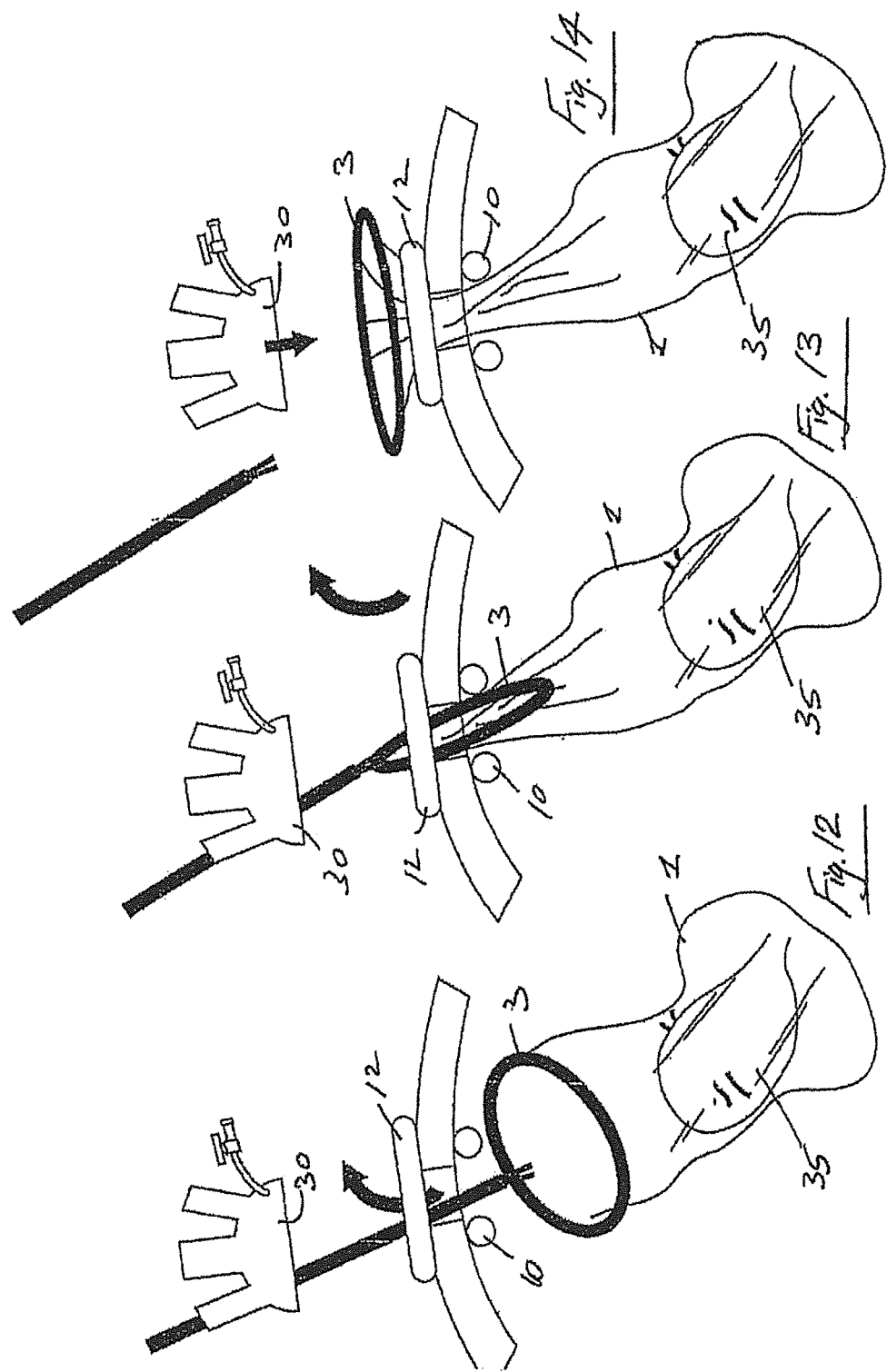

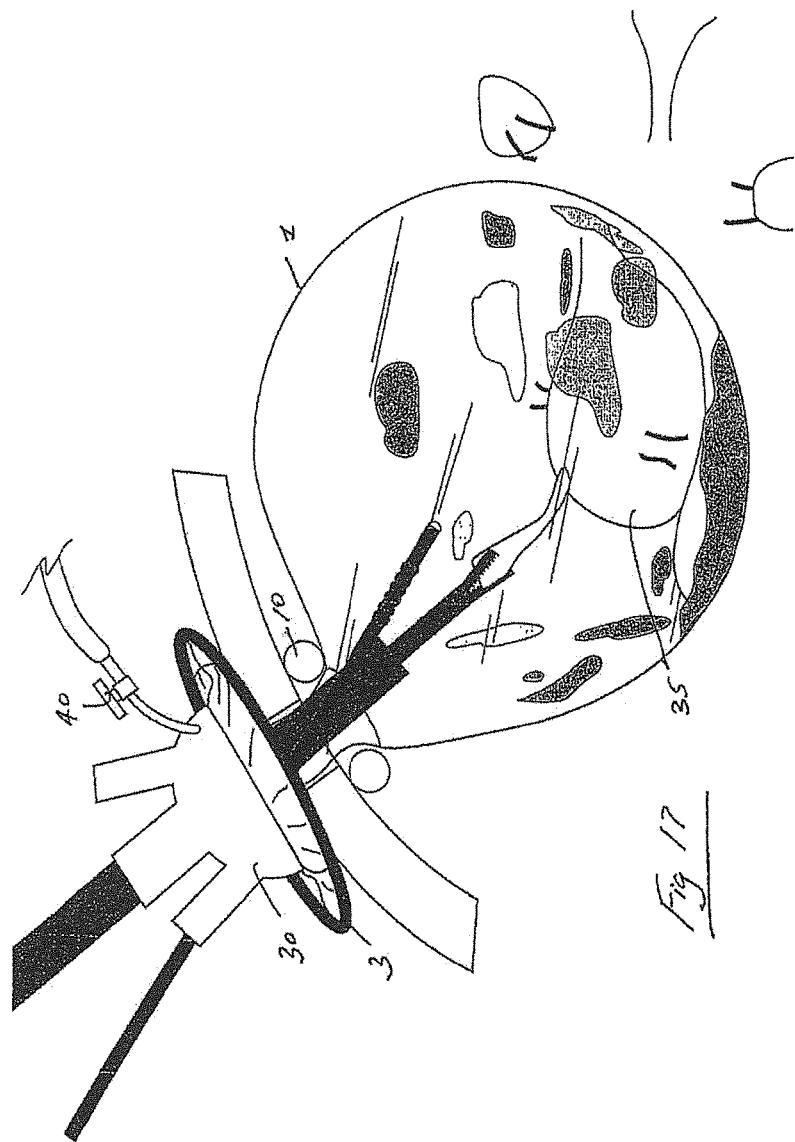

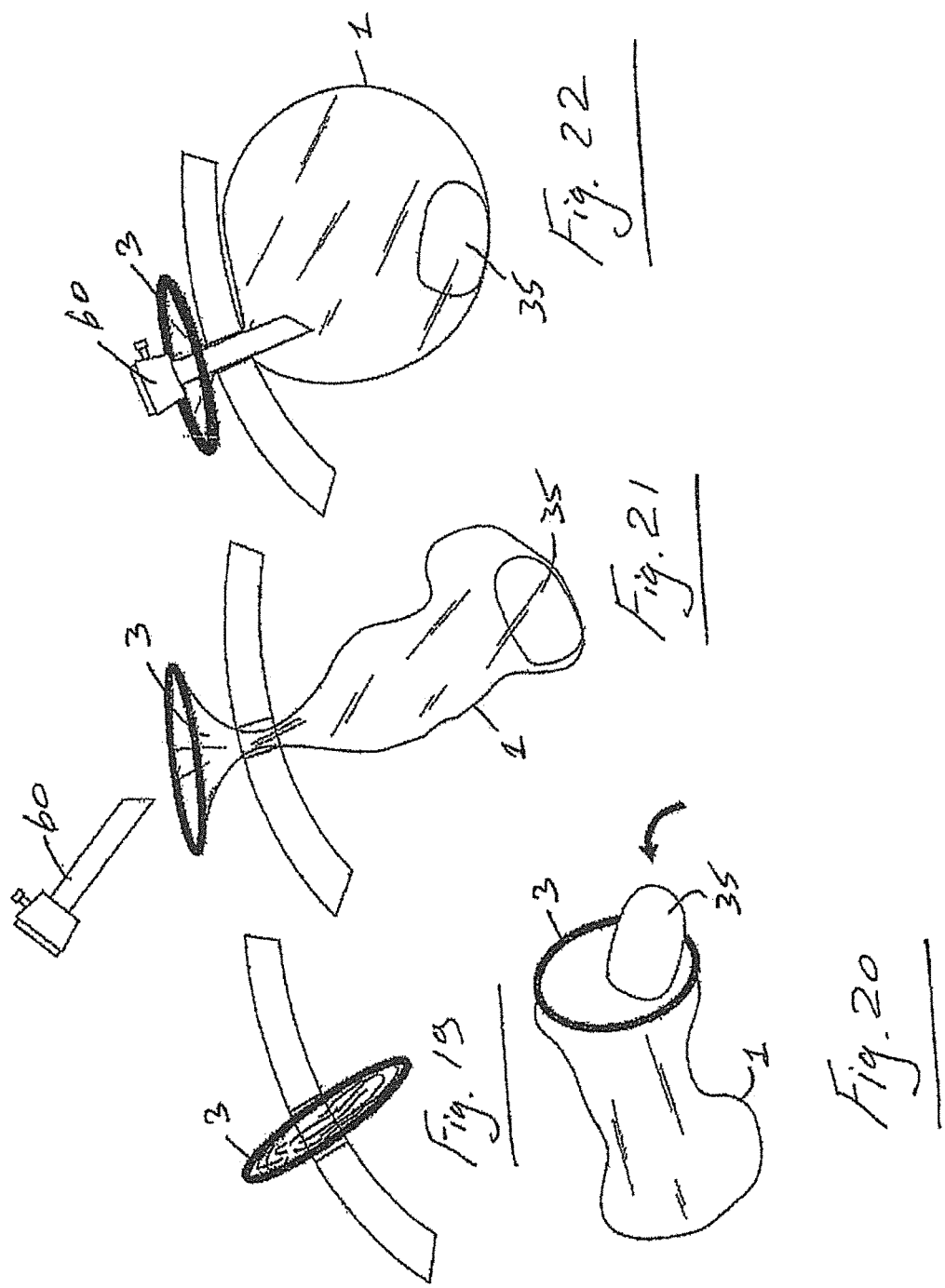

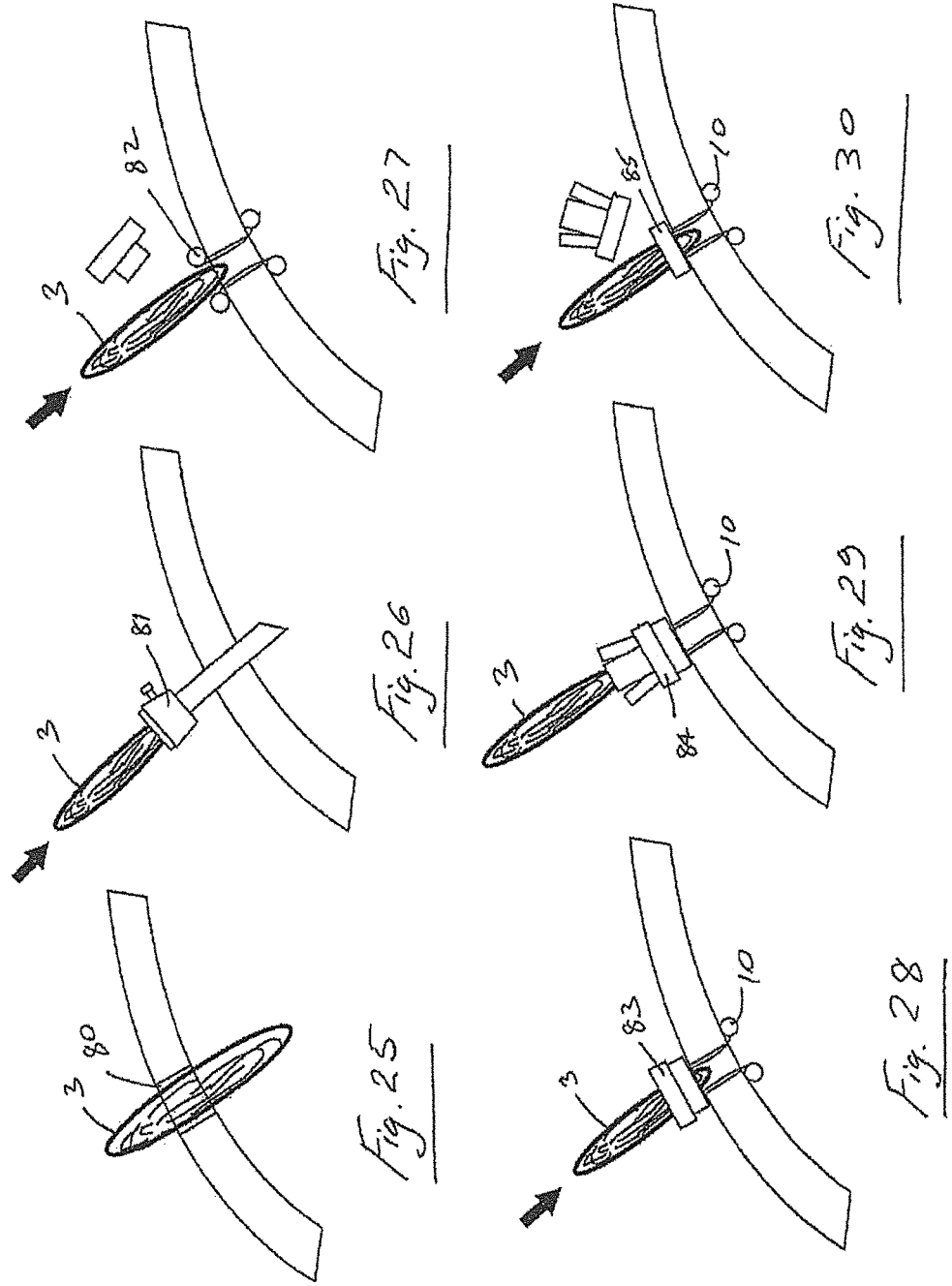

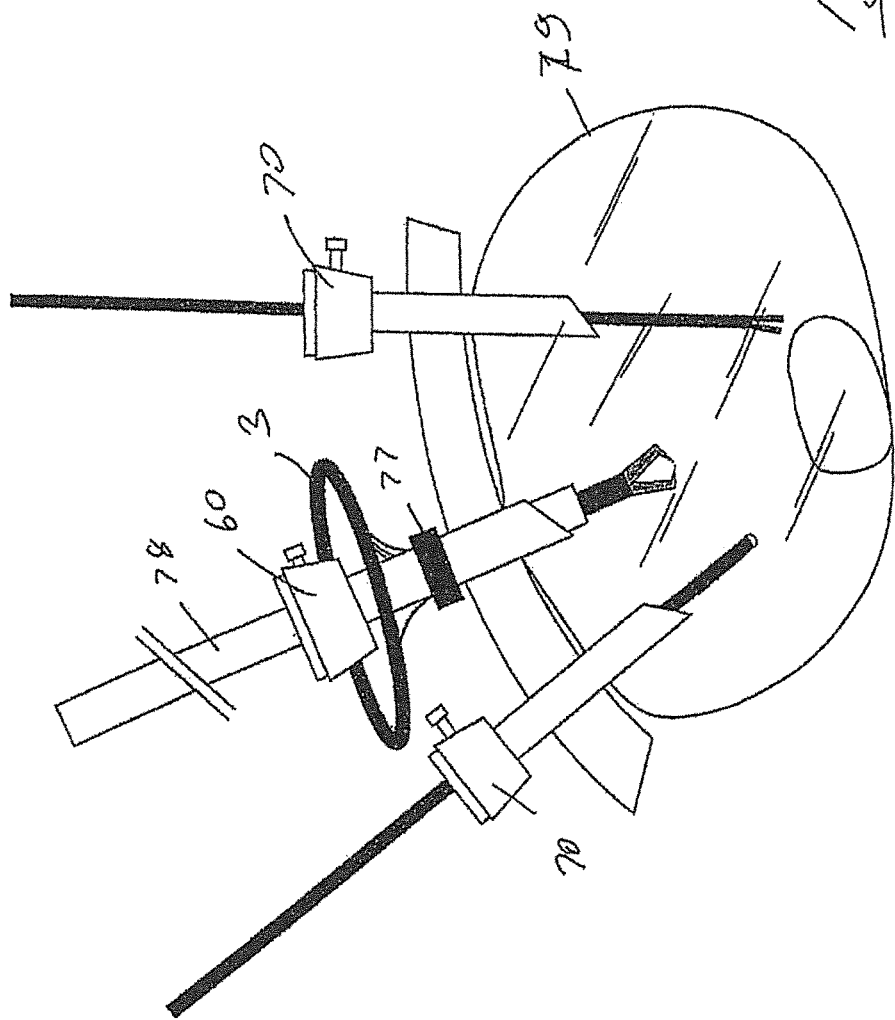

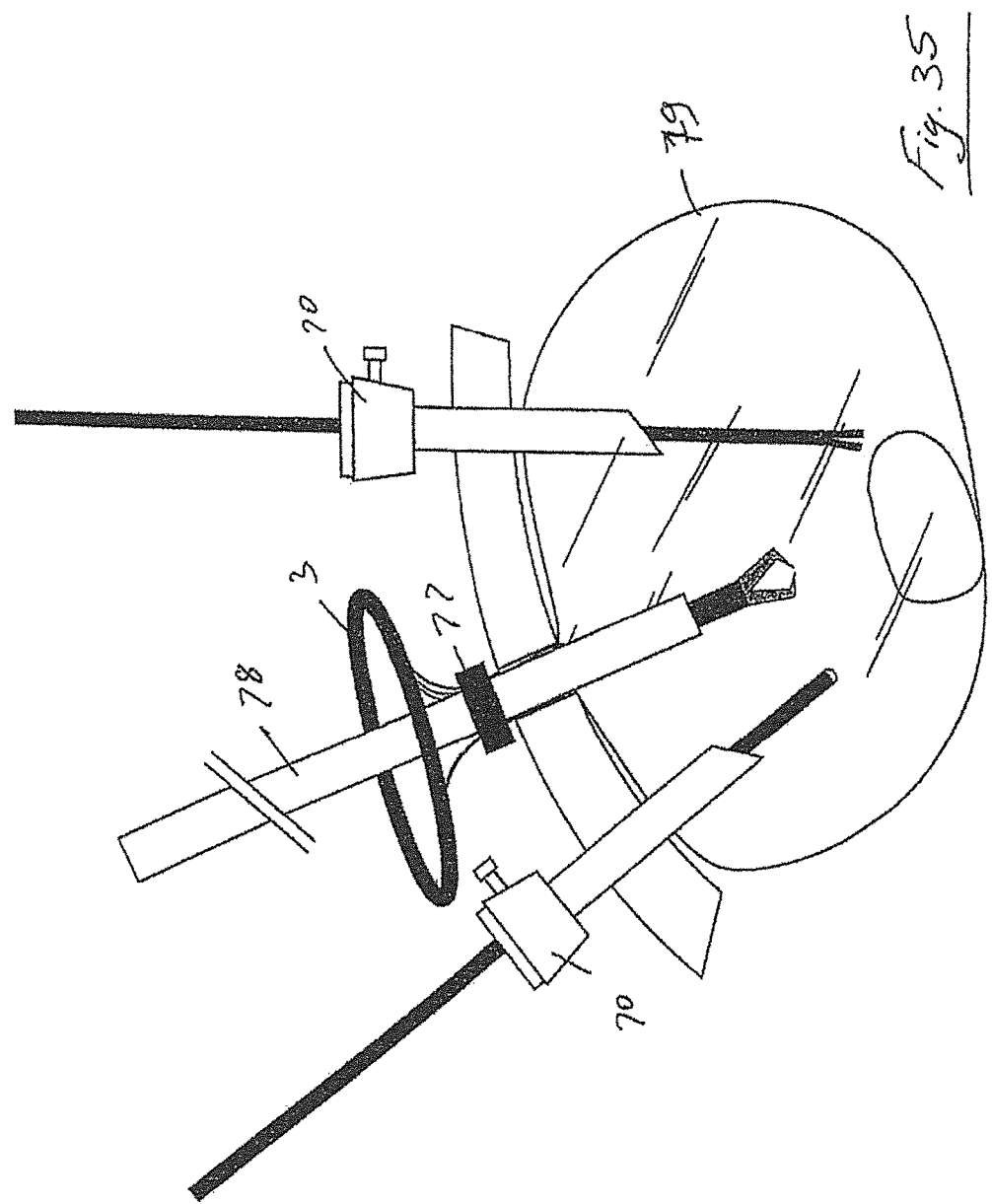

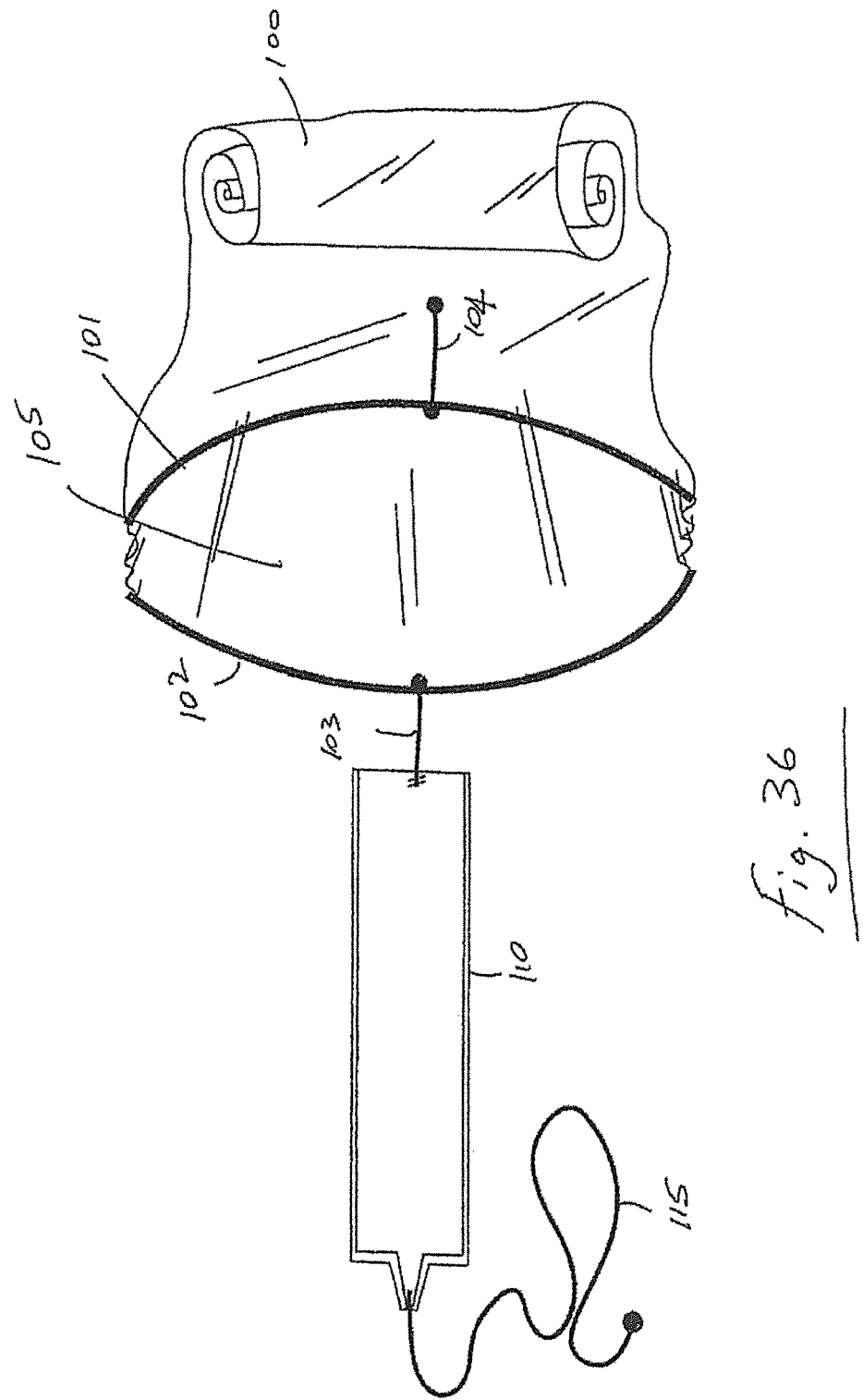

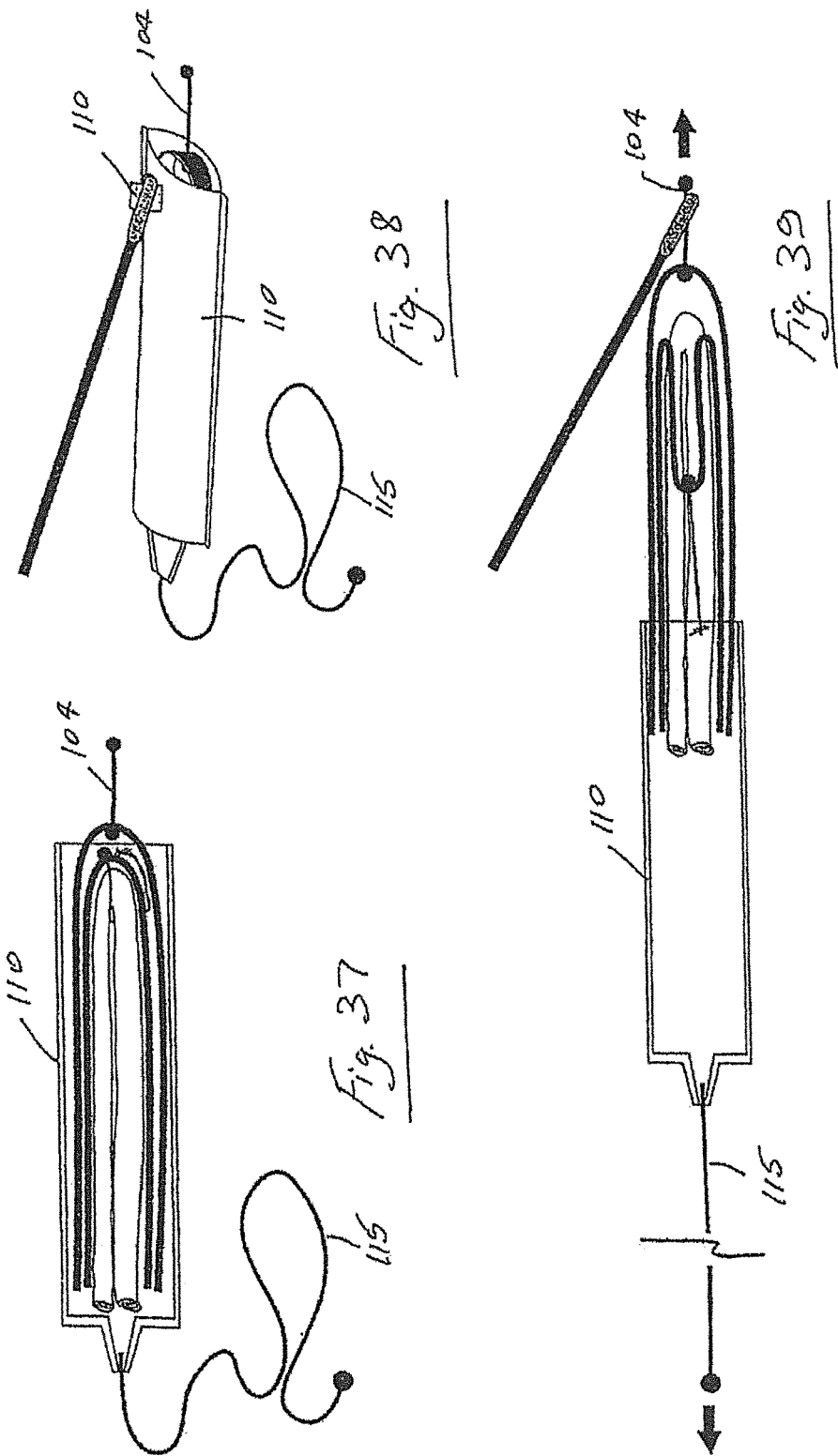

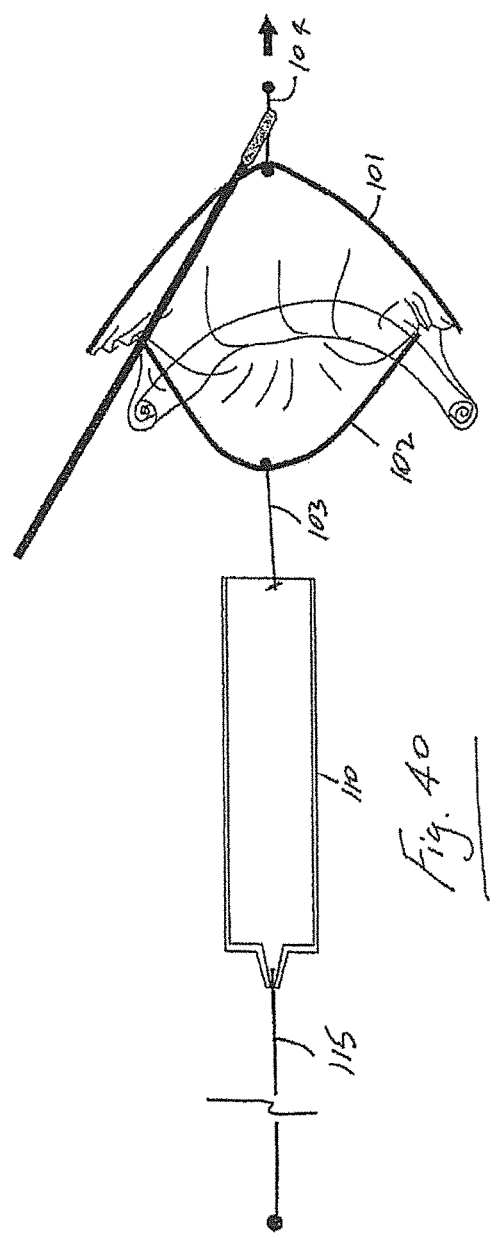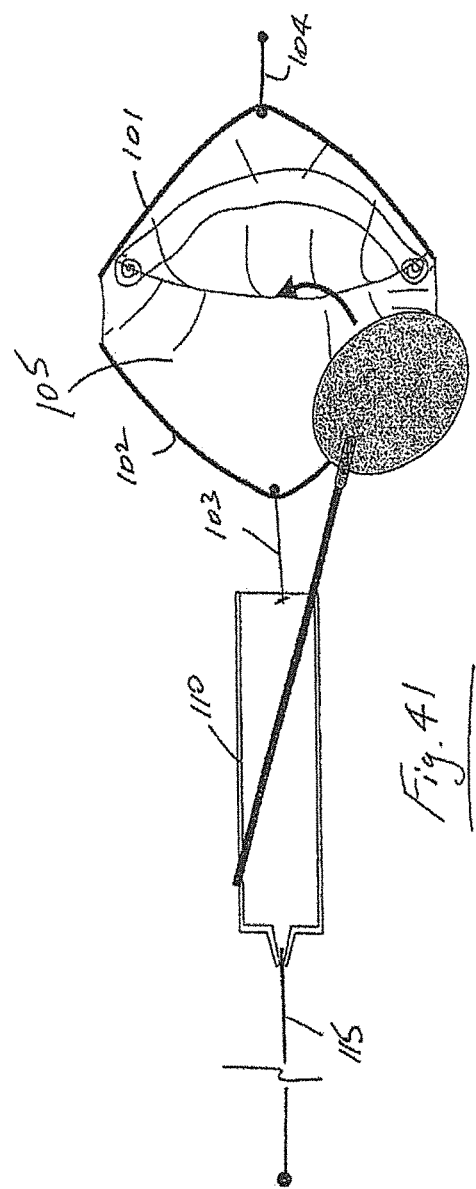

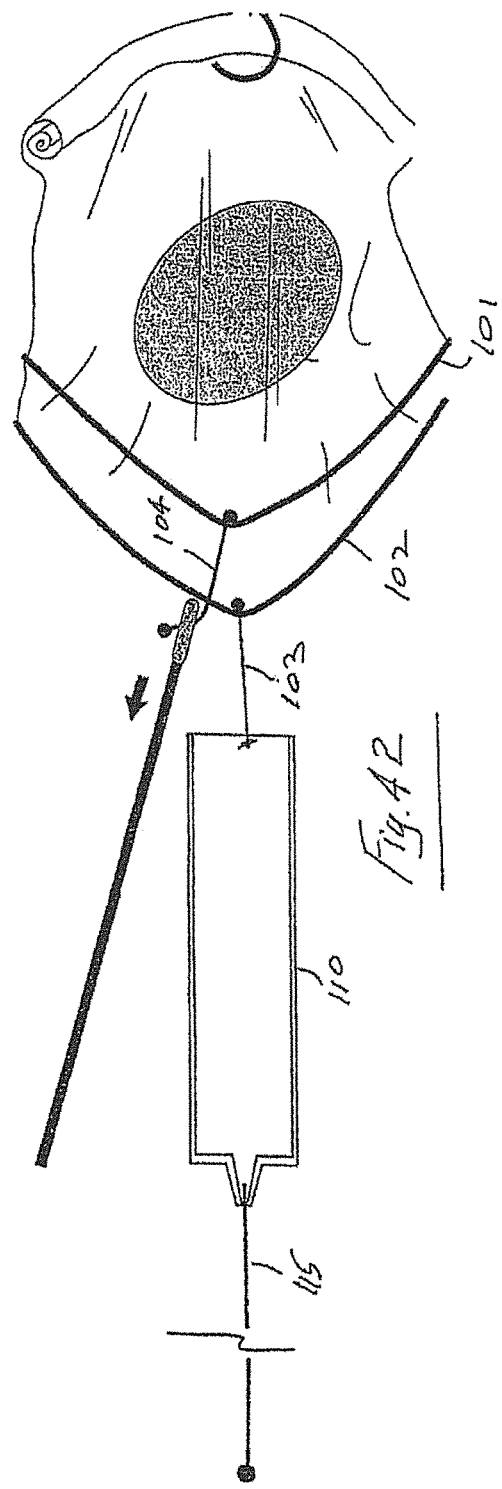
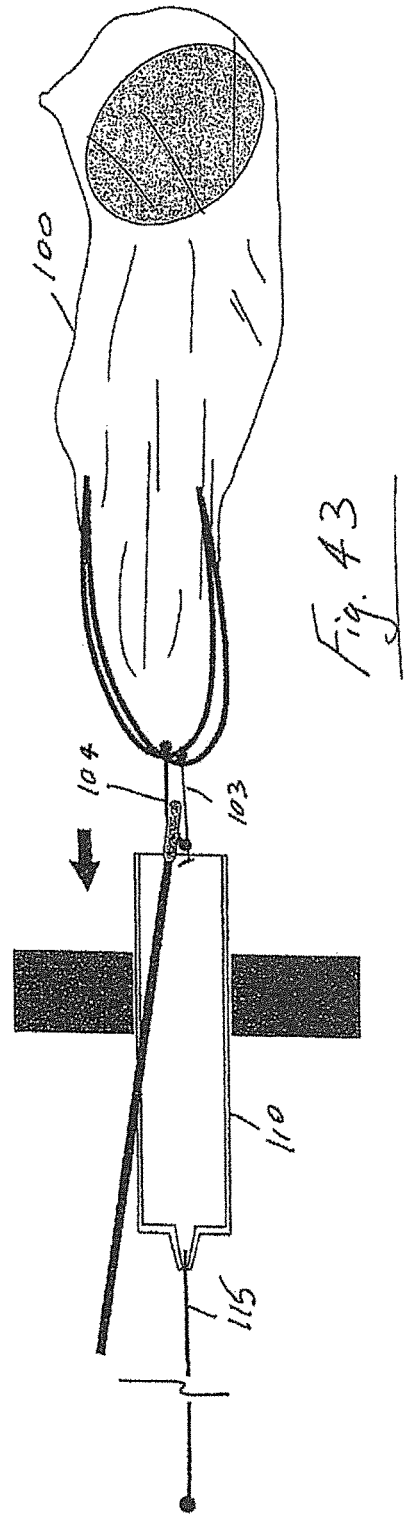

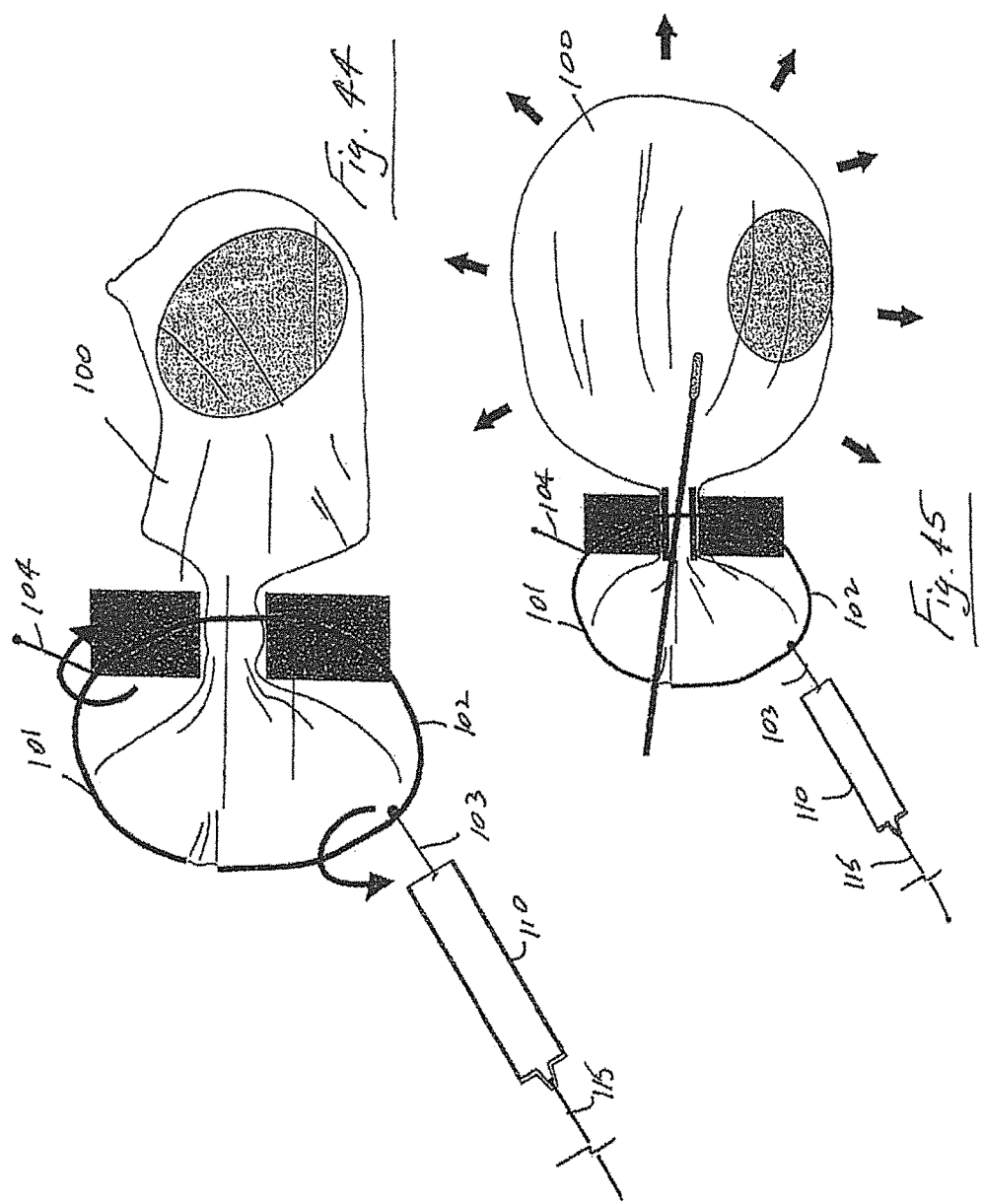

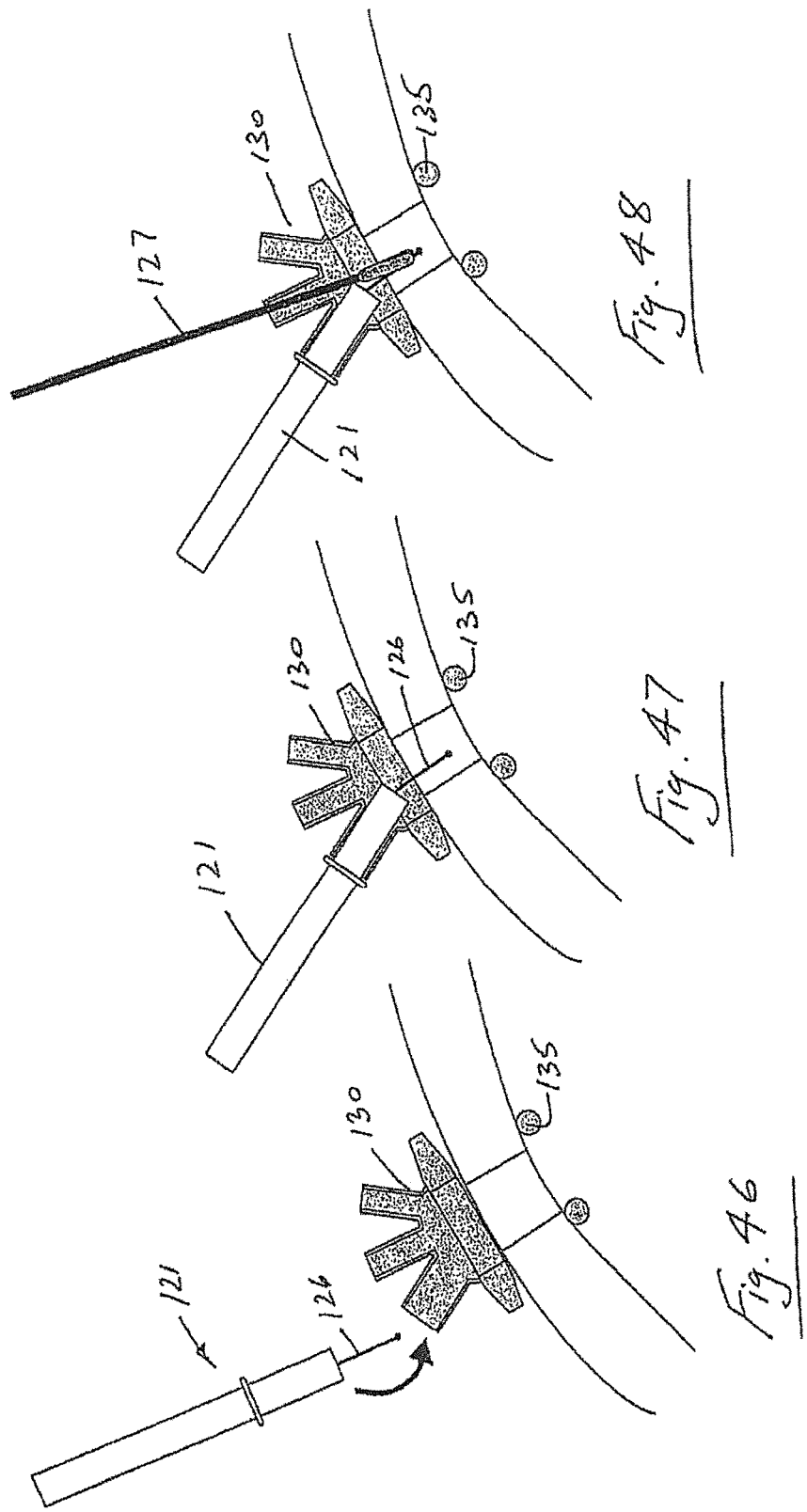

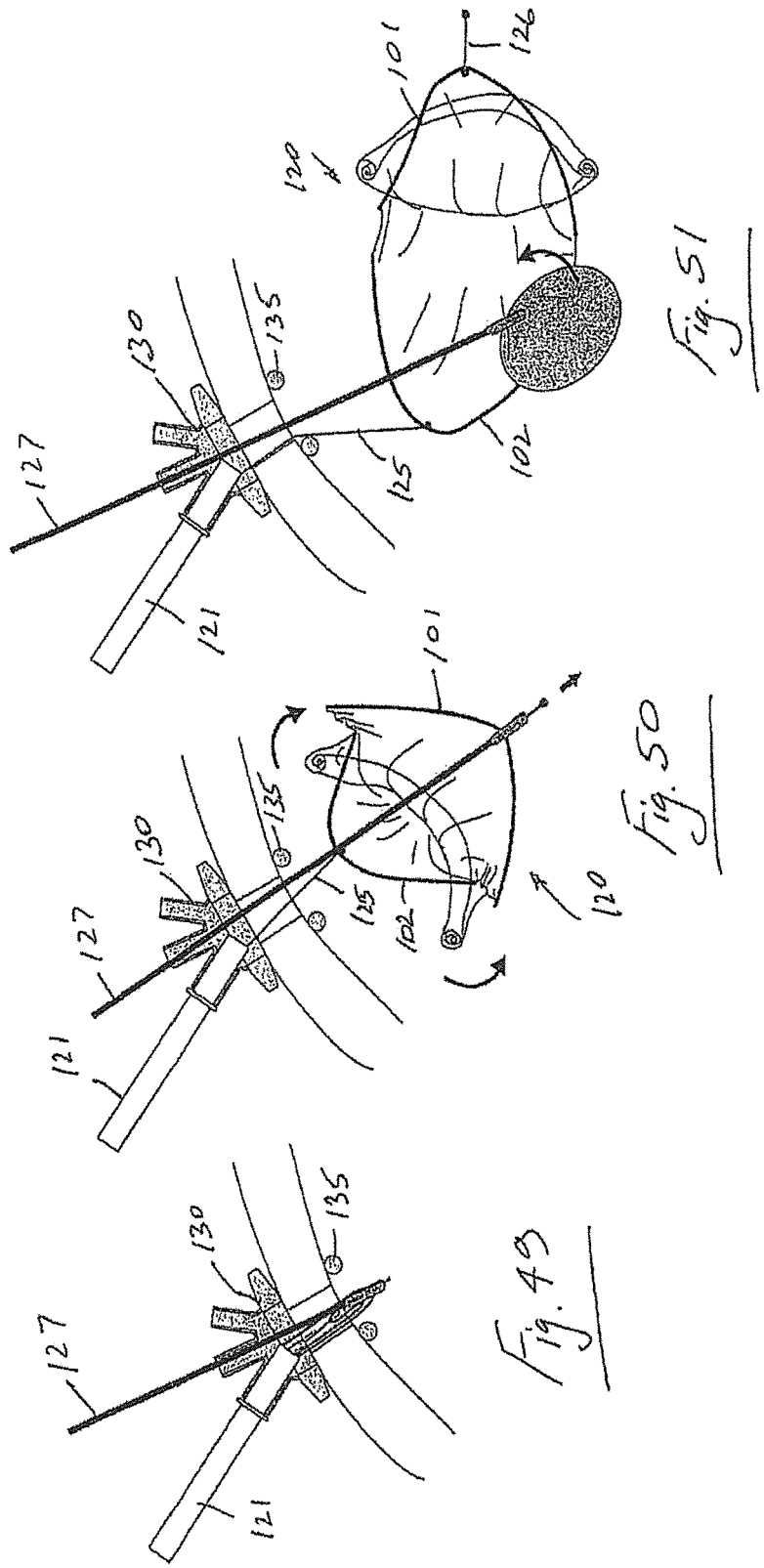

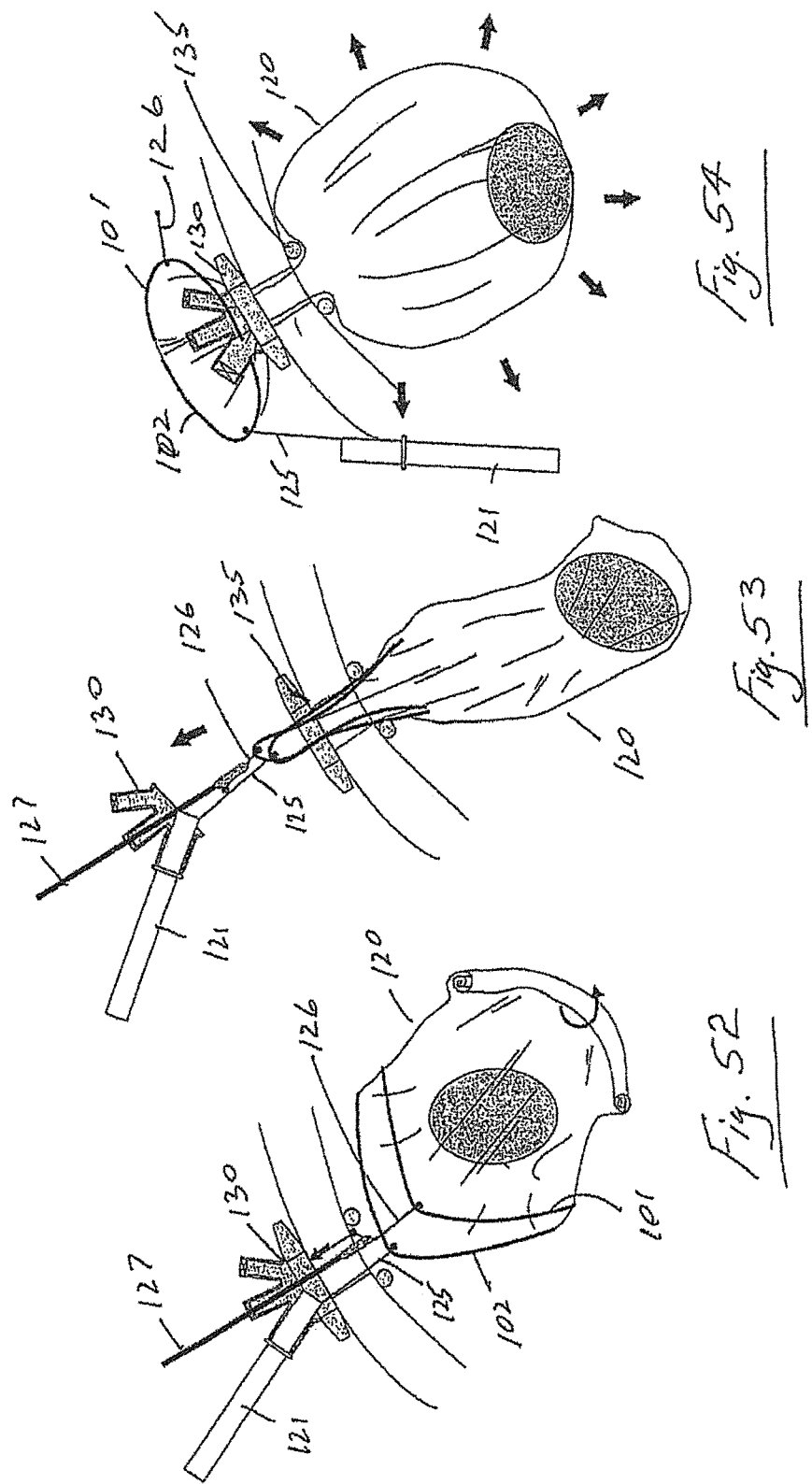

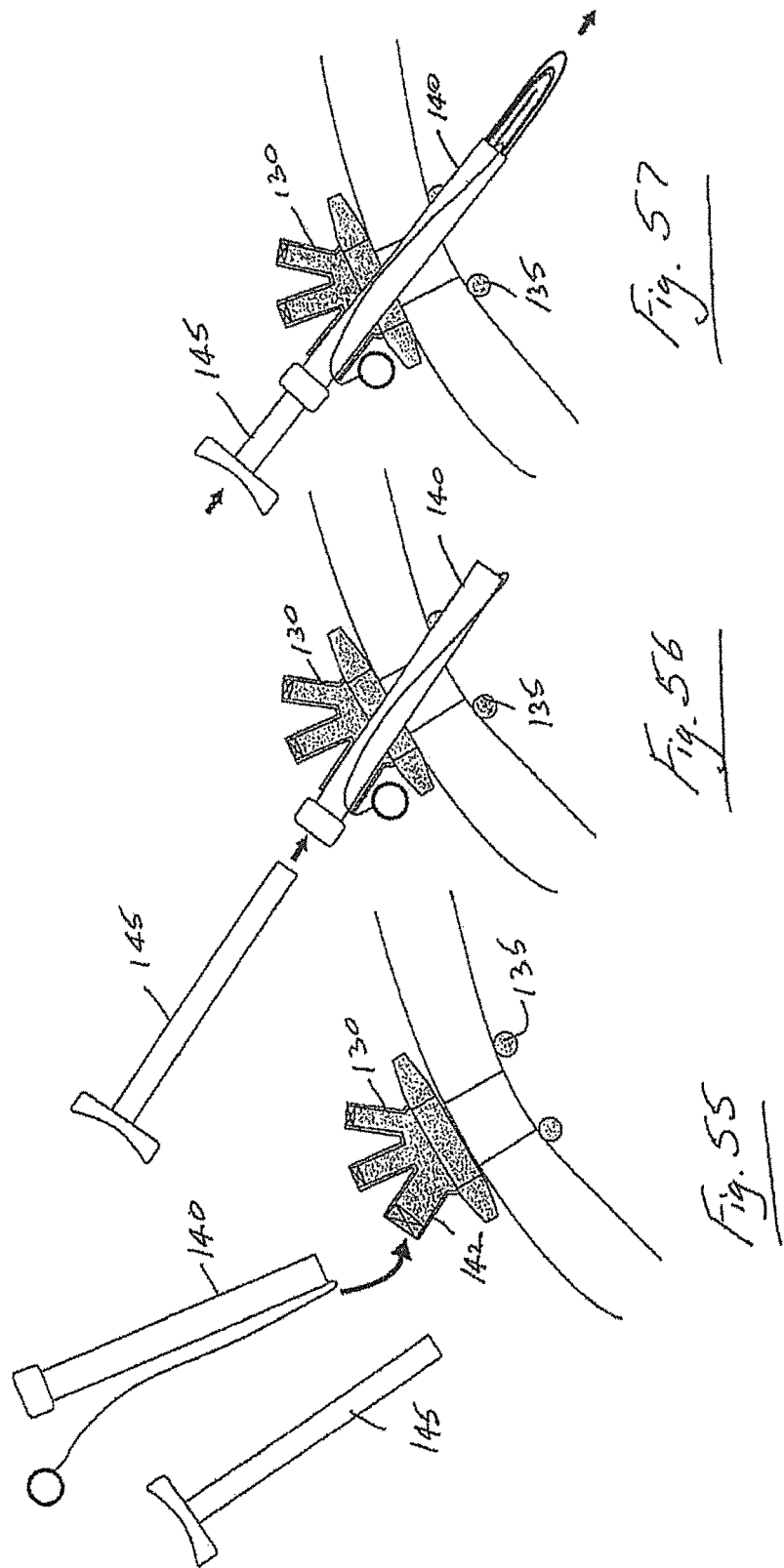

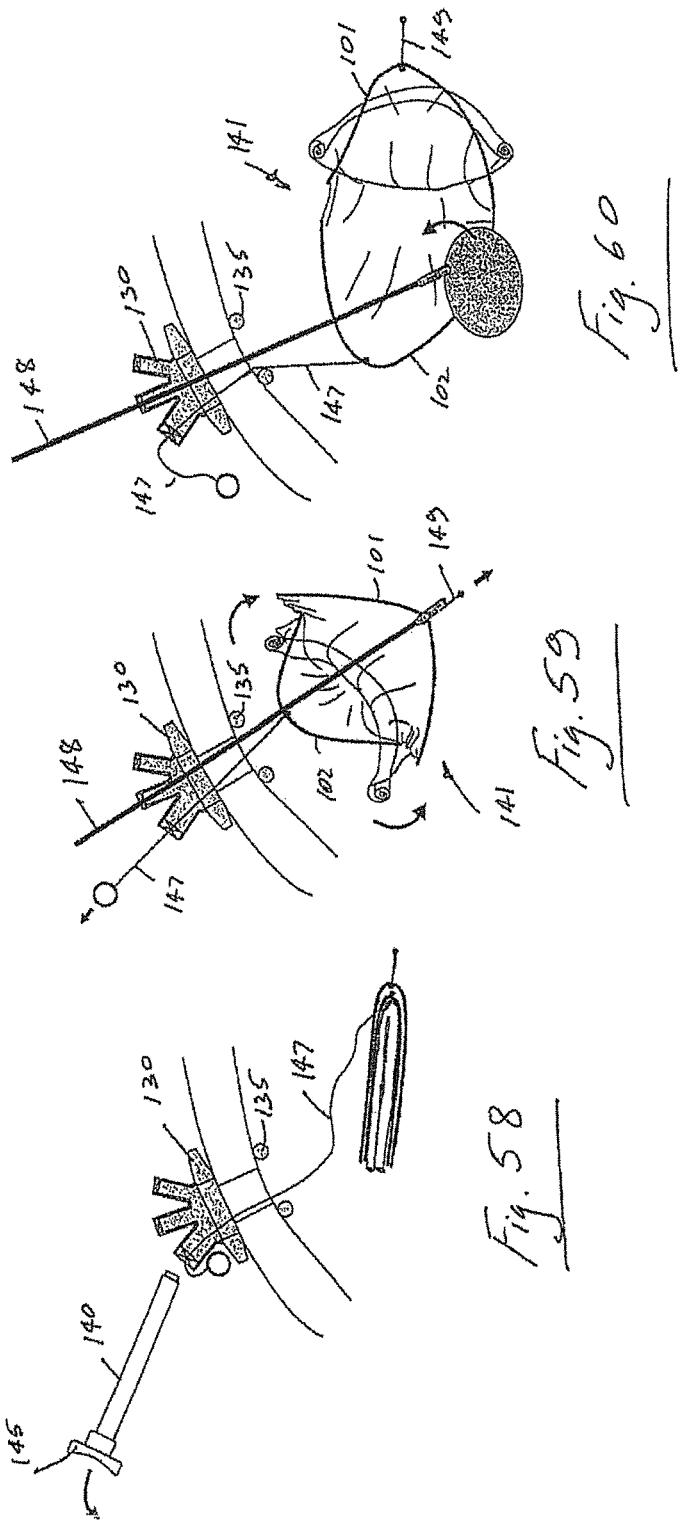

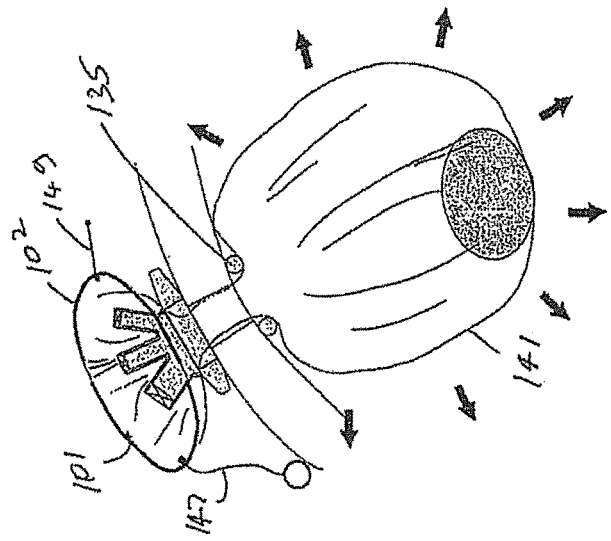
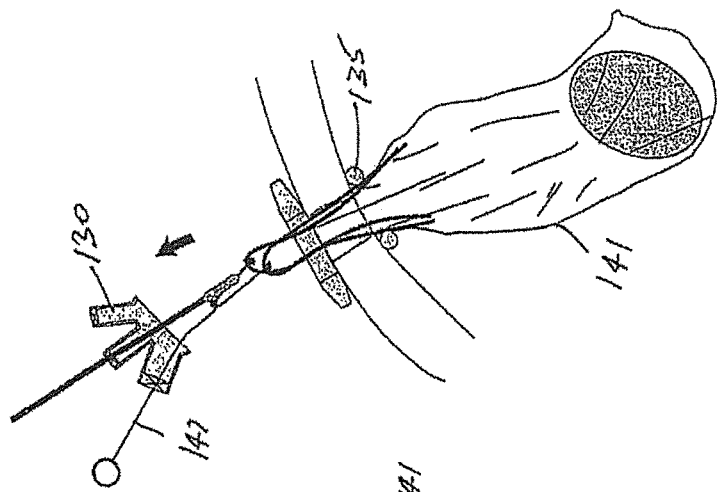
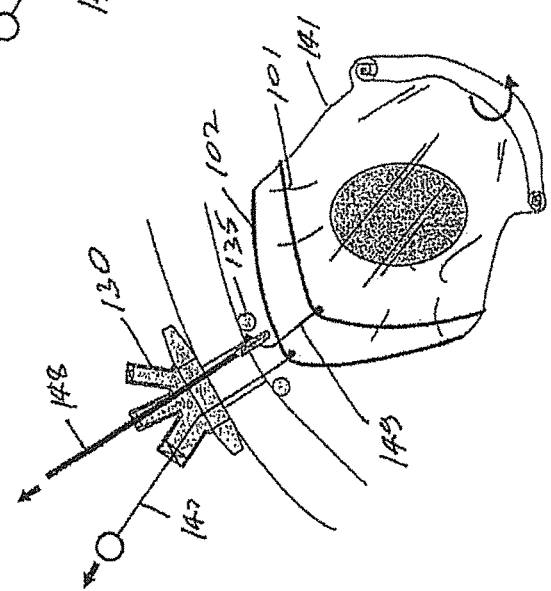

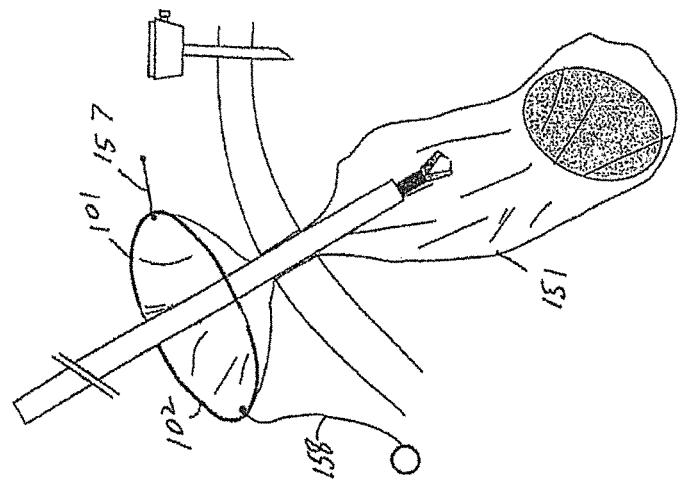
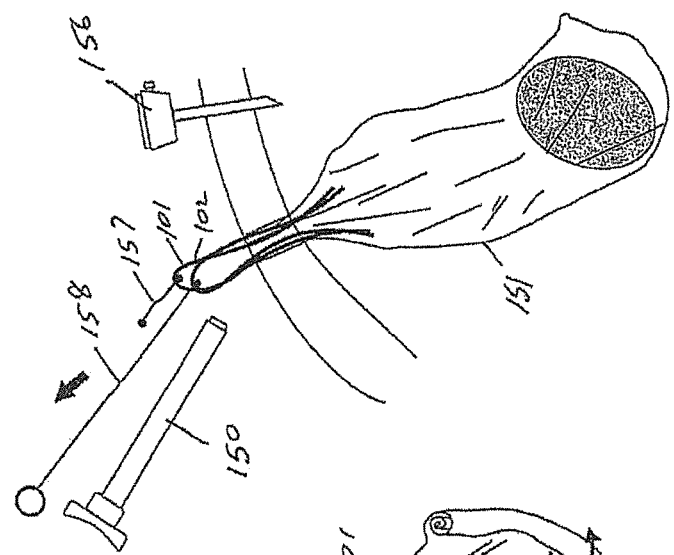
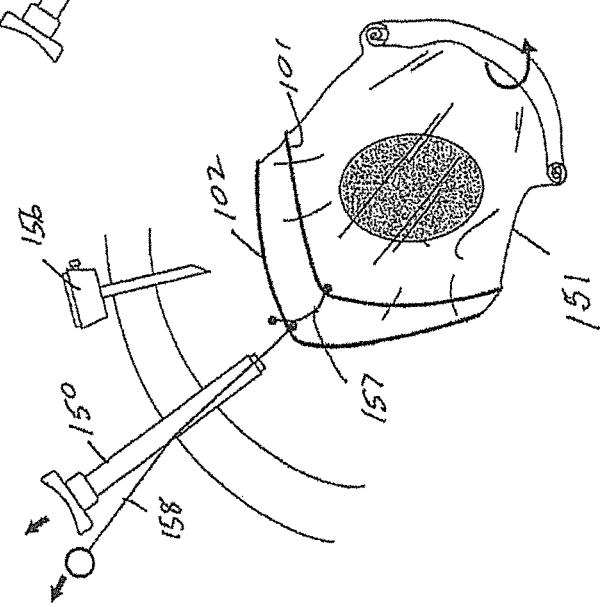

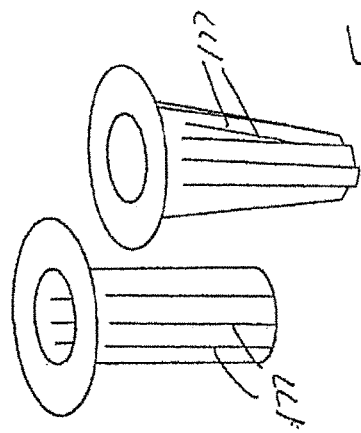
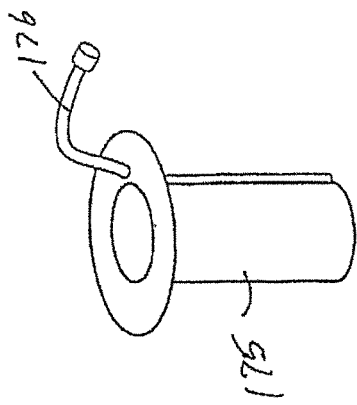
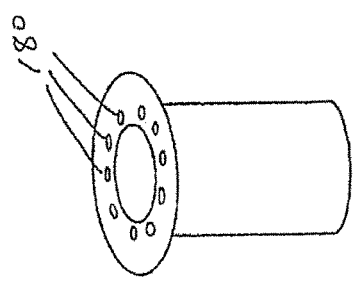
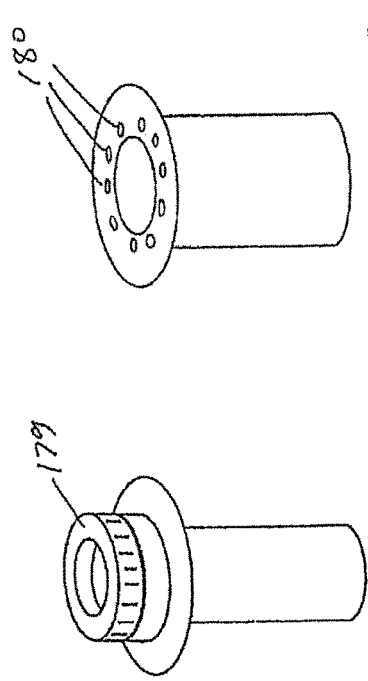
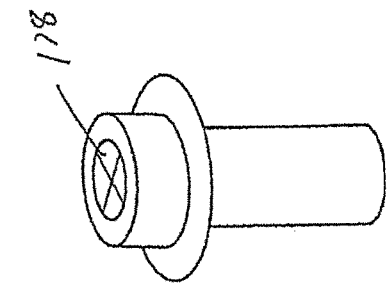

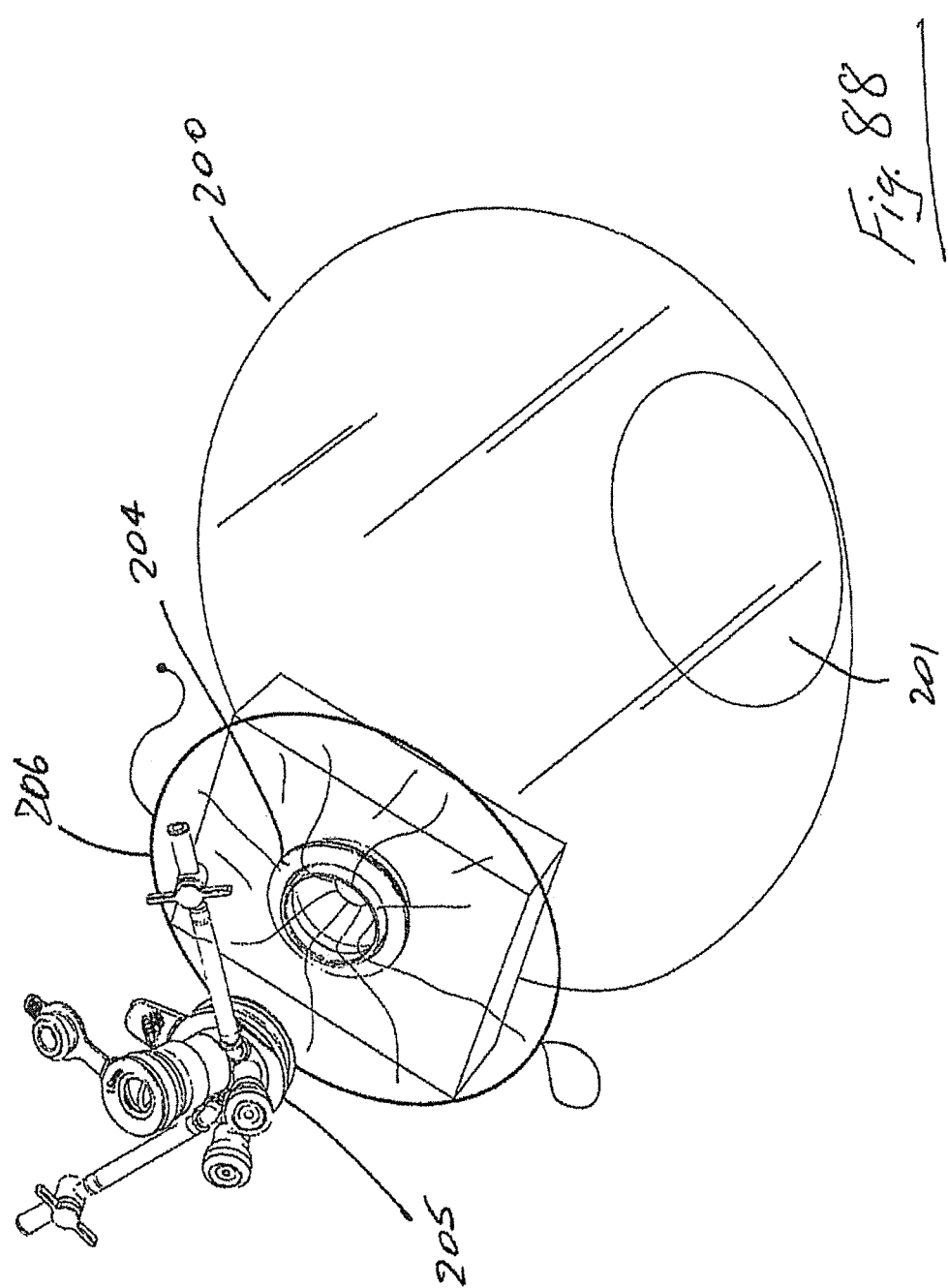

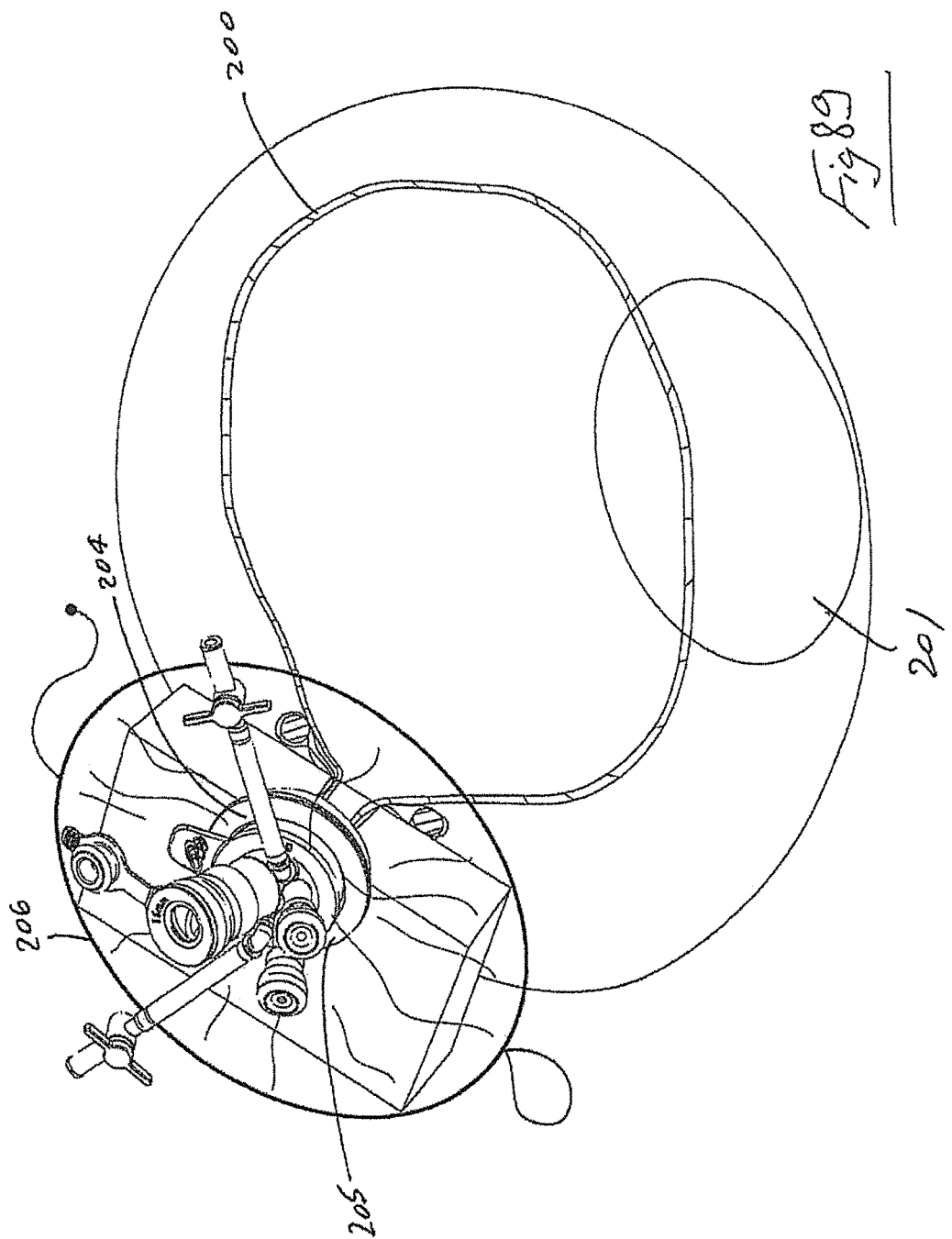

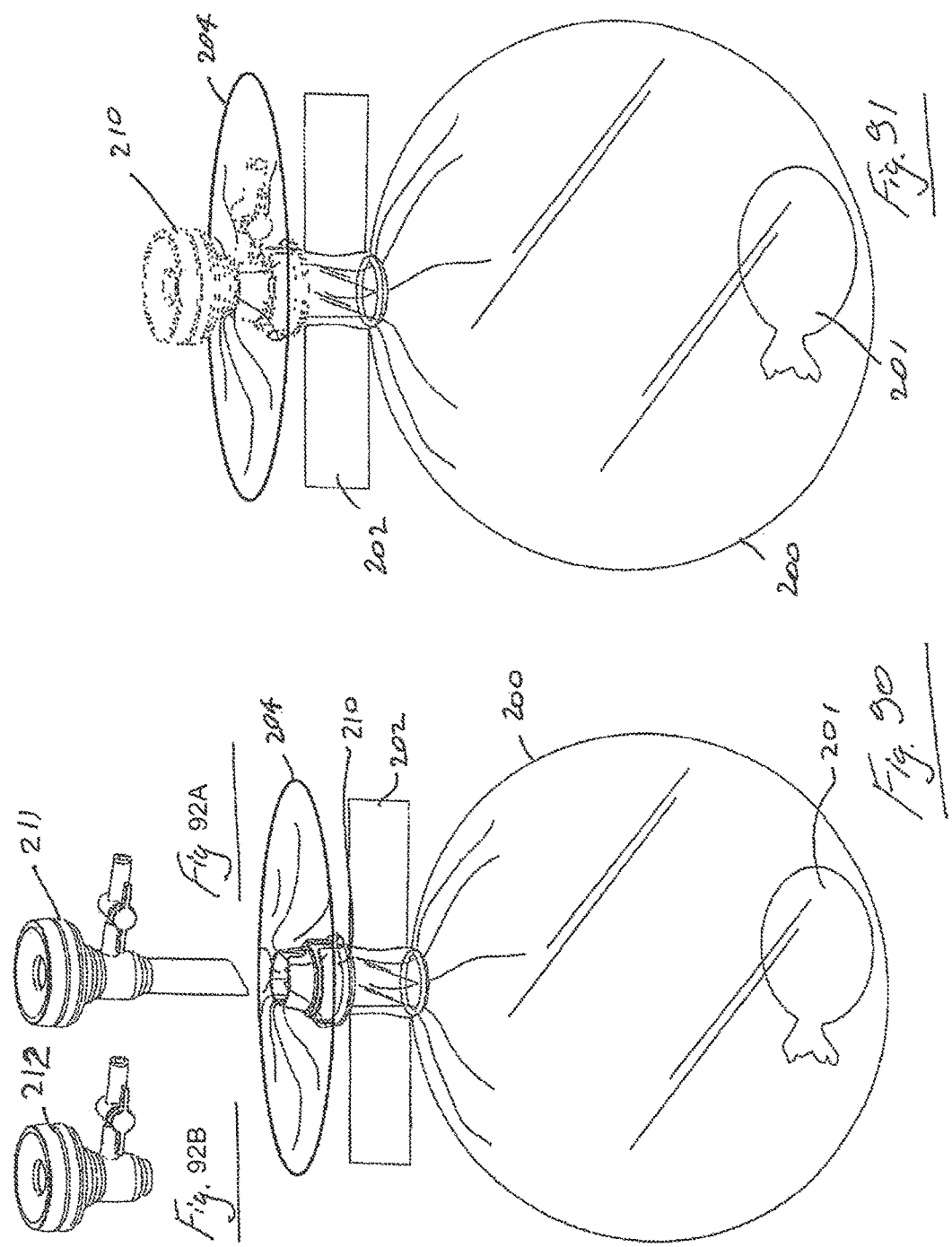

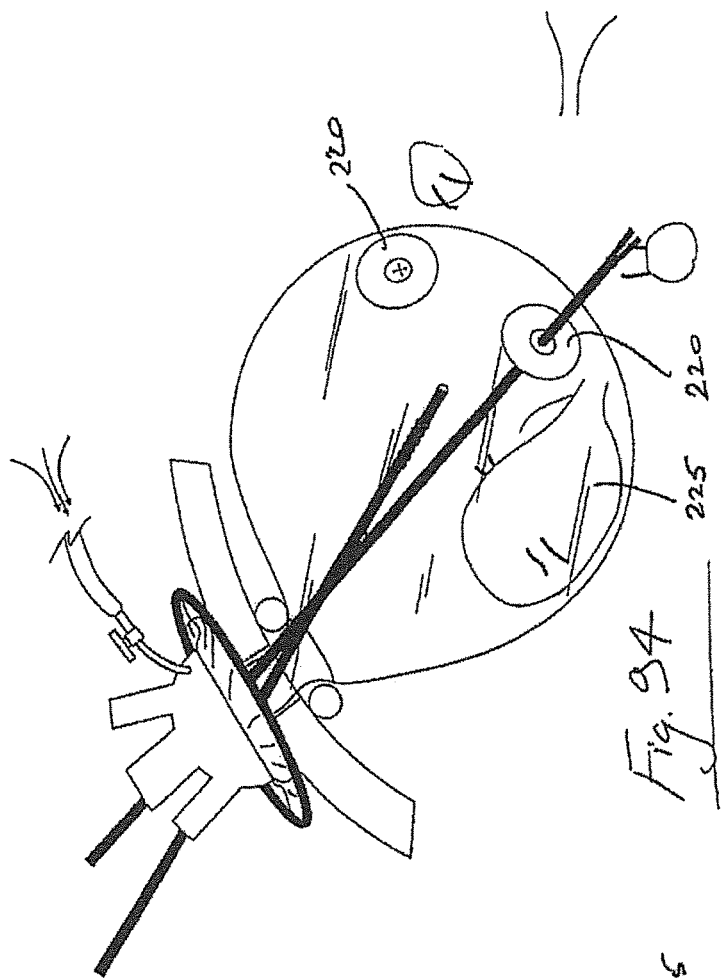
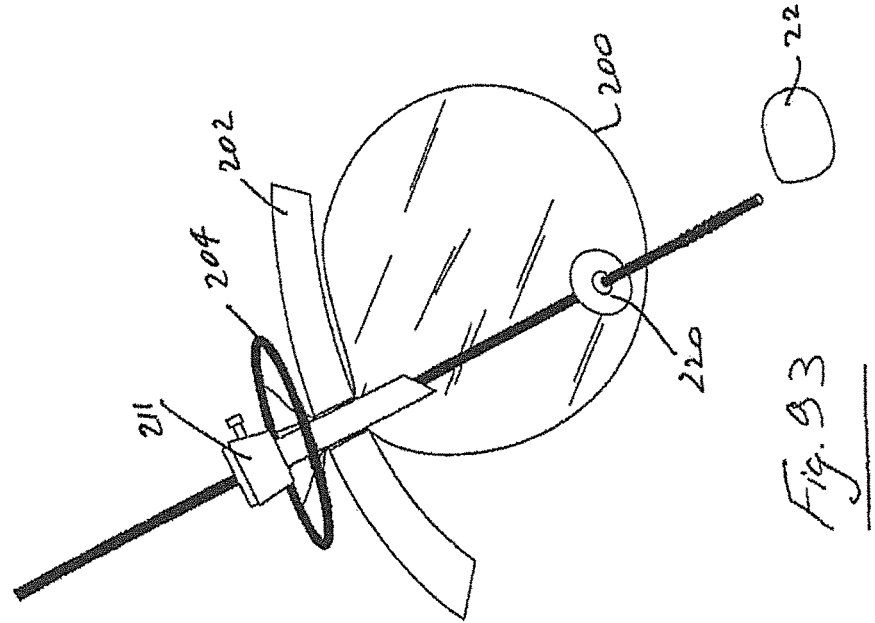

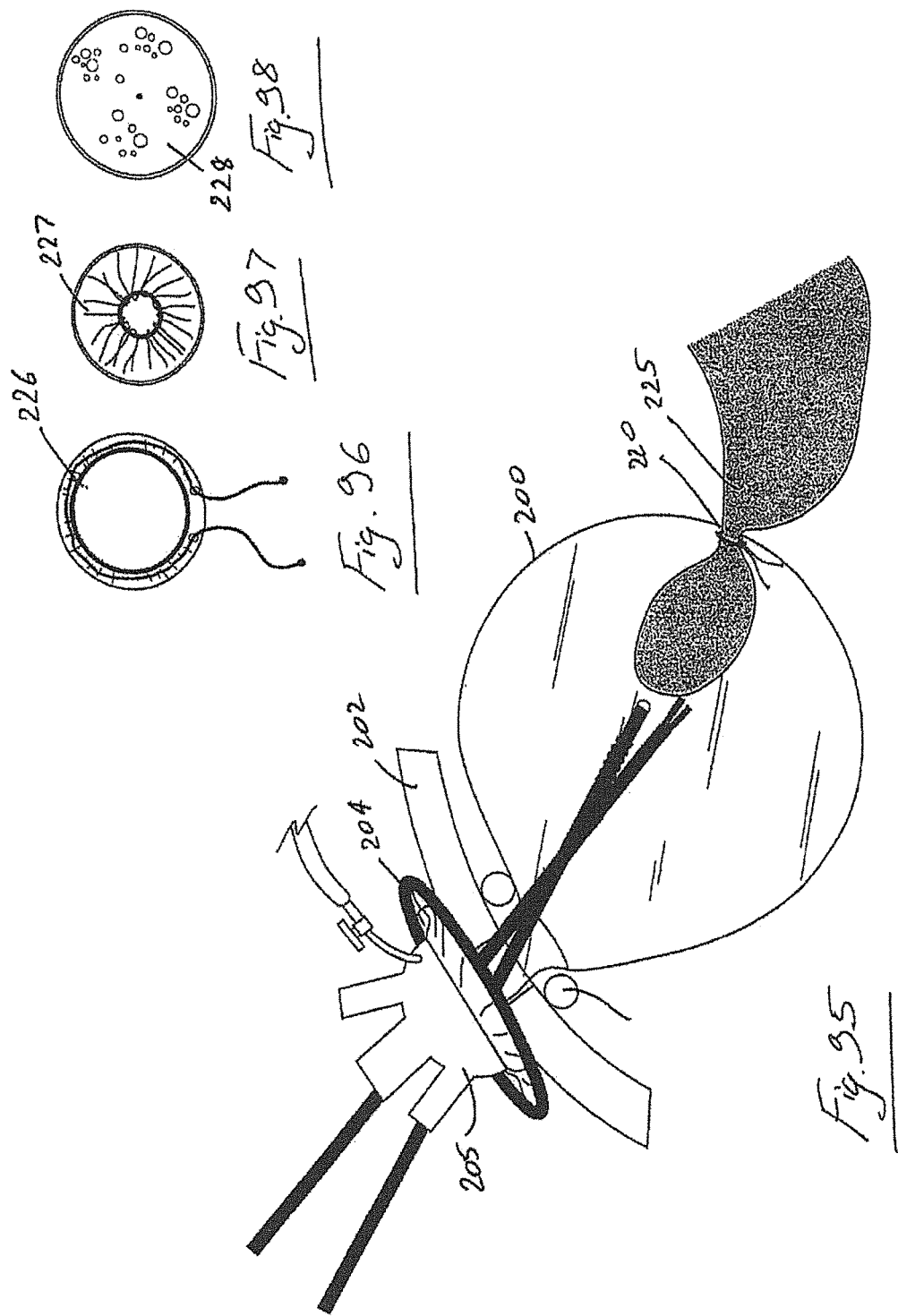

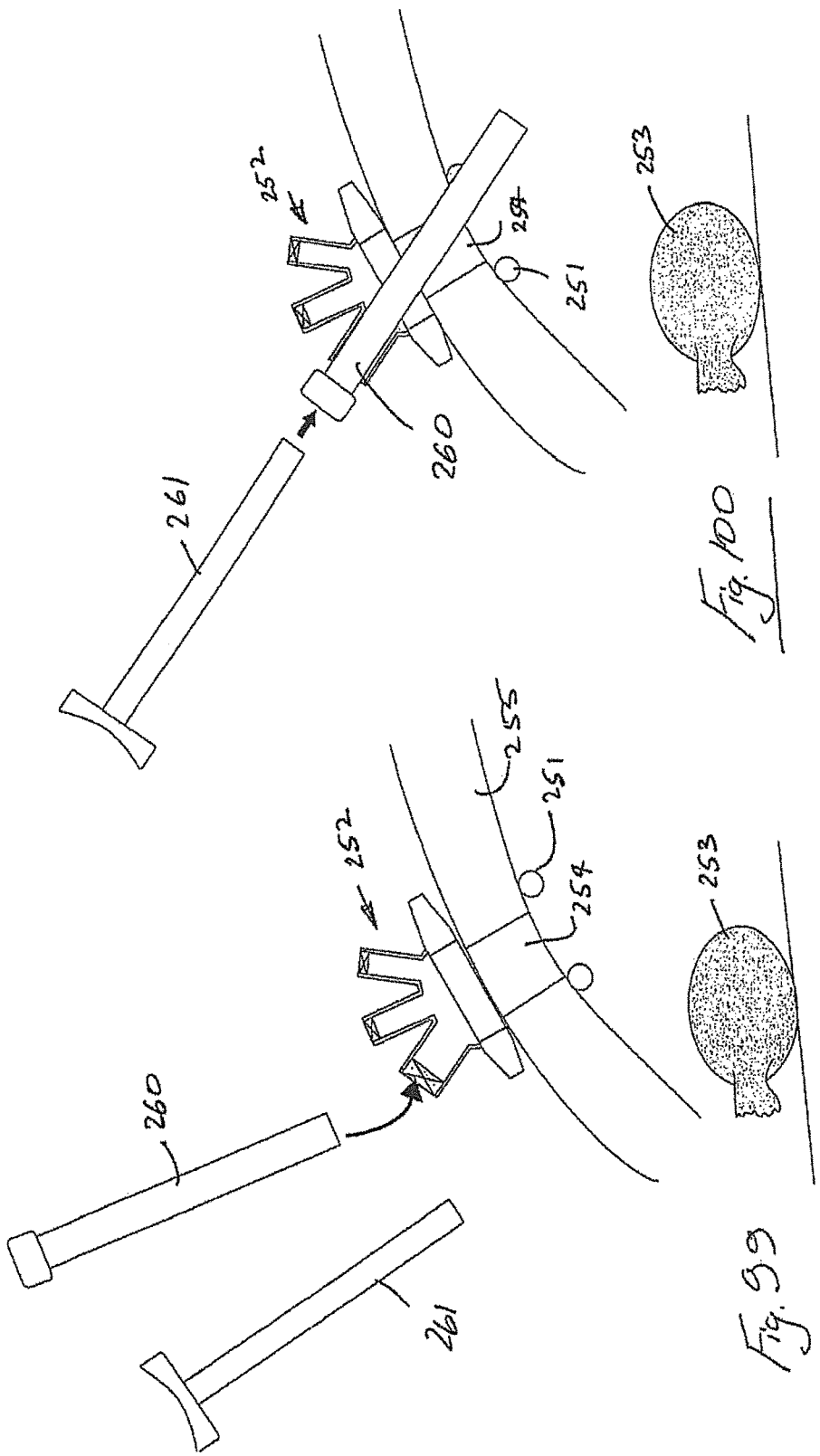

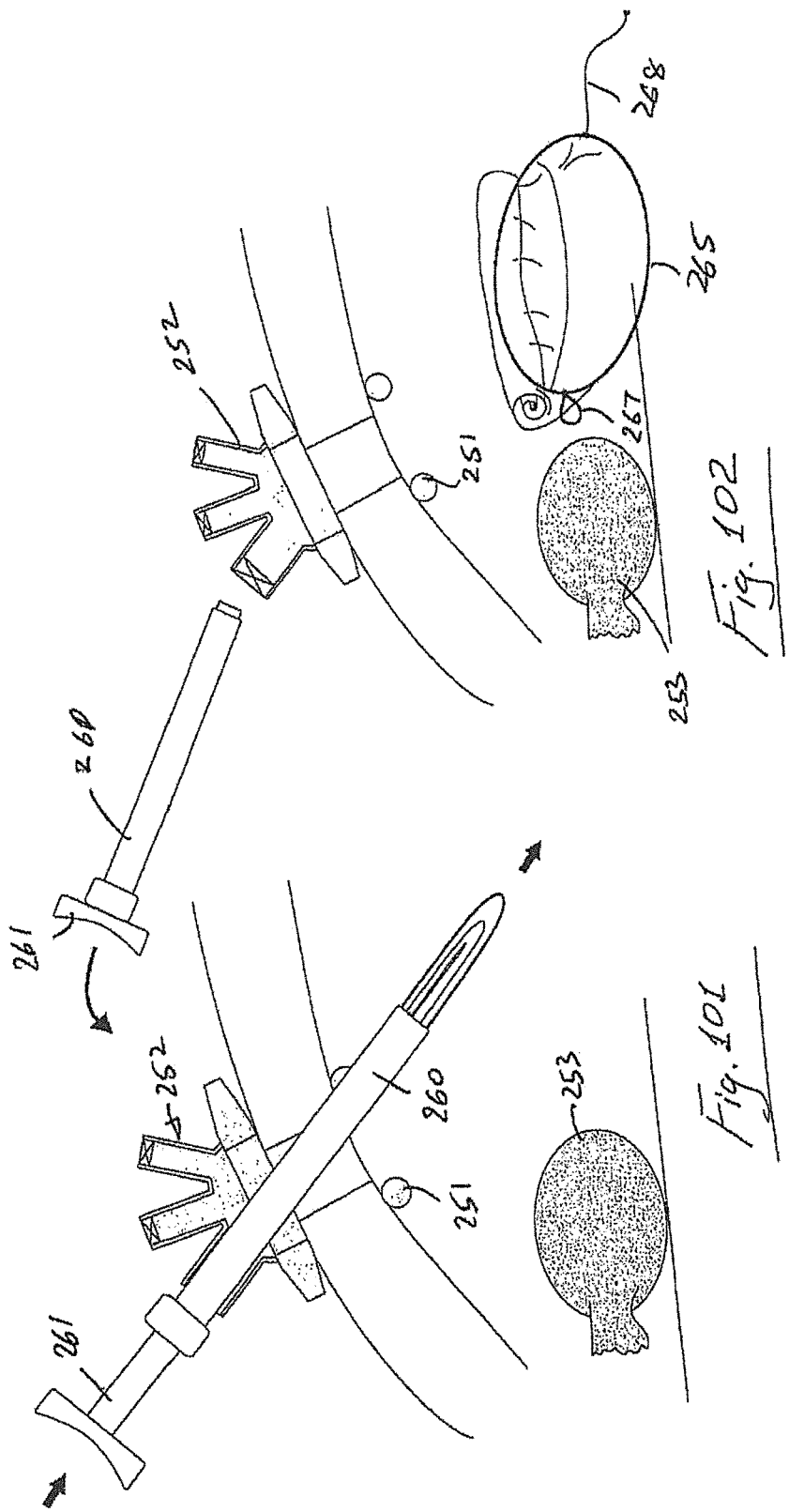

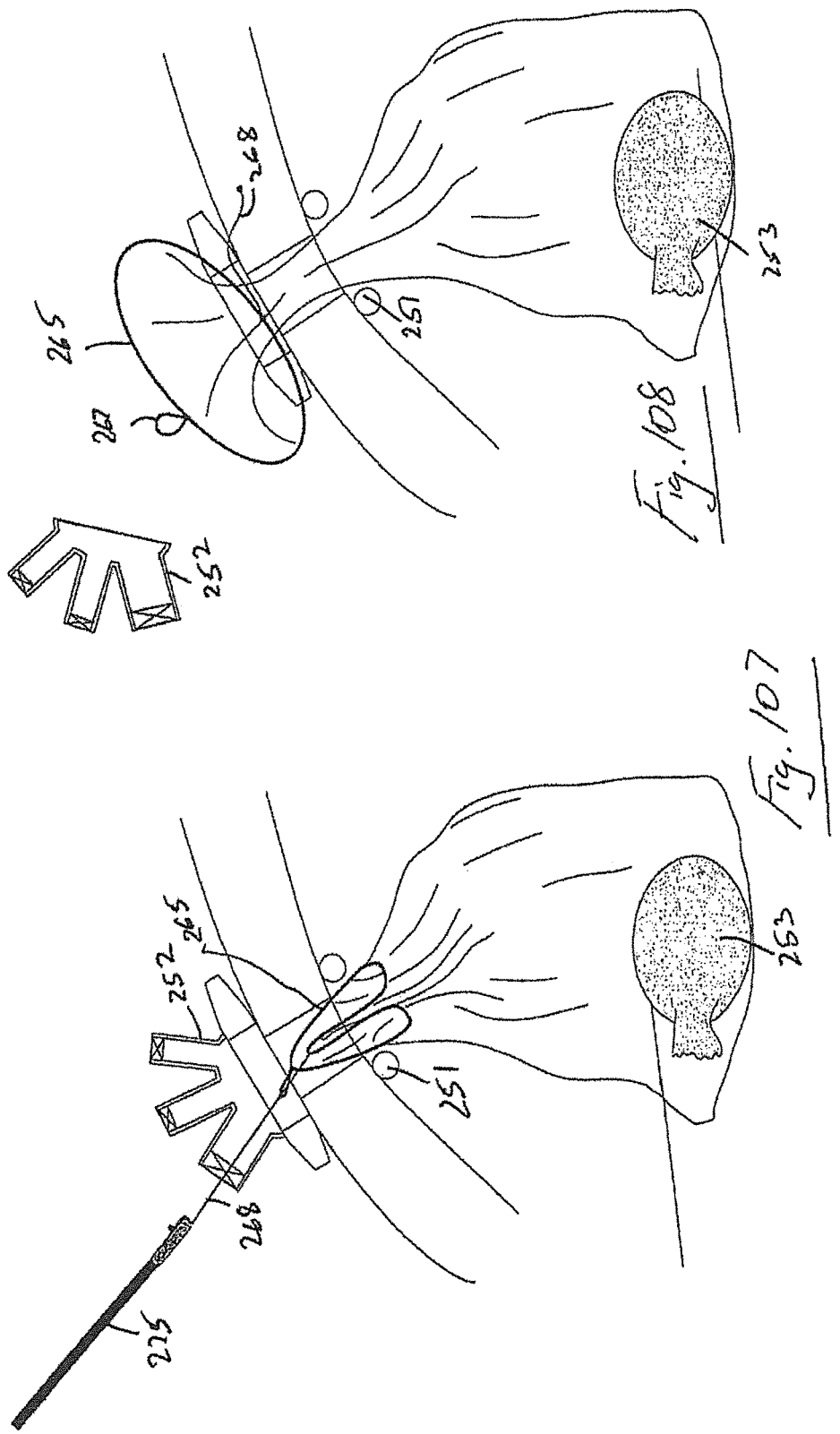

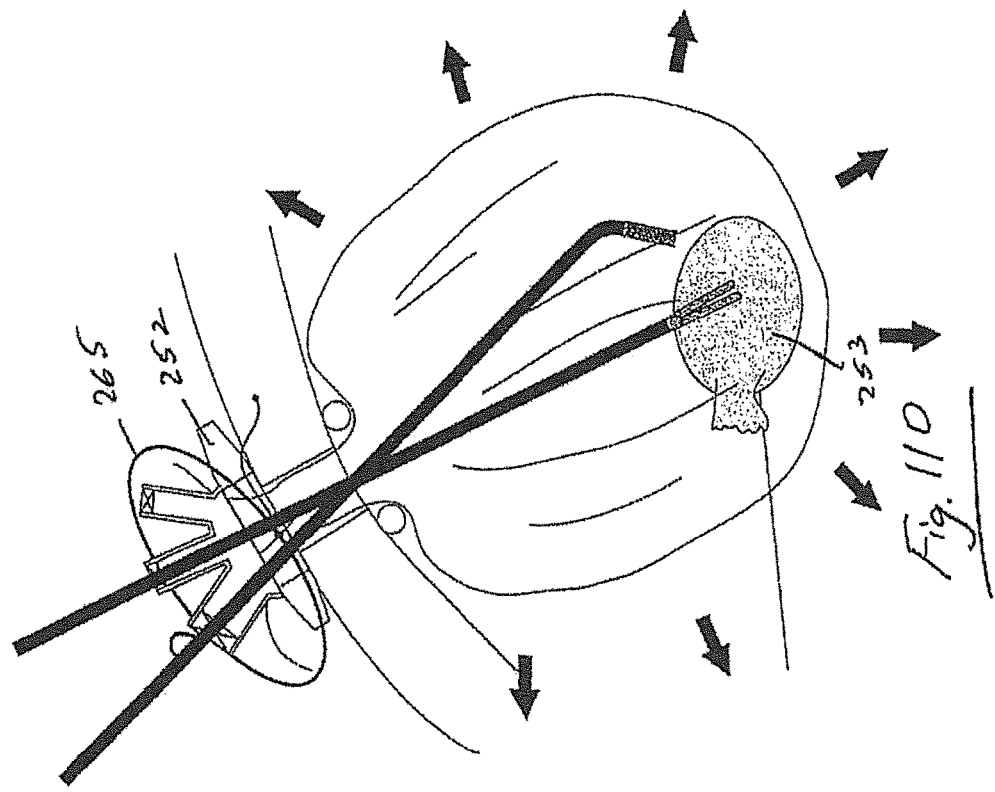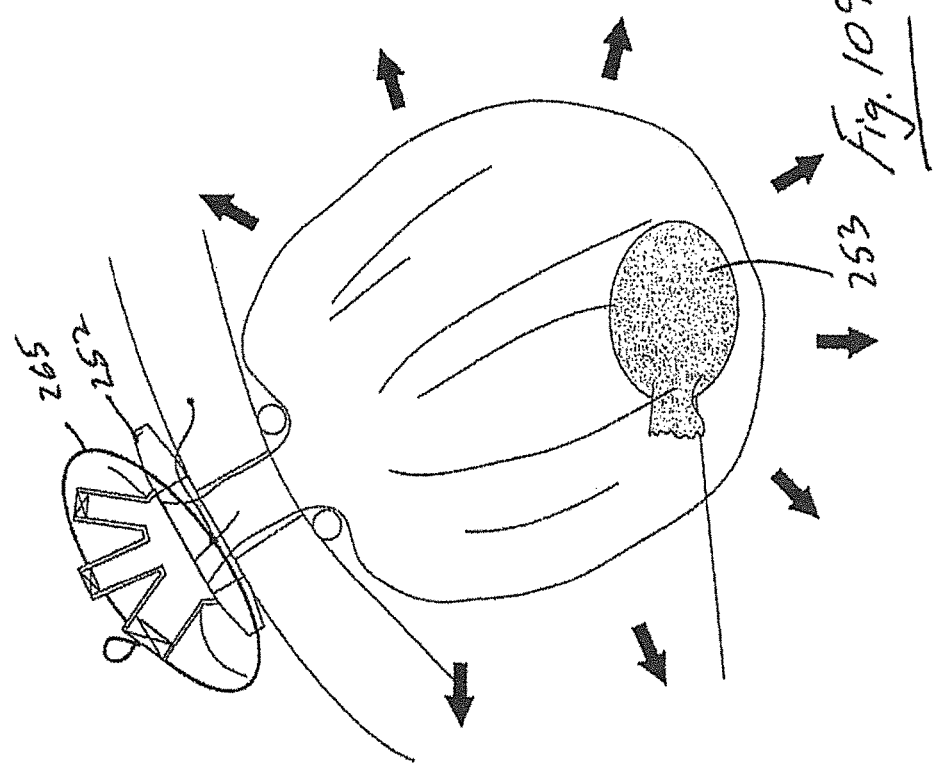

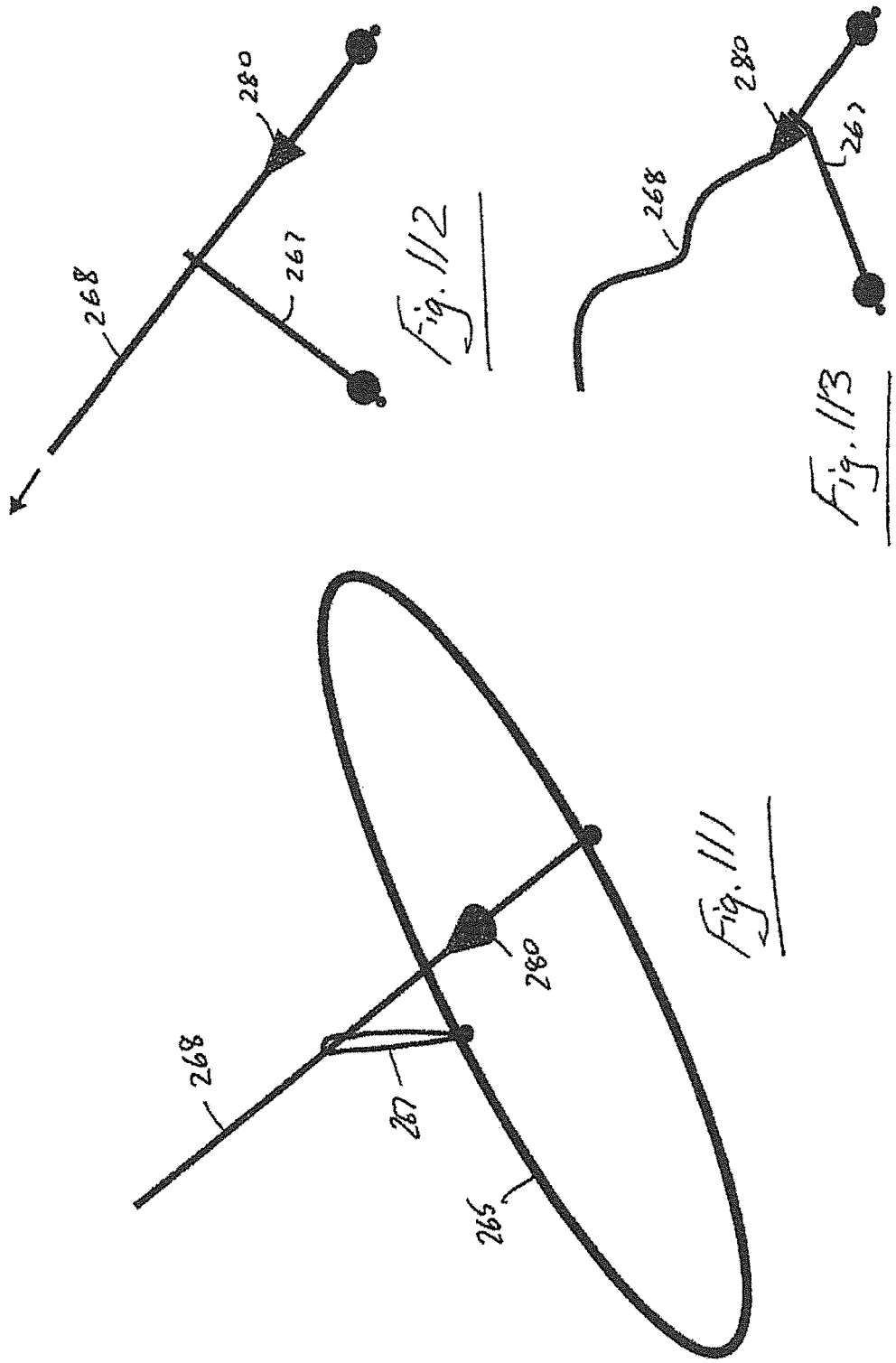

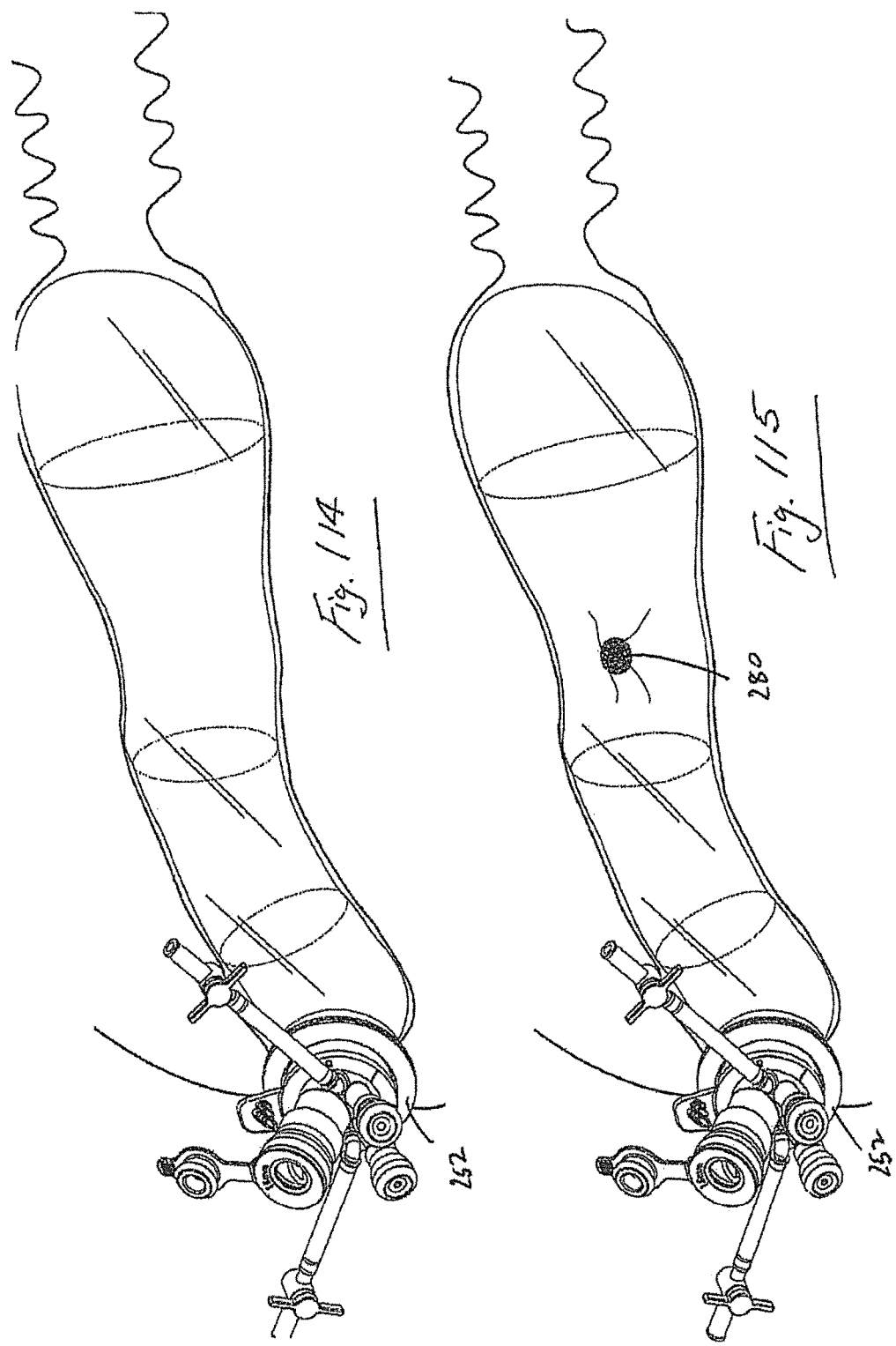

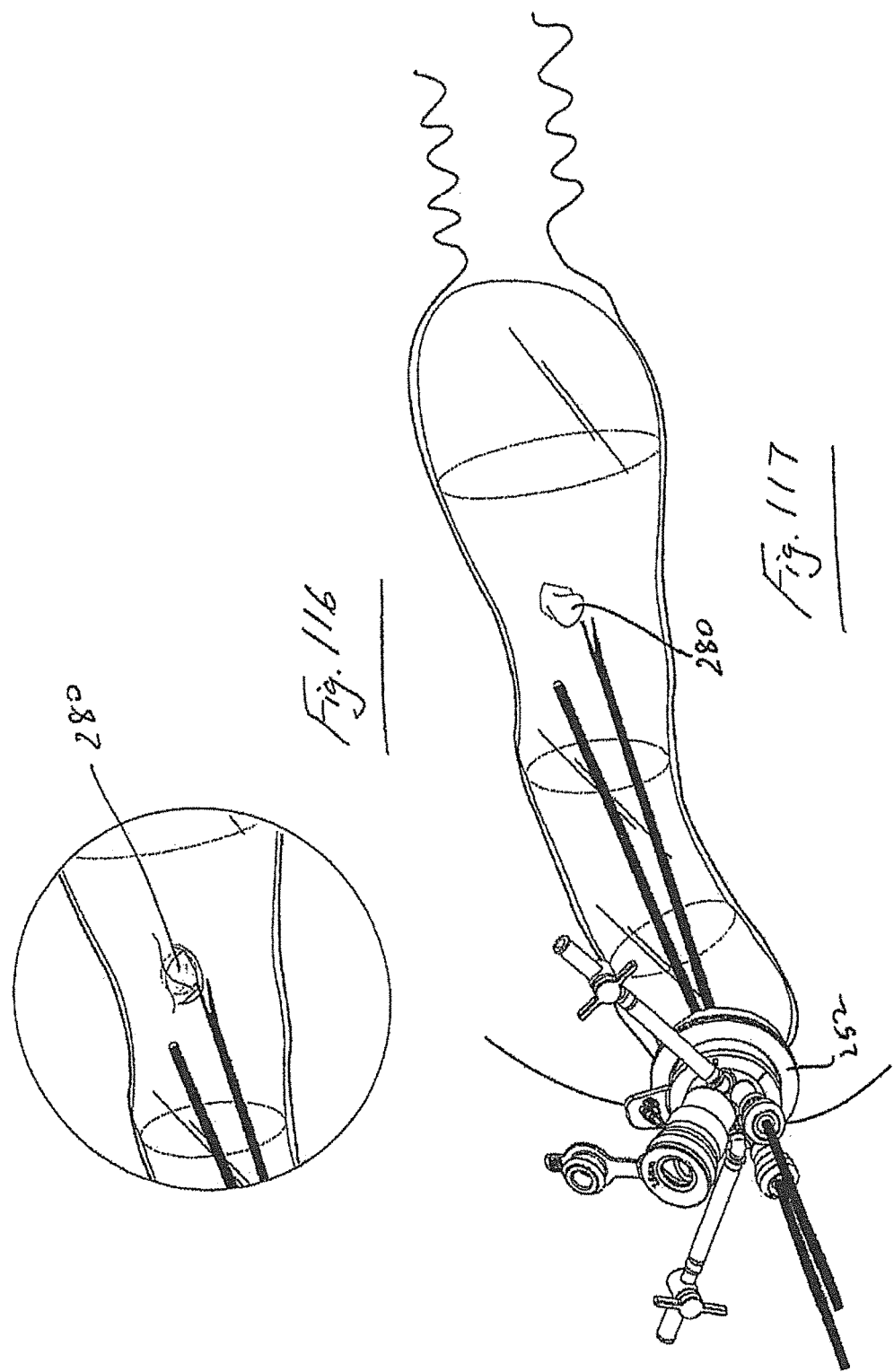

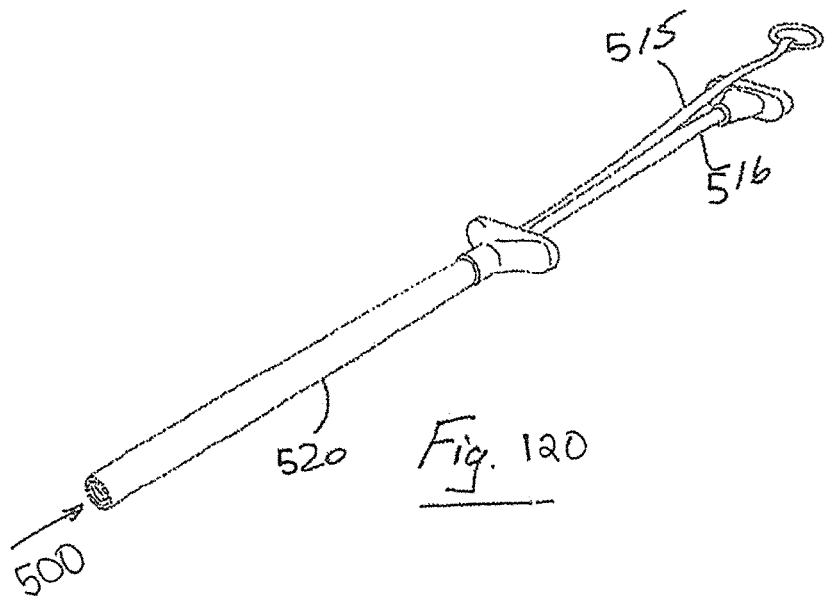
Fig. 120
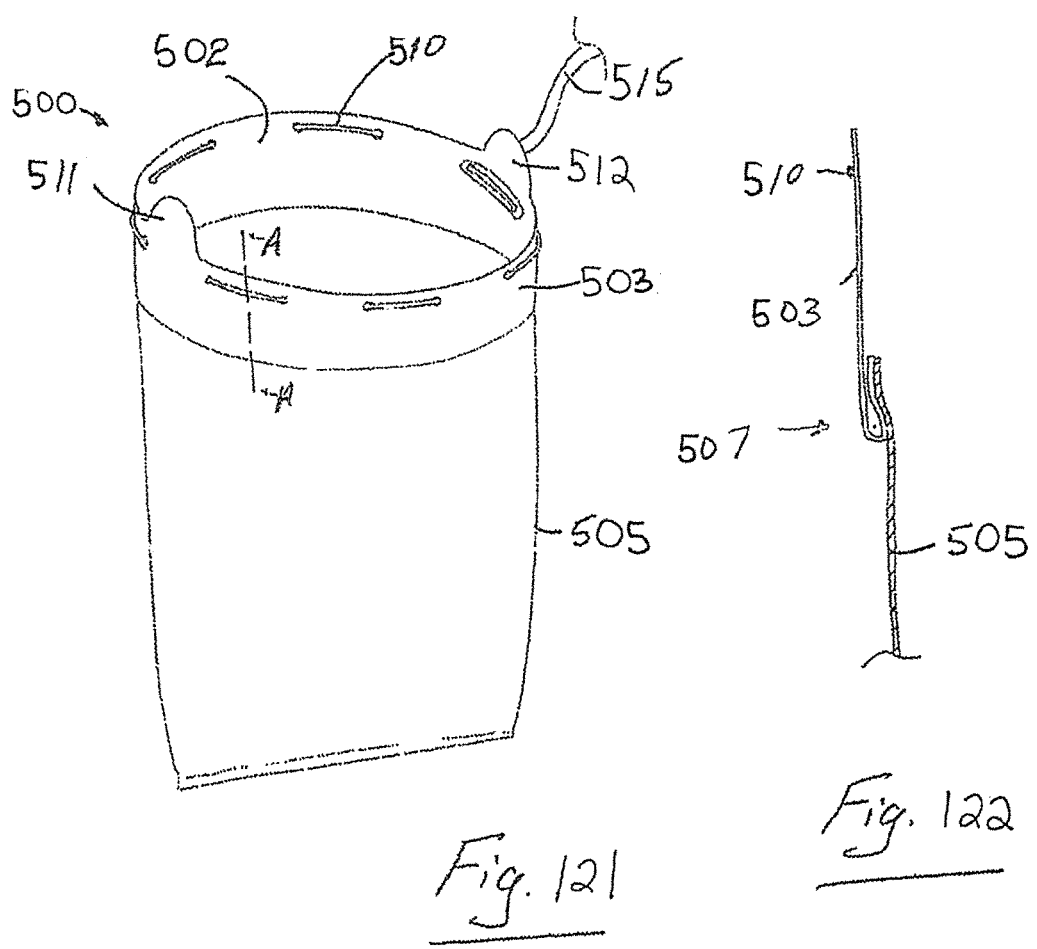
Fig. 121
Fig. 122

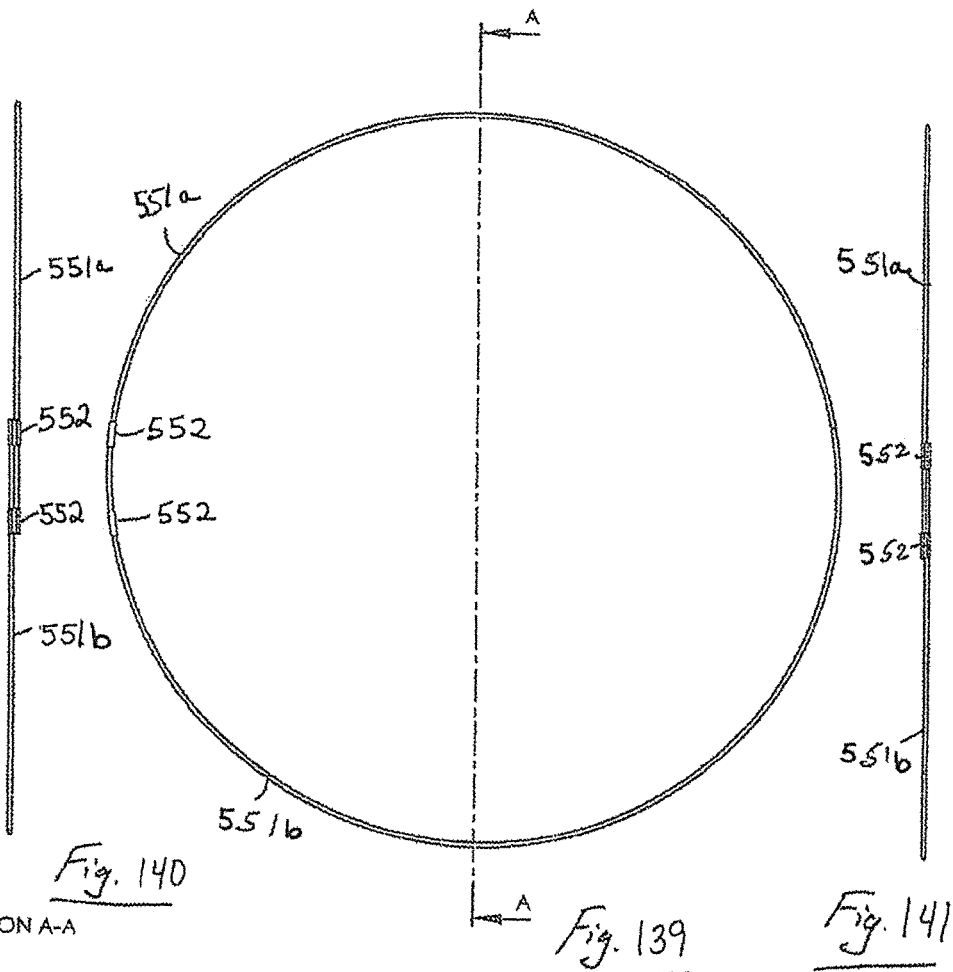
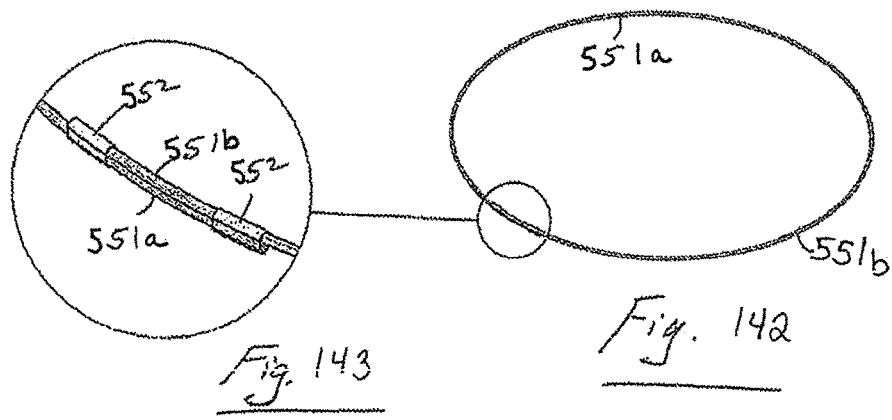

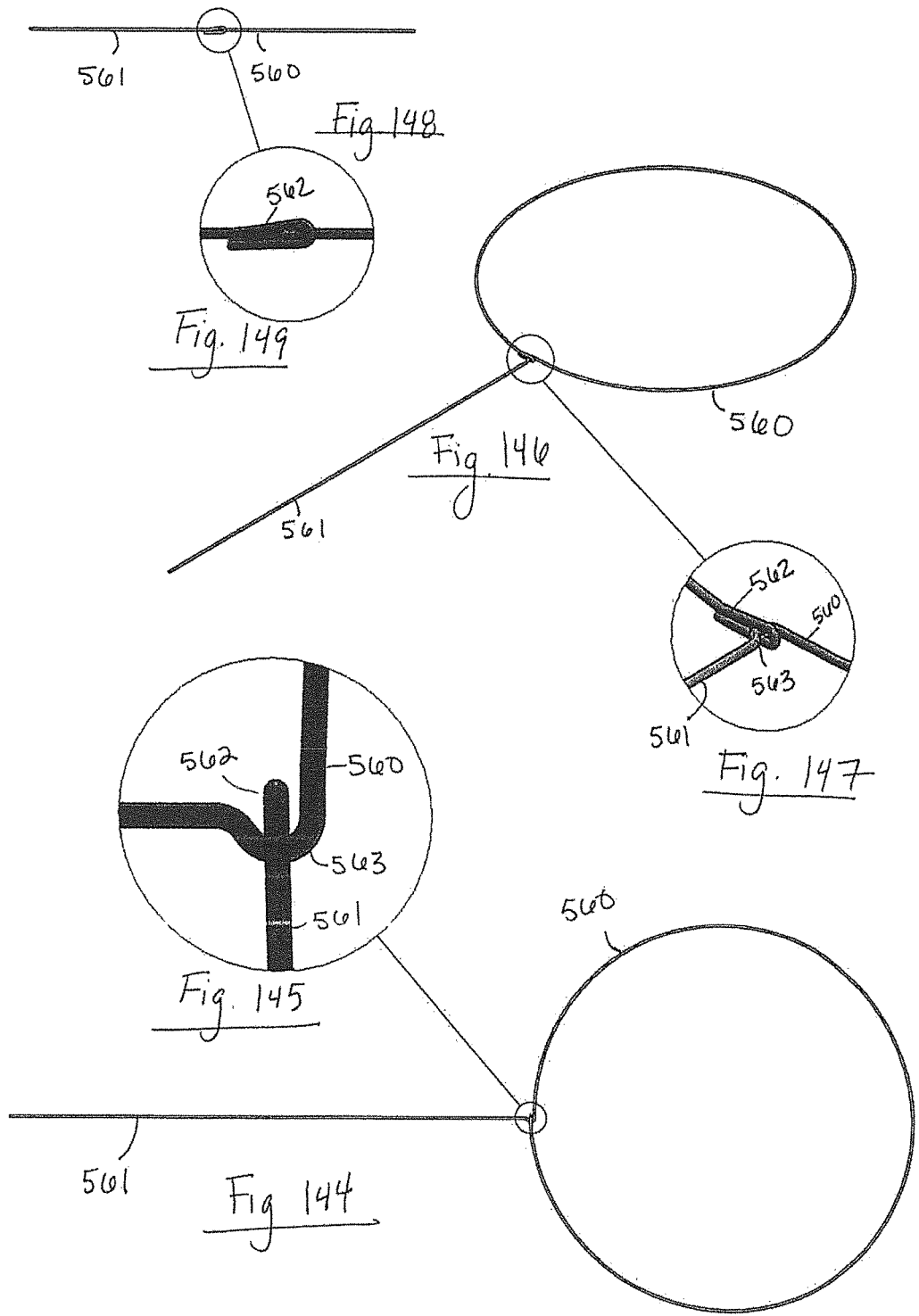

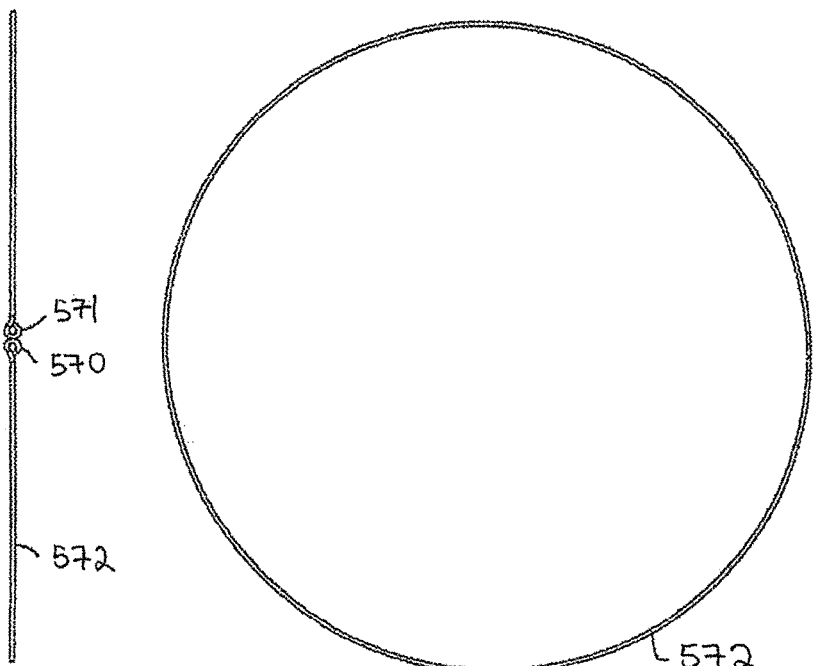
Fig. 150
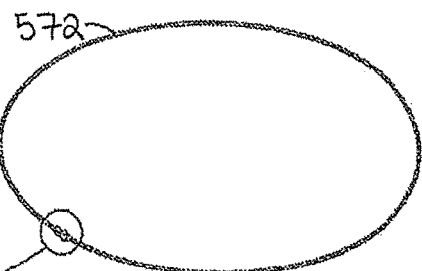
Fig. 151
Fig. 152
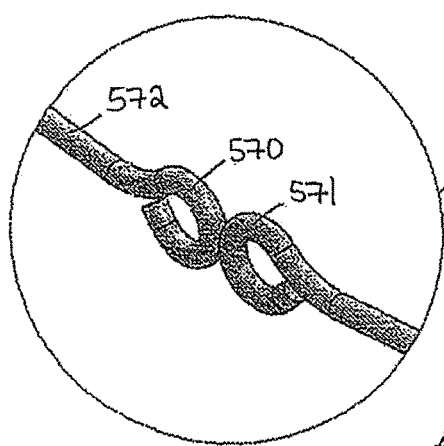
Fig. 153

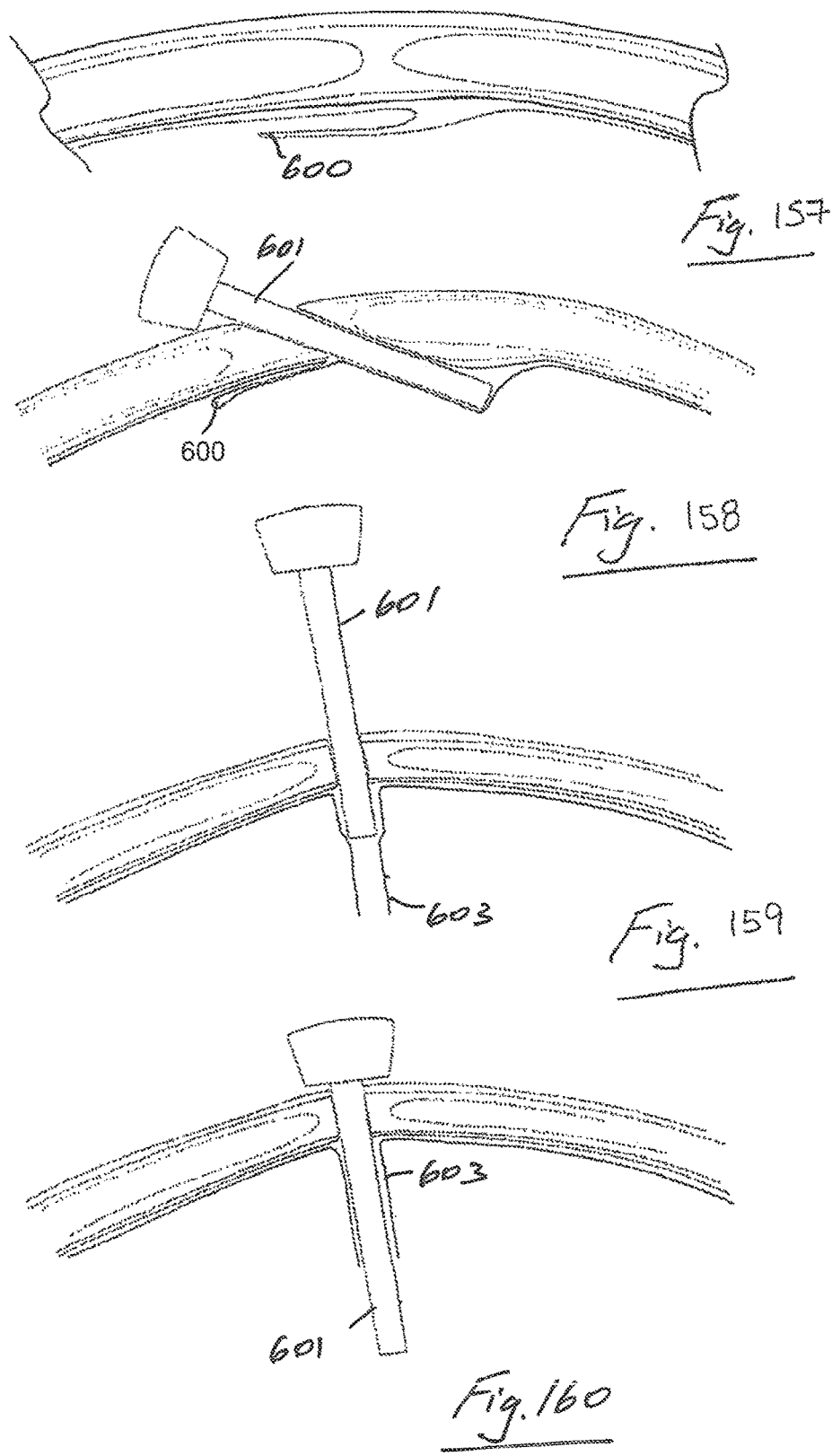

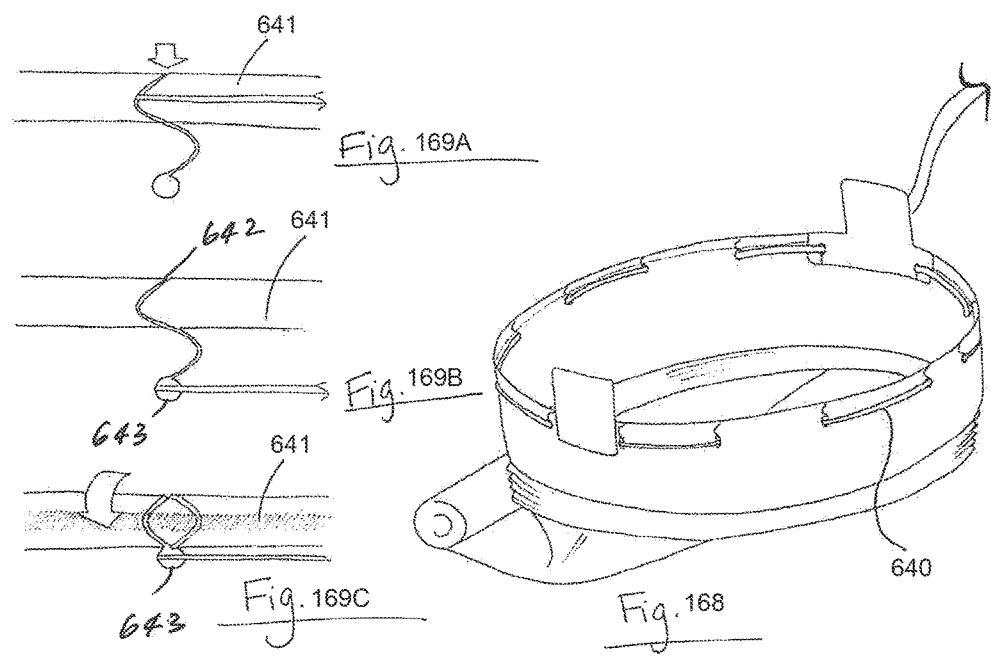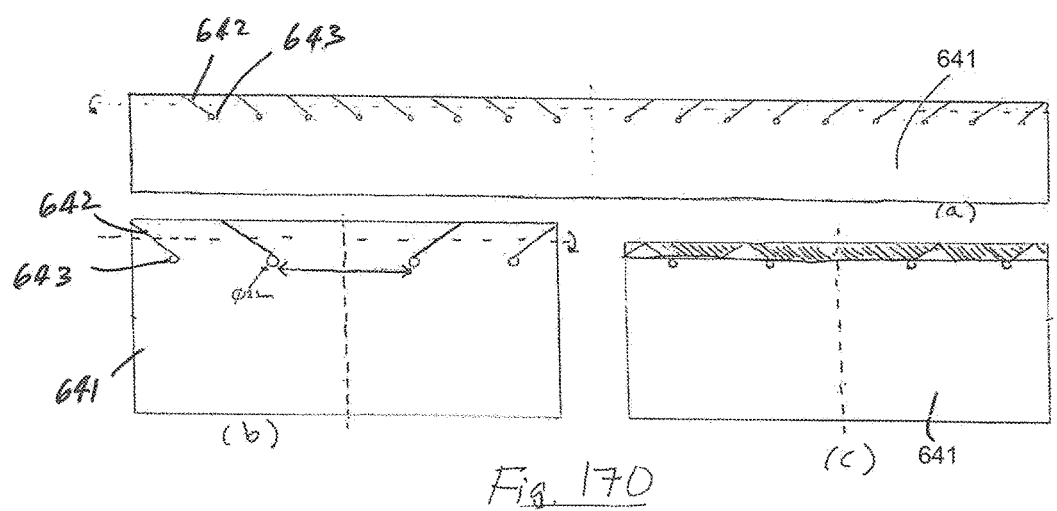

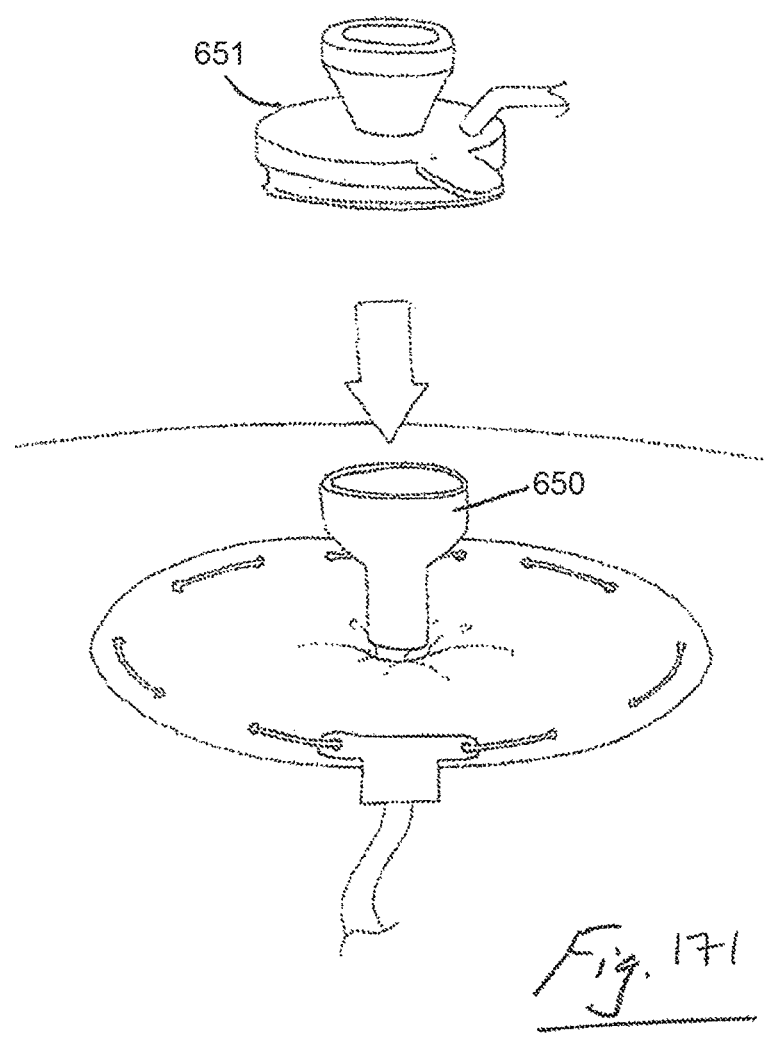

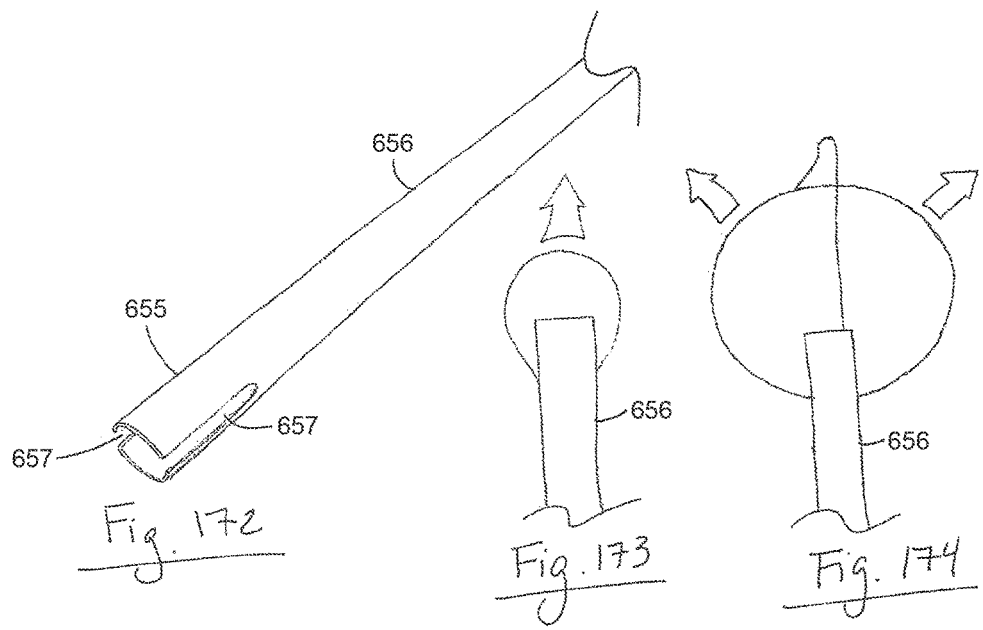
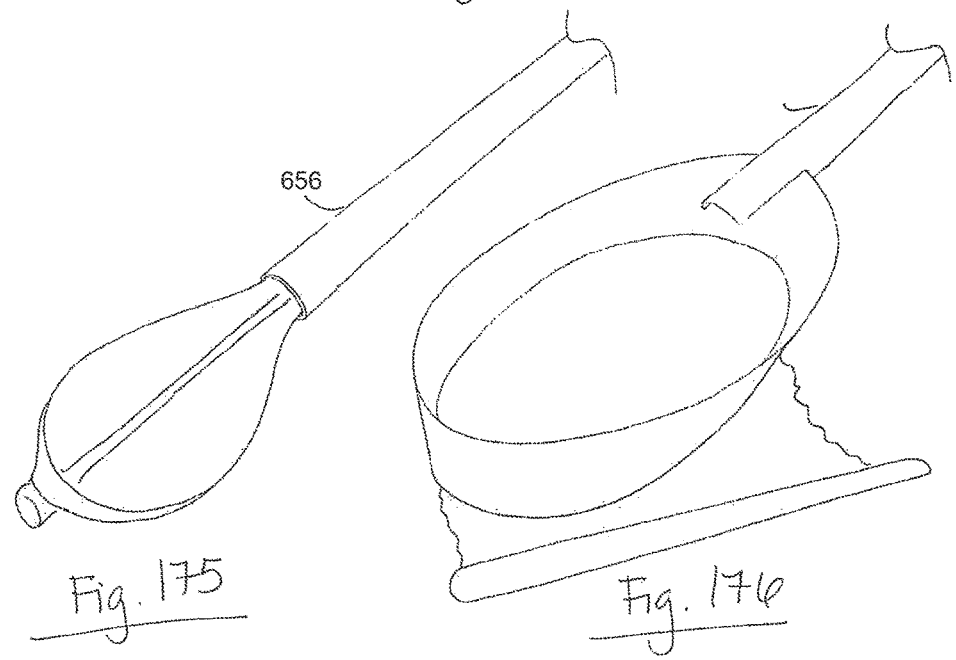

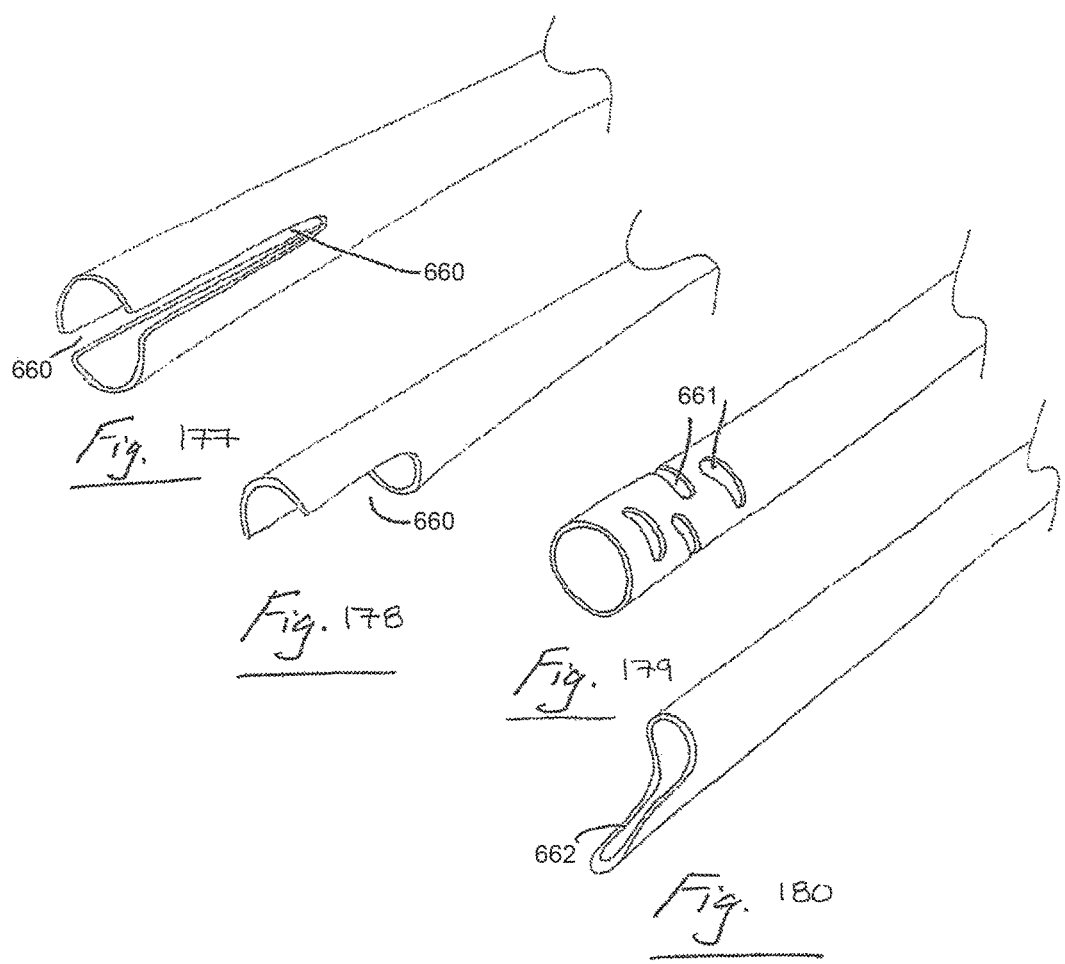

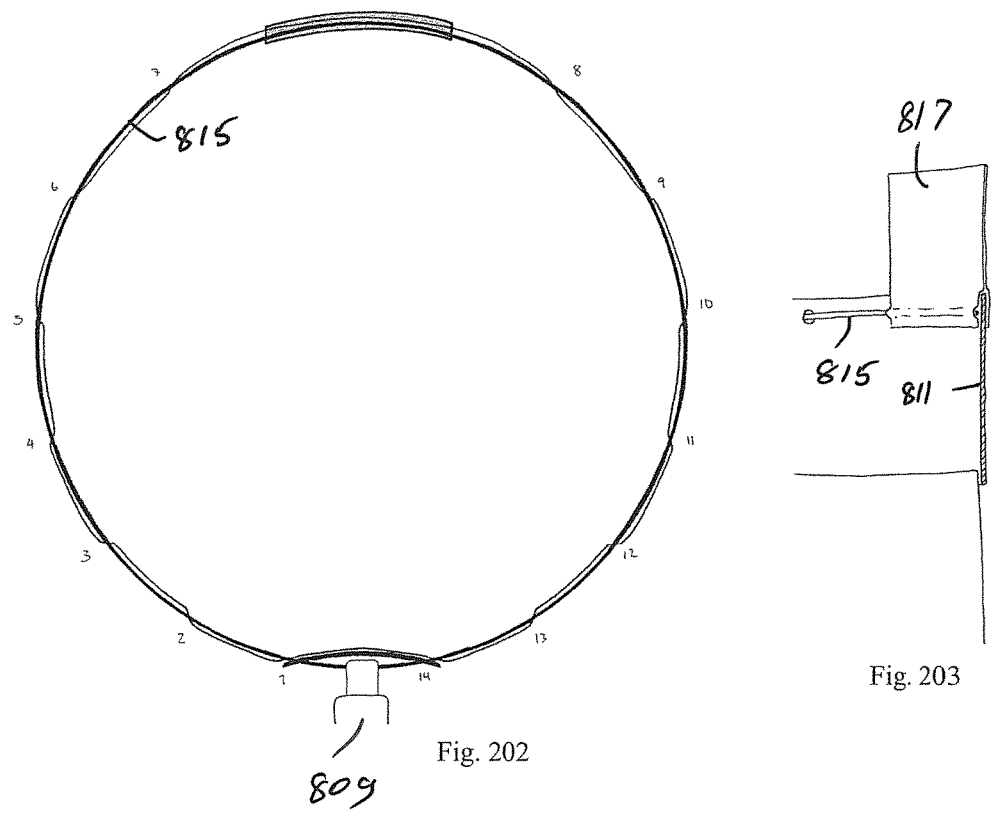
Fig. 202
Fig. 203
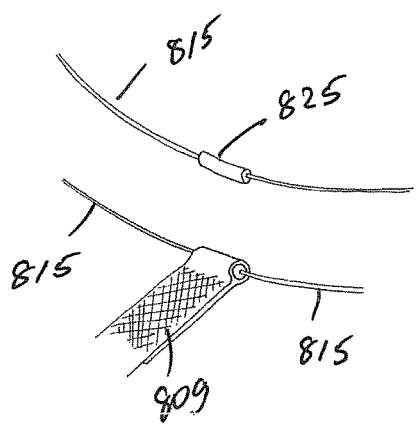
Fig. 204
Fig. 205

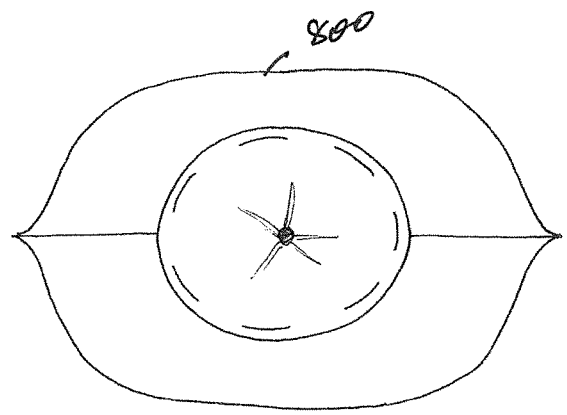
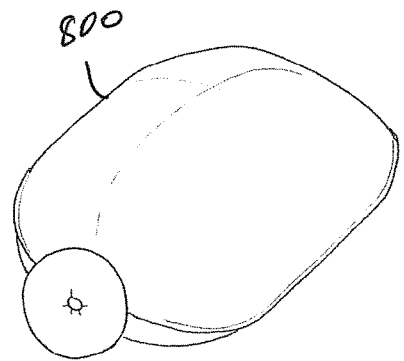
Fig. 213
Fig. 214
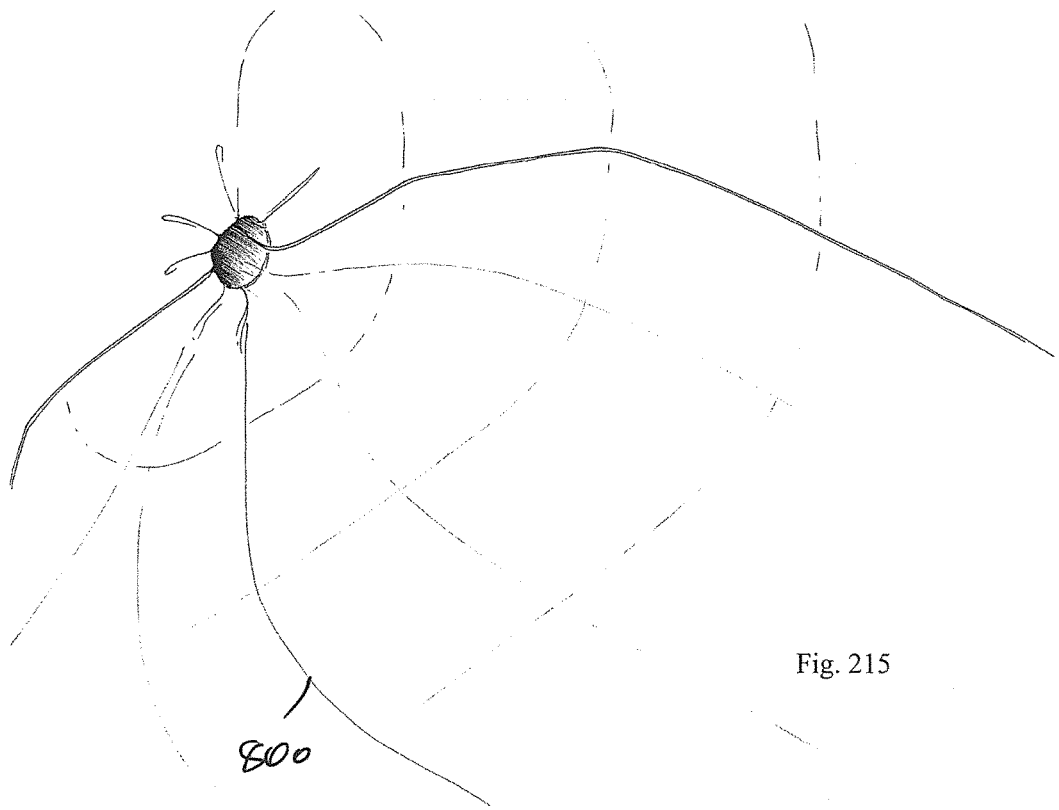
Fig. 215

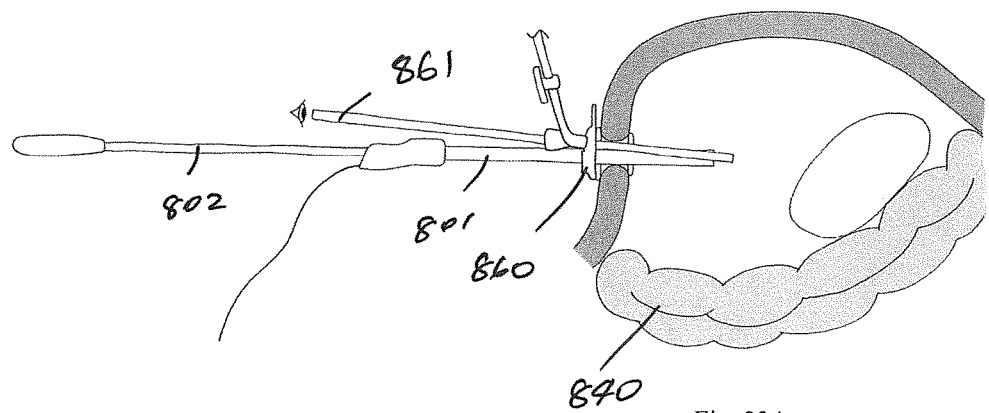
Fig. 224
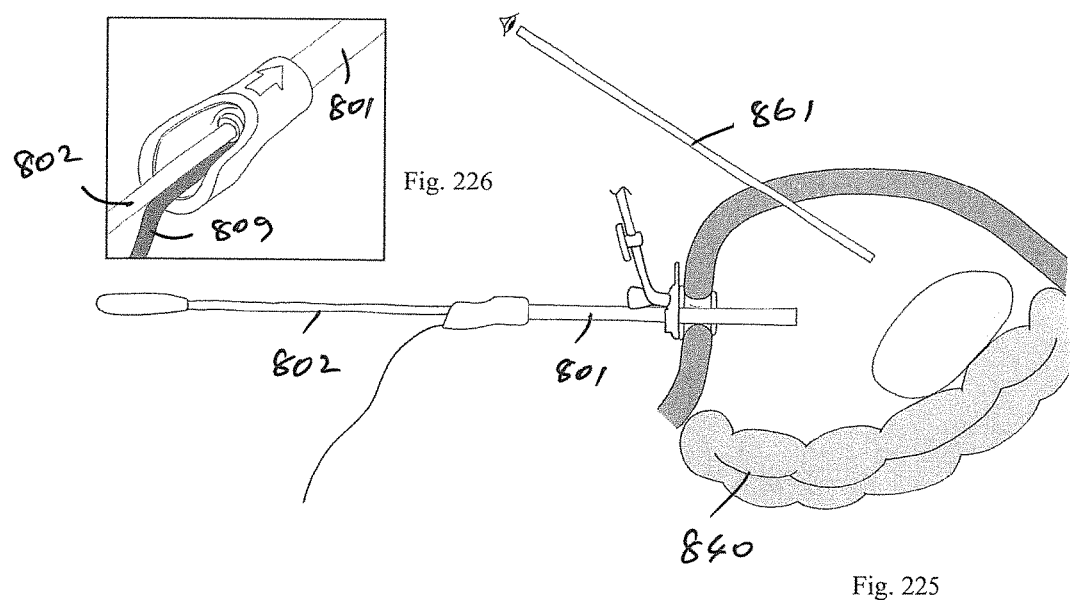
Fig. 226
Fig. 225

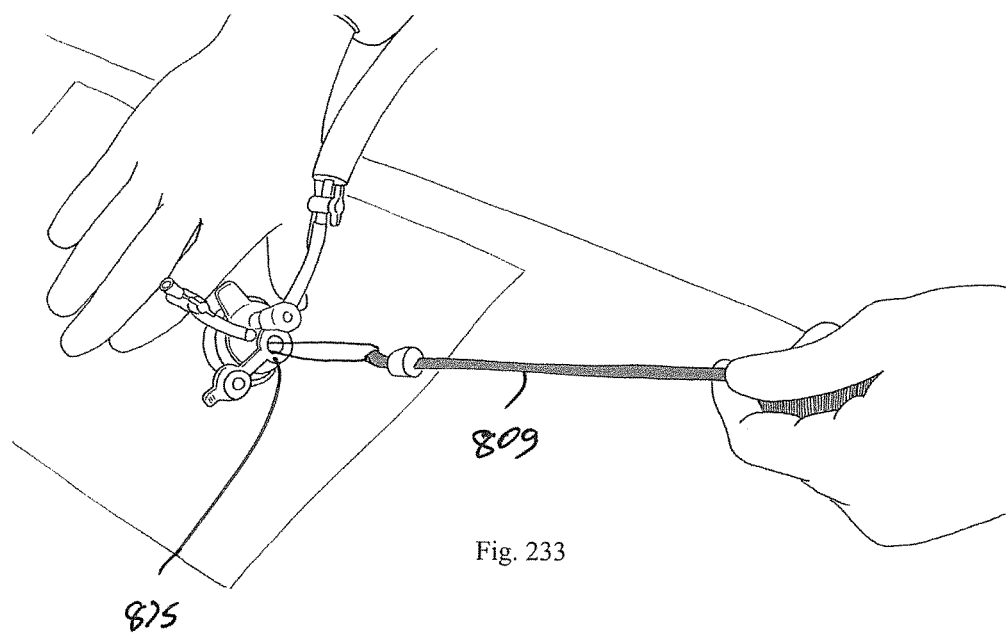
Fig. 233
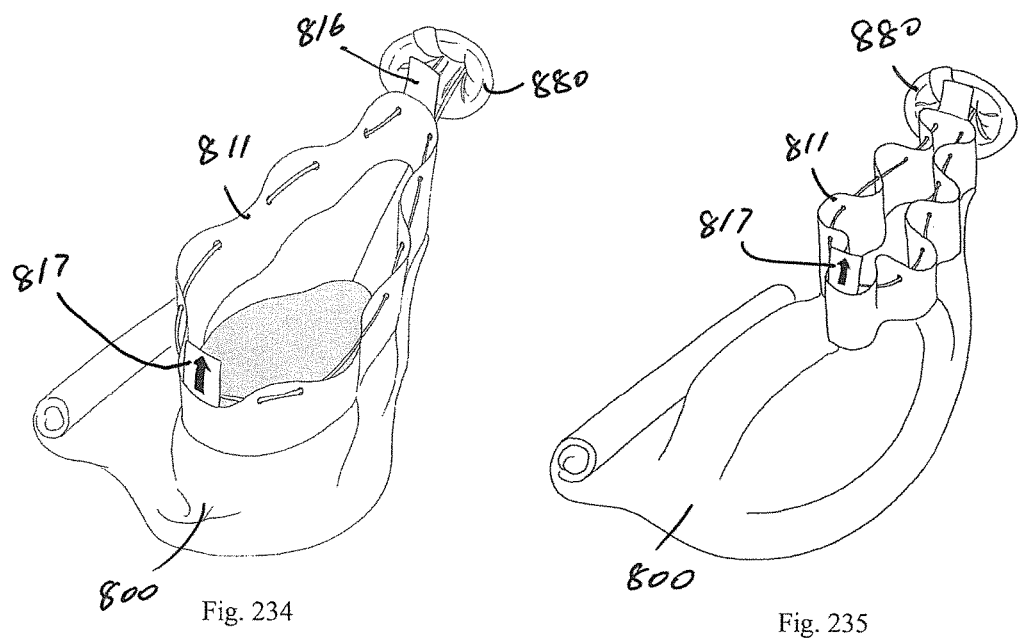
Fig. 234
Fig. 235

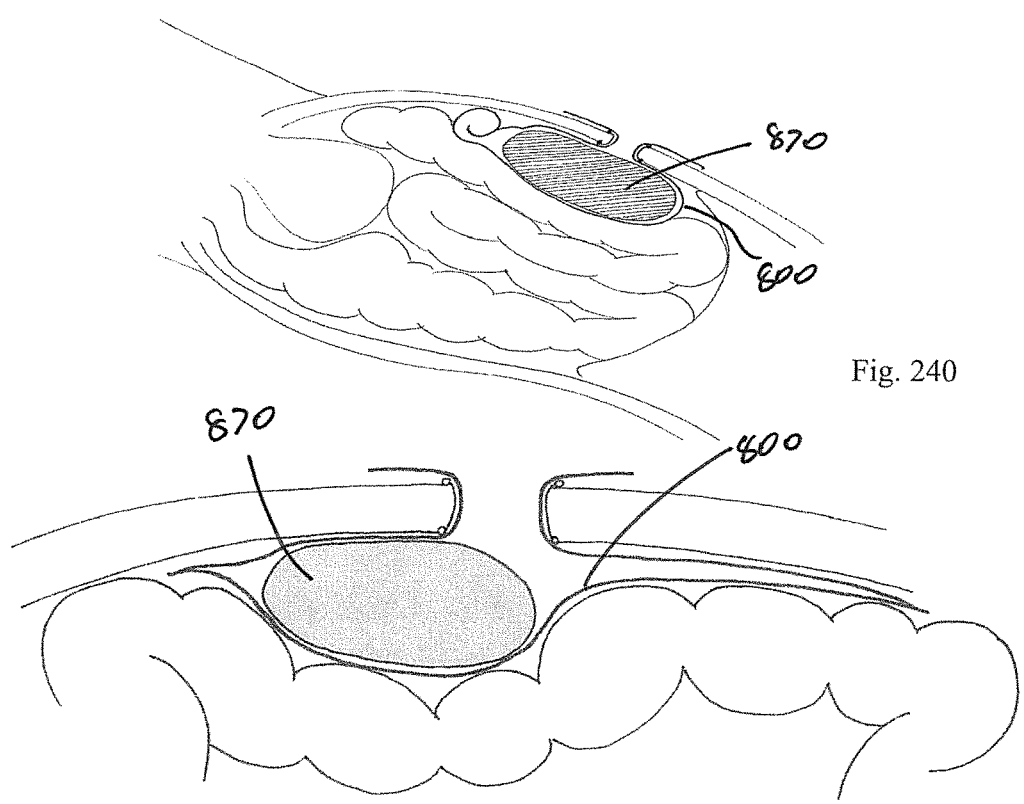
Fig. 240
Fig. 241
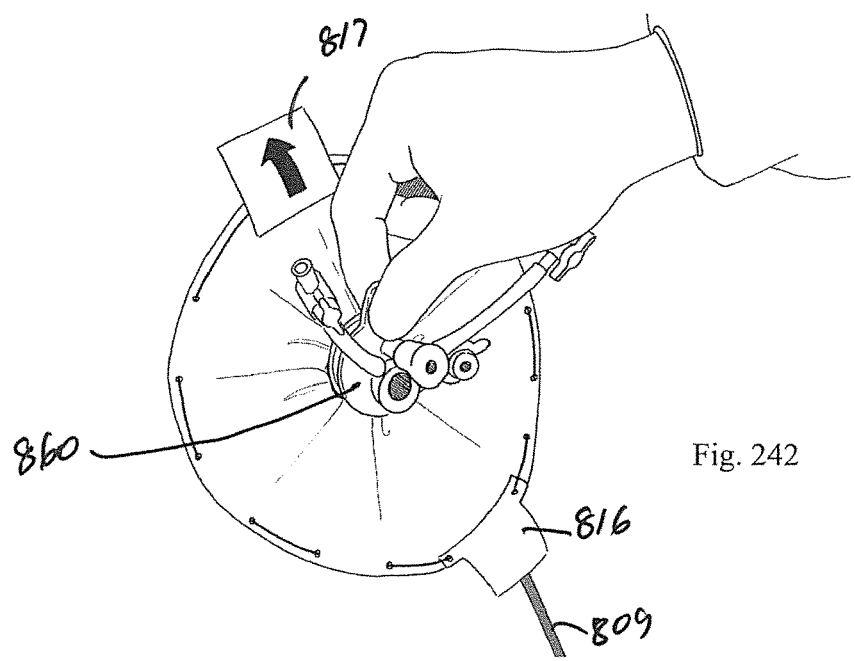
Fig. 242

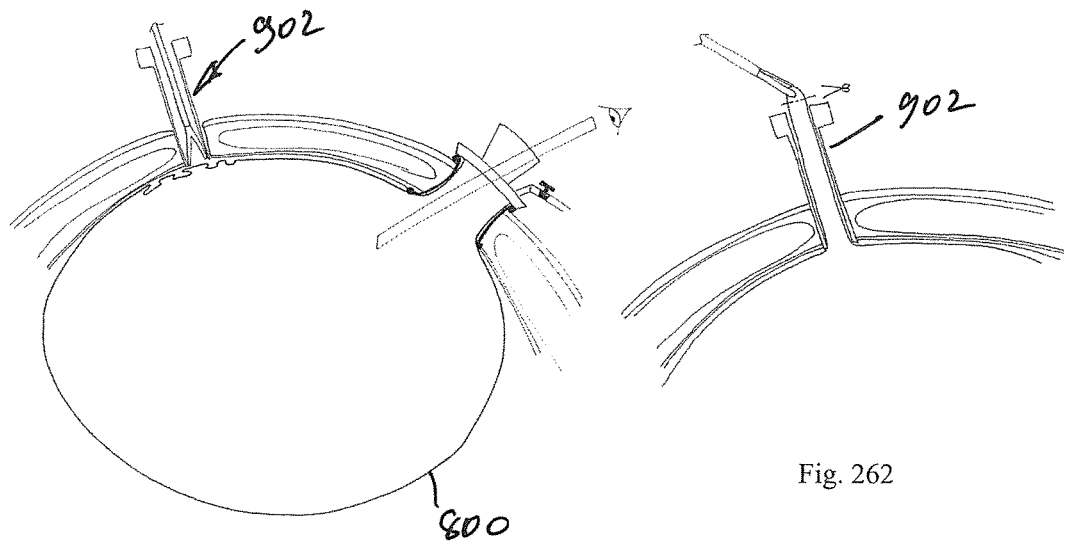
Fig. 262
Fig. 261
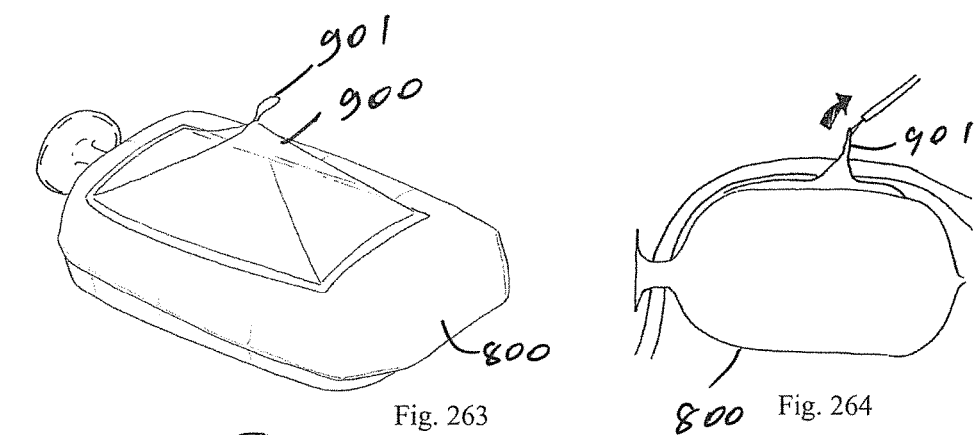
Fig. 263
Fig. 264
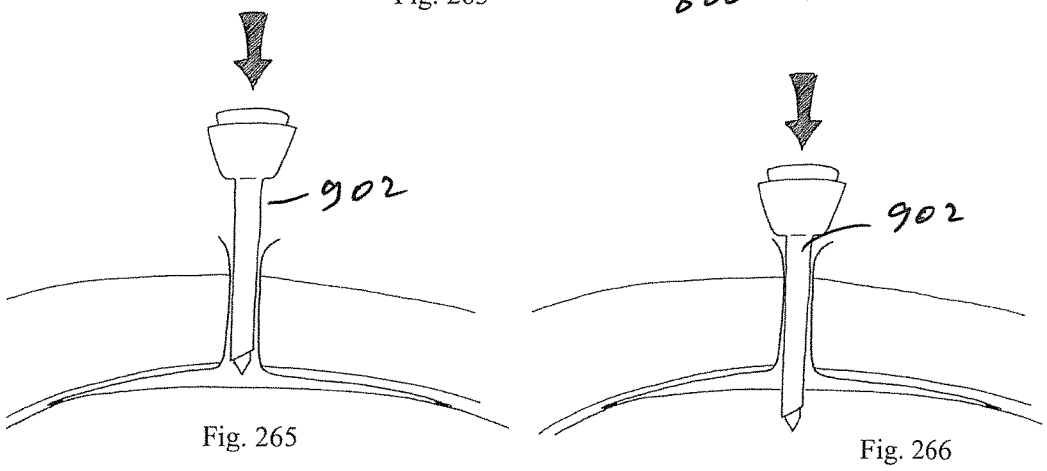
Fig. 265
Fig. 266

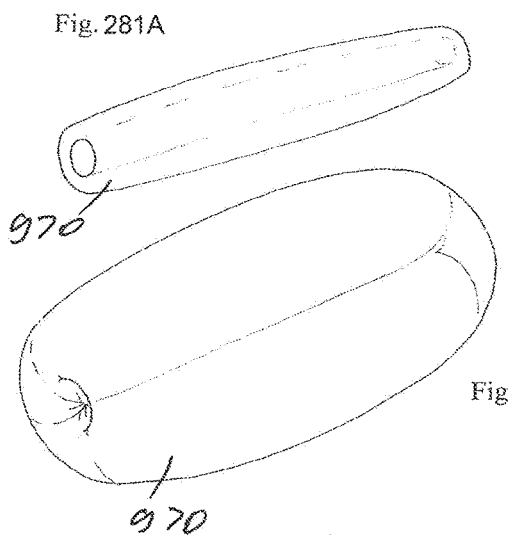
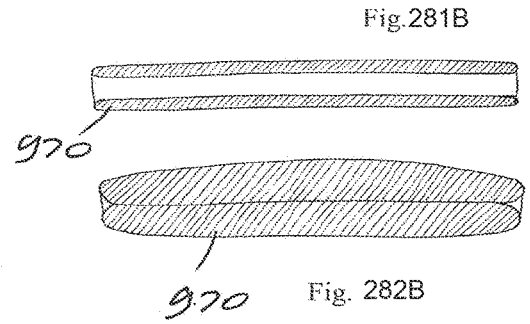
Fig. 281A
Fig. 281B
Fig. 282A
Fig. 282B
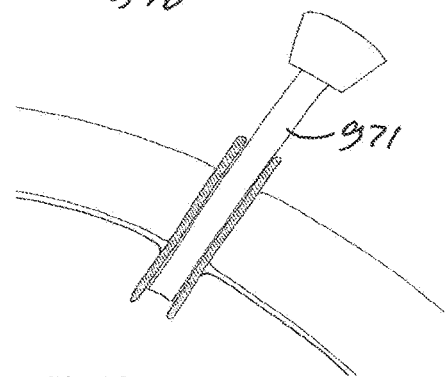
Fig. 283
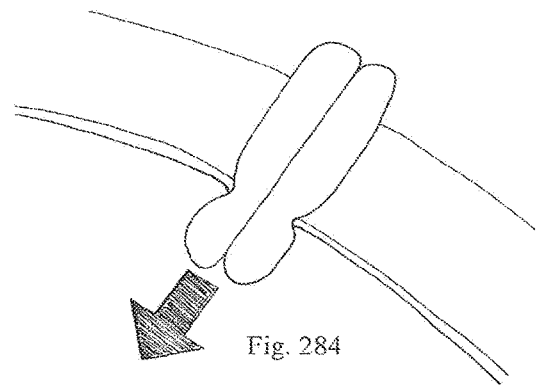
Fig. 284
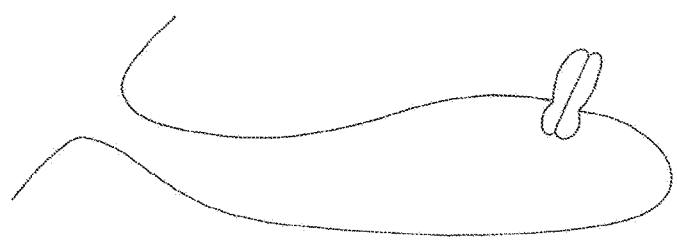
Fig. 285

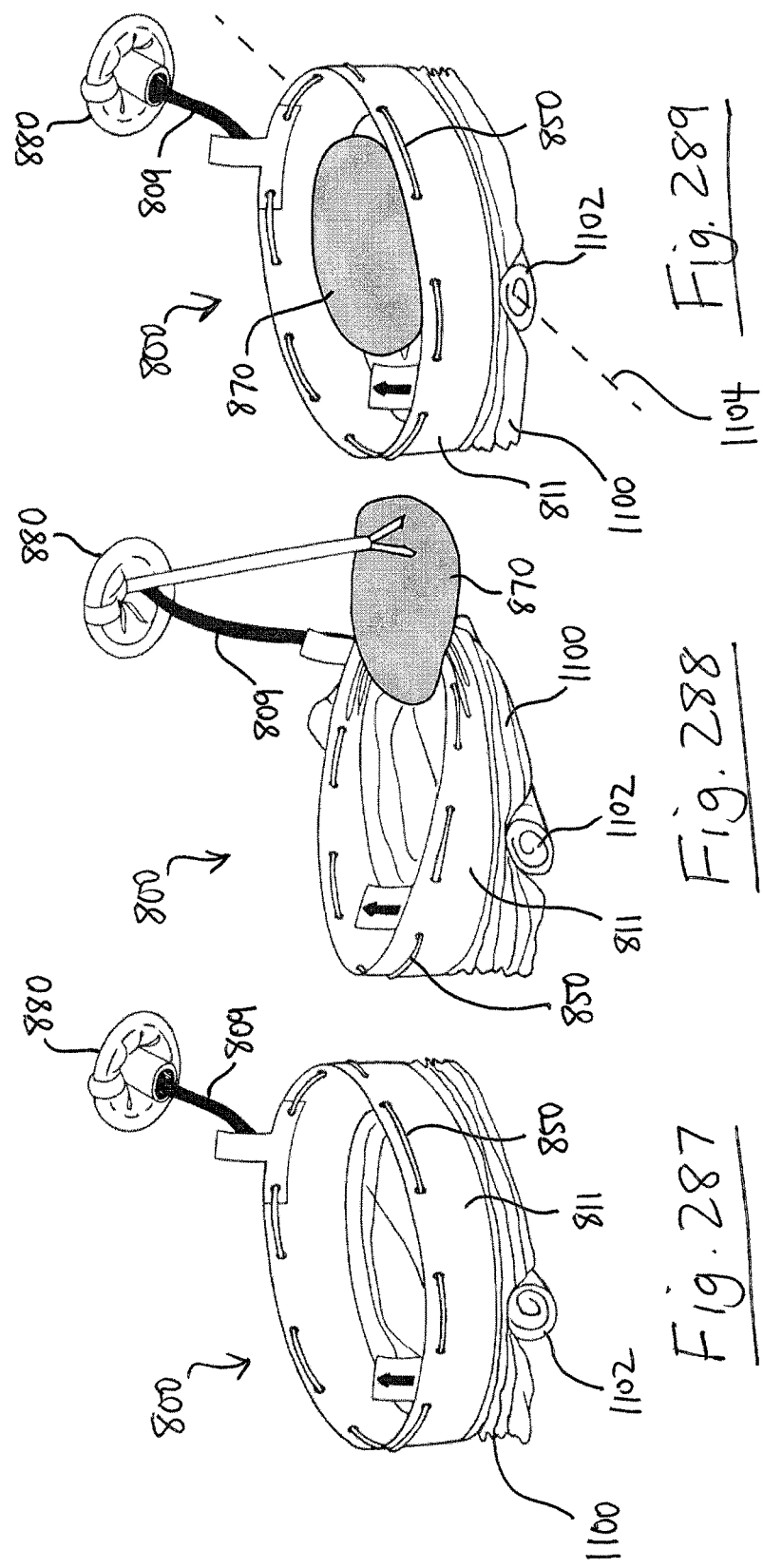

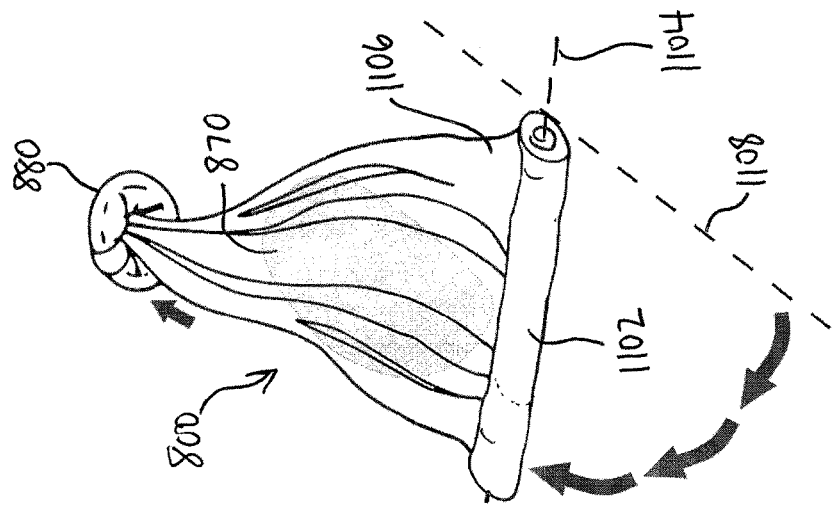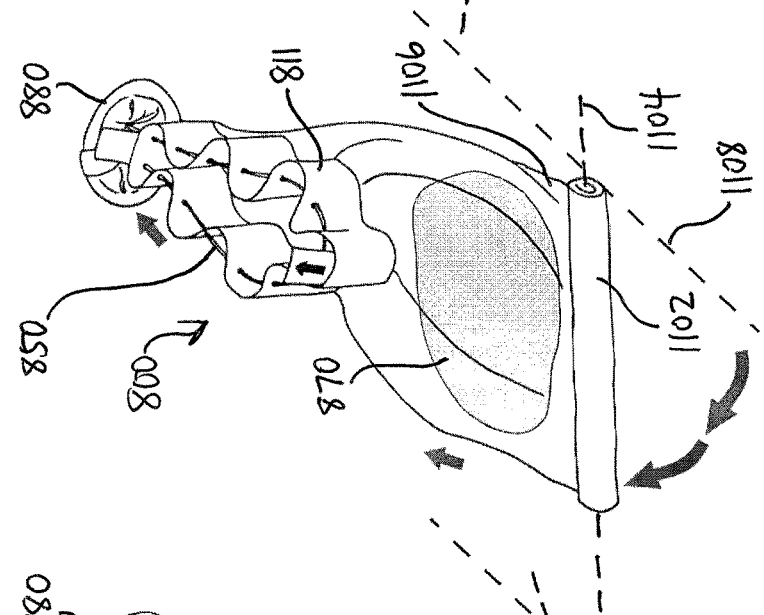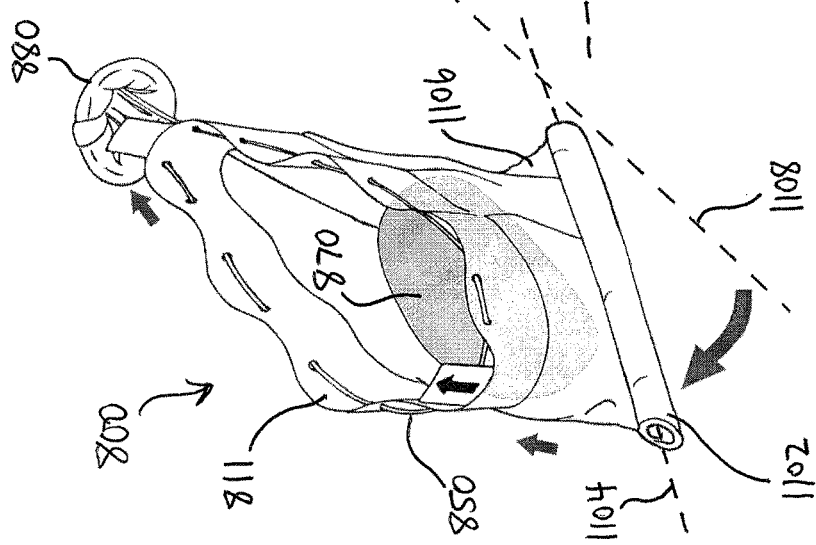

INFLATABLE PNEUMOPERITONEUM DEVICE

PRIORITY

This application claims the benefits of priority of U.S. Provisional Application No. 62/089,722, filed Dec. 9, 2014, and is a Continuation-In-Part of International Application No. PCT/EP2014/063458, filed Jun. 25, 2014, which claims the benefits of priority of U.S. Provisional Application No. 61/839,461, filed Jun. 26, 2013, U.S. Provisional Application No. 61/940,681, filed Feb. 17, 2014, U.S. Provisional Application No. 61/968,770, filed Mar. 21, 2014, and U.S. application Ser. No. 14/251,362, filed Apr. 11, 2014, now U.S. Pat. No. 8,920,431.

This application is also a Continuation-In-Part of U.S. application Ser. No. 14/584,865, filed Dec. 29, 2014, which is a Continuation of U.S. application Ser. No. 14/251,362, filed Apr. 11, 2014, which claims the benefits of priority of U.S. Provisional Patent No. 61/839,461, filed Jun. 26, 2013, U.S. Provisional Application No. 61/940,681, filed Feb. 17, 2014, and U.S. Provisional Application No. 61/968,770, filed Mar. 21, 2014, and is a Continuation-in-Part of U.S. application Ser. No. 13/725,148, filed Dec. 21, 2012, which claims the benefits of priority of U.S. Provisional Application No. 61/580,088, filed Dec. 23, 2011, and U.S. Provisional Application No. 61/742,125, filed Aug. 3, 2012.

This application is also a Continuation-In-Part of U.S. application Ser. No. 13/725,148, filed Dec. 21, 2012, which claims the benefits of priority of U.S. Provisional Application No. 61/580,088, filed Dec. 23, 2011, and U.S. Provisional Application No. 61/742,125, filed Aug. 3, 2012.

The entire contents of all of the above are incorporated herein by reference.

INTRODUCTION

This disclosure relates to a pneumoperitoneum device. The disclosure also relates to methods involving the use of the device.

STATEMENTS OF DISCLOSURE

According to aspects of the disclosure, there is provided an artificial pneumoperitoneum device (e.g., a bag) for receiving tissue, tissue isolation, and/or extraction in a laparoscopic procedure.

Aspects of the disclosure provide an apparatus for use in during laparoscopic surgery including an inflatable bag having a tissue-receiving opening at a proximal end thereof and a cuff at the proximal opening, the cuff having a closed configuration for delivery and retrieval of the bag and an open configuration to receive tissue, the cuff being biased into the open configuration.

Aspects of the disclosure provide an inflatable artificial pneumoperitoneum bag for receiving tissue during laparoscopic surgery, the bag having a tissue-receiving opening at a proximal end thereof and a cuff at the proximal opening, the cuff having a closed configuration for delivery and retrieval of the bag and an open configuration to receive tissue, the cuff being biased into the open configuration, the bag having a main body which extends from the cuff and the main body of the bag is more flexible than the cuff, and a biasing element to bias the cuff into the open configuration.

According to one aspect, the bag has a main body which extends from the cuff and the main body of the bag is more flexible than the cuff. The cuff may be of a different material than that of the main body of the bag. The cuff may be of a stiffer material than that of the main body of the bag.

According to one aspect, the main body of the bag includes a neck region extending from the cuff. The neck region may be more flexible than the cuff.

According to one aspect, the cuff extends for a distance of between 2 and 20 cm, between 2 and 10 cm, or about 5 cm.

According to one aspect, the bag includes a biasing element (e.g., a ring) that extends at least partially around the opening. The biasing element (e.g., ring) is preferably flexible to facilitate entry through an incision and/or an instrument access port. That is, the biasing element (e.g., ring) may bias the cuff into the open configuration.

In one case the biasing element (e.g., ring) includes a loop (e.g., an O-ring) extending around the cuff. The loop may be of a shape memory material such as Nitinol. The loop may include a single loop element which is open or closed.

In one case the loop includes a plurality of loop parts.

According to one aspect, at least one of the loop parts is movable relative to another of the loop parts. At least one of the loop parts may be movable circumferentially relative to another ring element.

In one case the apparatus includes a retainer for opening the bag.

The retainer may include at least one ring element which extends at least partially around the opening. The ring element may be flexible to facilitate entry through an incision and/or an instrument access port. In one case the ring element includes an O-ring.

According to one aspect, the retainer includes ring parts. There may be two separate ring parts.

According to one aspect, the apparatus (e.g., bag) includes a tether for each of the ring parts.

According to one aspect, the bag may include a tether extending proximally from the cuff. The cuff may include a tab for use in grasping the bag. In one case the bag includes tabs arranged on opposite sides of the cuff.

The or each tab may include an indicator to indicate a preferred orientation of the bag.

According to one aspect, the bag is configured to be foldable into a reduced size for insertion through an incision or an opening.

In one aspect the retainer has an insertion configuration and an expanded deployed configuration. The retainer may be biased into the deployed configuration.

The disclosure also provides an apparatus including an introducer sheath or pouch for containing the bag in an insertion configuration. The introducer sheath or pouch may be at least partially insertable through an opening and/or an incision and/or an access port.

In one case the apparatus includes an activator for delivering the bag from the pouch, on insertion. The activator may include a tab. In one case the activator includes a plunger.

According to one aspect, the apparatus includes a user tether attached to the bag.

In one case the bag includes a neck region. The neck region may be adjacent to the retainer.

According to one aspect, the bag itself includes a port. The port may be an exit port and/or an entrance port. The bag may include a plurality of ports.

According to one aspect, the port includes a valve. The valve may include a choke valve or a cuff valve. In one case the valve includes an elastomeric material such as a gel.

According to one aspect, the apparatus includes a proximal tether and a distal tether. The distal tether may be movable relative to the proximal tether.

In one case the proximal tether includes a loop through which the distal tether is movable.

There may be a lock to restrict movement of the distal tether. In one case the lock is provided by or on the proximal and/or the distal tether. The lock may include a projection on the distal tether which is engagable by the proximal tether.

According to one aspect, the apparatus further includes an access port to which the bag is mounted or mountable. The access port may include a retractor having a distal anchoring element for location within a wound interior, a proximal member for location externally of a wound opening and a retractor member extending proximally from the distal anchoring element to retract laterally the sides of an incision.

The bag may be mountable to the proximal member of the retractor.

According to one aspect, the apparatus further includes a cap for closing the proximal side of the retractor. The cap may include an access device for an instrument or a surgeon's hand/arm. The access device may be mountable to the proximal member of the retractor.

The disclosure also provides an apparatus for use in laparoscopic surgery including a bag of the disclosure and a retractor. The apparatus may further include an access port.

The disclosure also provides a viscera retainer including an apparatus of the disclosure.

Other aspects of the disclosure provide a method for performing a laparoscopic procedure including the steps of:—
inserting a bag according to the disclosure through an opening;
inflating the bag;
delivering tissue into the bag before or after inflating the bag; and
carrying out a procedure on the tissue located in the inflated bag.

According to one aspect, the opening is an opening into a body cavity.

The opening may be provided, at least in part, by an incision.

According to one aspect, the method includes providing a trocar and inserting the bag through the trocar.

The method may include providing a retractor in the opening and inserting the bag through the retracted opening.

The tissue may be delivered into the bag before inflating the bag.

The method may include the step, either before or after delivery of the tissue into the bag, of mounting the bag to the retractor.

According to one aspect, the method includes passing an instrument into the inflated bag to carry out a procedure.

According to one aspect, the method includes inserting a trocar into the bag.

The method may include the steps of providing an access port in the bag and passing an instrument and/or tissue through the access port.

According to one aspect, the method includes sealing the access port prior to and/or subsequent to passage of an instrument and/or tissue through the access port.

According to one aspect, a device of the disclosure includes at least one instrument seal to effect a seal around at least one instrument extended through the device, the instrument seal being configured to be arranged in sealing relationship to a body of a patient. The device preferably has a distal anchoring member for location within a wound interior. The device preferably also has a retractor member extending proximally from the distal anchoring member to retract laterally the sides of a wound opening. Preferably the device includes a first instrument seal to effect a seal around a first instrument extended through the device, and a second instrument seal to effect a seal around a second instrument extended through the device. By providing the two seal arrangement, this ensures that insertion or manipulation or removal of the second instrument does not adversely effect the seal around the first instrument. The device may include a third instrument seal to effect a seal around a third instrument extended through the device. The first instrument seal may be spaced apart from the second instrument seal. The first instrument seal may be formed separately from the second instrument seal. The first instrument seal may have a larger radial dimension than the second instrument seal. The instrument seal may be a valve. Alternatively, the seal is of a gelatinous elastomeric material.

In one case the device includes a proximal member for location externally of a wound opening. The retractor member may extend at least between the distal anchoring member and the proximal member. The retractor member may extend in two layers between the distal anchoring member and the proximal member. A first end portion of the retractor member may be fixed to the proximal member. The retractor member may be movable relative to the distal anchoring member. A second end portion of the retractor member may be movable relative to the proximal member. The retractor member may extend distally from the proximal member to the distal anchoring member, may be looped around the distal anchoring member, and may extend proximally from the distal anchoring member to the proximal member. The proximal member may include an inner part and an outer part. The retractor member may extend between the inner part and the outer part.

According to one aspect, the instrument seal is spaced proximally of the proximal member. The device may include at least one connector member to connect the proximal member to the at least one instrument seal. The connector member facilitates a degree of lateral movement of the instrument while maintaining the seal. The connector member may include a sleeve. The connector member may be of a laterally flexible material. The connector member may be of a longitudinally rigid material. The connector member may be of a rubber-like material. The connector member may be of a longitudinally flexible material.

In another case the instrument seal is mounted to the connector member. The instrument seal may be releasably mounted to the connector member. The instrument seal may include a mounting part to mount the instrument seal to the connector member. The mounting part may be of a rigid material. The instrument seal may include a sealing part to effect a seal around an instrument extended through the device, the sealing part being overmoulded over at least part of the mounting part.

According to one aspect, a method for performing a laparoscopic procedure may include inserting a bag through a patient opening, delivering tissue into a bag opening of the bag, withdrawing the bag opening back through the patient opening, sealing the bag, inflating the bag to create an artificial pneumoperitoneum that extends the abdomen, conforms to the peritoneal cavity, and provides additional working and viewing space; and carrying out a procedure on the tissue located in the inflated bag.

According to one aspect, a method for performing a laparoscopic procedure includes inserting a bag through a patient opening and into a peritoneal cavity, delivering tissue into the bag in an insufflated peritoneal cavity, sealing the bag, inflating the bag to apply a retracting force to the materials outside the bag thereby enlarging the peritoneal cavity, carrying out a procedure on the tissue located in the inflated bag; and allowing the peritoneal cavity to uninsufflate so that the inflated bag is located in an uninsufflated peritoneal cavity.

According to one aspect, a method for performing a laparoscopic procedure includes inserting a bag through a patient opening and into a peritoneal cavity, delivering tissue into the bag, sealing the bag, inflating the bag to retract surrounding structures and organs and urge the bag against the abdominal wall, piercing the bag by one or more trocars at a location where the bag is urged against the abdominal wall, carrying out a procedure on the tissue located in the inflated bag, and communicating the peritoneal cavity with the atmosphere prior to carrying out a procedure on the tissue located in the inflated bag.

According to one aspect, a method for performing a laparoscopic procedure includes insufflating the peritoneal cavity to provide a working and viewing space, excising tissue within the working and viewing space, inserting a bag into the working and viewing space, delivering the excised tissue into the bag, sealing the bag, inflating the bag to replace the working and viewing space of the insufflated peritoneal cavity with a working and viewing space within the bag, and carrying out a procedure on the tissue located in the inflated bag.

The methods for performing a laprascopic procedure may further include one or more of the following features: the opening may be a naked incision in the abdominal wall; the opening may be one of an opening through a retractor device coupled to an incision, or an opening through a trocar coupled to an incision; the inserting of a bag through an opening may include inserting the bag through a valve; the extending of the abdomen includes the bag contacting both the anterior abdominal wall and the abdominal viscera; the opening may be an opening through the retractor device, and the sealing of the bag may include sealing the bag to a proximal end of the retractor device with a cap; the delivering of tissue into the bag may be performed in an insufflated peritoneal cavity; the carrying out of a procedure in the inflated bag may be performed in an uninsufflated peritoneal cavity; the inflating of the bag may include inflating the bag to retract surrounding structures and organs and urge the bag against the abdominal wall; piercing the bag with one or more trocars at a location where the bag may be urged against the abdominal wall; the carrying out of a procedure may include sealably inserting a morcellator into the bag and morcellating the tissue; and retrieving the tissue by pulling the bag out through the opening.

According to one aspect, an inflatable artificial pneumoperitoneum bag includes a length and a width, an artificial pneumoperitoneum bag neck portion having a first end and a second end, the first end forming a bag opening, an artificial pneumoperitoneum bag body portion forming a closed cavity in fluid communication with the second end of the neck portion, the body portion having a length and width greater than a length and width of the neck portion, and a ring located at the bag opening, the ring configured to bias the bag opening toward an open condition.

According to one aspect, an inflatable artificial pneumoperitoneum bag, including a first planar sheet portion and a second planar sheet portion, the first and second planar sheet portions having joined edges to form the pneumoperitoneum bag having a length and a width, a neck portion having a first end and a second end, the first end forming a bag opening, a body portion forming a closed cavity in fluid communication with the second end of the neck portion, the body portion having a length and width greater than a length and width of the neck portion, and a ring located at the bag opening, the ring configured to bias the bag opening toward an open condition.

The inflatable artificial pneumoperitoneum bag may further include one or more of the following features: a length of the bag is between 300 and 600 mm when the bag is uninflated, and a maximum width of the bag is between 200 and 500 mm when the bag is uninflated; the neck portion has a diameter of between 100 and 220 mm when in the open condition; the neck portion has a length of between 100 and 300 mm when the bag is uninflated; a width-extending cross-section of the body portion includes an oval shape when the bag is inflated; the bag includes sterilized polyester polyurethane planar sheet portions having joined edges; the bag is symmetric about two planes that are normal to one another; the neck portion includes edges that extend parallel to a lengthwise axis of the bag; and the ring is formed of a shape memory material and is received through loops in the neck portion.

According to one aspect, a method includes creating an artificial pneumoperitoneum in a patient using an artificial pneumoperitoneum bag, the artificial pneumoperitoneum bag including a length and a width, a neck portion having a first end and a second end, the first end forming a bag opening, a body portion forming a closed cavity in fluid communication with the second end of the neck portion, the body portion having a length and width greater than a length and width of the neck portion, and a ring located at the bag opening, the ring configured to bias the bag opening toward an open condition.

According to one aspect, a method includes creating an artificial pneumoperitoneum in a patient using an artificial pneumoperitoneum bag, the artificial pneumoperitoneum bag including a first planar sheet portion and a second planar sheet portion, the first and second planar sheet portions having joined edges to form the pneumoperitoneum bag having a length and a width, a neck portion having a first end and a second end, the first end forming a bag opening, a body portion forming a closed cavity in fluid communication with the second end of the neck portion, the body portion having a length and width greater than a length and width of the neck portion, and a ring located at the bag opening, the ring configured to bias the bag opening toward an open condition, and the creating of the artificial pneumoperitoneum includes positioning the joined edges in alignment with the lateral walls of the abdomen.

The methods for performing a laprascopic procedure may further include one or more of the following features: the length of the bag is between 300 and 600 mm when the bag is uninflated, and a maximum width of the bag is between 200 and 500 mm when the bag is uninflated; the neck portion has a diameter of between 100 and 220 mm when in the open condition; the neck portion has a length of between 100 and 300 mm when the bag is uninflated; a width-extending cross-section of the body portion includes an oval shape when the bag is inflated; the bag is formed of sterilized polyester polyurethane planar sheet portions having joined edges; the bag is symmetric about two planes that are normal to one another; the neck portion includes edges that extend parallel to a lengthwise axis of the bag; the ring is formed of a shape memory material and is received through loops in the neck portion.

According to one aspect, there is provided an inflatable artificial pneumoperitoneum bag, including:
  a length and a width;
  an artificial pneumoperitoneum bag neck portion having a first end and a second end, the first end forming a bag opening;
  an artificial pneumoperitoneum bag body portion forming a closed cavity in fluid communication with the second end of the neck portion, the body portion having a length and width greater than a length and width of the neck portion; and
  a ring located at the bag opening, the ring configured to bias the bag opening toward an open condition.

According to one aspect, the length of the bag is between 300 and 600 mm when the bag is uninflated, and a maximum width of the bag is between 200 and 500 mm when the bag is uninflated.

According to one aspect, the neck portion has a diameter of between 100 and 220 mm when in the open condition.

The neck portion may have a length of between 100 and 300 mm when the bag is uninflated.

According to one aspect, a width-extending cross-section of the body portion includes an oval shape when the bag is inflated.

In one case the bag includes sterilized polyester polyurethane planar sheet portions having joined edges.

According to one aspect, the bag is symmetric about two planes that are normal to one another.

In one case the neck portion includes edges that extend parallel to a lengthwise axis of the bag.

According to one aspect, the ring is formed of a shape memory material and is received through loops in the neck portion.

The disclosure also provides an inflatable artificial pneumoperitoneum bag, including:
  a first planar sheet portion and a second planar sheet portion, the first and second planar sheet portions having joined edges to form the pneumoperitoneum bag having
    a length and a width;
    a neck portion having a first end and a second end, the first end forming a bag opening;
    a body portion forming a closed cavity in fluid communication with the second end of the neck portion, the body portion having a length and width greater than a length and width of the neck portion; and
    a ring located at the bag opening, the ring configured to bias the bag opening toward an open condition.

According to one aspect, the length of the bag is between 300 and 600 mm when the bag is uninflated, and a maximum width of the bag is between 200 and 500 mm when the bag is uninflated.

In one case the neck portion has a diameter of between 100 and 220 mm when in the open condition.

According to one aspect, the neck portion has a length of between 100 and 300 mm when the bag is uninflated.

In one case a width-extending cross-section of the body portion includes an oval shape when the bag is inflated.

According to one aspect, the bag includes sterilized polyester polyurethane.

In one case the bag is symmetric about two planes that are normal to one another.

According to one aspect, the neck portion includes edges that extend parallel to a lengthwise axis of the bag.

In one case the ring is formed of a shape memory material and is received through loops in the neck portion.

The disclosure also provides a method, including:
  creating an artificial pneumoperitoneum in a patient using an artificial pneumoperitoneum bag, the artificial pneumoperitoneum bag including
    a length and a width,
    a neck portion having a first end and a second end, the first end forming a bag opening;
    a body portion forming a closed cavity in fluid communication with the second end of the neck portion, the body portion having a length and width greater than a length and width of the neck portion; and
    a ring located at the bag opening, the ring configured to bias the bag opening toward an open condition.

According to one aspect, the length of the bag is between 300 and 600 mm when the bag is uninflated, and a maximum width of the bag is between 200 and 500 mm when the bag is uninflated. In one case the neck portion may have a diameter of between 100 and 220 mm when in the open condition. The neck portion may have a length of between 100 and 300 mm when the bag is uninflated. In one case a width-extending cross-section of the body portion includes an oval shape when the bag is inflated. The bag may include sterilized polyester polyurethane planar sheet portions having joined edges. The bag may be symmetric about two planes that are normal to one another. The neck portion may include edges that extend parallel to a lengthwise axis of the bag. The ring may be formed of a shape memory material and is received through loops in the neck portion.

The disclosure also provides a method, including:
  creating an artificial pneumoperitoneum in a patient using an artificial pneumoperitoneum bag, the artificial pneumoperitoneum bag including
    a first planar sheet portion and a second planar sheet portion, the first and second planar sheet portions having joined edges to form the pneumoperitoneum bag having
      a length and a width;
      a neck portion having a first end and a second end, the first end forming a bag opening;
      a body portion forming a closed cavity in fluid communication with the second end of the neck portion, the body portion having a length and width greater than a length and width of the neck portion; and
      a ring located at the bag opening, the ring configured to bias the bag opening toward an open condition; and
    the creating of the artificial pneumoperitoneum includes positioning the joined edges in alignment with the lateral walls of the abdomen.

According to one aspect, the length of the bag is between 300 and 600 mm when the bag is uninflated, and a maximum width of the bag is between 200 and 500 mm when the bag is uninflated. The bag may be symmetric about two planes that are normal to one another.

The disclosure also provides a method for performing a laparoscopic procedure, including:
  inserting a bag through a patient opening;
  delivering tissue into a bag opening of the bag;
  withdrawing the bag opening back through the patient opening;
  sealing the bag;
  inflating the bag to create an artificial pneumoperitoneum that extends the abdomen and provides additional working and viewing space; and
  carrying out a procedure on the tissue located in the inflated bag.

According to one aspect, the patient opening is a naked incision in the abdominal wall. The patient opening may be one of an opening through a retractor device coupled to an incision, or an opening through a trocar coupled to an incision. According to one aspect, the inserting of a bag through a patient opening includes inserting the bag through a valve. According to one aspect, the extending of the abdomen includes the bag contacting both the anterior abdominal wall and the abdominal viscera. In one case the patient opening is an opening through the retractor device, and the sealing of the bag includes sealing the bag to a proximal end of the retractor device with a cap. According to one aspect, the delivering of tissue into the bag is performed in an insufflated peritoneal cavity. The carrying out of a procedure in the inflated bag may be performed in an uninsufflated peritoneal cavity. The inflating of the bag may create an artificial pneumoperitoneum that extends the abdomen includes urging the bag against the abdominal wall, and the method further includes piercing the bag with one or more trocars at a location where the bag is urged against the abdominal wall. According to one aspect, the carrying out of a procedure includes sealably inserting a morcellator into the bag and morcellating the tissue, and the method further includes retrieving the tissue by pulling the bag out through the patient opening.

The disclosure also provides a method for performing a laparoscopic procedure, including:
 inserting a bag through a patient opening and into a peritoneal cavity;
 delivering tissue into the bag in an insufflated peritoneal cavity;
 sealing the bag;
 inflating the bag to apply a retracting force to the materials outside the bag thereby enlarging the peritoneal cavity;
 carrying out a procedure on the tissue located in the inflated bag; and
 allowing the peritoneal cavity to uninsufflate so that the inflated bag is located in an uninsufflated peritoneal cavity.

According to one aspect, the application of the retracting force to the materials outside the bag includes the bag contacting both the anterior abdominal wall and the abdominal viscera. The patient opening may be one of an opening through a retractor device coupled to an incision, or an opening through a trocar coupled to an incision. The inserting of a bag through an opening may include inserting the bag through a valve. The patient opening may be an opening through the retractor device, and the sealing of the bag includes sealing the bag to a proximal end of the retractor device with a cap. The method may further include pulling an open end of the bag out through the patient opening prior to inflating the bag. The allowing of the peritoneal cavity to uninsufflate may be performed before the carrying out of a procedure on the tissue located in the inflated bag. The inflating of the bag may be performed in an uninsufflated peritoneal cavity. The inflating of the bag to apply a retracting force may include urging the bag against the abdominal wall, the method further including piercing the bag with one or more trocars at a location where the bag is urged against the abdominal wall. The carrying out of a procedure may include sealably inserting a morcellator into the bag and morcellating the tissue, and the method further includes retrieving the tissue by pulling the bag out through the opening.

The disclosure also provides a method for performing a laparoscopic procedure, including:
 inserting a bag through a patient opening and into a peritoneal cavity;
 delivering tissue into the bag;
 sealing the bag;
 inflating the bag to retract surrounding structures and organs and urge the bag against the abdominal wall;
 piercing the bag by one or more trocars at a location where the bag is urged against the abdominal wall;
 carrying out a procedure on the tissue located in the inflated bag; and
 communicating the peritoneal cavity with the atmosphere prior to carrying out a procedure on the tissue located in the inflated bag.

According to one aspect, the patient opening is one of an opening through a retractor device coupled to an incision, or an opening through a trocar coupled to an incision. In one case the patient opening is an opening through the retractor device, and the sealing of the bag includes sealing the bag to a proximal end of the retractor device with a cap. The method may further include pulling an open end of the bag out through the patient opening prior to inflating the bag, and wherein the retraction of the surrounding structures and organs includes the bag contacting both the anterior abdominal wall and the abdominal viscera. The delivering of tissue into the bag may be performed in an insufflated cavity. The inflating of the bag may be performed in an uninsufflated peritoneal cavity.

The disclosure also provides a method for performing a laparoscopic procedure, including:
 insufflating the peritoneal cavity to provide a working and viewing space;
 excising tissue within the working and viewing space;
 inserting a bag into the working and viewing space;
 delivering the excised tissue into the bag;
 sealing the bag;
 inflating the bag to replace the working and viewing space of the insufflated peritoneal cavity with a working and viewing space within the bag; and
 carrying out a procedure on the tissue located in the inflated bag.

According to one aspect, the method further includes pulling an open end of the bag out through a patient opening prior to inflating the bag, and wherein the inflating of the bag includes the bag contacting both the anterior abdominal wall and the abdominal viscera. The method may further include uninsufflating the peritoneal cavity after delivering the excised tissue into the bag. The inflating of the bag may be performed in an uninsufflated peritoneal cavity.

According to one aspect, an artificial pneumoperitoneum bag device may include an inflatable bag having an opening at an end of the bag. The bag device may also include an indicator including at least one repeating pattern on a wall of the bag. The pattern may extend across at least one side of the bag.

According to one aspect, an artificial pneumoperitoneum bag device may include an inflatable bag that has an opening at an end of the bag. The bag device may also include a grid. The grid may include a plurality of lines extending across at least a first side of the bag.

According to one aspect, an artificial pneumoperitoneum bag device may include at least one patterned membrane forming at least a portion of an inflatable bag that has an opening at an end of the bag. The at least one patterned membrane may include a neck portion having a width defined between opposing lateral edges of the neck portion. The patterned membrane may also include an enlarged body portion having a width defined between opposing lateral edges of the body portion. The width of the body portion may be greater than the width of the neck portion. The patterned membrane may also include a shoulder portion connecting the neck portion with the enlarged body portion.

According to one aspect, a method for performing a surgical procedure may include inserting an artificial pneumoperitoneum bag device through a patient opening and into a peritoneal cavity. The bag device may include an inflatable bag with an opening at an end of the bag. The bag device may also include at least one repeating pattern on the bag. The at least one pattern may extend across at least one side of the bag. The method may also include inflating the bag to cause the bag to conform to a shape of the peritoneal cavity. The method may also include visually observing the pattern after inflating the bag.

According to one aspect, a method for deploying an artificial pneumoperitoneum bag in a peritoneal cavity may include inflating the bag. The bag may include an open end, an opposite closed end, a longitudinal axis extending between the open end and closed end, and a pair of side portions located between the open end and the closed end. Inflating the bag may cause a rolled portion of the bag to unroll away from the open end. The rolled portion may include the side portions with the side portions folded toward the longitudinal axis. As the rolled portion unrolls, unrolled portions of the side portions may unfold away from the longitudinal axis.

BRIEF DESCRIPTION OF THE DRAWINGS

The disclosure will be more clearly understood from the following description of some aspects thereof, given by way of example only, with reference to the accompanying drawings, in which:

FIG. 1 is an isometric view of a pneumoperitoneum device according to an aspect of the disclosure;

FIG. 2 is another isometric view of the device of FIG. 1;

FIGS. 3 to 5 are views of another pneumoperitoneum device according to an aspect of the disclosure;

FIGS. 6 to 18 are diagrams illustrating the use of the device of FIGS. 1 to 5;

FIGS. 19 to 22 are diagrams illustrating another use of the device of FIGS. 1 to 5;

FIGS. 25 to 30 are diagrams illustrating various ways in which a device according to an aspect of the disclosure may be introduced;

FIGS. 31 to 35 are diagrams illustrating the device, in use;

FIG. 36 is a diagram of another device according to an aspect of the disclosure;

FIGS. 37 to 45 are diagrams illustrating the device of FIG. 36, in use;

FIG. 46 is a diagram of another device according to an aspect of the disclosure;

FIGS. 47 to 54 are diagrams illustrating the device of FIG. 46, in use;

FIG. 55 is a diagram of a further device according to an aspect of the disclosure;

FIGS. 56 to 63 are diagrams illustrating the device of FIG. 55, in use;

FIGS. 65 to 74 are diagrams illustrating the device of FIG. 64, in use;

FIGS. 82 to 87 are isometric views of alternative grommets;

FIG. 88 is an isometric view of another device according to an aspect of the disclosure with a multi-lumen access port removed;

FIG. 89 is an isometric, partially cut-away view of the device of FIG. 88 with an access port in position for use;

FIG. 90 is an isometric view of a device according to an aspect of the disclosure.

FIG. 91 is another view of the device of FIG. 90 with an access port in position for use;

FIGS. 92A and 92B are isometric views of single lumen access ports for use with the devices of aspects of the disclosure;

FIG. 93 is an isometric view of a pneumoperitoneum device according to another aspect of the disclosure with an exit port from the device;

FIG. 94 is an isometric view of another device similar to FIG. 93 with a number of exit ports;

FIG. 95 is an isometric view illustrating devices of the types of FIGS. 93 and 94, in use;

FIGS. 96 to 98 are views of various seals that may be used in association with the device;

FIGS. 99 to 110 illustrate one method of use of devices according to an aspect of the disclosure;

FIGS. 111 to 113 are views illustrating a locking detail of the device of FIGS. 99 to 110;

FIGS. 114 to 117 are views of a device according to an aspect of the disclosure, in use in the colon;

FIG. 120 is an isometric view of a pneumoperitoneum device according to an aspect of the disclosure loaded in an introducer;

FIG. 121 is an isometric view of a bag according to an aspect of the disclosure;

FIG. 122 is a cross sectional view on the line A-A in FIG. 121;

FIGS. 139 to 143 are various views of a biasing loop including loop sections which are movable relative to one another;

FIGS. 144 to 149 are various views of another biasing loop;

FIGS. 150 to 153 are various views of a further biasing loop;

FIGS. 157 to 160 are diagrams illustrating another bag device according to an aspect of the disclosure;

FIGS. 166 to 168 are isometric views of further bag devices according to an aspect of the disclosure with a retaining ring in place in a cuff of the bags;

FIGS. 169A to 169C and 170 illustrate the mounting of a ring to the cuff of the bag of FIG. 168;

FIG. 171 shows a protector cap for a bag device;

FIGS. 172 to 176 illustrate an introducer for use in deploying and manipulating a bag device;

FIGS. 177 to 180 are views of further introducers with various pressure dissipating features;

FIG. 202 illustrates the threading of a wire through a collar of the bag device;

FIG. 203 is a cross sectional view of a detail of FIG. 202;

FIG. 204 illustrates the joint between ends of the wire;

FIG. 205 shows the attachment of a tether to the joint of FIG. 204;

FIGS. 211 to 218 illustrate the artificial pneumoperitoneum device at different stages of use;

FIGS. 224 to 253 illustrate the artificial pneumoperitoneum device according to an aspect of the disclosure at various stages during use;

FIGS. 261 to 266 illustrate further artificial pneumoperitoneum devices according to an aspect of the disclosure;

FIGS. 281A, 281B, 282A, 282B, and 283 to 285 illustrate a trocar cover;

FIGS. 287 to 289 are isometric views illustrating the delivery of tissue into the device;

FIGS. 290 to 292 are isometric views illustrating the closing of the device.

DETAILED DESCRIPTION

Figure 18:
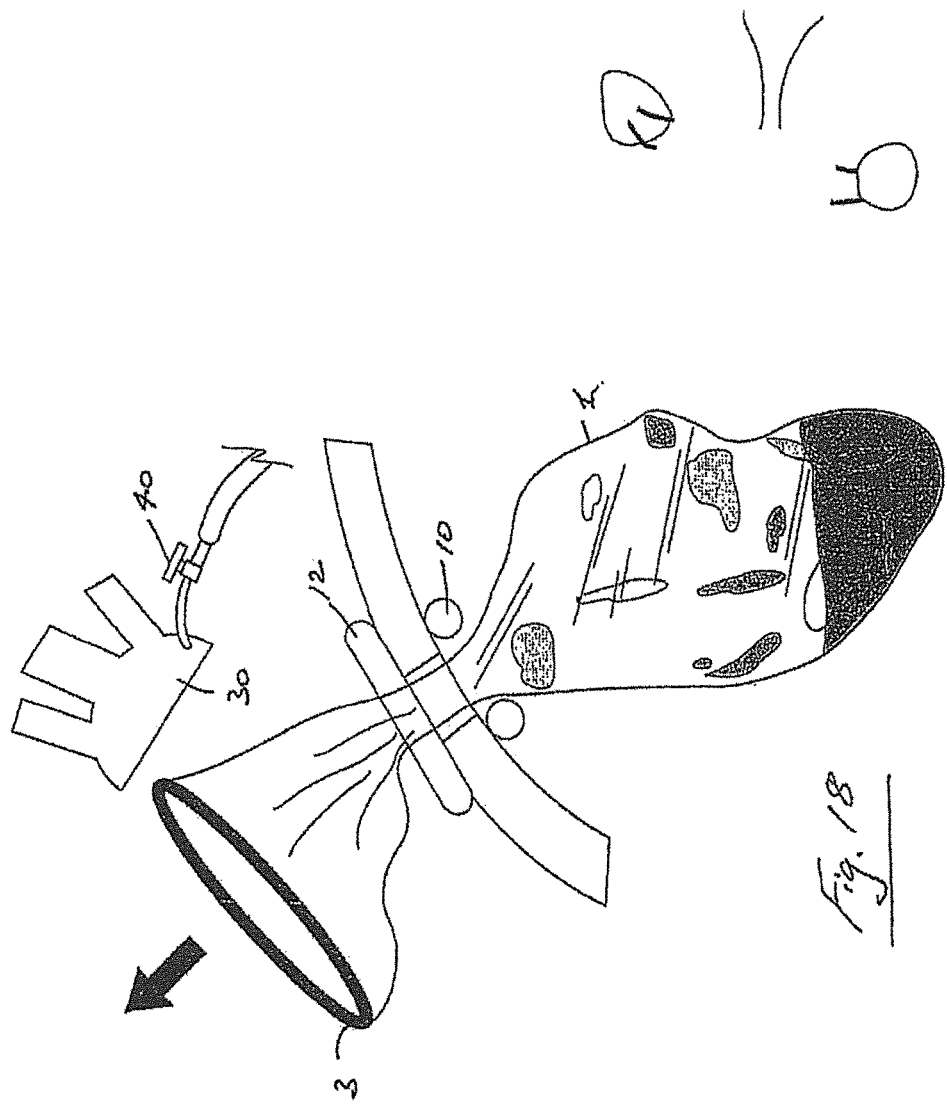

Aspects of the disclosure provide an artificial pneumoperitoneum device for tissue isolation and/or extraction in a laparoscopic procedure The device is used to safely reduce and remove resected tissue from within the abdomen via small laparoscopic incisions. The bag creates an artificial pneumoperitoneum containing the specimen and eliminating the dissemination of tissue and cellular fluids within the peritoneal cavity. The device facilitates effective and safe isolation of tissue/organs within an artificial pneumoperitoneum for improved surgical procedures and subsequent safe tissue extraction.

A tissue bag is inserted within the peritoneal cavity through an incision in the abdominal wall or vagina.

In one case the bag with one or more openings is placed within the abdomen. Excised tissue is placed within the opening of a deflated bag. One or more openings of the bag are withdrawn outside the abdomen and the bag is inflated. Instruments including laparoscopic visualization are placed within the inflated bag that remains within the peritoneal cavity. Visualisation tools may also be provided external of the bag. The tissue retained within the bag is morcellated/crushed/reduced and removed. The bag is deflated and removed with residual tissue/blood/fluids inside. A major advantage is that the tissue to be removed is retained in the bag which prevents potentially harmful material such as cancerous cells from being released in the body cavity.

Referring to the drawings, and initially to FIGS. 1 and 2 thereof, there is illustrated an apparatus for use in laparoscopic surgery including a bag 1 having an opening 2 to receive tissue and a ring element 3 extending around the opening 2. The bag is inflatable.

Referring to FIGS. 3 to 5, there is illustrated another bag device according to an aspect of the disclosure which is similar to the bag device of FIGS. 1 and 2 and like parts are assigned the same reference numerals. In this case the bag 1 has a necked region 5 to reduce the amount of material near the ring 3. This facilitates attachment of the bag 1 to an external element.

The bag device 1 is suitable for use during laparoscopic surgery to facilitate procedures on tissue in an insufflated cavity while maintaining pneumoperitoneum.

The bag device 1 may be mounted to a retractor. One such retractor includes a distal anchoring ring 10, a retractor member such as a sleeve 11, and a proximal ring assembly 12.

One such retractor is described in US 2005-0090717 A, the entire contents of which are incorporated herein by reference. The distal anchoring ring 10 is located within a wound interior, in use. In this case the distal anchoring ring 10 is provided in the form of an O-ring. The proximal ring assembly 12 is located externally of a wound opening, in use. The retractor member 11 may be employed to retract laterally the sides of a wound opening. In this case, the retractor member is provided in the form of a sleeve.

The proximal end of the retractor 11 is closable by a cap which in this case includes an instrument access device 30 which may have a number of instrument ports 31 to effect a seal around an instrument extended through the device 30. The instrument access device 30 may be releasably mountable to the proximal ring assembly 12. At least some of the instrument ports may include a stalk 32 which is laterally flexible and longitudinally rigid.

FIG. 6 illustrates an instrument 51 being introduced under vision provided by a camera 52 through an instrument access port 31.

FIG. 7 shows an organ or tissue such as an uterus 35 which has been severed from its retaining structures.

FIG. 8 illustrates the bag device 1 being inserted into the abdominal cavity at the beginning of a procedure or as and when required. The bag 1 is inserted in a small flattened state for ease of insertion through a small opening such as an incision. As shown in FIG. 8, the bag device 1 is inserted through an opening that is open to the atmosphere, and thus the peritoneal cavity is uninsufflated. The bag may also be introduced through a valve without the need to remove the access cap 30. One such arrangement is illustrated in FIG. 10, and this allows the bag device to be inserted into an insufflated peritoneal cavity.

When the bag 1 is inserted in the insufflated or uninsufflated peritoneal cavity, it is opened up (FIG. 9). An organ is then readily manipulated for insertion into the bag 1 as illustrated in FIG. 11. The rigidity of the O-ring 3 keeps the bag open to facilitate insertion of an organ.

Figure 76:
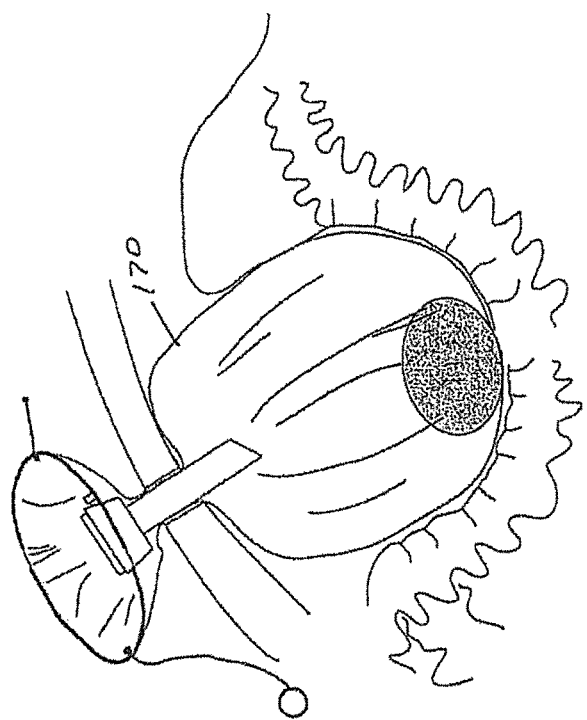
FIGS. 76 to 78 are diagrams illustrating the device of FIG. 75, in use.

FIG. 12 shows the organ located in the bag 1 and the O-ring 3 being grasped to facilitate manipulation of the bag towards the opening. As shown in FIG. 12, removal of access cap 30 provides an uninsufflated peritoneal cavity prior to inflating the bag device 1. The uninsufflated nature of the peritoneal cavity helps the bag device 1 expand as shown in FIG. 16, and apply a retracting force to the materials outside the bag thereby creating additional space (FIG. 76). It is understood that the bag device 1 could be inflated while the peritoneal cavity is insufflated if there is one or more openings to the peritoneal cavity that allow the insufflation gas to escape to the cavity. One such opening could be provided through an open trocar device or trocar incision opening that was used to carry out the tissue excising explained above. The O-ring 3 is pulled out through the opening (FIG. 13) and the bag 1 is mounted to the proximal ring assembly 12 and the cap 30 is mounted to the proximal assembly 12 (FIG. 14). FIG. 15 illustrates the device in place with an organ enclosed within the bag 1.

The bag 1 is then inflated through an insufflation port 40. The inflation of the bag has the additional benefit of applying a retracting force to the materials outside the bag 1 thereby creating additional space (FIG. 16). Thus, the artificial pneumoperitoneum created in the uninsufflated peritoneal cavity, and within the inflated bag device 1, serves to extend the abdomen and provide additional working and viewing space within the bag device 1.

FIG. 17 shows an organ being worked on in the inflated bag 1. In this case the organ is morcellated. The material is all retained safely within the bag and is not released into the cavity which could cause major difficulties.

When the organ has been morcellated, the bag is readily removed through the original opening. All waste, blood, tissue and the like are safely removed and sealed within the bag 1.

FIG. 19 shows the bag device being inserted through a standard naked incision. Once the specimen has been inserted into the bag 1 (FIG. 20) the ring 3 is pulled back out through the incision (FIG. 21) and a trocar 60 is inserted to create a gas seal (FIG. 22). It may also be possible to insert the bag device 1 directly through a trocar.

In all cases there may be one or more access trocars used in addition to the primary port. Thus, the disclosure includes procedures which involve two or more incision laparoscopy.

Figure 24:
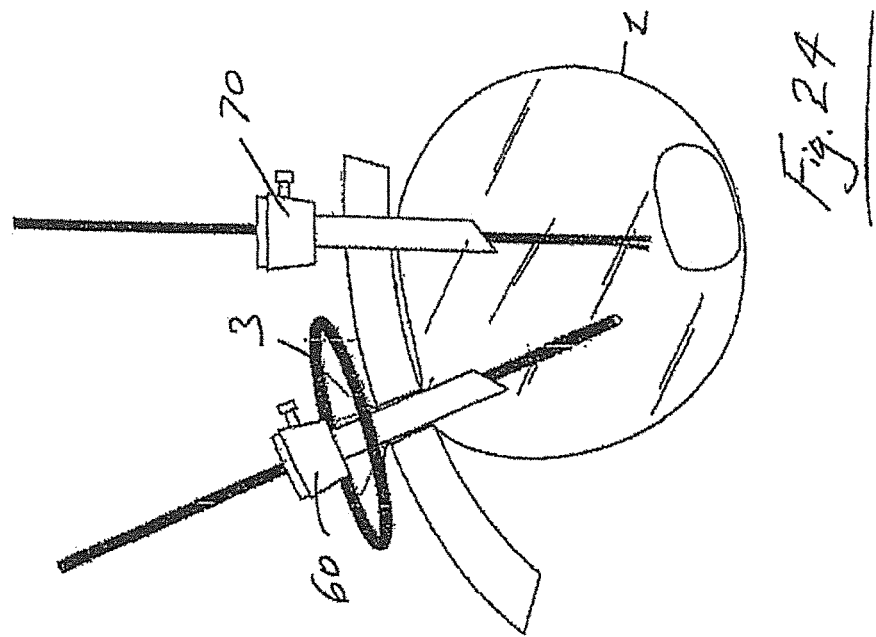
FIGS. 23 to 24 are diagrams illustrating a further use of the device of FIGS. 1 to 5.
Figure 23:
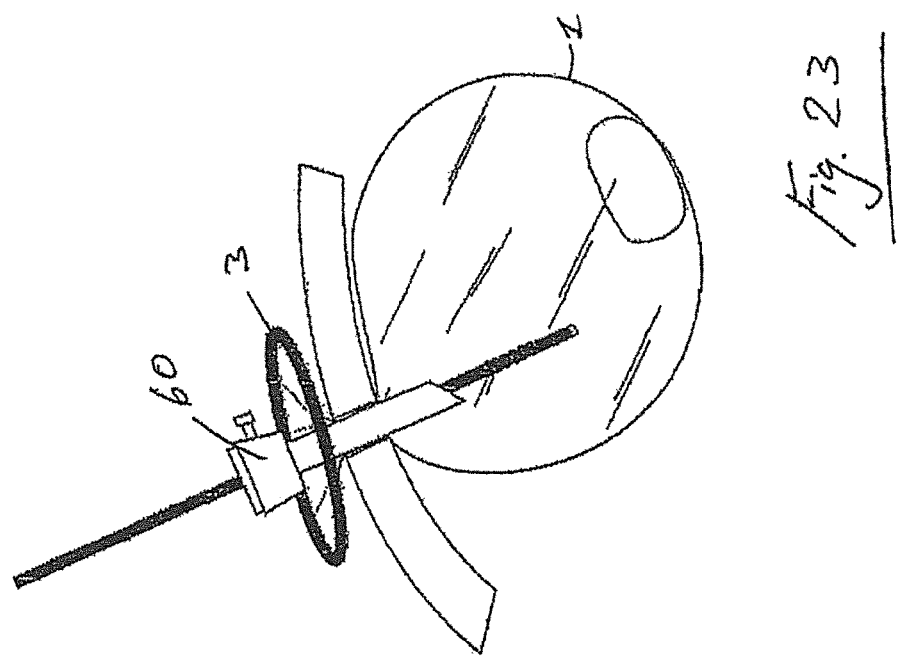

For example, FIGS. 23 and 24 show one arrangement in which an additional trocar 70 is inserted. In some cases, the additional trocar 70 may be extended through the bag whilst maintaining a seal.

A bag 1 is illustrated which has some depth which is preferred. However, a flat material can be used to form a holder in situ and the edges of the material pulled out through an incision and sealed outside, for example by an access device 30.

Aspects of the disclosure provide a method of inserting a large bag into the abdominal cavity to allow the insertion of a specimen into the bag. The bag is then sealed and inflated and procedure carried out within the bag.

FIGS. 25 to 30 show various ways a bag 79 may be introduced into the abdomen.

In FIG. 25 the device may be inserted directly through an incision 80.

Referring to FIG. 26, the device may be inserted through a trocar 81.

In FIG. 27 a device may be inserted through a base retractor 82.

Referring to FIG. 28 a device may be inserted through a low profile port 83.

As shown in FIG. 29 the device may be inserted through a Multi-port device 84. The multiport device may, for example, be of the type described in U.S. Pat. No. 8,187,178 or US 20110071359A, the entire contents of which are incorporated herein by reference.

Referring to FIG. 30 the device may be inserted through the base 85 of a multi-port device.

Figure 31:
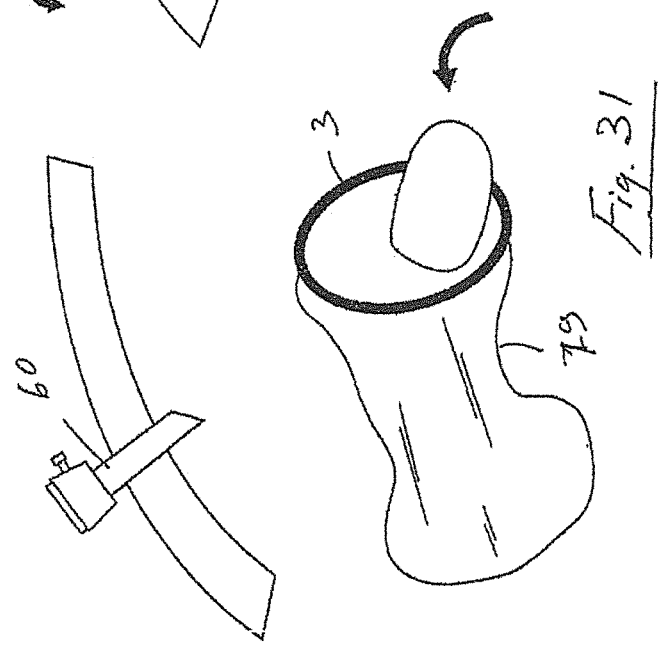

As illustrated in FIG. 31, once the bag 79 has been inserted the specimen is placed inside.

Figure 32:
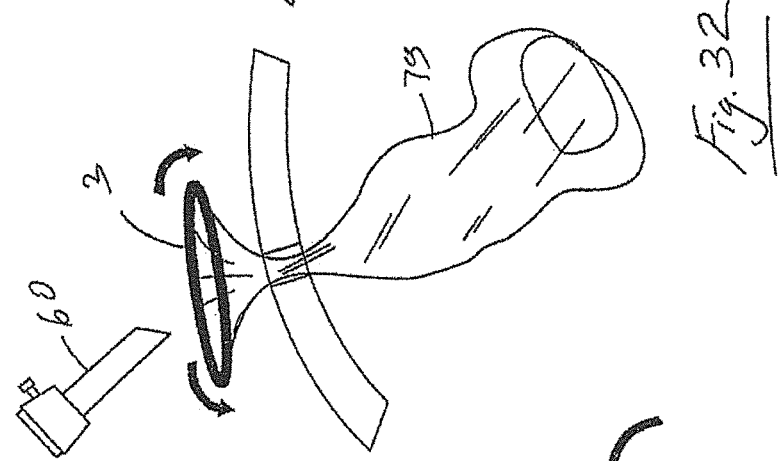

FIG. 32 the lip of the bag 79 is pulled out through the opening.

Figure 33:
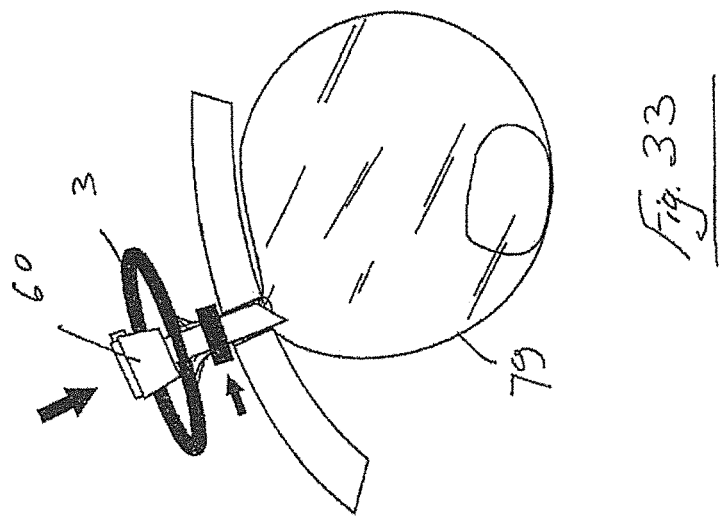

FIG. 33 the bag 79 is sealed by re-inserting the trocar 60, replacing the cap or inserting a morcellator 78. If necessary an extra seal may be applied to the neck of the bag 79.

As shown in, FIG. 34, once the bag 79 is inflated additional trocars may be inserted into the abdomen as normal and pierced through the bag 79. FIG. 34 also shows a morcellator 78 inserted through a trocar 60.

FIG. 35 shows the morcellator 78 being inserted without the need for a trocar. A sealing ring 77 may be applied around the shaft of the morcellator 78 if necessary to hold back gas.

Referring to FIGS. 36 to 45 a method of inserting a large bag 100 into an abdominal cavity which may automatically open to allow the insertion of a specimen is illustrated. The bag 100 is foldable and has a top opening 105 which may be biased into the open configuration by retaining elements which in this case include semi-circular ring parts 101, 102 which have attached tether elements 104, 103 respectively. A pouch 110 is used to house the bag 100 in a folded/retracted configuration. The pouch 110 has a grasping tab 111 and a pull string 115.

FIG. 36 illustrates the main components of the automatically opening bag device.

FIG. 37 illustrates a folded bag 100 inside the pouch 110. In FIG. 38 the pouch 110 is inserted into the abdominal cavity with the aid of the grasping tab 111. When the pouch is inside, the distal pull tether 104 is pulled forward and the bag 100 is released. A rear pull string 115 is pulled in the opposite direction to aid release.

Referring to FIG. 40, it will be noted that as the distal end of the bag 100 is pulled forward the rear of the bag 100 is pulled in the opposite direction as it is attached to the pouch 110 with the connecting tether 103. This action opens the mouth of the bag 100 sufficient to ease the inserting of specimens.

FIG. 41 shows specimens being placed on top of the bag opening 105.

Referring to FIG. 42, by pulling the distal pull tether 104 back and over the specimen, the bag 100 begins to unroll and the specimen travels deeper insider the bag 100. Referring to FIG. 43, as the front and back retaining elements 101, 102 of the bag opening are pulled outwards, the specimen travels further into the bag 100.

FIG. 44 shows the rim of the bag being opened up and the incision being cleared of excess bag material.

Referring to FIG. 45, the opening is re-sealed by attaching a cap, by inserting a trocar, or by inserting a morcellator through the opening.

Referring to FIGS. 46 to 54 there is illustrated another device according to an aspect of the disclosure. The device is similar to that of FIGS. 36 to 45 and like parts are assigned the same reference numerals. In this case a bag 120 is housed within a cartridge 121 for delivery and automatically opens when it exits the cartridge 121 on insertion into the abdominal cavity. In this case the ring part 102 remains attached to the cartridge 121. A tether 125 extends between the distal end of the cartridge 121 and the ring element 102. The ring element 101 has a tether element 126 which is grasped by an instrument 127 to pull the bag 120 from the cartridge 121.

FIGS. 46 to 54 show the bag 120 housed in the cartridge 121 which can be inserted into a valve on an access port/trocar 130. The cartridge 121 remains in place during the procedure.

Referring to FIG. 46, the loaded cartridge 121 is placed through a valve on the port 130. FIG. 47 shows the distal pull tether 126 that is positioned so that it is easily grasped with an instrument 127. In FIG. 48 an instrument 127 is inserted and the pull tether 126 is grasped.

Referring to FIG. 49, as the instrument/grasper 127 is pushed forward the bag 120 is released from the cartridge 121. As shown in FIG. 50, once the bag is in far enough, the tether 125 which connects the back side of the bag 120 to the cartridge 121 begins to open the bag 120 up.

Referring to FIG. 51, when the mouth of the bag 120 is sufficiently open a specimen may be placed inside. When the distal pull tether 126 is pulled back as illustrated in FIG. 52 this forces the bag 120 to unroll and the specimen to travel deeper into the bag 120.

Referring to FIG. 53, the cap/trocar 130 is then removed and the rim of the bag 120 is pulled out through the incision and mounted to the retractor 135. FIG. 54 shows the cap, trocar, or morcellator reconnected. The bag 120 is then inflated.

Referring to FIGS. 55 to 63, there is illustrated a removable cartridge 140 with a manually opened bag 141 for insertion through a single port 142. These drawings illustrate a method of inserting a large bag 141 which will be manually opened by the user when inserted into the abdominal cavity. FIGS. 55 to 63 show a bag 141 housed in a cartridge 140 which plugs into a valve 142 on an access port/trocar 130. The bag 141 is ejected from cartridge 140 using a plunger 145 and the cartridge 140 is removed. As shown, for example, in FIG. 54, inflating the bag device 1 creates the artificial pneumoperitoneum and urges the bag against the abdominal wall. This arrangement allows one or more additional trocars 70 to extend through the abdominal wall and directly and sealingly pierce the inflated bag device 1 where the bag device is urged against the abdominal wall. See, for example, FIGS. 24, 34, and 35. Further facilitating this sealing of the additional trocars 70 to the inflated bag device 1 is the fact that the inflated bag device 1 is applying a retracting force to the materials outside the bag device and is thus secured in place against the abdominal wall.

Referring to FIG. 55, the bag 141 is loaded into a cartridge 140 which is then inserted through a valve 142 on the port/trocar 130. When the cartridge 140 is in place of the plunger 145 is inserted through the proximal end of the cartridge 140 as illustrated in FIG. 56. Pushing the plunger 145 down as illustrated in FIG. 57 forces the bag 141 to eject into the abdominal cavity.

Referring to FIG. 58, when the bag 141 has been ejected, the cartridge 140 may be removed, leaving an activation tether 147 in place. An instrument 148 is inserted as illustrated in FIG. 59 and the instrument 148 is used to grasp the distal pull tether 149 which is attached to the front band or ring part/element 101 on the bag 141.

Referring to FIG. 60, the specimen is then lifted into the open mouth of the bag 141. The surgeon can control the mouth of the bag 141 using the activation tether 147. When both the front and the back ring elements 101, 102 of the bag 141 are grasped as illustrated in FIG. 61, the bag 141 can be pulled towards the incision, forcing the specimen to travel deeper into the bag 141.

FIG. 62 shows the valve/trocar 130 being removed and the rim of the bag being pulled out through the incision. In FIG. 63, the rim of the bag 141 is opened up, and the valve/trocar 130 are replaced to seal the bag 141. The bag 141 is then inflated and the procedure carried out within.

Referring to FIGS. 64 to 74 there is illustrated a removable cartridge 150 with a manually opened bag 151 (laparoscopic). These drawings show a method of inserting a large bag 151 which can be manually opened by the user when inserted into the abdominal cavity.

Figure 64:
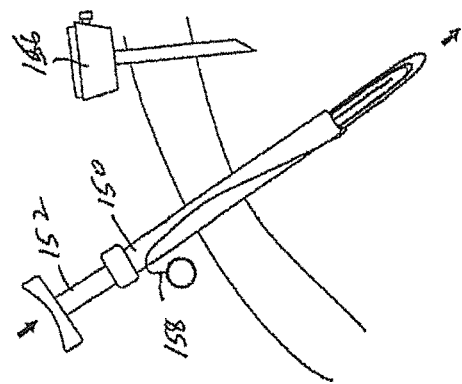
FIG. 64 is a diagram of another device according to an aspect of the disclosure.
Figure 65:
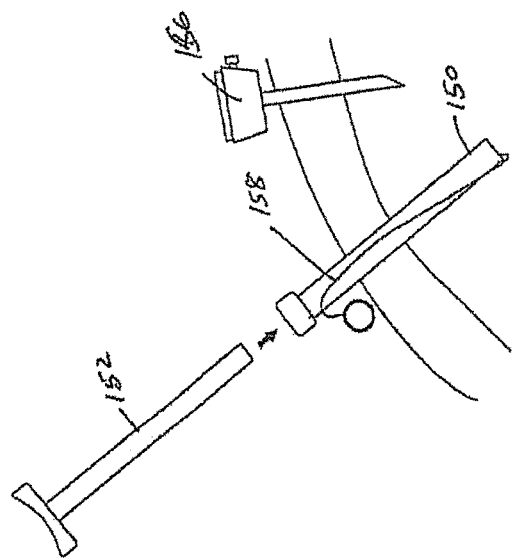
Figure 66:
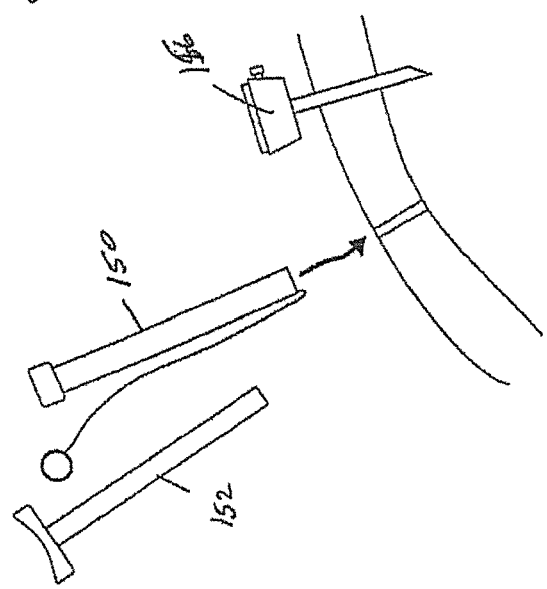
Figure 65:
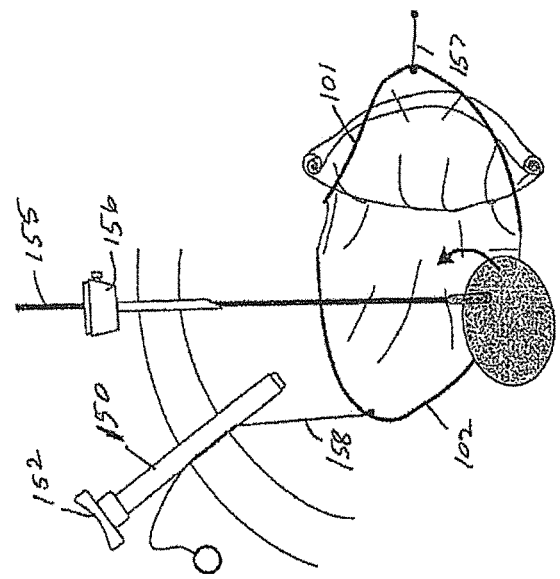
Figure 66:
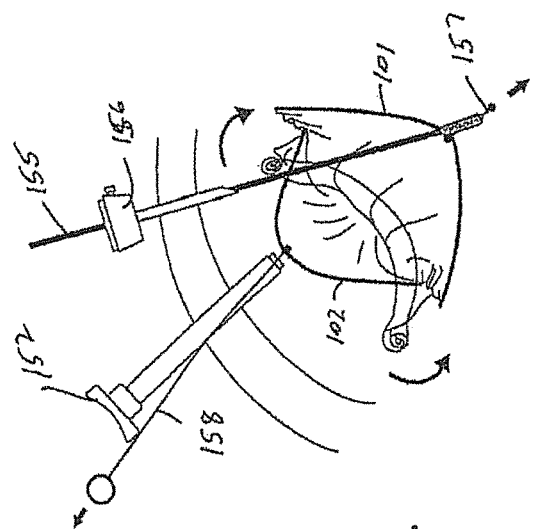
Figure 67:
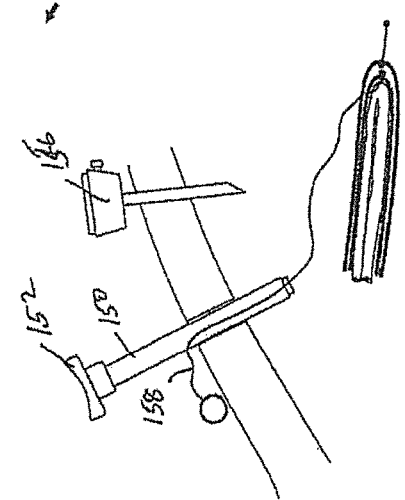

Referring to FIG. 64, the loaded cartridge 150 is inserted through a pre-made incision. When the cartridge 150 is in place a plunger 152 is inserted as illustrated in FIG. 65. The plunger 152 is pushed all the way down and the bag 151 is ejected as shown in FIGS. 66 and 67.

Referring to FIG. 68 an instrument 155 is inserted through a trocar/access port 156 and is used to grasp a distal pull tether 157 which is attached to the front band on the bag. Once the distal tether 157 is held, pulling on the activation tether 158 opens the mouth of the bag 151 and forces the excess material to unroll. The specimen may now be lifted into the open mouth of the bag as shown in FIG. 69. The surgeon can control the mouth of the bag 151 to some degree with an activation tether 158.

Referring to FIG. 70, with the back end of the bag 151 grasped, the bag 151 can be pulled towards the incision, forcing the specimen to travel deeper into the bag 151. The valve/trocar is removed and the rim of the bag is pulled out through the incision as illustrated in FIG. 71. The rim of the bag 151 is opened up, and the morcellator is inserted to seal the bag as shown in FIG. 72. The bag is then inflated and the procedure carried out within.

Figure 74:
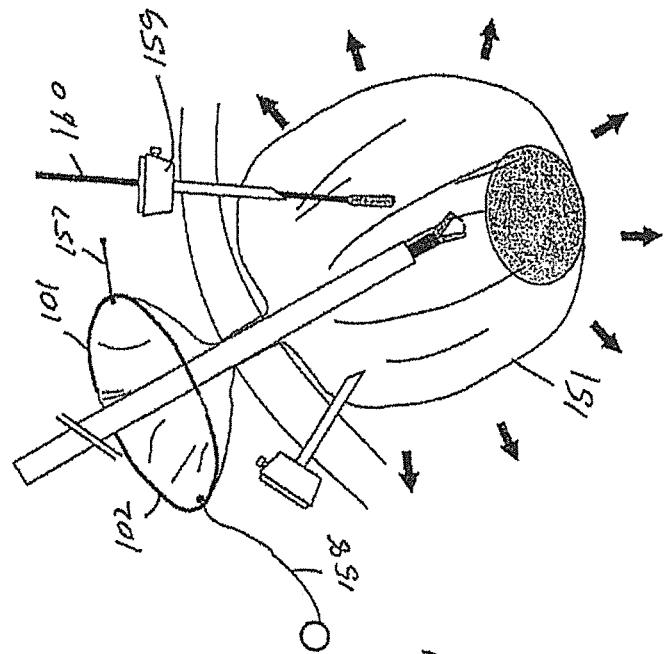
Figure 73:
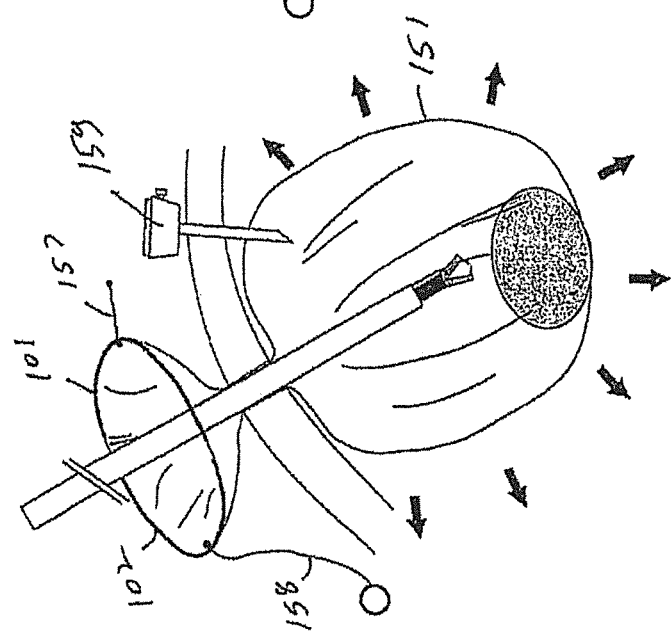

As illustrated in FIGS. 73 and 74, when the bag 151 is inflated trocars 159 can be pierced through to allow access for additional instruments 160.

Figure 75:
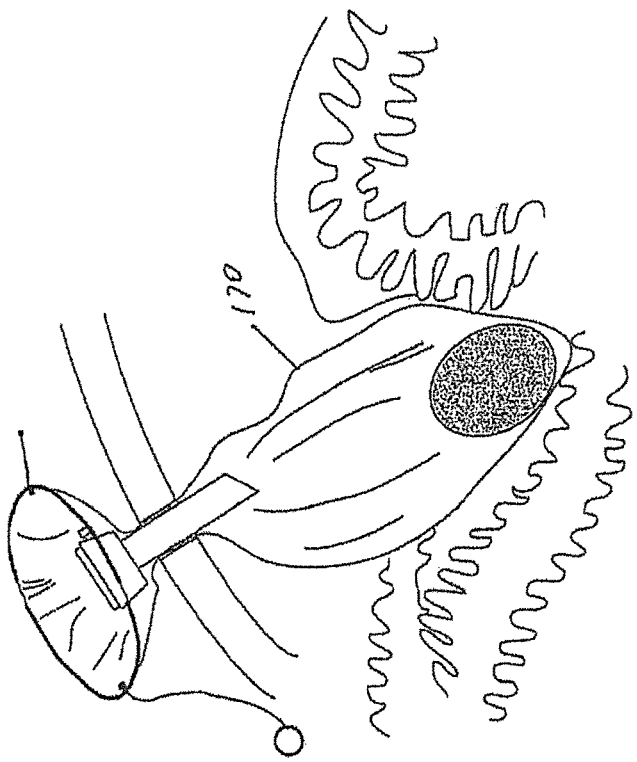
FIG. 75 is a diagram of a device according to an aspect of the disclosure for use as a visceral retainer.

Referring to FIGS. 75 to 87 there is illustrated the use of a bag 170 as described above as a visceral retainer. The bag 170 is first inserted and positioned where required (FIG. 75). As the bag 170 is inflated, surrounding structures and organs (abdominal viscera) are retracted as shown in FIG. 76.

Figure 78:
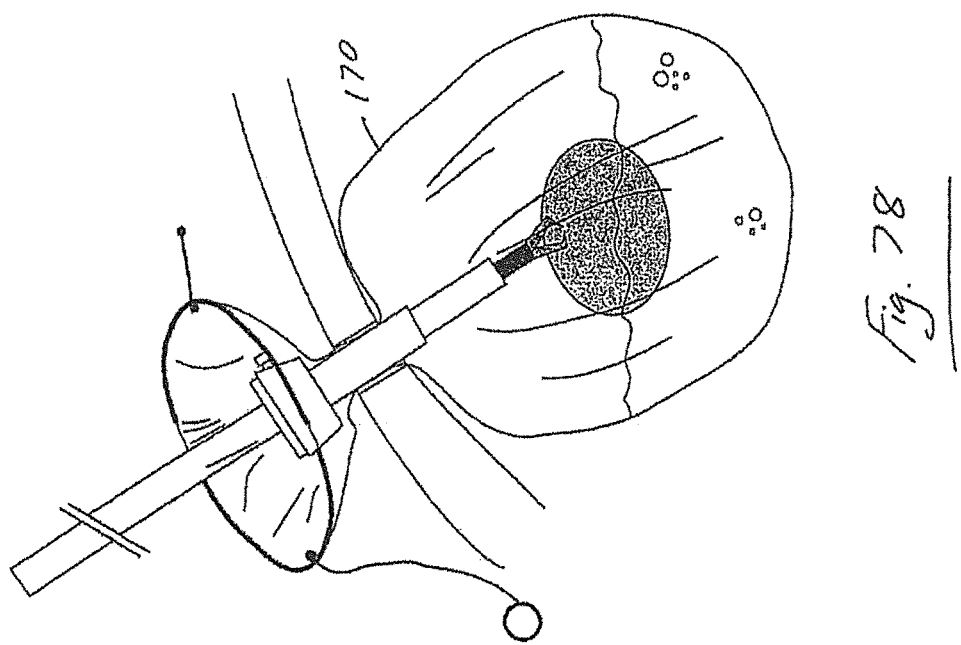
Figure 77:
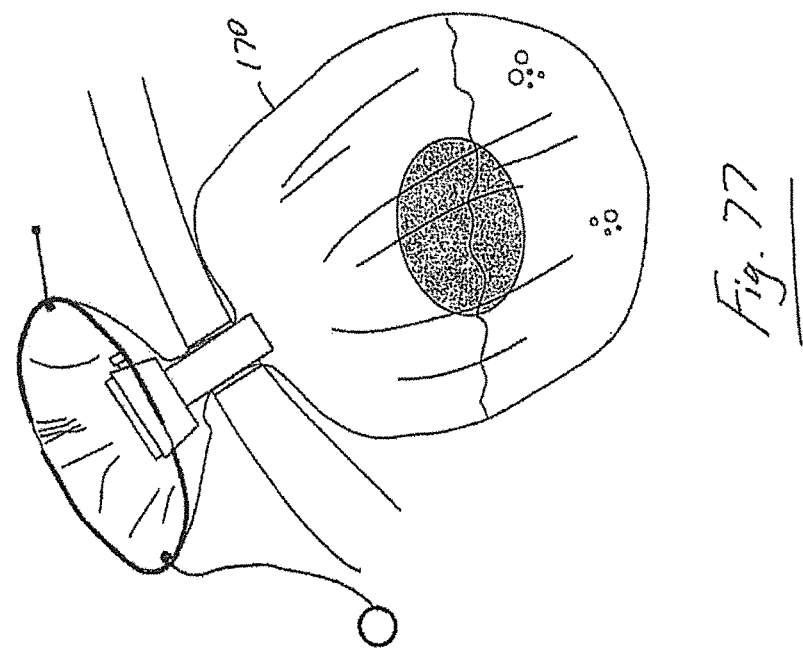

As shown in FIGS. 77 and 78, it may be of benefit to fill, or partially fill the bag 170 with a liquid. These benefits may include: 1) The specimen floats to the top of the bag and therefore the risk of bag damage at the base may be reduced. 2) Liquid may reduce smoke build up in the bag. 3) Blood will be diluted and may therefore allow for enhanced visibility.

Figure 79:
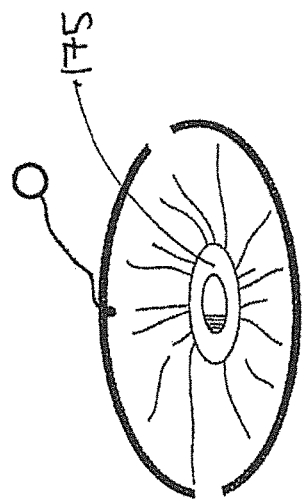
FIG. 79 is a diagram of the device of FIGS. 75 to 78 with an associated grommet.
Figure 80:
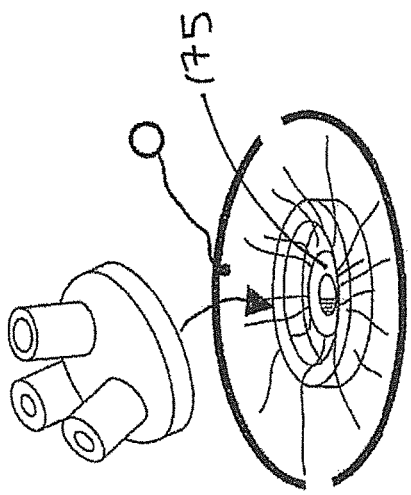
FIGS. 80 and 81 are diagrams illustrating the device of FIGS. 75 to 78 in use.
Figure 81:
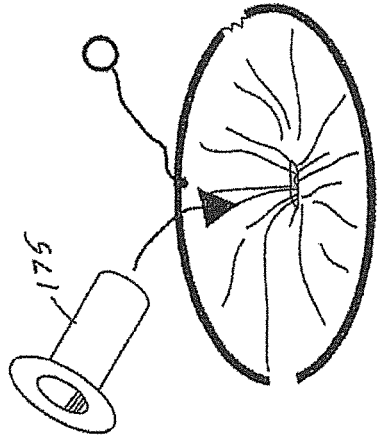

Referring to FIG. 79, when the bag 170 is in place and the neck has been pulled through the incision there is often a lot of excess material in the incision. A grommet 175 may be inserted through the bag/incision to keep excess material away from the incision as illustrated in FIG. 80. This will help prevent damage to the bag 170 and aid visibility and gas flow. With the grommet 175 in place instruments can be inserted with ease as shown in FIG. 81.

Figure 82:
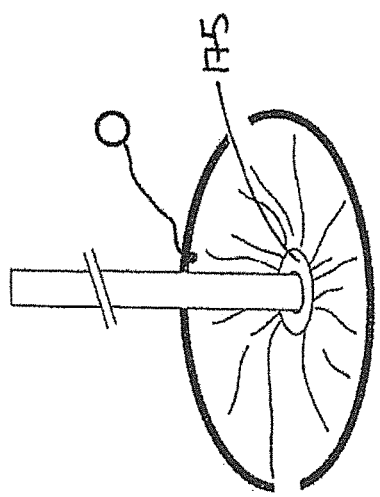

The grommet 175 may be used with multiport or single port access devices (FIG. 82).

In some cases the grommet 175 have an insufflation/desufflation line 176 built in (FIG. 83).

As illustrated in FIG. 84 the grommet may include a series of slits 177 which allow it to conform to various incision dimensions.

The grommet may include a valve system 178 as illustrated in FIG. 85.

An instrument locking mechanism 179 may also be included (FIG. 86).

In some cases, as illustrated in FIG. 87, the grommet may have a series of lumens 180 to aid with ventilation/insufflation.

Referring to FIGS. 88 and 89 there is illustrated a bag device 200 according to an aspect of the disclosure. In this case, the bag 200 is shown in the inflated configuration within a body cavity such as the abdomen. A tissue sample 201 is contained within the bag. An incision is made in the abdomen 202 and the incision is retracted using a retractor 203 as described above. In this case the retractor 203 has an outer proximal ring 204 and a multilumen access port 205 is releasably mounted to the ring 204. The bag 200 extends through the retracted incision and terminates in a retainer ring 206.

FIGS. 90 and 91 illustrate a bag device similar to that shown in FIGS. 88 and 89 but in this case a single instrument lumen access port 211 is mountable to a proximal part of the retractor assembly. The access port 211 may have a cannula section that extends through the retractor or may be an access port 212 with a short proximal leg.

The bag device may itself have an access port to facilitate passage of instruments into and out of the bag and/or to facilitate passage of a tissue sample into the bag.

Referring to FIG. 93 the bag has a single access port 220. However, there may be a plurality of such access ports as illustrated in FIG. 94. Passage of a tissue sample 225 through an access port 220 is illustrated in FIG. 95. The access port 220 may be provided with any suitable valve such as a choke valve, for example, for example a drawstring 226 as illustrated in FIG. 96, a cuff valve 227 as illustrated in FIG. 97, or an elastomeric valve 228 as illustrated in FIG. 98. The valve 228 may be of any suitable plastics, rubber or gel material.

Referring to FIGS. 99 to 110 there is illustrated various steps in methods involving the use of the bag devices according to aspects of the disclosure. In the example illustrated the device is of the type described above. The methods involve the use of a bag device 250, a retractor 251, an external access port system 252 and is used to access tissue 253 such as a specimen or an organ through an opening 254 in the body, in this particular case in the abdomen 255. The bag device has a delivery configuration in which it is housed in a retracted condition in a cartridge 260. A plunger 261 is used to deliver the retracted bag device out of the cartridge 260. The bag device 250 has an opening which is biased into an open configuration by a retainer ring 265. The ring 265 may be of a shape memory material as described above. A proximal tether which in this case is in the form of a ring or loop 267 is provided on one side of the ring 265 and a distal tether 268 extends from the side of the ring 265 generally opposite to the proximal tether 267.

Figure 104:
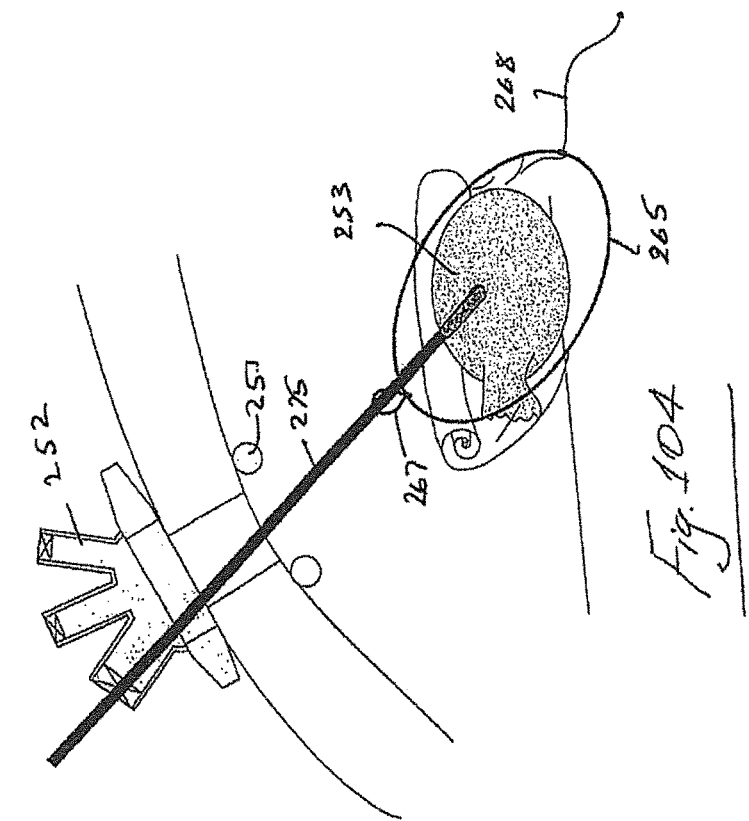
Figure 103:
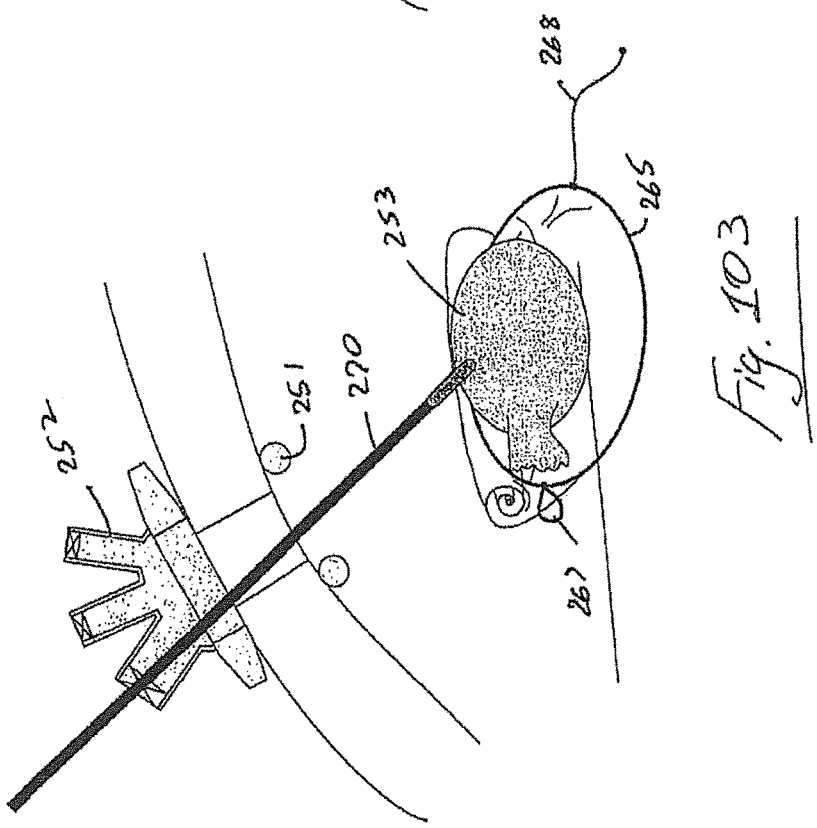
Figure 106:
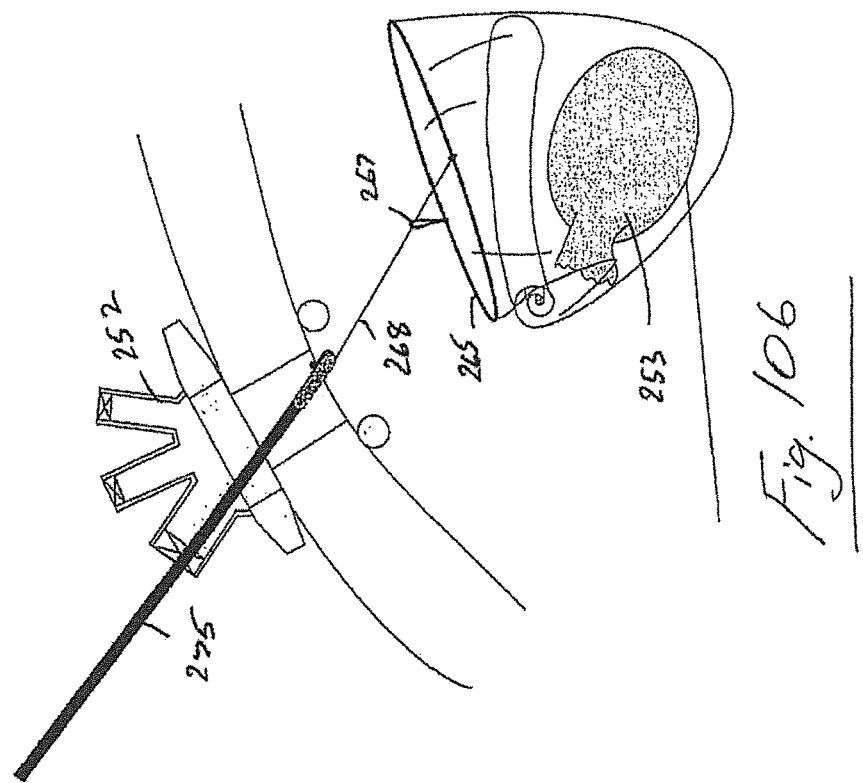
Figure 105:
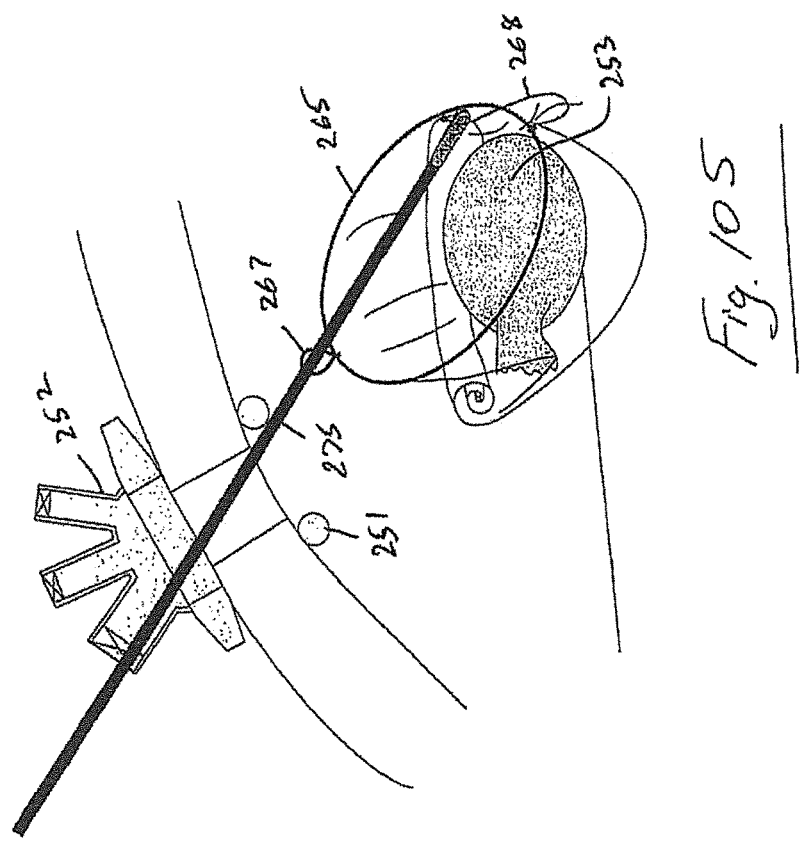

In FIG. 99 the bag device is placed in the delivery configuration in the cartridge or pouch 260. In this case the access port device 252 is in situ on top of the retractor 251 and the cartridge 260 is inserted through one lumen of the access port (FIG. 100). The plunger 261 is used to push the bag device 250 out of the cartridge 260 (FIG. 101). In this particular case the bag device is not tethered to the user, on delivery. On delivery into the body cavity, such as the abdomen, the retractor ring is free to move to its normally expanded configuration in which it opens up the bag opening (FIG. 102). The bag is folded in the delivery configuration. Using various instruments 268 a clinician manipulates a tissue specimen, organ or the like and then delivers it into the bag 250 through the open mouth of the bag (FIGS. 103, 104). FIGS. 105 and 106 illustrate one particular way in which the bag containing the tissue is retrieved. A grasper type instrument 273 is led through the proximal tether loop 267 and is used to grasp the distal tether 268 (FIG. 105). The distal tether 268 is pulled through the proximal tether loop 267 which ensures that the clinician has control over the bag as it is moved up towards the body opening (FIG. 106). As the retaining ring 265 engages with the retractor 251 it retracts allowing it to be pulled up through the body opening (FIG. 107). The access port 252 is removed and the retaining ring 265 is again free to expand (FIG. 108).

The access port 252 is re-attached and the bag is inflated to increase the operative field. The tissue sample can then readily by worked on (FIGS. 109, 110) without the risk of any potentially harmful material being released into the body cavity.

In some cases there may be a lock feature which prevents movement of one tether relative to the other in some directions. One such lock feature is illustrated in FIGS. 111 to 113. The distal tether has a one-way step feature 280 which permits the distal tether to pass through the proximal loop tether but once it has passed through this reverse movement is prevented as illustrated in FIG. 113. This ensures even greater control on the movement of the retaining ring 265 to aid closing of the bag as the ring 265 is being withdrawn.

As discussed above, the devices according to aspects of the disclosure may be used in any suitable body cavities. One such use is in the colon and one device for this use is illustrated in FIGS. 114 to 117. The device may be inserted as described above. Once in place and inflated a clinician can inspect the wall of the colon for any unusual features such as a growth. One such growth 280 is illustrated in FIG. 115. In this case, when a growth 280 is identified some or all of the growth 280 may be accessed by cutting a hole in the wall of the bag which remains in place by virtue of its engagement with the rest of the colon. Using various instruments, at least a portion of the growth 280 can be excised and removed through the bag. As in the other devices described a major advantage is that the tissue to be removed is retained in the bag which prevents potentially harmful material such as cancerous cells from being released in the body cavity.

Figure 118:
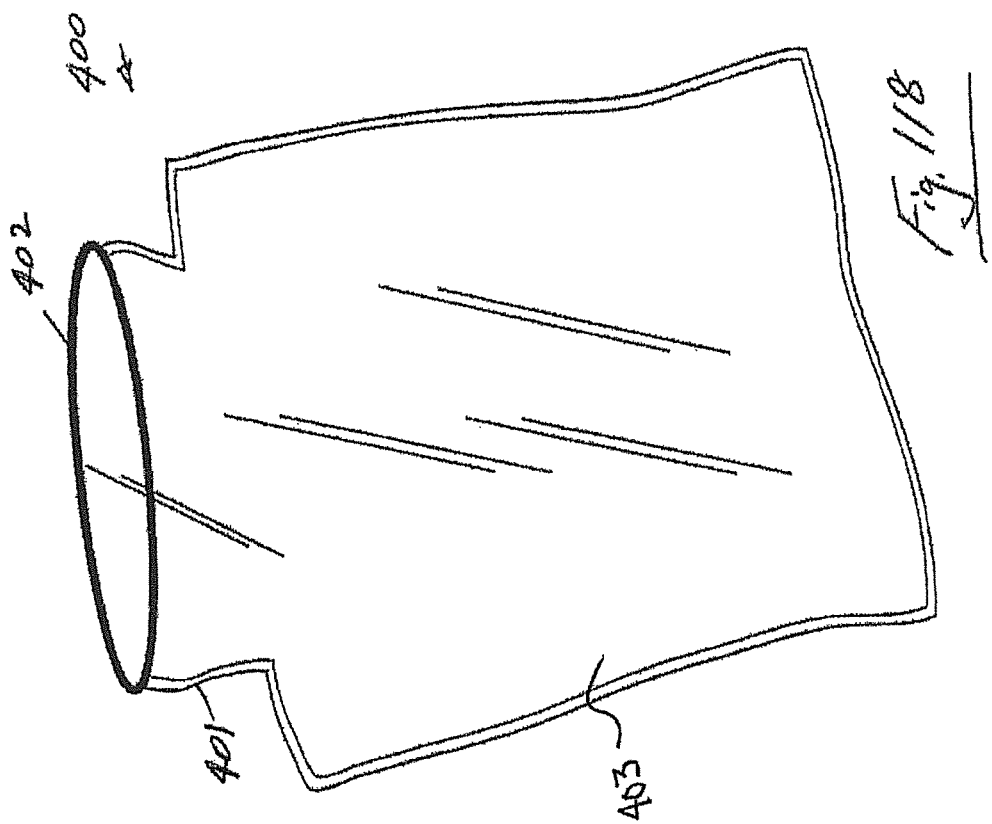
FIG. 118 is an isometric view of another device according to an aspect of the disclosure.
Figure 123:
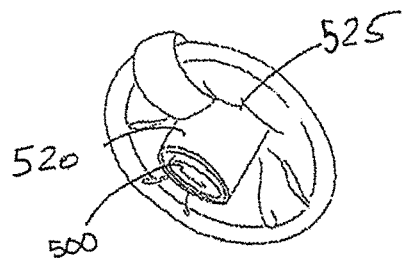
FIGS. 123 to 126 are isometric views illustrating the insertion of the bag through an opening.
Figure 124:
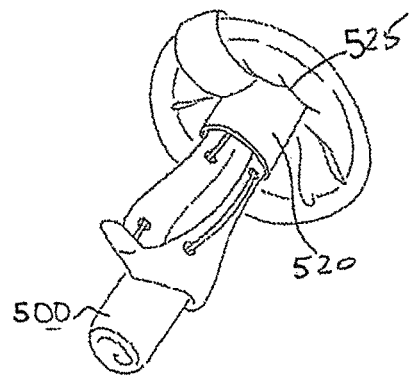
Figure 125:
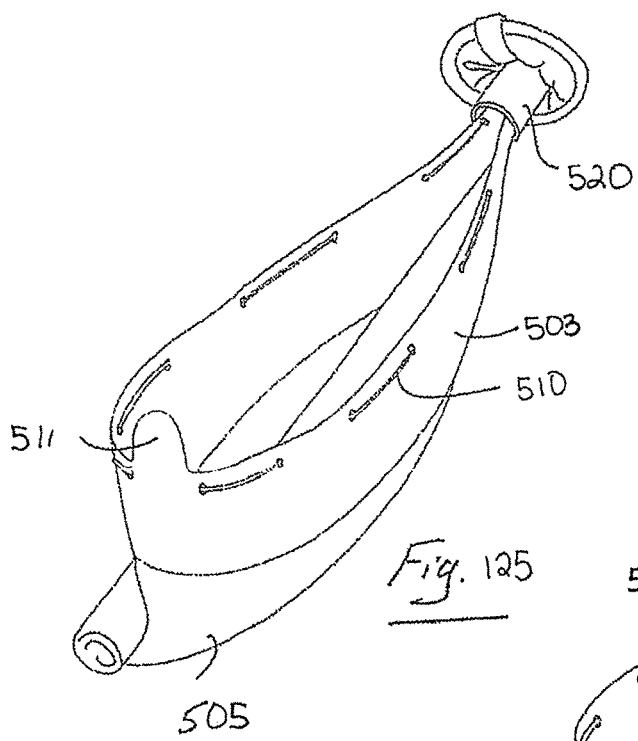
Figure 126:
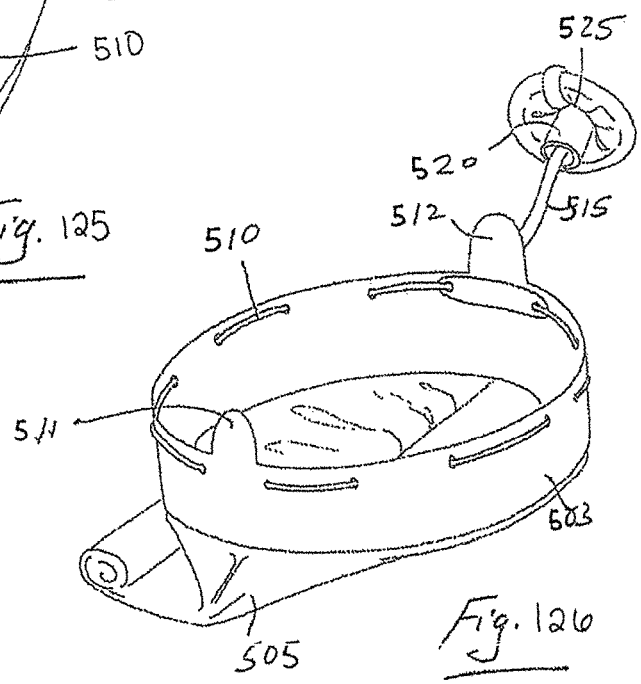

Referring to FIG. 118 there is illustrated another bag device 400 according to an aspect of the disclosure. The bag device has a neck or collar region 401 between a retaining ring 402 and the main body of the bag. Because the retaining ring 402 is of smaller diameter than that of the bag it is more easily inserted through an access port. As shown in FIG. 118, the bag device 400 includes joined planar sheet portions forming the neck region 401 and a body portion 403. Also as shown in FIG. 118, the body portion 403 forms a closed cavity in fluid communication with the neck region 401, and the body portion 403 has a length and width greater than a length and width of the neck region 401. As also shown in FIG. 118, the retaining ring 402 is configured to bias the bag opening toward an open condition.

Figure 119:
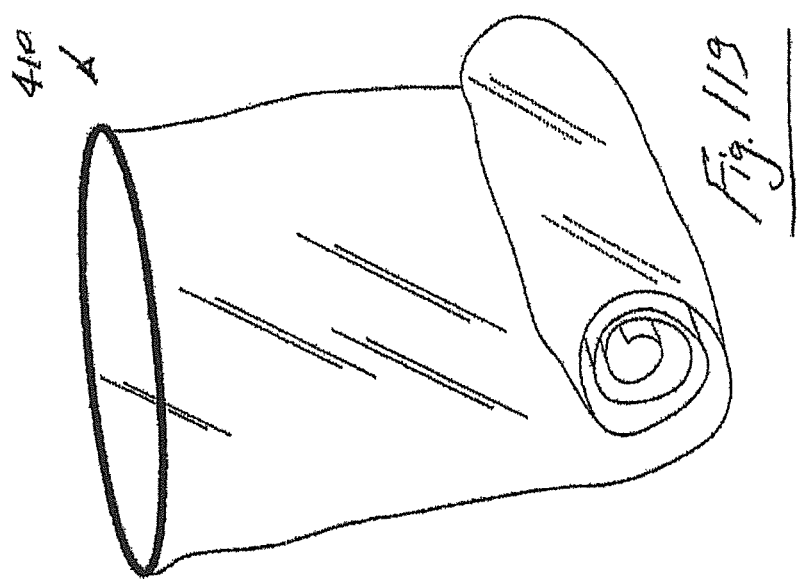
FIG. 119 is an isometric view of a further device according to an aspect of the disclosure.

FIG. 119 illustrates another bag device 410 and shows how the main body of the bag may be folded in the retracted delivery configuration.

Referring to FIGS. 121 and 122, there is illustrated a bag 500 for use in laparoscopic surgery having an opening 502 to receive tissue and a cuff or collar 503 extending around the opening 502. The bag 500 may be inflatable.

The bag 500 includes a main body 505 which extends from the cuff 503. The main body 505 is more flexible than the cuff 503 to assist in retaining the bag 500 open in the deployed configuration.

The cuff 503 may be of a different material than that of the bag 500 or may include the same or a similar material which is thicker than that of the main body 505 of the bag 500. In one case the cuff 503 is of a plastics material and the main body 505 of the bag 500 is of a plastics material which is more flexible than that of the cuff 503. However, the cuff 503 is sufficiently flexible to allow closing of the opening 502. A joint 507 between the cuff 503 and the main body 505 of the bag may be reinforced in any suitable manner such as by using a double layer of the cuff material as illustrated in FIG. 22.

The cuff 503 has an axial extent which is important in maintaining the opening 502 in a fully open configuration. This has the major advantage that tissue can be more readily manoeuvred into the opening 502 by the surgeon performing a laparoscopic procedure through a small opening. When the bag 500 is in the open configuration the surgeon is able to concentrate on manipulation of the tissue/material to be inserted into the bag 500 without the added task of complex manipulation of the bag 500 at the same time as the material is being manipulated. Thus, the bag 500 greatly facilitates the laparoscopic surgical procedure.

The cuff 503 extends axially for a length which is sufficient to ensure that the opening 502 remains open to provide an axially extending delivery mouth into the main body 505 of the bag 500. For example the cuff 503 may extend for an axial length of from 2 to 20 cm, 2 to 10 cm, or about 5 cm. Alternative size dimensions for the cuff or collar 503, as well as sizes for other features of the bag, will be discussed in more detail below.

According to one aspect of the disclosure, the cuff 503 is biased into the open configuration. In this case the bag 500 includes a biasing element to bias the cuff 503 into the open configuration.

The biasing element may include a loop 510 extending around the cuff 503. The loop may be of a shape memory material such as Nitinol. The loop 510 extends round the cuff 503 in any suitable manner. It may, for example, be threaded through the cuff as illustrated or may extend through a table or track provided in or on the cuff 503.

The cuff 503 has tabs 511, 512 which may be used for more readily grasping the bag during a laparoscopic procedure.

A tether 515 extends from the cuff 503 and may be used to activate the opening and/or closing of the bag 500.

Referring to FIG. 120, the bag 500 is folded and housed in an introducer sheath or pouch 520 ready for deployment. Any suitable insertion tool may be used to deliver the bag 500 through an opening. The bag 500 may be deployed in any suitable manner such as by using a plunger 516 which a user activates to deliver the bag from the introducer 520.

Figure 127:
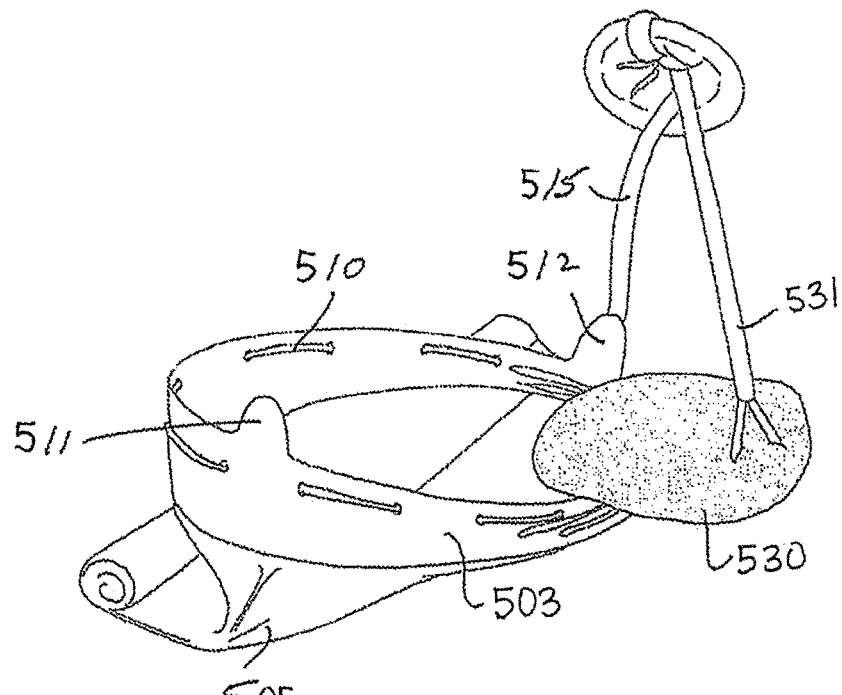
FIGS. 127 and 128 are isometric views illustrating the delivery of tissue into the bag.
Figure 128:
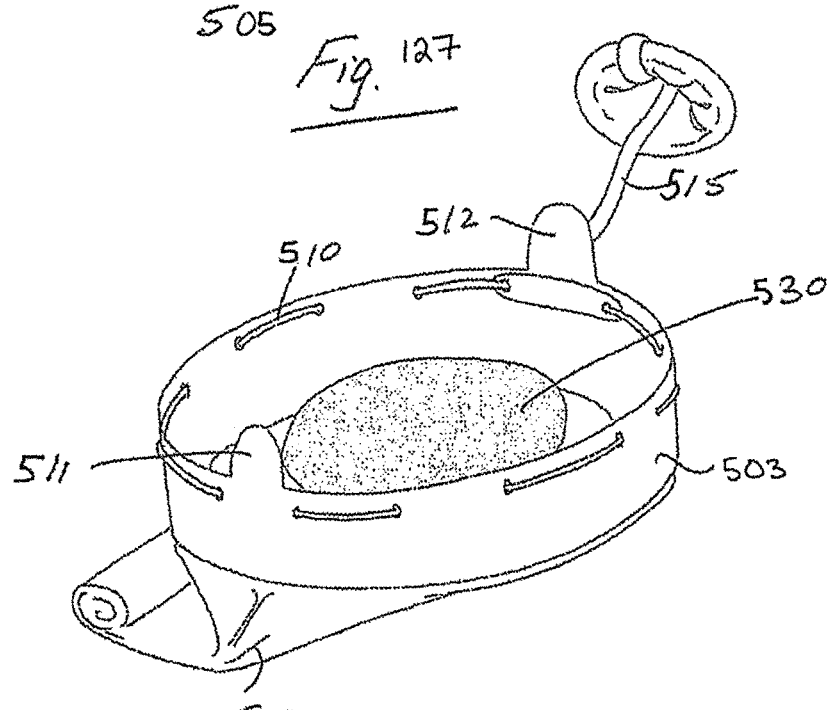
Figures 131, 132, 133:
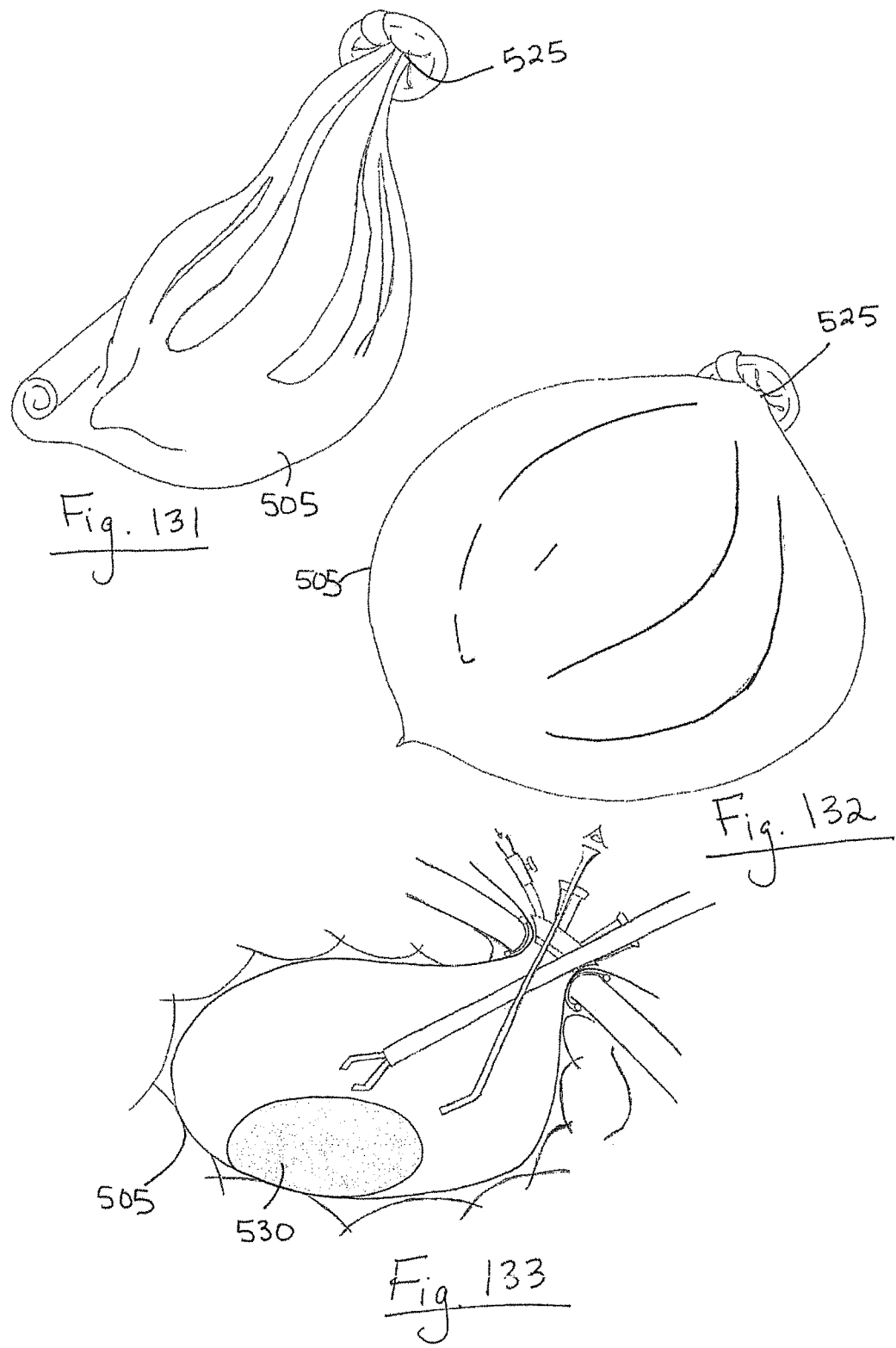
FIGS. 131 to 133 are isometric views illustrating the presentation of the bag to the tissue opening, subsequent inflation of the bag, and procedures such as morcellation being carried out on tissue in the inflated bag.
Figure 134:
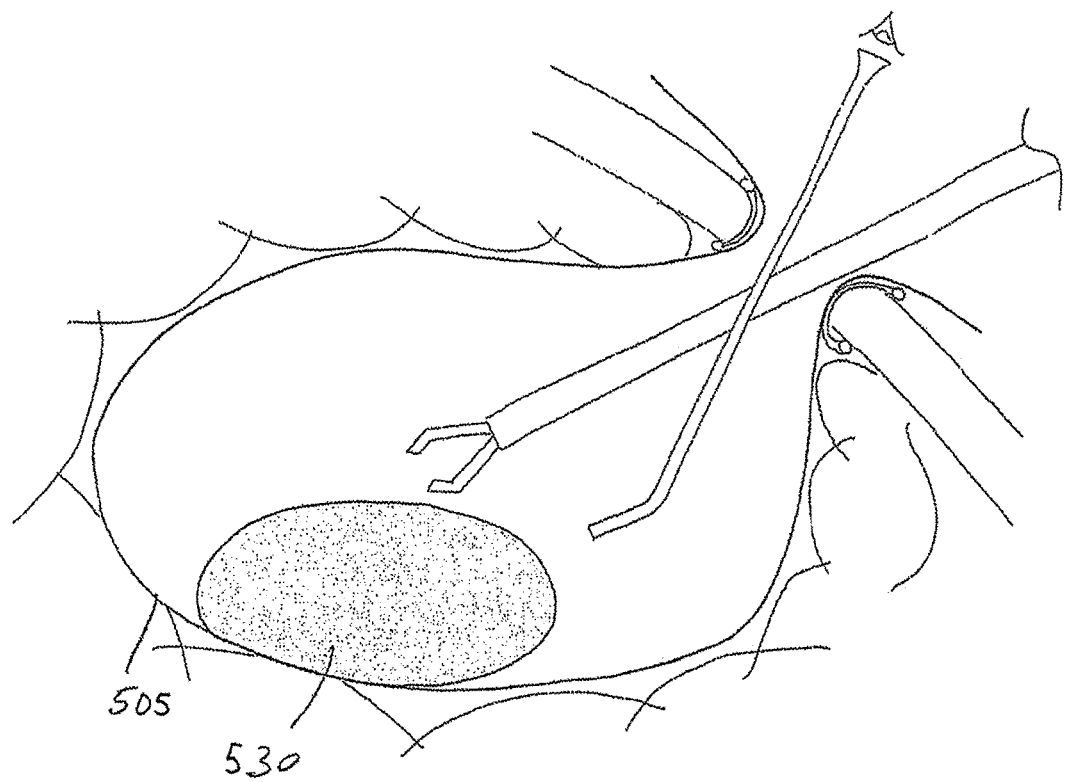
FIGS. 134 to 138 are diagrams illustrating various alternative arrangements of trocar(s) and instrument(s) used in performing procedures on tissue in the inflated bag.
Figure 135:
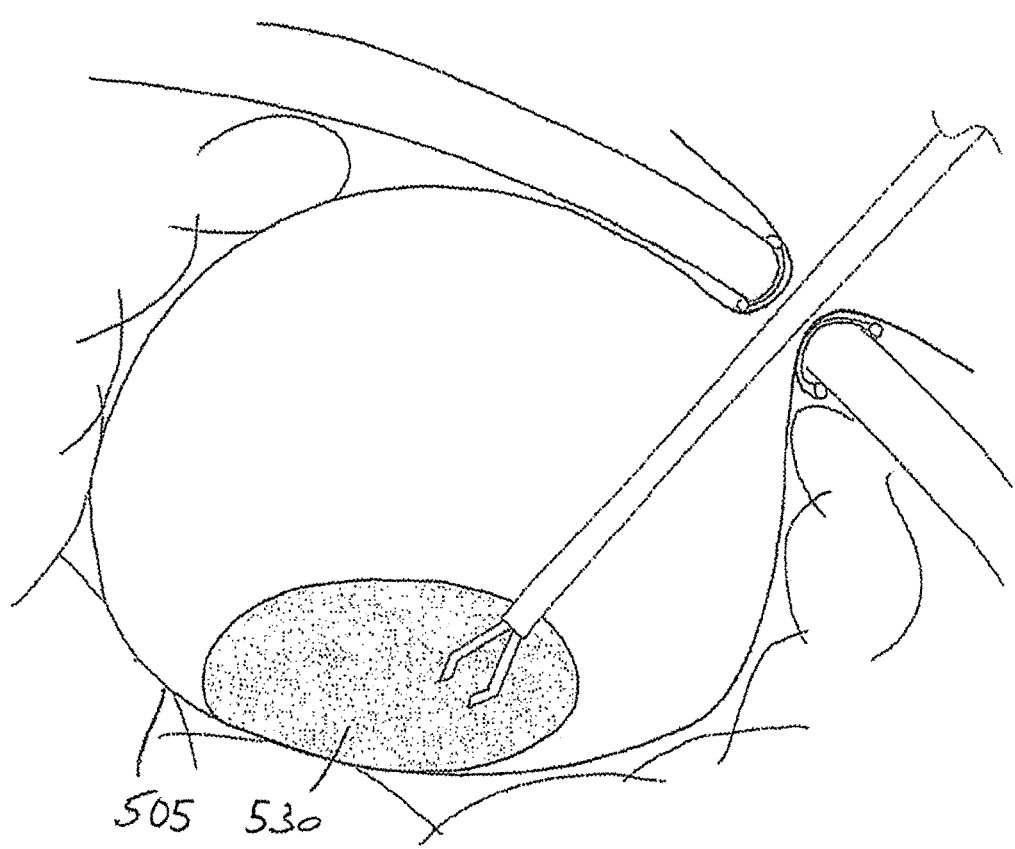
Figure 136:
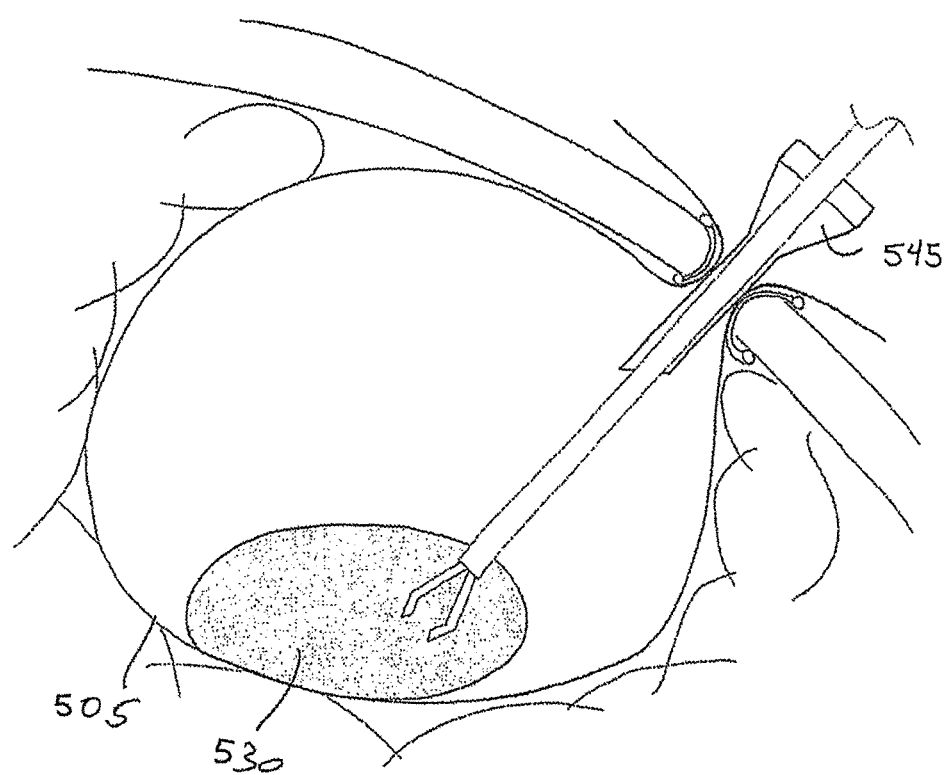

The deployment of the bag 500 through an opening such as a retracted incision 525 is illustrated in FIGS. 123 to 126. As soon as the bag starts to exit the pouch the cuff 503 opens up and when fully deployed defines an axially extending open mouth. FIGS. 127 and 128 illustrate tissue 530 being manipulated into the open mouth of the bag 500 using an instrument such as a grasper 531. When the tissue 530 is in the bag 500 the tether 515 is used to pull the cuff 503 which initially closes the opening and is then pulled out through the tissue opening 525. When the proximal end of the bag 500 has passed through the tissue opening the bag 500 may be inflated and a procedure carried out on the tissue isolated within the bag 500. This may be carried out in several different ways, depending on the procedure being performed. For example, the bag entrance may be closed with an access port 540 as illustrated in FIG. 133 which facilitates access of any suitable instruments to perform procedures such as morcellation of the tissue within the bag 500. Alternatively access is gained to the captured tissue without a requirement for an access port—see FIGS. 134, 135 and 138. Alternatively a trocar 545 may be provided through which an instrument is passed (FIG. 136). There may be additional trocars 550 used (see FIG. 137, for example).

The collar/cuff 503 may be collapsible to allow tissue to be rolled into the bag opening 502 rather than being lifted into the bag opening 502.

The bag 500 may be mounted to a retractor. One such retractor includes a distal anchoring ring, a retractor member such as a sleeve, and a proximal ring assembly. One such retractor is described in US 2005-0090717 A, the entire contents of which are incorporated herein by reference. The distal anchoring ring is located within a wound interior, in use. In this case the distal anchoring ring is provided in the form of an O-ring. The proximal ring assembly is located externally of a wound opening, in use. The retractor member may be employed to retract laterally the sides of a wound opening. In one case the retractor member is provided in the form of a sleeve.

The proximal end of the retractor is closable by a cap which may include an instrument access device 540 which may have a number of instrument ports to effect a seal around an instrument extended through the device. The instrument access device may be releaseably mountable to a proximal ring assembly of a retractor. At least some of the instrument ports may include a stalk which is laterally flexible and longitudinally rigid. One such instrument access port is described in U.S. Pat. No. 8,187,178 or US20110071359A, the entire contents of which are incorporated herein by reference.

FIG. 127 shows an organ or tissue such as an uterus which has been severed/amputated from its retaining structures.

FIGS. 123 to 126 illustrate the bag device being inserted into the abdominal cavity at the beginning of a procedure or as and when required. The bag is inserted in a small flattened state for ease of insertion through a small opening such as an incision. The bag may also be introduced through a valve without the need to remove an access cap.

When the bag is inserted it is opened up. An organ 530 is then readily manipulated for insertion into the bag as illustrated in FIG. 128. The relative rigidity of the cuff 503 keeps the bag open to facilitate insertion of an organ.

Figure 129:
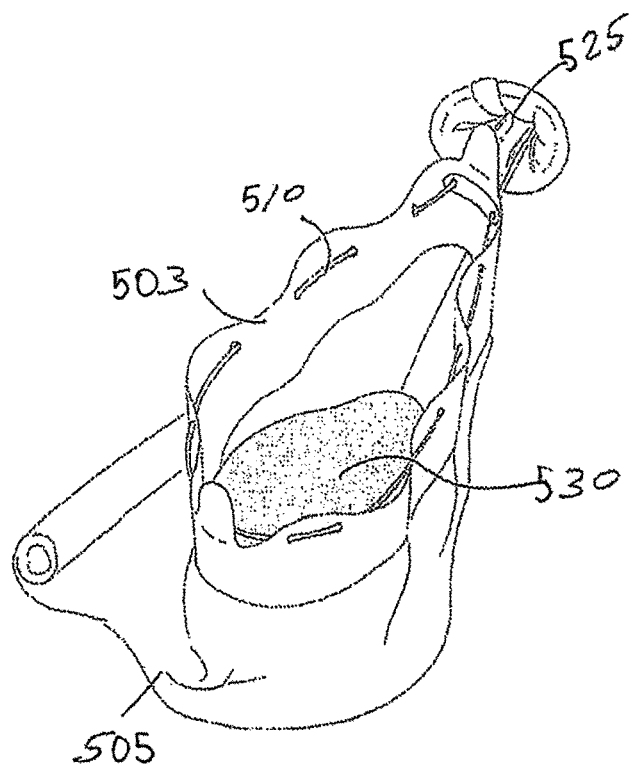
FIGS. 129 and 130 are isometric views illustrating the closing of the bag.
Figure 130:
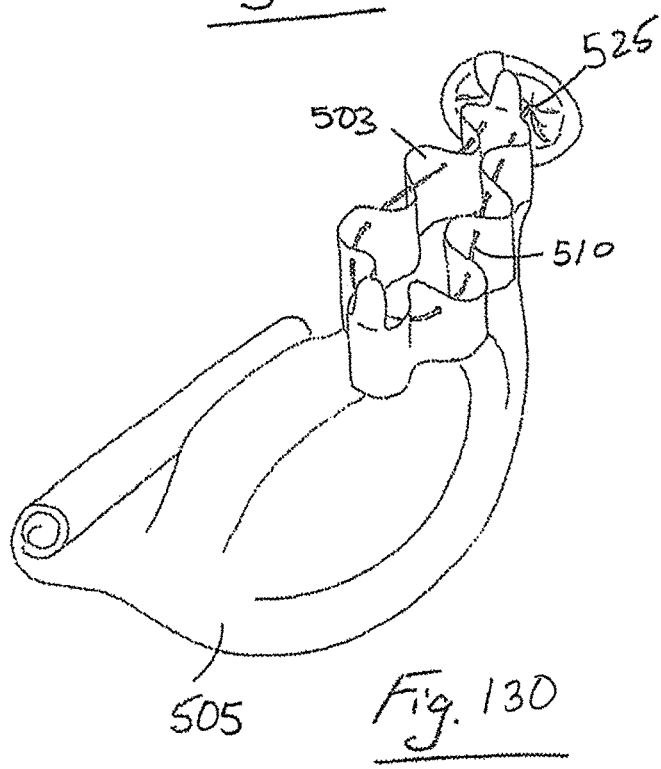

FIG. 129 shows the organ located in the bag and the cuff 503 being grasped to facilitate manipulation of the bag towards the opening. The cuff 503 is pulled out through the opening. The bag may be mounted to a proximal ring assembly of a retractor and a cap may be mounted to the proximal assembly. FIG. 131 illustrates the device in place with an organ enclosed within the bag.

The bag is then inflated (FIG. 132) through an insufflation port. The inflation of the bag has the additional benefit of applying a retracting force to the materials outside the bag thereby creating additional space.

FIG. 133 shows an organ being worked on in the inflated bag. The organ may be morcellated. The material is all retained safely within the bag and is not released into the cavity which could cause major difficulties. The bag is retained externally, for example by clamping/connecting to a retractor.

When the organ has been morcellated the bag is readily removed through the original opening. All waste, blood, tissue and the like are safely removed and sealed within the bag.

The bag device may be inserted through a standard naked incision. Once the specimen has been inserted into the bag an opening such as a cuff 503 is pulled back out through the incision and a trocar may be inserted to create a gas seal. The bag device may also be inserted directly through a trocar as illustrated in FIG. 136.

In some cases there may be one or more access trocars used in addition to the primary port. Thus, an aspect of the disclosure includes procedures which involve two or more incision laparoscopy.

Figure 137:
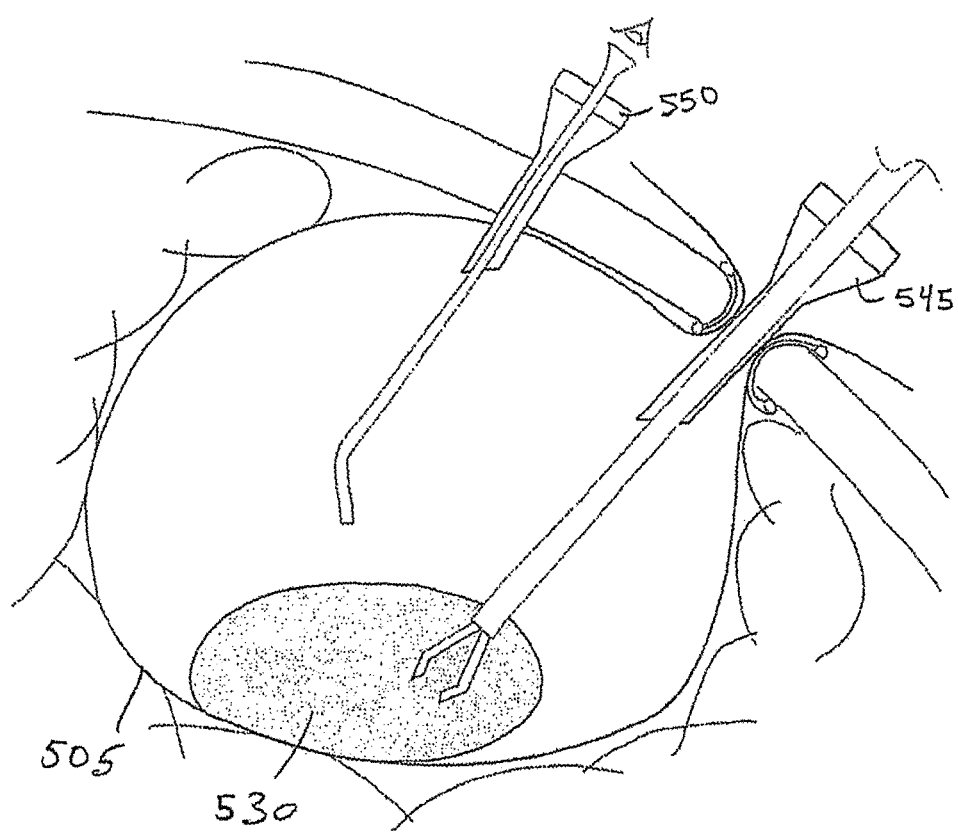
Figure 138:
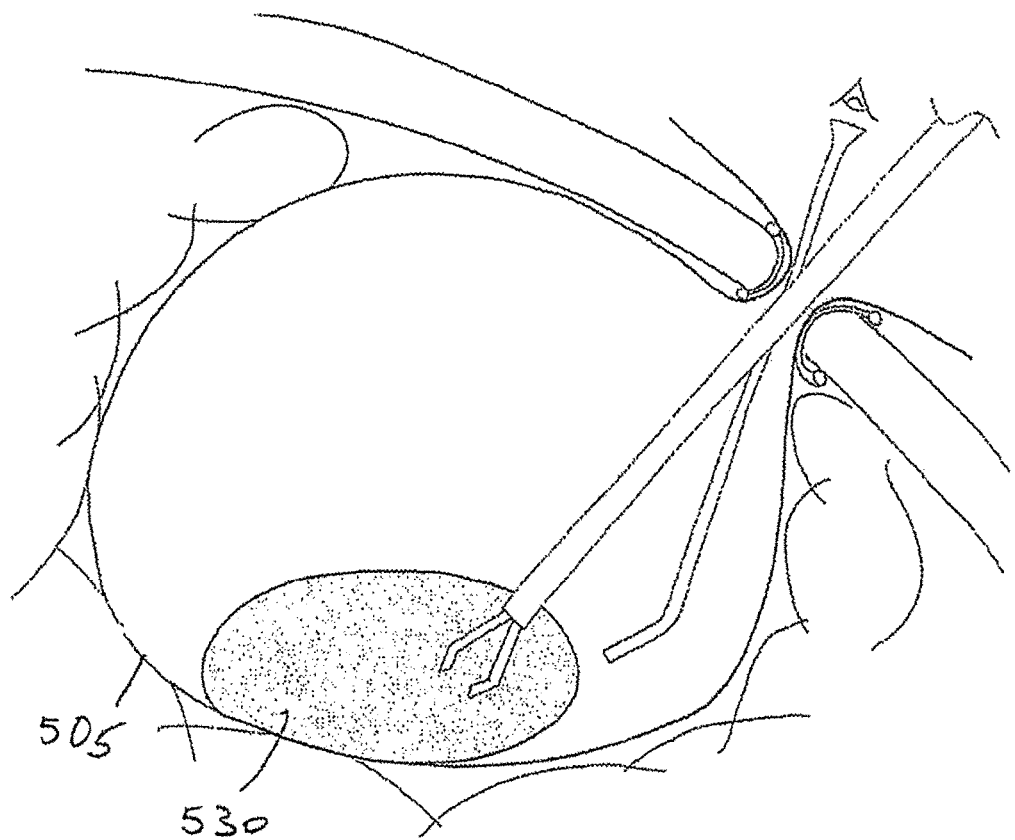

For example, FIG. 137 shows one arrangement in which an additional trocar is inserted. In some cases, the additional trocar may be extended through the bag whilst maintaining a seal.

Aspects of the disclosure provide a method of inserting a large bag into the abdominal cavity to allow the insertion of a specimen into the bag. The bag is then sealed and inflated and procedure carried out within the bag.

As discussed above, the devices according to aspects of the disclosure may be used in any suitable body cavities. One such use is in the colon. The device may be inserted as described above. Once in place and inflated a clinician can inspect the wall of the colon for any unusual features such as a growth. In this case, when a growth is identified some or all of the growth may be accessed by cutting a hole in the wall of the bag which remains in place by virtue of its engagement with the rest of the colon. Using various instruments, at least a portion of the growth can be excised and removed through the bag. As in the other devices described a major advantage is that the tissue to be removed is retained in the bag which prevents potentially harmful material such as cancerous cells from being released in the body cavity.

Referring to FIGS. 139 to 155 various aspects of biasing loop elements which may be used in the bag device, according to an aspect of the disclosure, to assist in maintaining the bag open, are illustrated. In these cases the loop includes a number of loop parts which are movable relative to one another for loading deployment, and/or retrieval.

Referring to FIGS. 139 to 143 in this case there are two joined loop parts 551*a*, 551*b* which are movable circumferentially through hoops 552. In some cases a single piece loop is sufficiently flexible to allow manipulation.

Referring to FIGS. 144 and 149 in this case a loop 560 is configured in the manner of a noose with a leg 561 extending from the loop which may be pulled to reduce the diameter of the loop. There is a closed loop 562 on one end and a kink 563 on the other end which links into the loop 562 to facilitate reducing the diameter of the loop 560.

Referring to FIGS. 150 to 153 in this case there may be closed loops 570, 571 at each end of the retaining loop 572. These may be used as tether attachment points.

Figures 154, 155, 156:
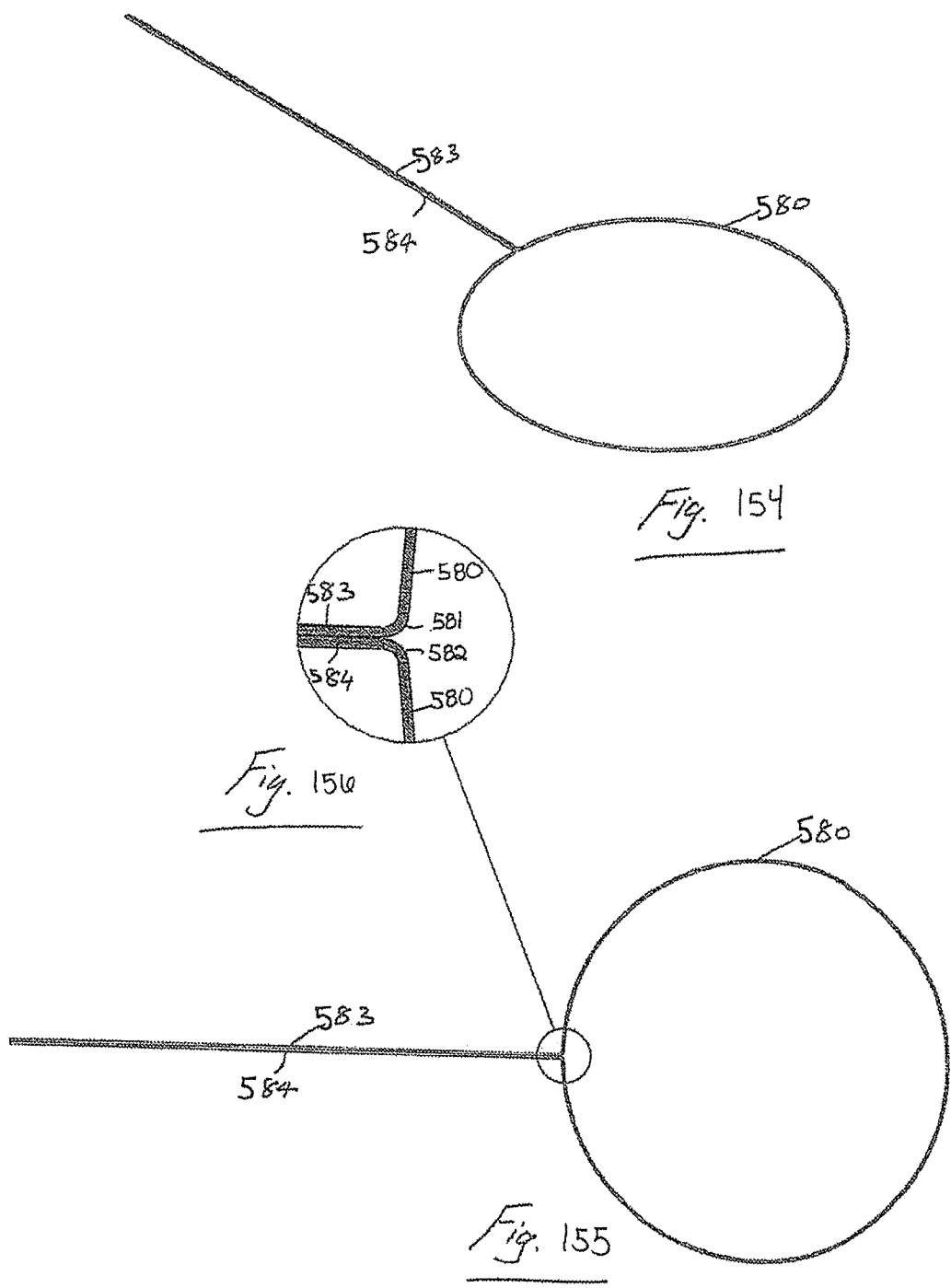
FIGS. 154 to 156 are various views of another biasing loop.

Referring to FIGS. 154 to 156 in this case the ends of a retaining loop 580 have bends 581, 582 and extend to define arms 583, 584 which facilitate manipulation of the loop for retrieval.

The device, according to an aspect of the disclosure, may include features to isolate the contents of the bag from the wound opening and hence protect from escape of material as could occur with seeding of cancer cells and the like.

Referring to FIGS. 157 to 160 in this case the bag includes a small opening 600 which remains closed under insufflation pressure. The opening 600 is opened on insertion of an implement such as a trocar 601 through the opening 600. The bag has excess material in the region of the opening 600 which defines a sleeve or chimney 603 which seals along part of the length of the trocar shaft when the shaft is in place in the opening 600. The opening 600 is located at the top of the bag, in use i.e. in the region that touches the abdominal wall. A trocar 601 may be inserted in a region of the abdominal wall remote from key organs and manipulated under full vision to locate the opening. The opening stays closed whilst there is internal insufflation pressure and the sleeve or chimney 603 collapses around the trocar to create a seal.

Figure 161:
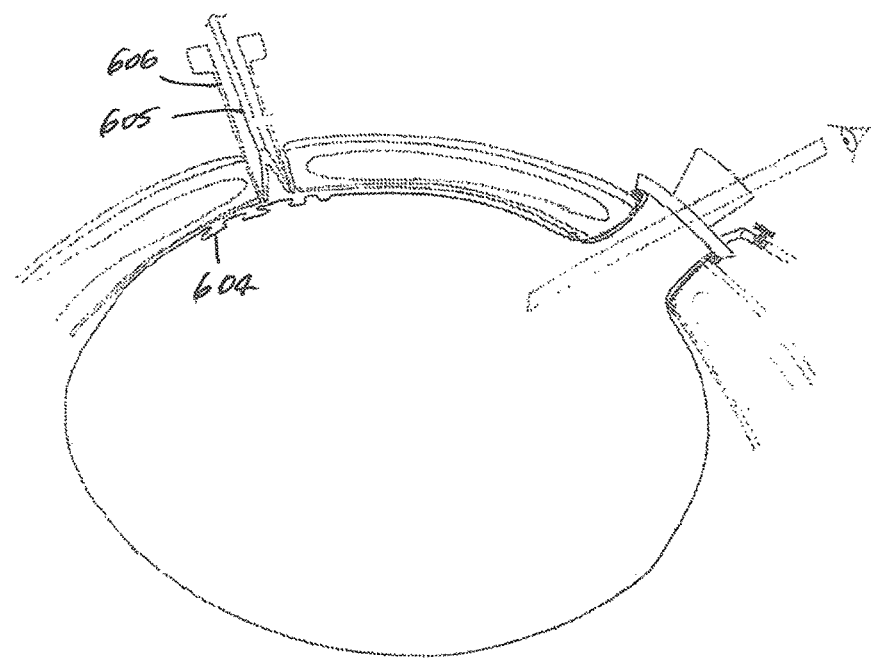
FIGS. 161 to 164 illustrate another bag device according to an aspect of the disclosure in use.
Figure 162:
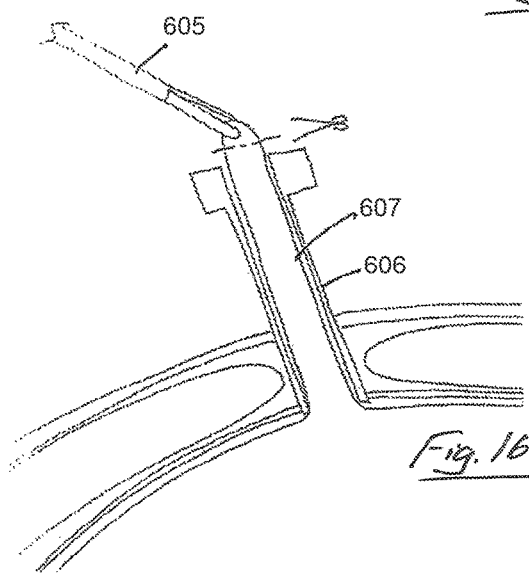
Figure 163:
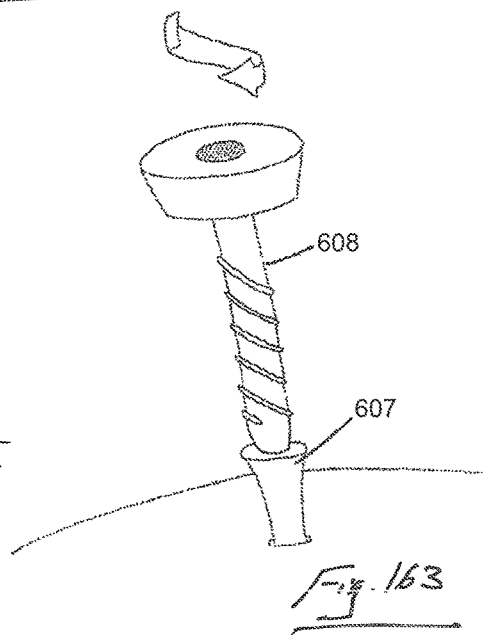

Referring to FIGS. 161 to 163, in this case any excess bag material 604 may be grasped using a grasper 605 inserted through a trocar 606. The end of the excess material may then be cut (FIG. 162) creating a chimney 607 extending from the bag. The chimney 607 is then sealed—for example using a threaded trocar 608 which is twisted inside the chimney 607 to create a seal. The chimney 607 prevents contact between the wound and debris created during morcellation. In this case the surgeon is provided with an additional port into the bag for use during the procedure. One such procedure may involve insertion of a laparoscope or a grasper, for example through the secondary port.

Figure 164:
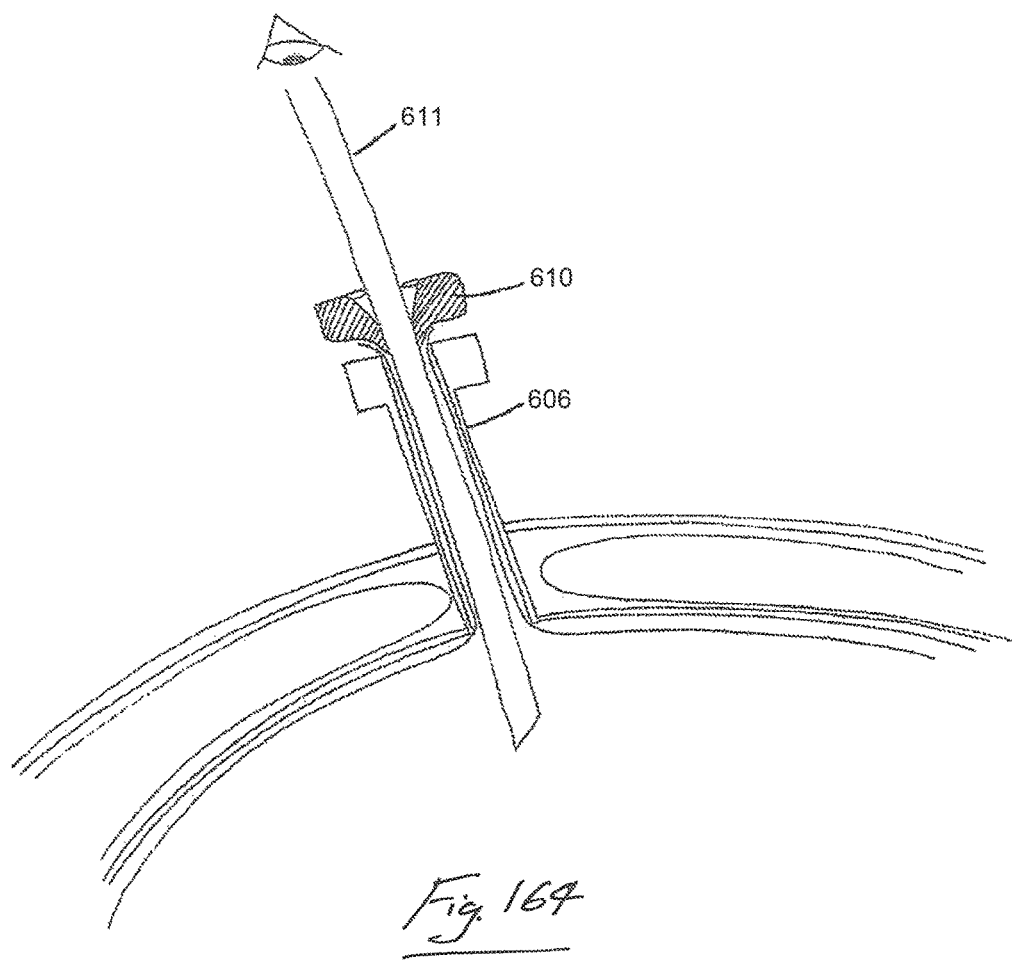

Referring to FIG. 164, in accordance with another aspect, a bung 610 may be placed inside the trocar 606, sealing the bag to the trocar. An implement such as a laparoscope 611 may be inserted through the bung 610.

Figure 165:
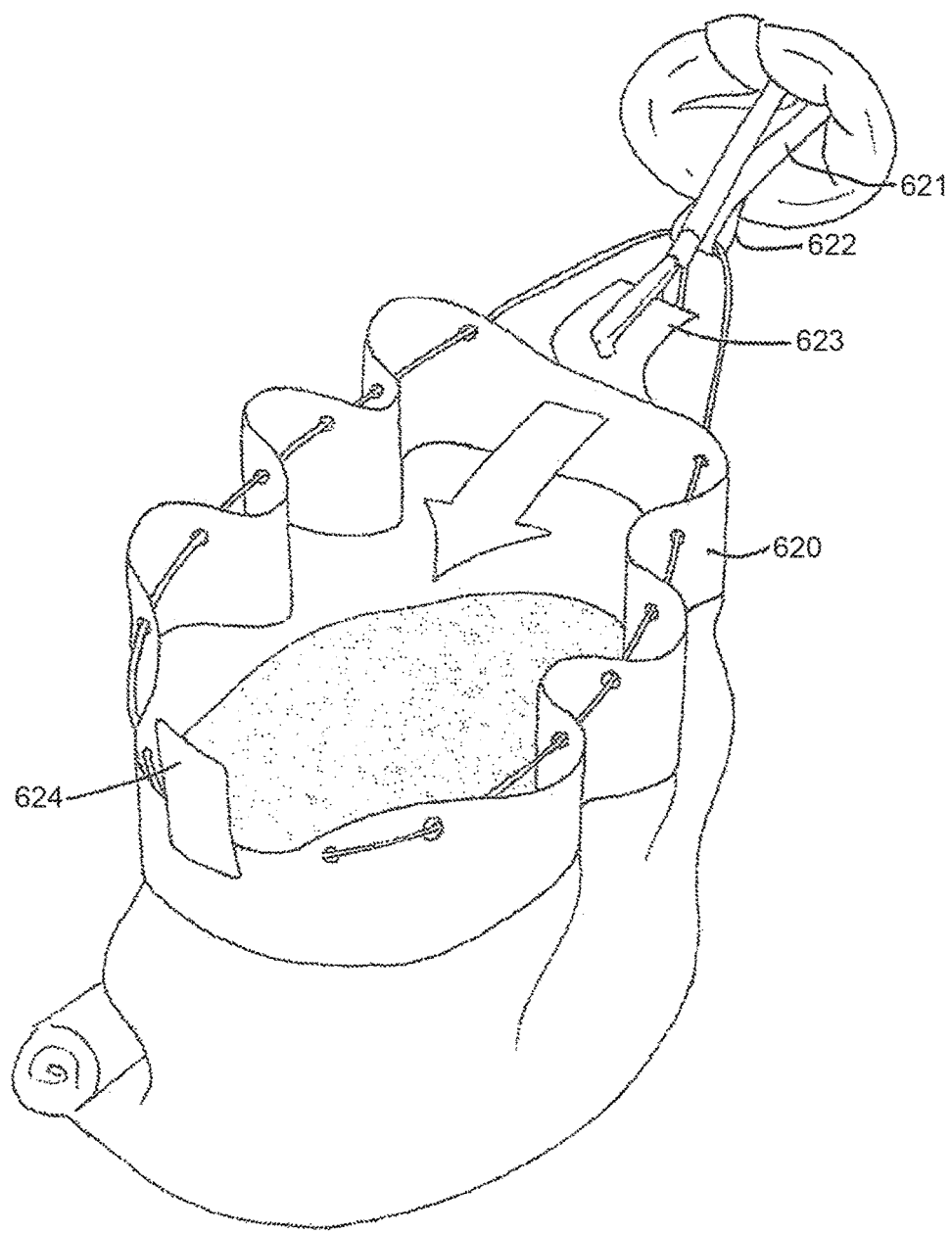
FIG. 165 is an isometric view illustrating closing of a bag device.

Referring now to FIG. 165, in this case the bag has a cuff 620 and a tether 621 loop is threaded through the cuff. The tether 621 has a strap 622 which may be used to pull on the tether from a location external of the abdomen. The cuff 620 also has grasping tabs 623, 624. In this case a grasper 625 may be used to grip the tab 623 as illustrated and then push the cuff towards the opposite side of the bag, towards the tab 624, thus closing the bag. The strap 622 enables the bag to be held firmly whilst being closed within the pneumoperitoneum.

Figure 185:
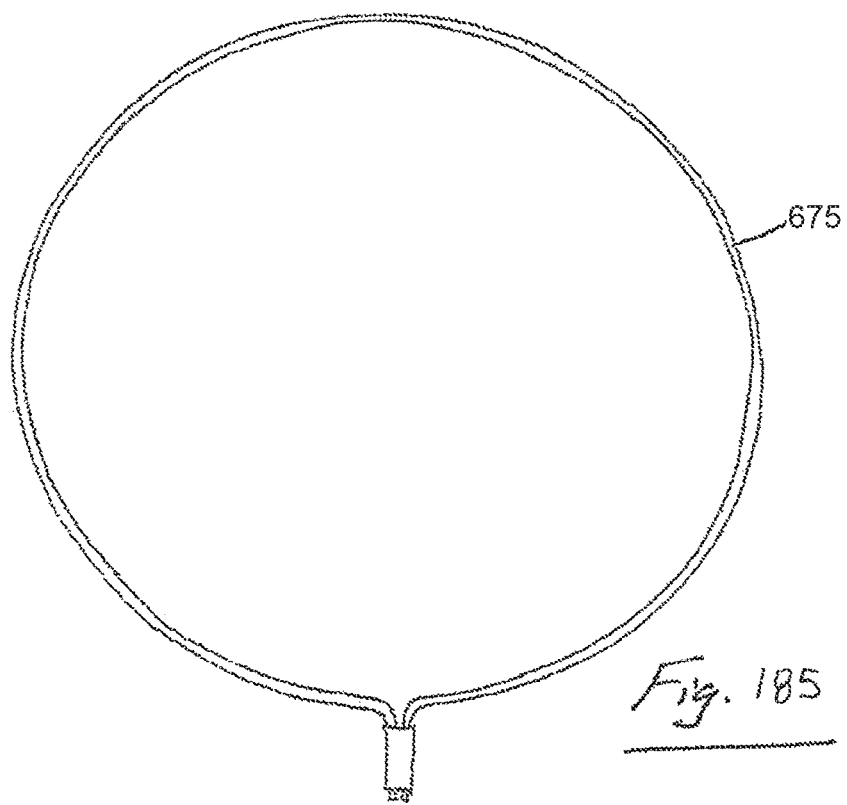
FIGS. 185 and 186 illustrate a retaining ring of the bag.
Figure 186:
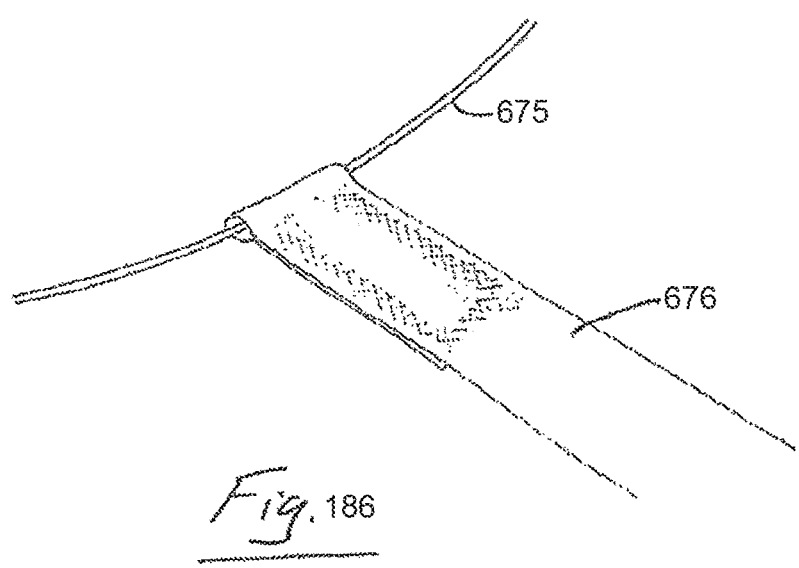
Figure 187A:
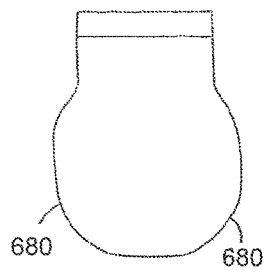
FIGS. 187A to 187F are views illustrating the loading of a bag device into an introducer.
Figure 187B:
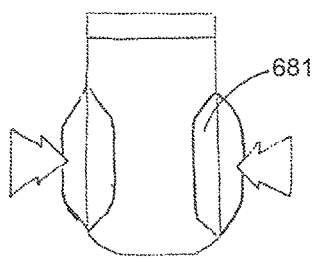
Figure 187C:
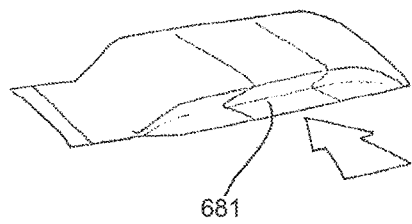
Figure 187D:
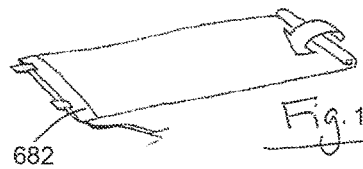
Figure 187E:
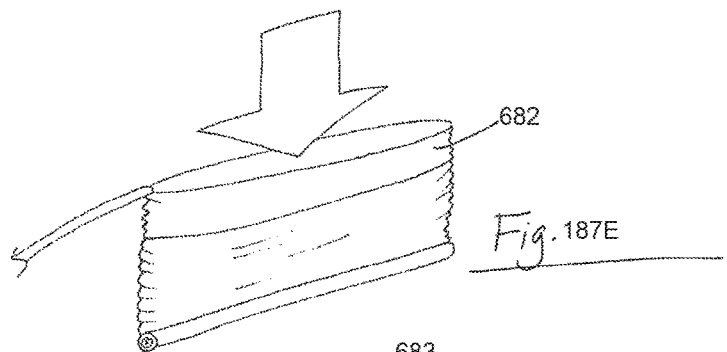
Figure 187F:
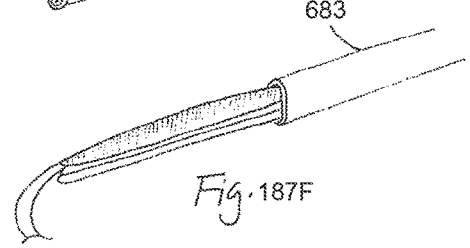

In some cases the bag is retained in the normally open configuration by a retainer ring of a shape memory material such as Nitinol. It has been found that a single ring formed by attaching, for example by welding, together the ends of a ring-forming member is most efficient in achieving rapid deployment. Referring to FIGS. 185 and 186 the retaining ring of the bag may be manufactured in any suitable manner. In one case, for example, a shape memory material 675 is formed into a loop, shape set and welded. A tether strap 676 may also be attached in any suitable manner.

In some cases the cuff of the bag may have features to facilitate mounting of the pre-formed ring to the bag.

Figure 166:
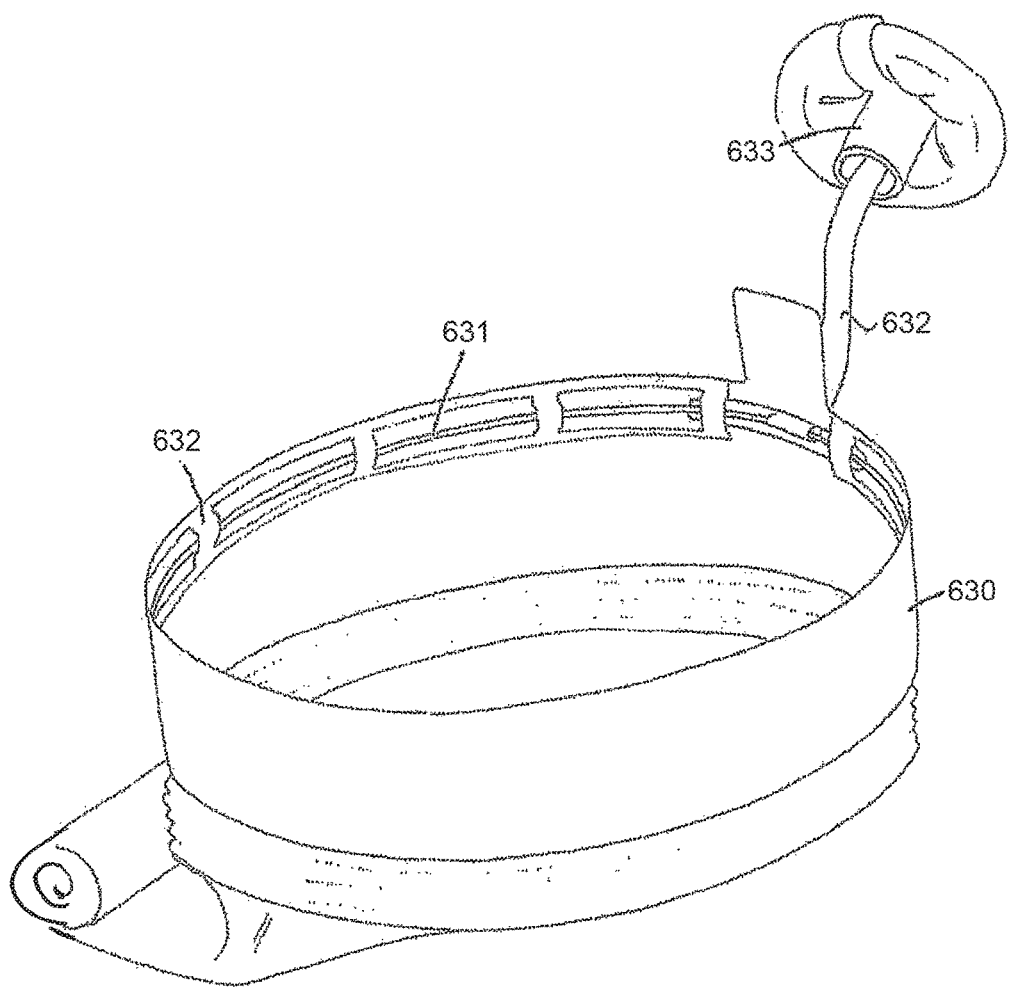

According to one aspect, illustrated in FIG. 166 the bag has a cuff 630 through which a loop 631 of a shape memory material such as Nitinol is led. Internal capturing regions 632 for the retaining loop 631 are created by cutting panels in the material of the bag and folding down over the retaining loop 631 and sealing using a suitable tool such as a circular sealing tool. A tether strap 632 is mounted to the loop 631 and extends through an access port 633 to maintain control over the bag.

Figure 167:
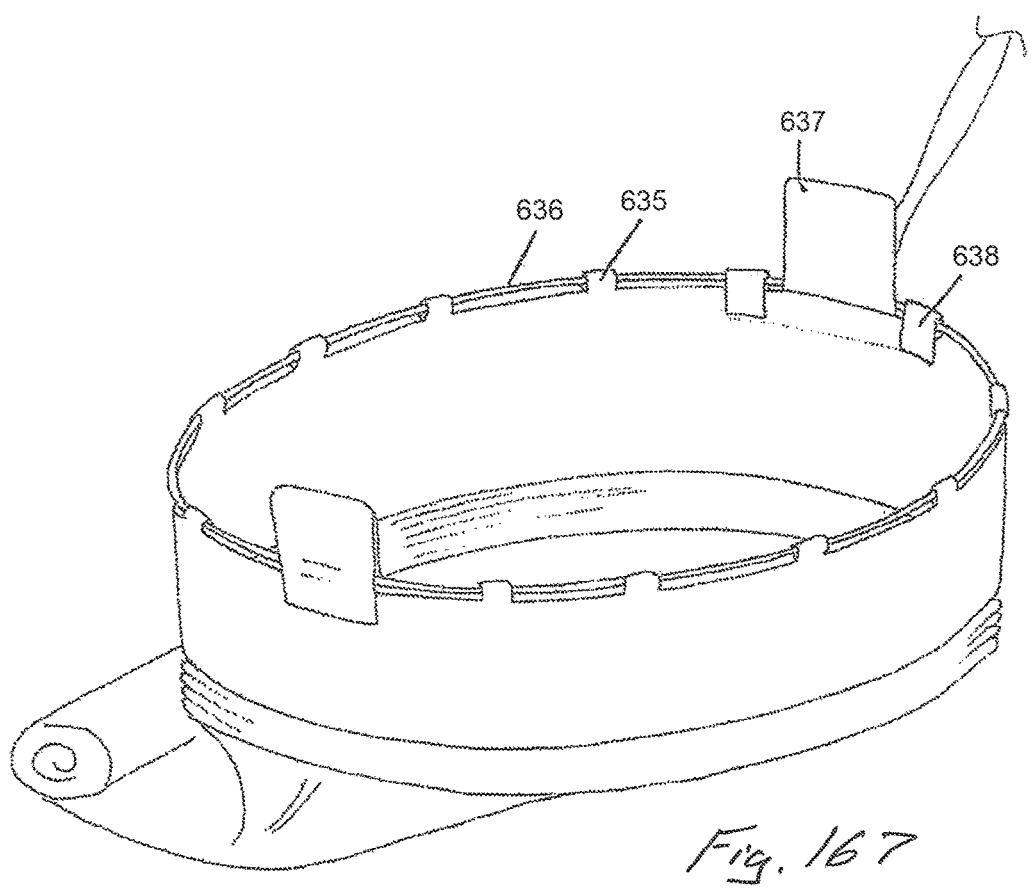

Referring to FIG. 167, in this case pressed out attachments 635 are folded over a closed retaining loop 636 of a shape memory material such as Nitinol and sealed, for example by heating. A front grasping tab 637 includes reinforced attachment loops 638.

FIGS. 168 to 170 illustrate another method of attaching a retaining loop 640 to a cuff 641 of a bag according to an aspect of the disclosure. In this case the material of the collar or cuff 641 is punched out with a cut detail 642 extending from a hole 643 (through which the retaining ring 640 is extended) to the edge of the cuff. The cuff is formed into a collar 641 as illustrated in FIGS. 169A to 169C. The retaining ring 640 is inserted through the cut details 642 and into the receiving holes 643. Using a circular sealing tool, the tabs are folded down to create an alternating overlap. The cuff is then sealed, for example by heat sealing to close the holes 643. In this way a closed loop 640 of a shape memory material such as Nitinol is attached to the bag to maximise the opening and facilitate insertion of tissue laparoscopically when the bag is within the abdomen.

According to one aspect, the abdominal bag is protected from damage during use of a morcellator. For example, as illustrated in FIG. 171 an insert/cannula 650 may be inserted to isolate a morcellator from the material of the bag. The insert 650 may for example be rigid, flexible or of a segmented rigid material. An access port or cap 651 may be releasably mountable to the insert 650.

The device used to introduce the bag into an insufflated abdomen may be adapted to control the opening of the bag. For example, as illustrated in FIGS. 172 to 176 a tip 655 of an introducer sheath 656 may have mirrored slots 657 which allow a retaining ring of the bag to start to expand before the full bag is inserted. Such an introducer will aid manoeuvring of the bag into a desired position before the bag becomes detached from the introducer. In addition, the deployed bag can be partially withdrawn into the introducer to enable further rigid movement of the bag to optimise positioning.

To limit blood or other material being pushed into the introducer by the positive insufflation pressure within the abdomen the tip of the introducer may have pressure dissipating features. For example, as illustrated in FIGS. 177 to 180 the introducer tip may have various slots 660, holes 661 and/or tapering features 662.

Figure 189:
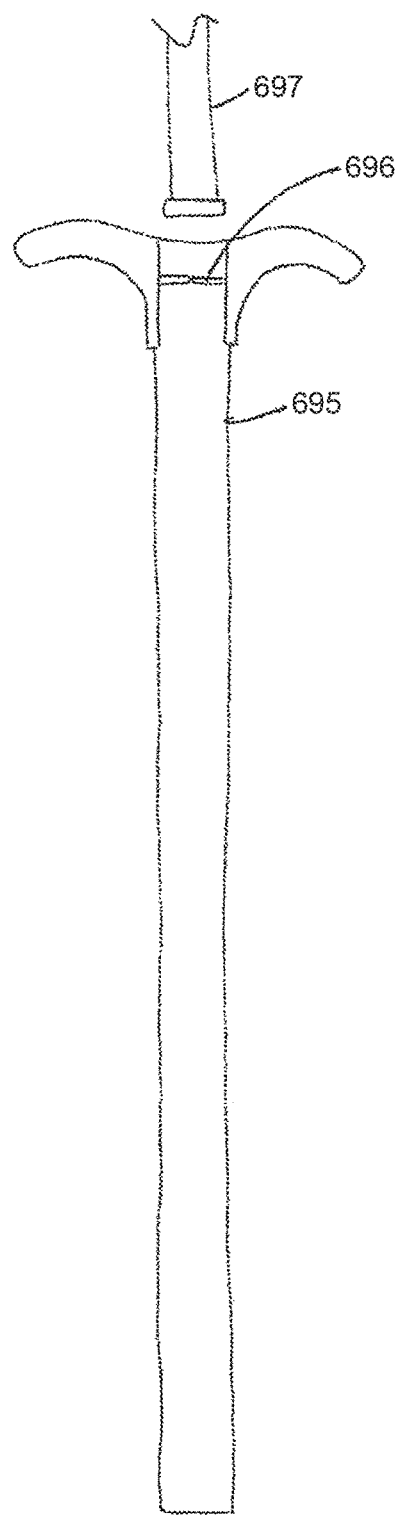
FIG. 189 shows an introducer with a valve.

According to one aspect, as illustrated in FIG. 189 to restrict blood or other material from entering the introducer, a shaft 695 of the introducer may have a valve 696 at the proximal end. The valve 696 may be openable on insertion of a pusher 697 used to deploy the bag device from the introducer.

Figure 181:
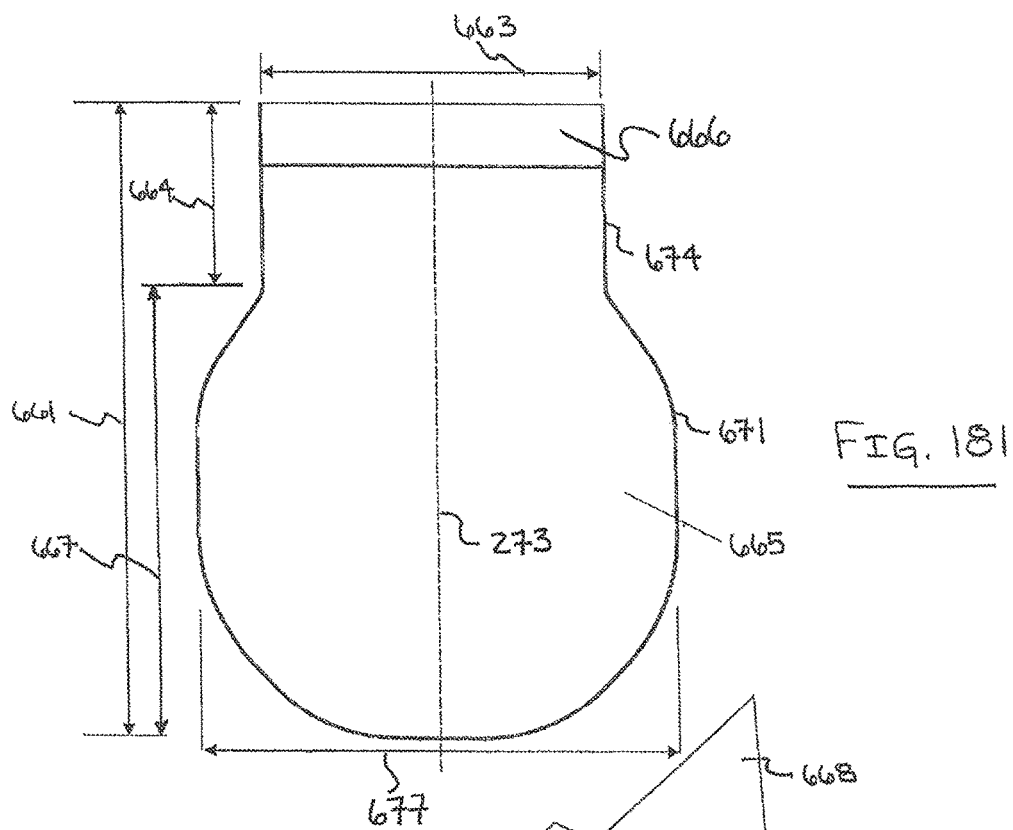
FIGS. 181 to 184 illustrate another bag device having a generally ovoid shape.
Figure 182:
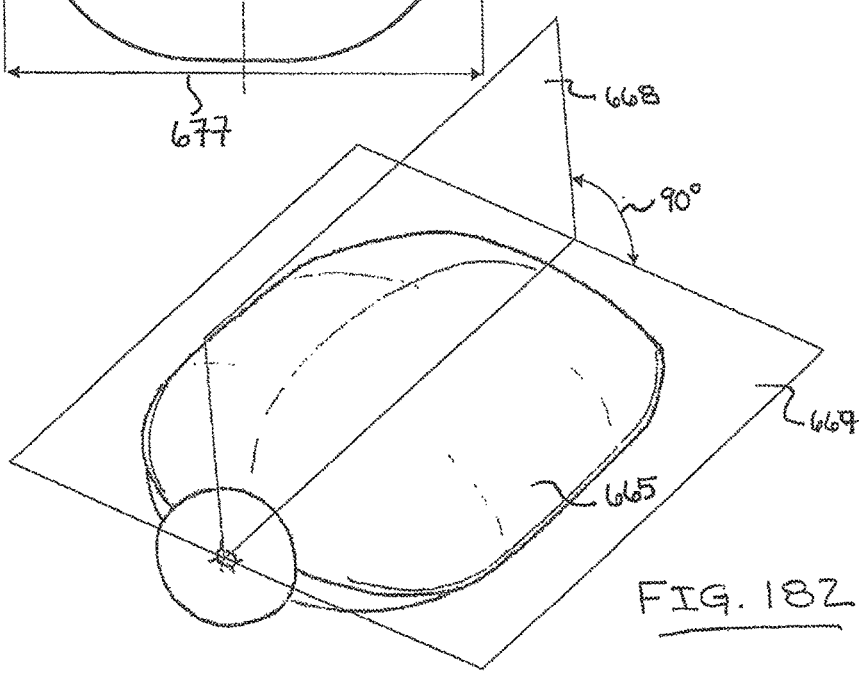

It will be appreciated that the bag, according to an aspect of the disclosure, may include different materials to fulfil different requirements for sections of the bag. For example, as illustrated in FIGS. 181 and 182 a main body 665 of the bag may be made from a relatively thin flexible material and a collar 666 of a thicker, more rigid material. For example, the main body 665 may include a sterilized polyester polyurethane, such as SS-1495-95 (95 shore A polyester polyurethane blown film with high slip surface and good clarity), and the collar or neck portion 666 may include a sterilized polyether polyurethane, such as ST-625-85 (85 Shore A polyether polyurethane formulated for medium/high slip with good sealability).

Figure 183:
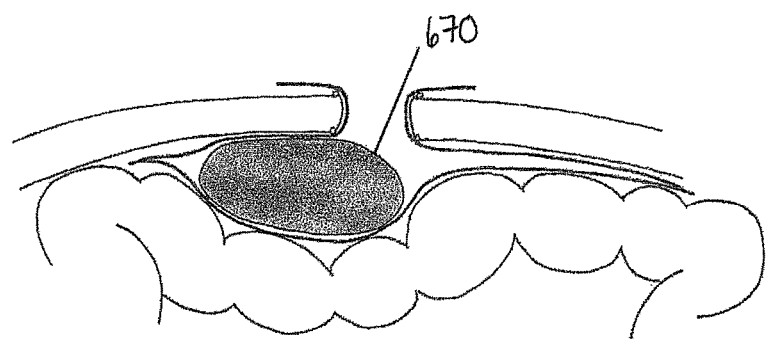
Figure 184:
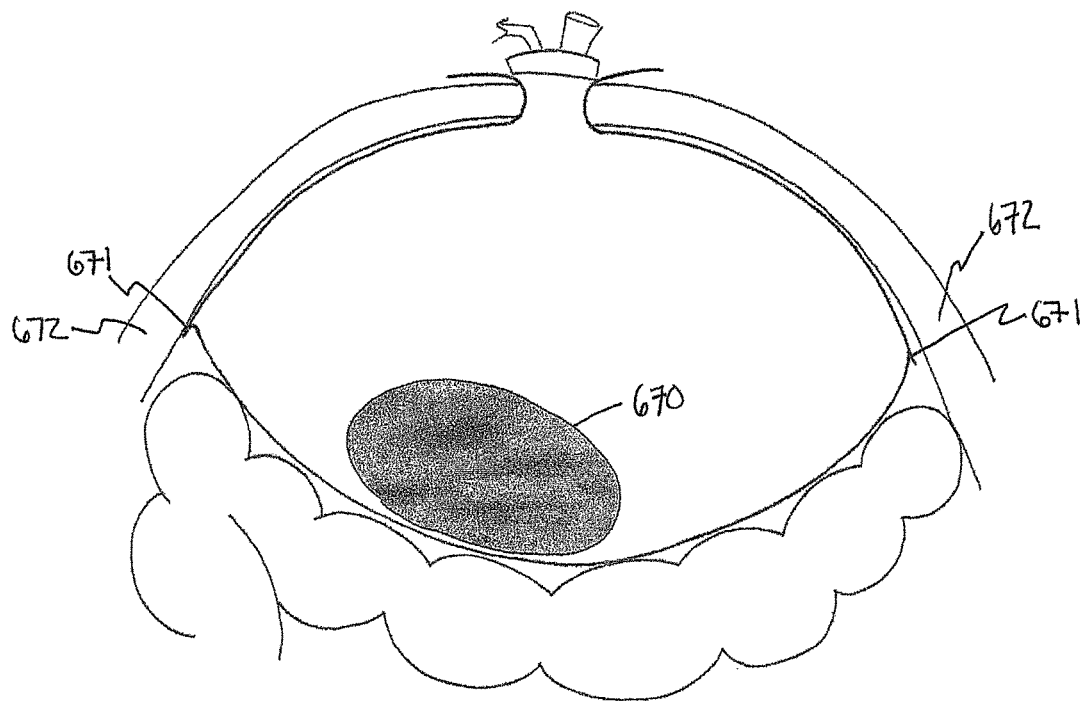

The bag may also be of any desired shape/profile. For example, the bag may be of oval or elliptical profile as illustrated in FIGS. 181 to 184. This shape assists in pushing organs such as a section of bowel away from the abdominal wall which prevents the bowel from migrating over the top of the bag. As shown in FIG. 184, the creation of the artificial pneumoperitoneum includes positioning the joined edges 671 of the bag in alignment with the lateral walls of the abdomen 672 such that one of the planar sheet portions of the bag faces, and is in contact with, the anterior abdominal wall, and the other sheet portion of the bag faces and contacts the viscera. Tissue 670 is illustrated in FIGS. 183 and 184 within the bag.

The bag may be sized to be larger than the peritoneal cavity of the patient so as to provide apposition against the abdominal wall after inflation. The oversized nature of the bag, and the loading of the bag into the introducer as described below in connection with FIGS. 187A to 187F, allows any additional bag material after inflation to remain rolled at the bottom of the bag. This helps to minimize pleats or folds of the inflated bag from extending into the artificial pneumoperitoneum. Consistent with this, and as shown in FIG. 181, the bag may be sized to include a total bag length 661 of between 300 and 600 mm, or between 400 and 550 mm, or approximately 500 mm, all in an uninflated condition. The bag may also include a maximum width 677, for example in the body portion 665, of between 200 and 500 mm, or between 300 and 400 mm, or approximately 350 mm, all in the uninflated condition. The collar or neck 666 may include a constant width 663 of between 150 and 350 mm, or between 180 and 320 mm, or approximately 250 mm, all in a bag uninflated condition and when the neck 666 is flattened as shown in FIG. 181. The collar or neck 666 may also include a length 664 of between 100 and 300 mm, or between 100 and 200 mm, or approximately 150 mm, in a bag uninflated condition. The main body 665 may include a main body length 667 (not including the neck) of between 200 and 500 mm, or between 300 and 400 mm, or approximately 350 mm. Also, main body 665 may be configured to have a maximum width to maximum length ratio of approximately 1:1.

Also, as noted above, the bag may be retained in the normally open configuration by a retainer ring of a shape memory material such as Nitinol. Referring to FIGS. 166-170, the retaining ring of the bag may be formed into a loop, shape set and welded. The diameter of the bag opening when the retaining ring is in an open configuration may be between 100 and 220 mm, or between 120 and 200 mm, or approximately 160 mm.

Referring again to FIGS. 181 and 182 the bag may be formed from shaped flat sheet laid on top of one another and attached at the edges 671, for example by welding. When inflated (FIG. 182), the bag expands into an ovoid type shape with rounder corners which can more closely align with the contours of the abdomen. Also as shown in FIGS. 118, 181, and 182, the bag may be shaped to be symmetric about two different planes (668, 669) that are normal to one another. In addition, as shown in FIGS. 118 and 181, neck or collar portion (401, 666) may be shaped to extend parallel to a longitudinal axis 271 of the bag, and thus edges 674 of the neck or collar portion (401, 666) may extend parallel to the longitudinal axis 271 of the bag.

The bag, according to an aspect of the disclosure, in some cases may be manipulated to optimise ease of loading into an introducer and/or to optimise deployment. For example, as illustrated in FIGS. 187A to 187F the bag may be wider at certain sections 680. These extra width sections may be folded inwardly from the side to form pleats 681. The bag may then be rolled from the bottom up towards the neck 682 of the bag. The neck 682 of the bag may then be scrunched down and loaded into an introducer 683.

Figure 188:
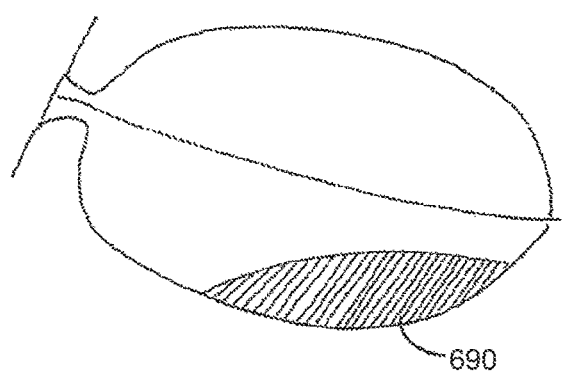
FIG. 188 is an illustration of a bag device with a reinforced section.

Referring to FIG. 188 in some cases sections of the bag may be of a different material and or material thickness in order to provide desired properties. For example, a bottom section 690 of the bag may be of a stranger/more rigid material to resist the action of a morcellator. The section 690 may be of a rip-stop nylon material, by way of example.

Figure 190A:
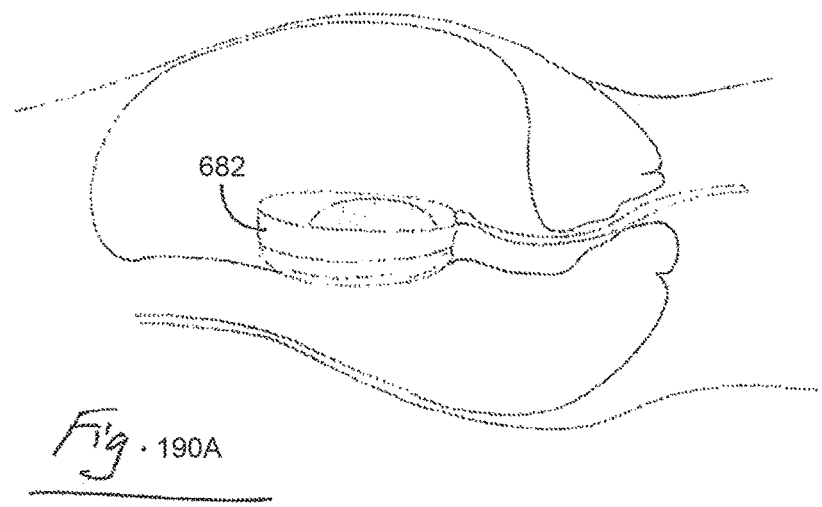
FIGS. 190A to 190C illustrate the use of a bag device in trans-vaginal procedures.
Figure 190B:
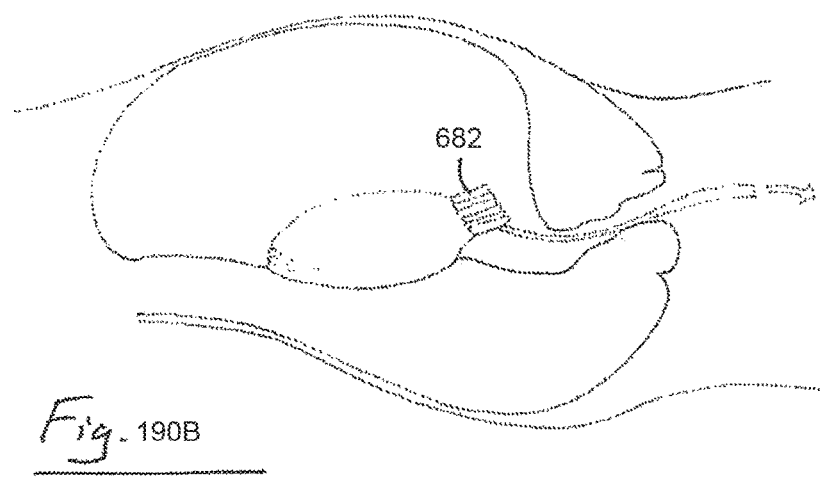
Figure 190C:
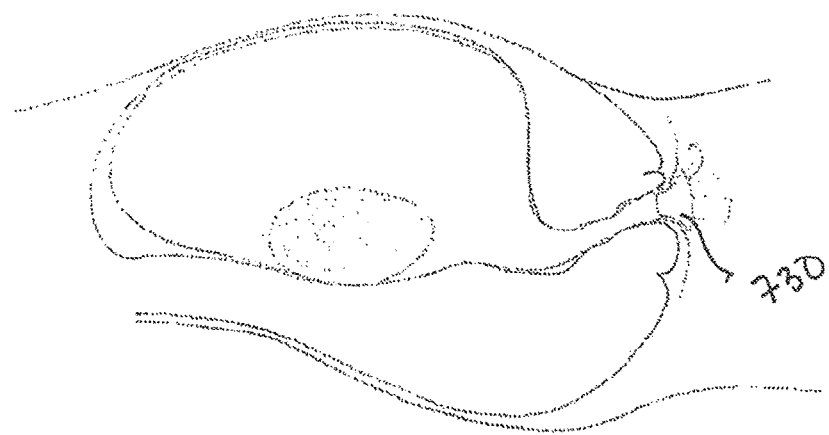

FIGS. 190A to 190C illustrate the use of the bag device, according to an aspect of the disclosure, in trans-vaginal procedures, for example hysterectomies. In some cases (FIGS. 190A and 190B) the bag device may be inserted and used directly without an access port. In other cases, the device may be used as described in accordance with other aspects with an access port 730 (FIG. 190C).

Figure 191:
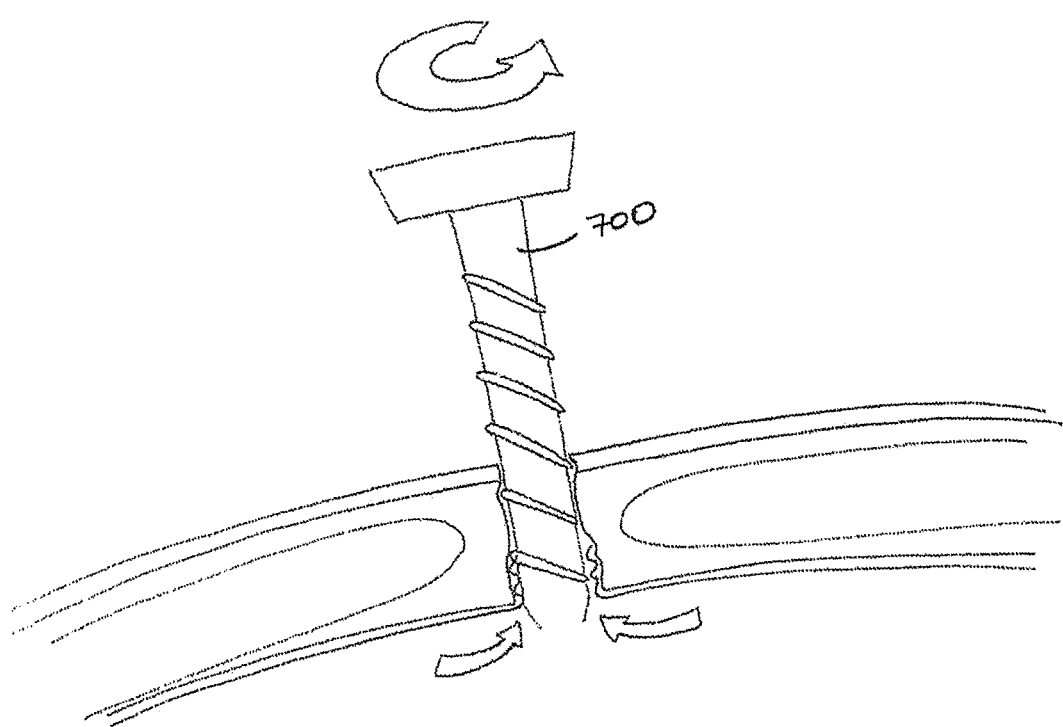
FIG. 191 is a view of a part of a bag with a threaded bung or trocar in place.

Referring to FIG. 191, in some cases the twisting action of a threaded trocar or bung 700 may assist in pulling the bag up through the wound.

Figure 192A:
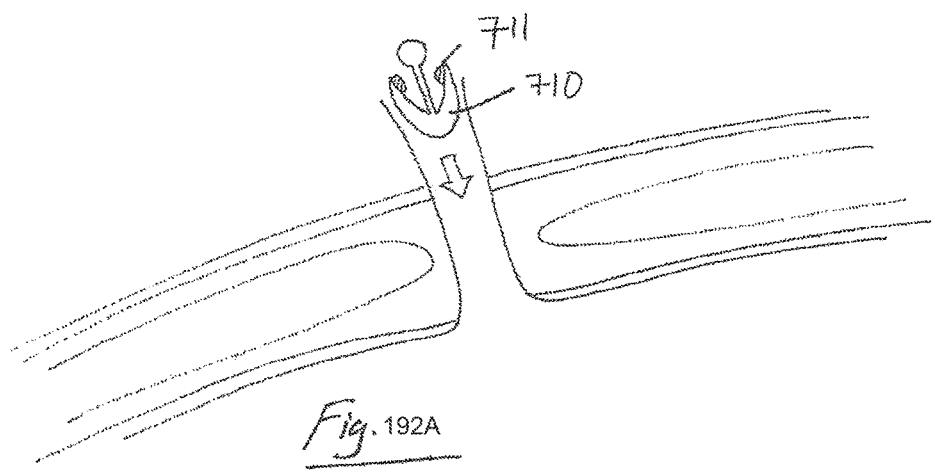
FIGS. 192A and 192B illustrate the closing of a chimney of a bag, prior to deflation.
Figure 192B:
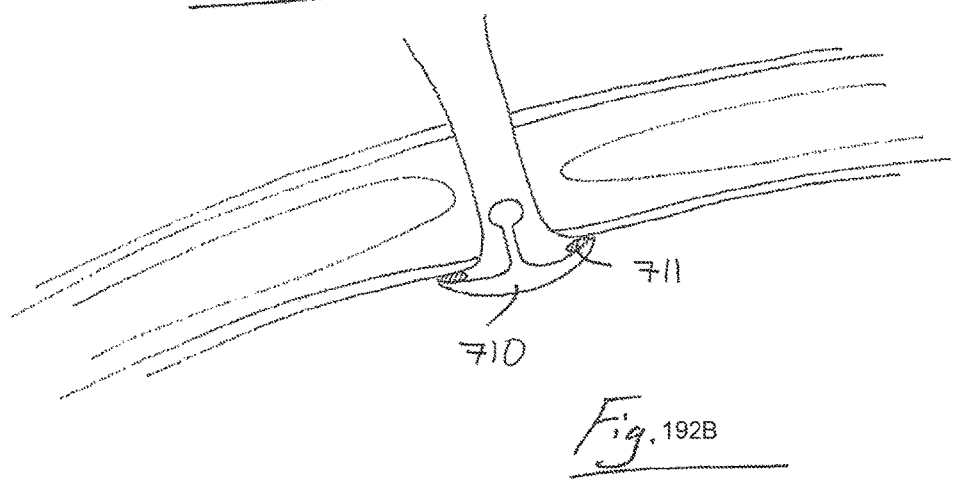

According to one aspect, in order to seal the hole into the chimney before the bag is deflated a closure device or valve may be deployed. For example, as illustrated in FIGS. 192A and 192B a closure device 710 may be inserted into the chimneys in a collapsed configuration and deployed at the distal end of the chimney. The closure device may be retained in place using any suitable retaining means such as an adhesive pad(s) 711.

Figure 193A:
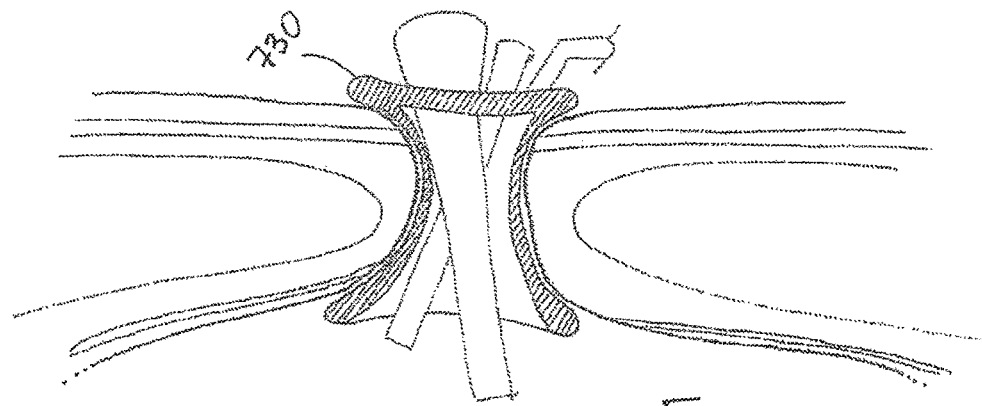
FIGS. 193A to 193C illustrate the use of the bag devices according to aspects of the disclosure with various access devices.
Figure 193B:
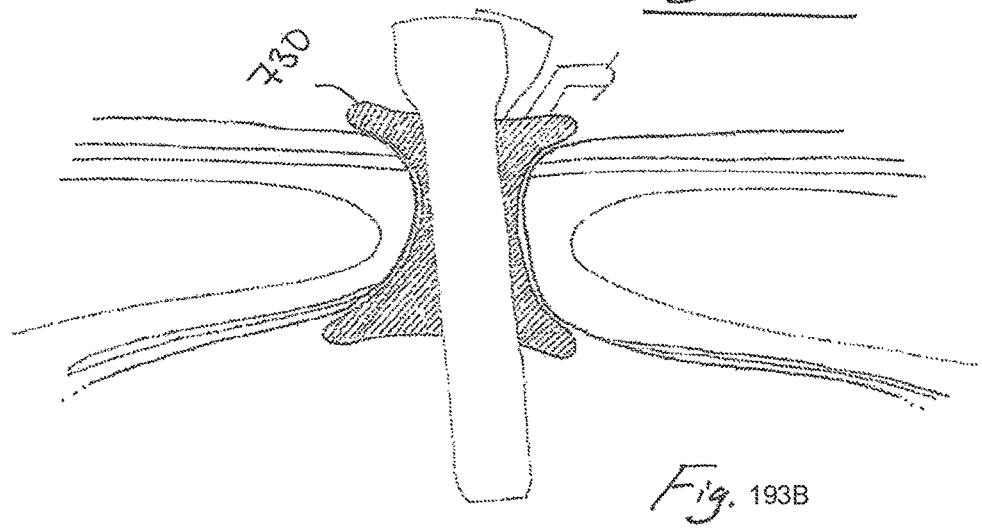
Figure 193C:
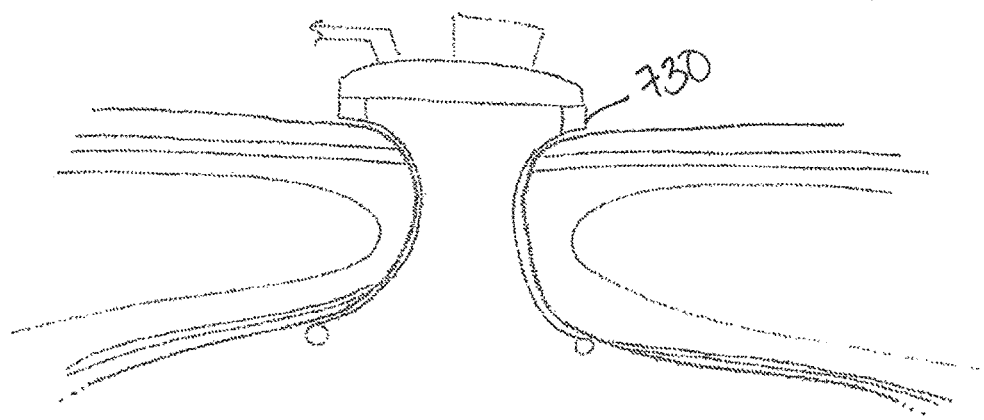

The abdominal bag device, according to an aspect of the disclosure, may be used with any suitable access port system 730 as illustrated, for example, in FIGS. 193A to 193C. In some cases the access port is mounted within the neck of the bag.

Figures 194, 195, 196:
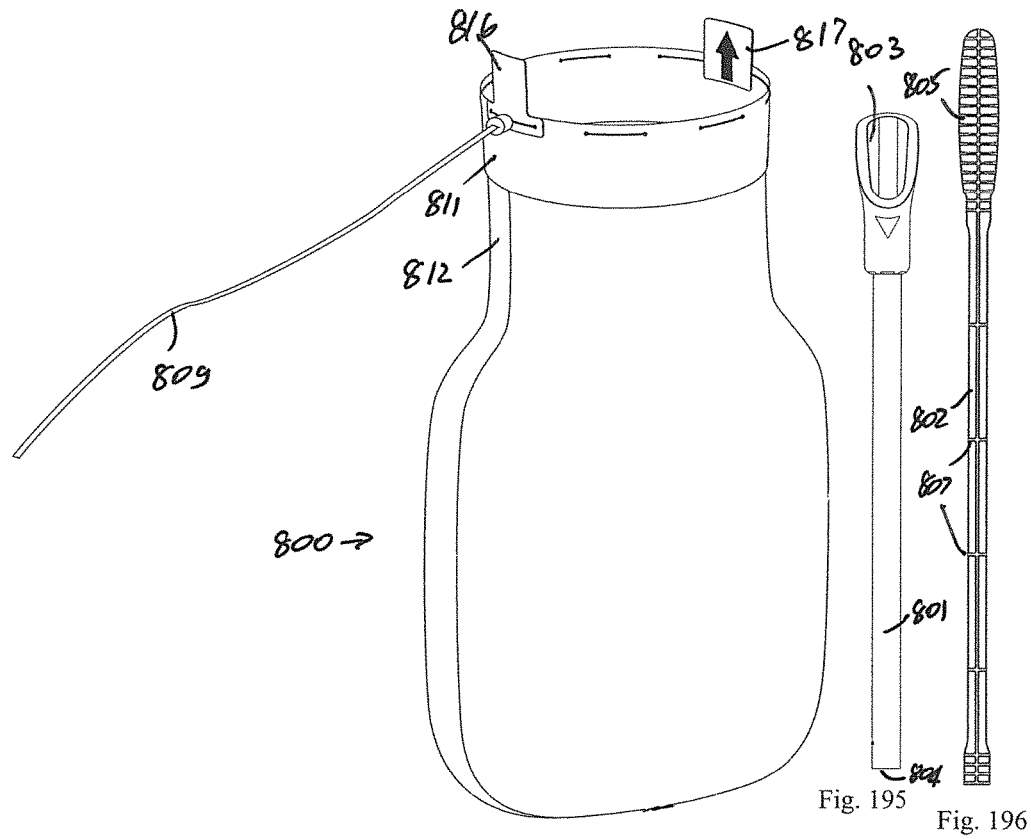
FIG. 194 is an isometric view of an artificial pneumoperitoneum device according to an aspect of the disclosure.
FIG. 195 is a view of an introducer sheath for the device of FIG. 194.
FIG. 196 is a view of a plunger for use with the introducer sheath.
Figures 197, 198:
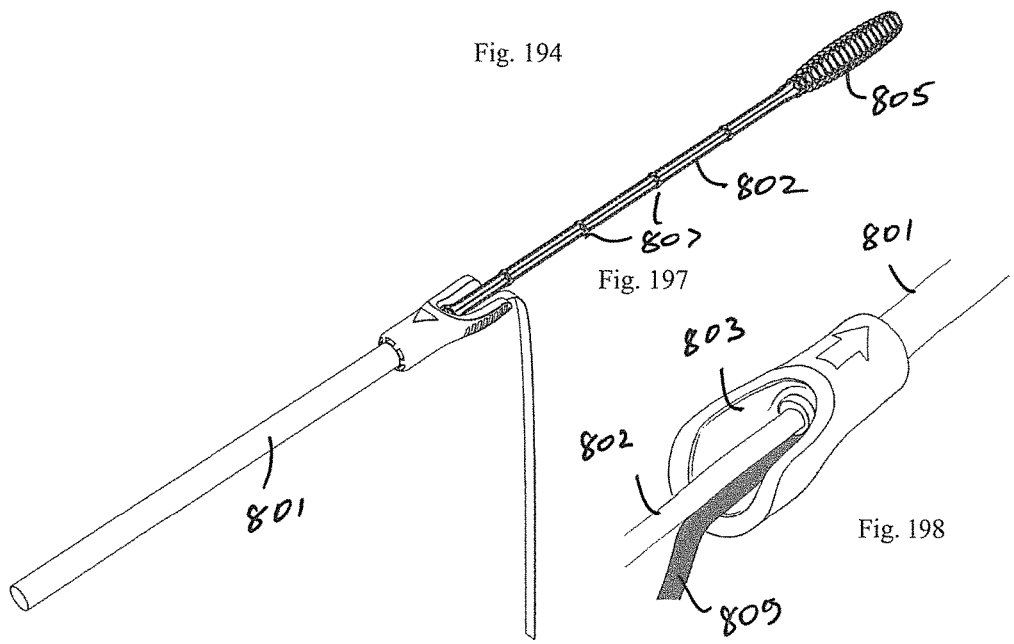
FIGS. 197 and 198 show the introducer sheath and plunger, in use.
Figure 295:
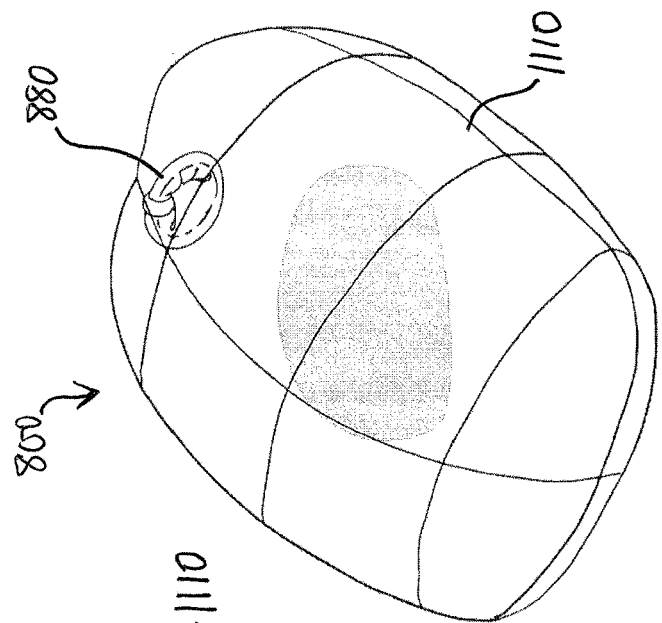
FIGS. 293 to 295 are isometric views illustrating inflation of the device.

Referring to FIGS. 194 to 295 there are illustrated further views of various artificial pneumoperitoneum devices and systems according to aspects of the disclosure. These devices and systems have several features in common with the devices described above and the relevant disclosures should be read in conjunction with the following.

Figure 210:
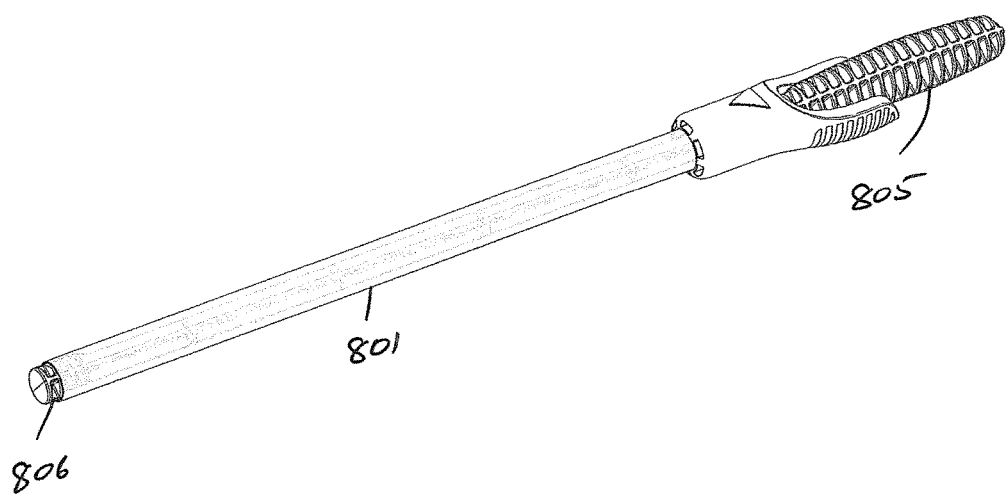
FIG. 210 illustrates the introducer and plunger after delivery of the device.

FIGS. 194 to 198 illustrate an artificial pneumoperitoneum device 800, an introducer sheath 801 for the device 800 and a plunger 802 for delivery of the device 800 from the sheath 801. Device 800 may include a container made of flexible material with an opening at the top. The sheath 801 has an open proximal end 803 with a tapered profile and an indicator arrow to indicate to the user the direction of travel of the plunger, and a distal end 804. The plunger 802 has a handle 805 at the proximal end and an enlarged sealing head 806 at the distal end. There are also seals 807 spaced-apart along the length of the plunger 802. Referring also to FIG. 210 the plunger 802 is sized to overshoot the distal end of the introducer 801 to ensure that the device 800 is always fully ejected from the introducer sheath 801. When the distal seal 806 has been ejected from the introducer sheath 801 the plunger 802 will sufficiently fill the introducer tube 801 to prevent significant loss of pneomo whilst being sufficiently loose to ensure that a tether 809 part of the device can be pulled freely.

Figure 199:
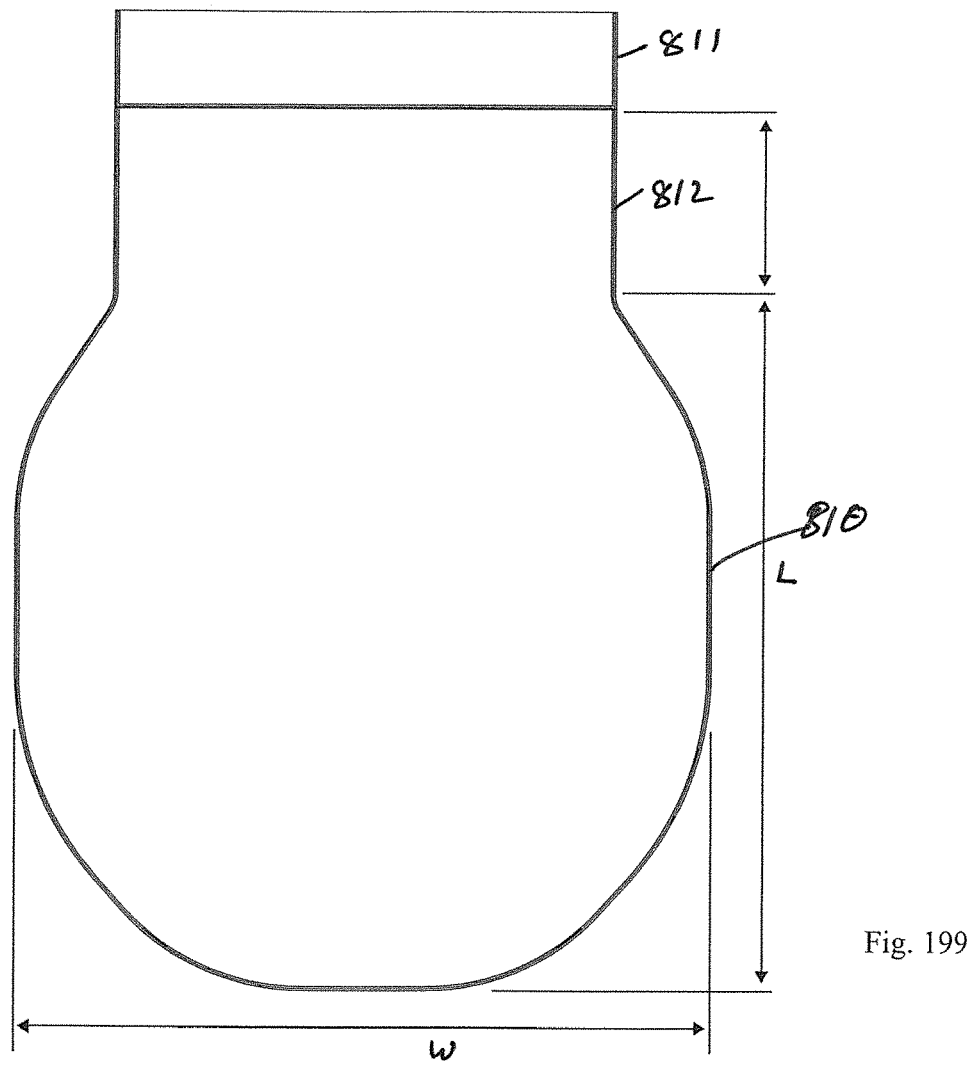
FIG. 199 is a view of a bag part of the device of FIG. 194.
Figure 200:
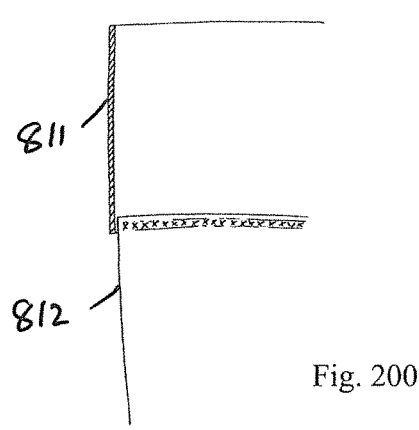
FIG. 200 is a cross sectional view of a detail of the bag device of FIG. 199.

As described in detail above and referring also to FIGS. 199 and 200 the shape and size of the device has several unique benefits. FIGS. 199 and 200 show a bag part of the device in a flattened configuration (i.e. without an opening ring structure). The bag has a main body region 810, a collar region 811 and a neck region 812 between the collar 811 and the main body 810. A length L of the main body is the same as the width W of the main body 810 whilst the neck region 812 is narrowed. The neck region 812 in use is used to line the incision or opening through which it is introduced. The collar 811 is stiffer than the neck and main body and is typically welded to the neck 81 region.

A biasing element in the form of a Nitinol loop 815 extends through and in this case is threaded through the collar 811. Pull tabs 816, 817 are mounted to and extend proximally from the collar 811. As described above, the collar is of stiffer material than the main body of the bag and in addition to assisting in maintaining an opening it also facilitates secure mounting of various elements such as the biasing loop 815 and the tabs 86, 817.

Figure 201:
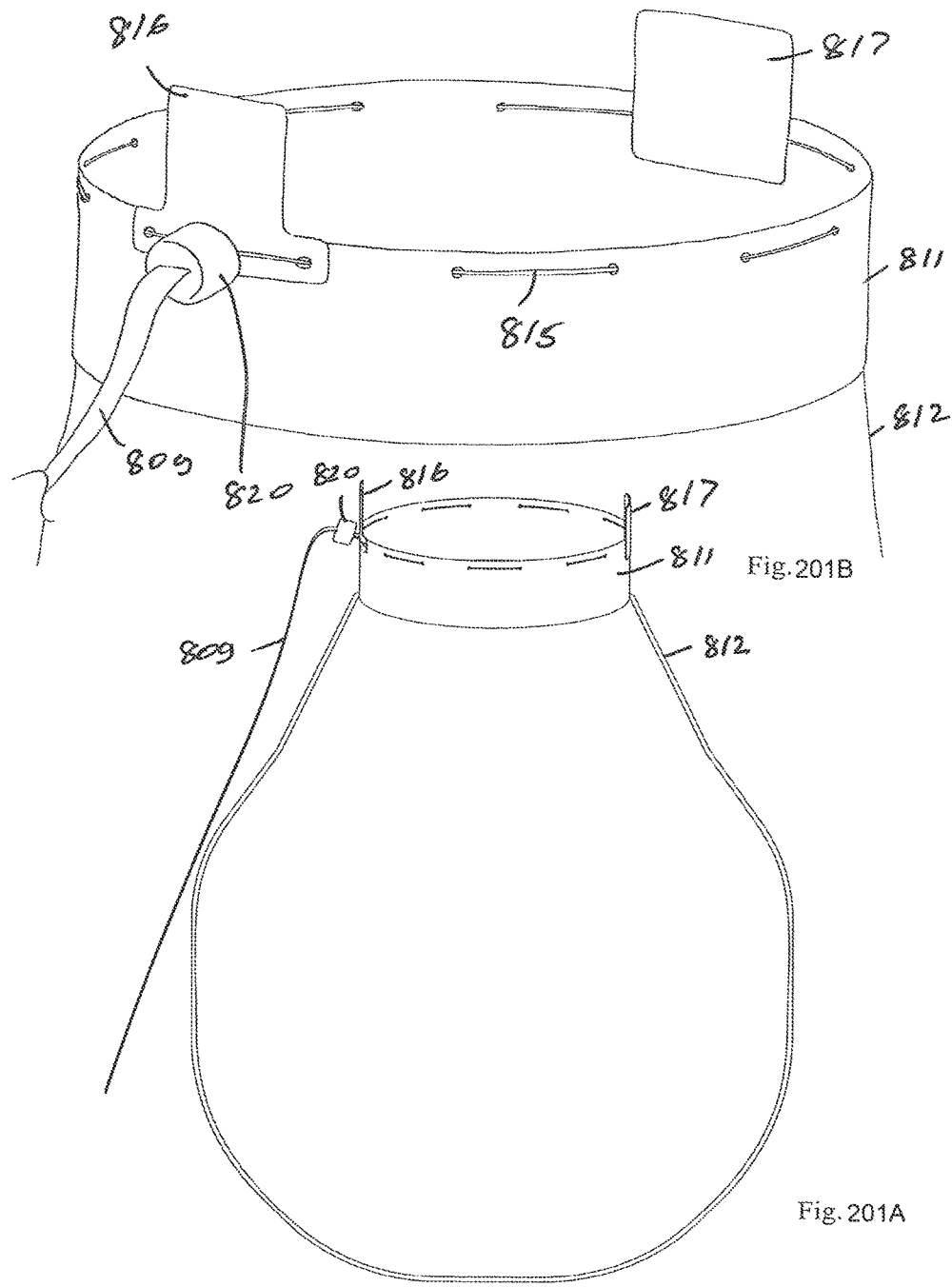
FIGS. 201A and 201B are views of an open end of the bag device.
Figures 206, 207:
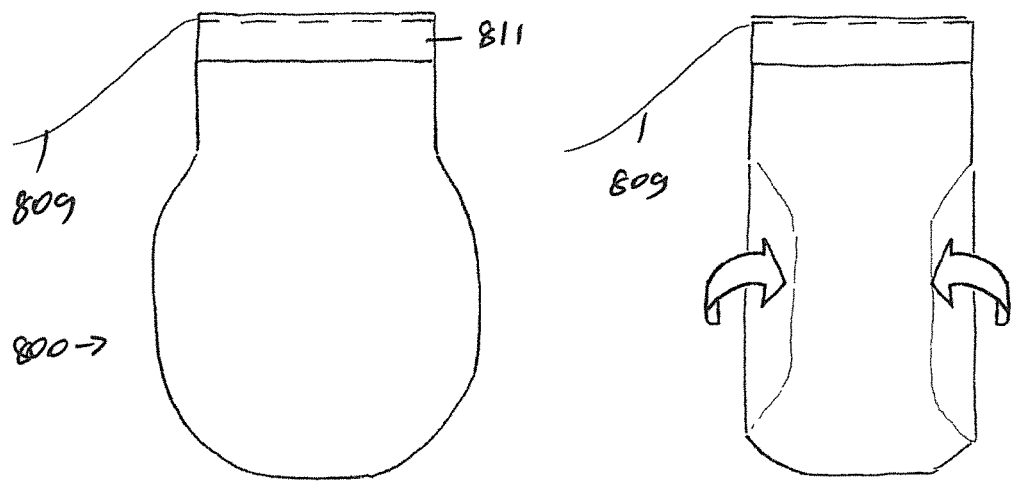
FIGS. 206 to 209 illustrate the folding of the device for loading into an introducer.
Figure 208:
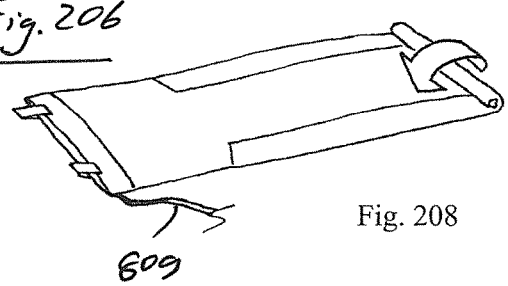
Figure 209:
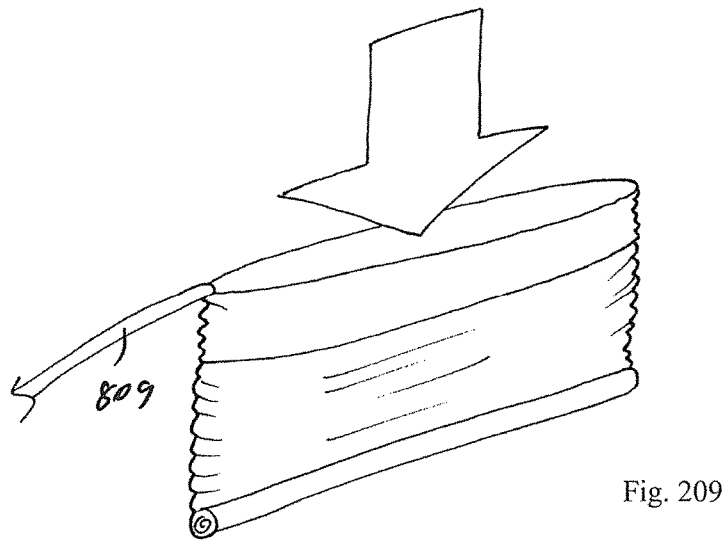

Referring to FIGS. 201A and 201B, in use a seal 820 is pressed out of closed cell foam with the slit in the middle. The tether is passed through this slit and glued into place. The seal 820 seals the introducer preventing blood being sucked up onto the introducer and possibly out of the handle. The proximal tab provides reinforcement for the two holes that the Nitinol wire passes.

Referring to FIGS. 202 to 205, the procedure for fitting the Nitinol ring 815 is a follows:

The collar 811 is formed before the Nitinol wire 815 is added.

The Nitinol wire 815 is threaded through holes in the collar, alternating inside and outside in a pattern as illustrated in FIG. 202.

The Nitinol wire 815 is on the inside of the collar at the distal side of the collar 811.

The Nitinol wire 815 is on the outside of the collar at the proximal side, where the tether 809 is attached.

The distal tab 817 captures the Nitinol 815 wire on the inside of the collar 811.

Due to the requirement to thread the Nitinol through the holes, a cold crimping process is used.

Both ends of the Nitinol wire 815 are placed inside a tube 825 (which may be of Nitinol) which is then cold pressed to hold the wire 815.

The tether 807 is formed over the crimp to ensure the crimp comes out first and to cover any sharp edges.

The crimp region is the first part of the wire to be pulled outside of the body by the tether 809.

FIGS. 206 to 209 illustrate the folding/rolling of the device 800 to ready it for loading. The procedure is as follows:

Fold in the excess width to make same width as flattened opening.

Roll from the bottom as far as the shoulder/neck.

Scrunch down the neck. This ensures that the tissue specimen has sufficient space to allow the device to close without the tissue getting caught in the opening into the device.

The device is then loaded into the introducer 801.

Figure 211:
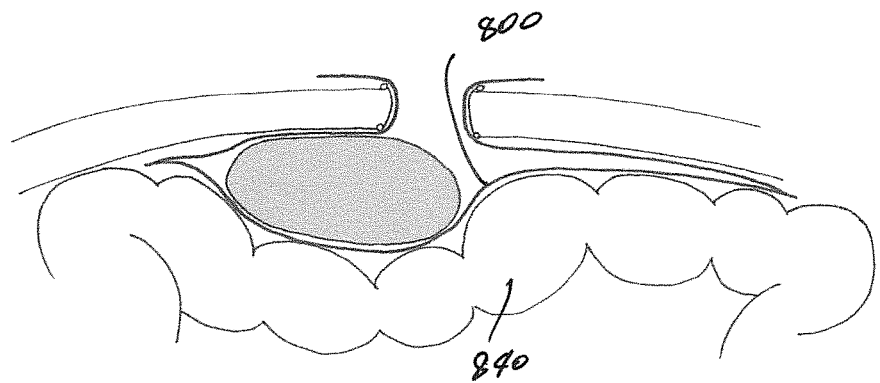
Figure 212:
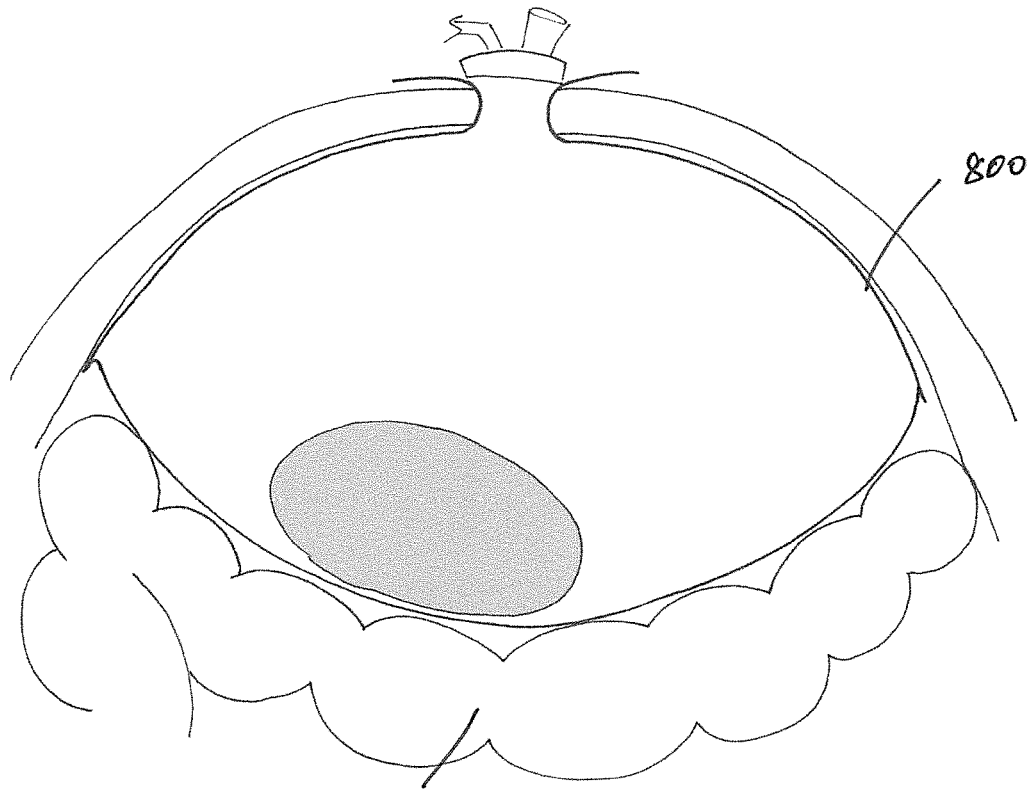

Referring to FIGS. 211 and 212 it will be apparent that the shape and the width of the bag device 800 retracts the viscera 840 whilst ideally preventing the viscera from creeping over the device to become trapped between the device and the abdominal wall.

Referring to FIGS. 213 to 215 it will be apparent that once inflated the bag device has no pleats, folds, curtains or excess material.

Figure 216:
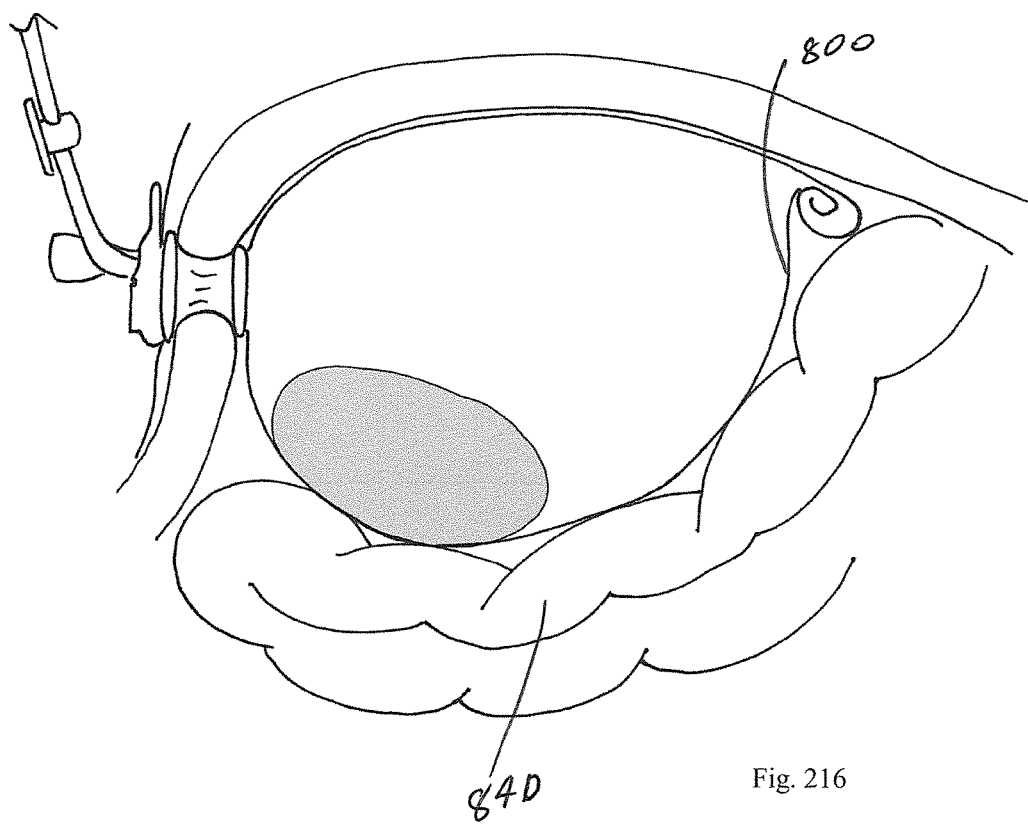

Referring to FIG. 216 it will be noted that the bag device 800 is larger than most abdominal cavities therefore ensuring all available space within the abdominal cavity is taken by the bag device. The device, its loading and how it inflates minimises internal folds in material and that any excess material is kept on the outside, therefore not providing any accidental grabbing hazards on the inside. As the bag device 800 inflates, it only unrolls as much material as necessary to fill the available space, leaving all excess material neatly rolled on the outside.

Figure 217:
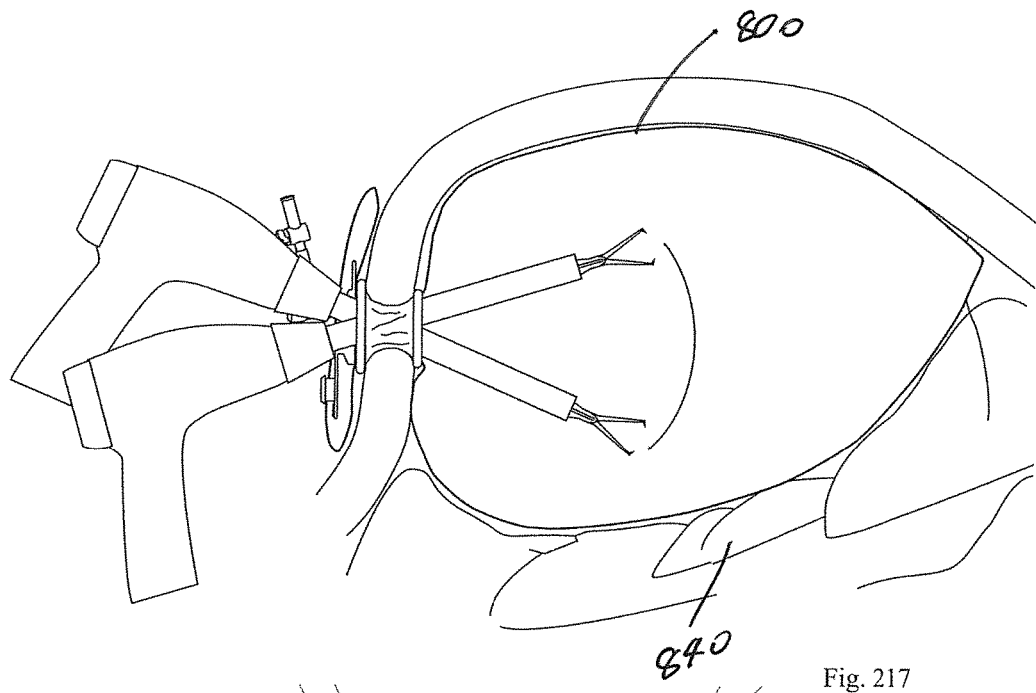
Figure 218:
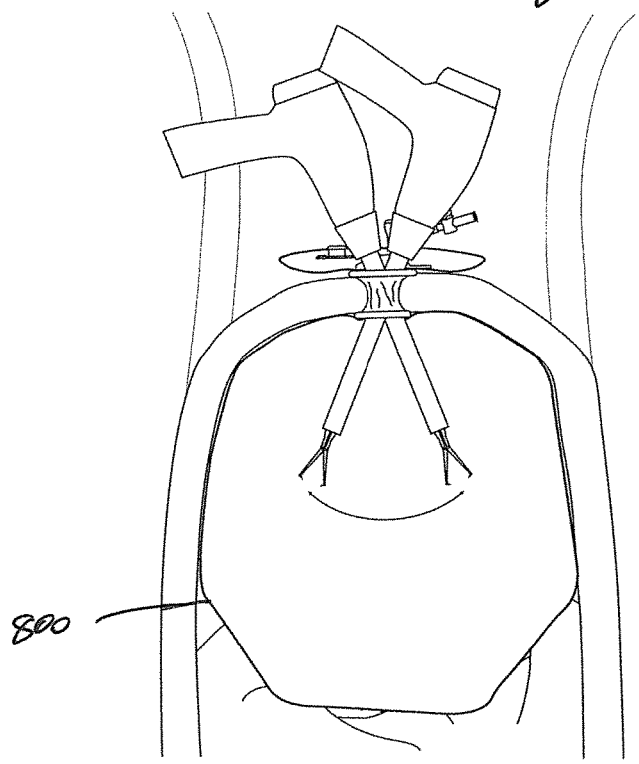

Referring in particular to FIGS. 217 and 218 it will be apparent that the viscera 840 is retracted away from a morcellator, making it difficult for the morcellator to accidentally touch off the body of the bag device 800.

Figure 219:
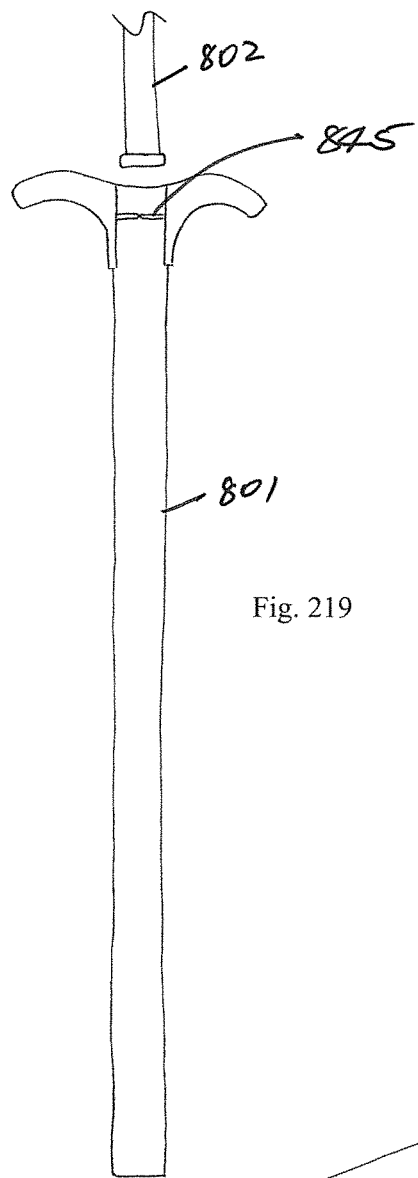
FIGS. 219 and 220 illustrate a seal between the introducer and the plunger.
Figure 220:
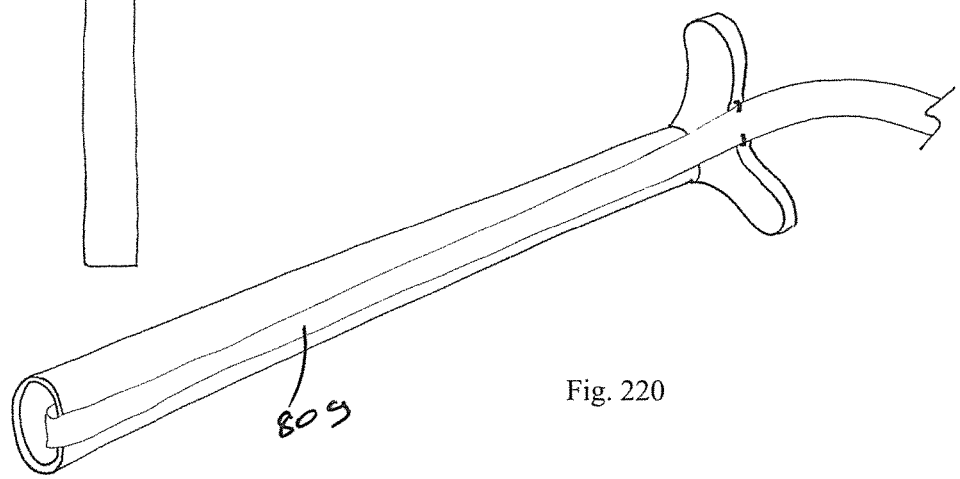
Figure 222A:
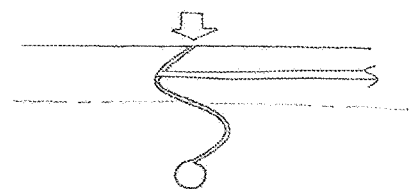
FIGS. 221 and 222A to 222C illustrate the mounting of a solid ring to the collar of a device according to an aspect of the disclosure.
Figure 222B:
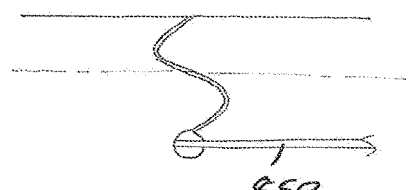
Figure 222C:
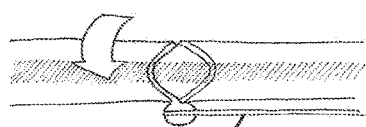
Figure 221:
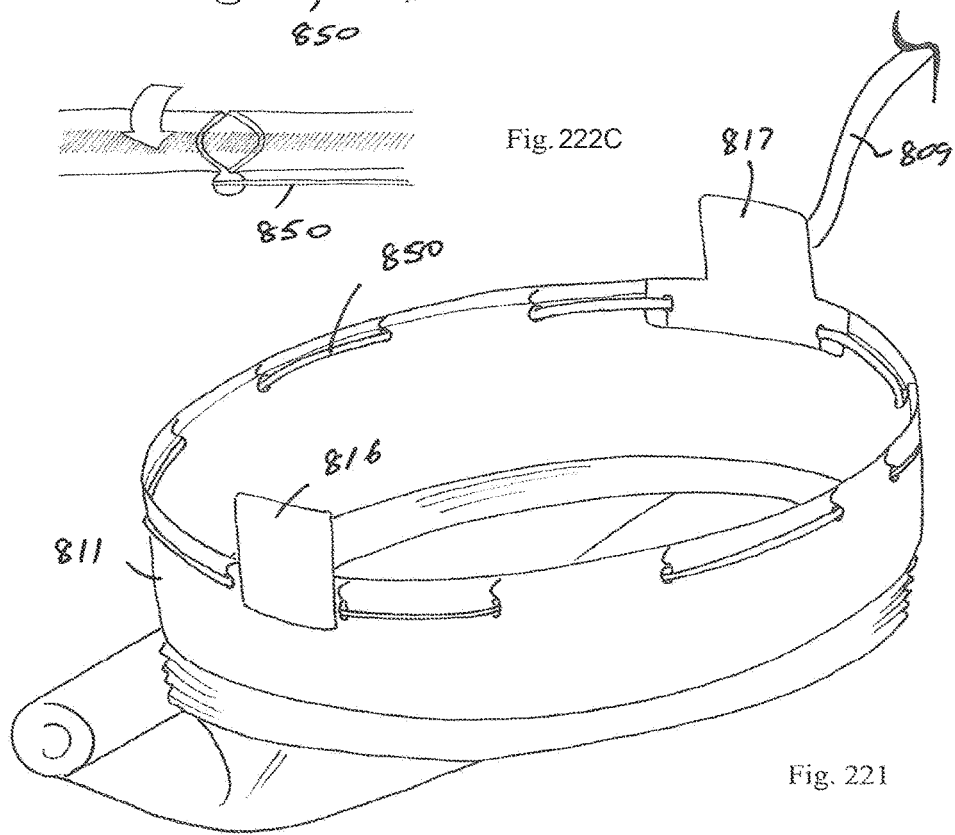

It will be apparent from FIGS. 219 and 220 that a zero seal and lip seal introducer 845 may be moulded into the introducer handle which is pierced by the plunger 802. In his case the tether 809 extends out from the front of the introducer 801 and up along the outside.

FIGS. 221 and 222A to 222C illustrate an alternative manufacture described above in which for assembly with a solid Nitinol ring; the cuff 811 is attached to a pre-formed Nitinol ring 850.

Figure 223:
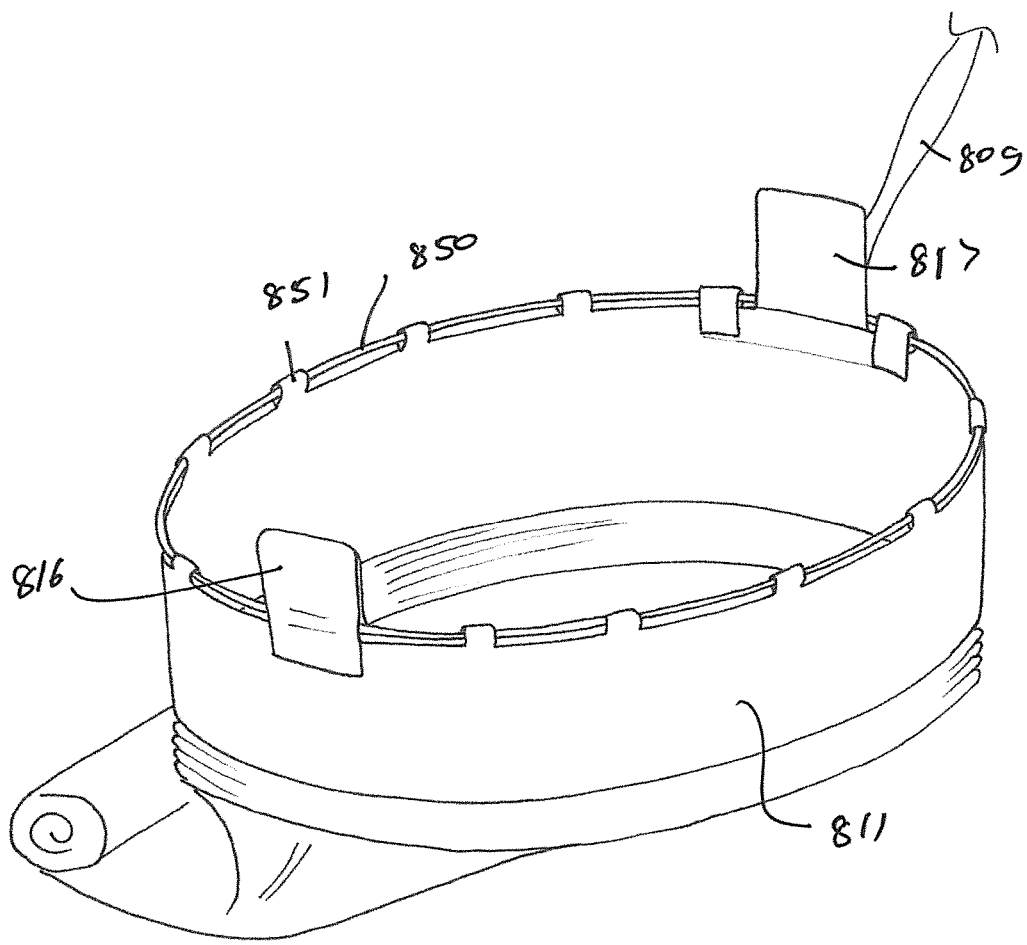
FIG. 223 illustrates another method of attachment of a ring to a device according to an aspect of the disclosure.

FIG. 223 illustrates an alternative manufacturing procedure for assembly with a solid Nitinol ring 850. This uses loops 851 instead of threading the Nitinol through holes.

Referring to FIG. 224 there is illustrated a bag device 800 being introduced through an access port 860. A scope 861 is also inserted.

FIGS. 225 and 226 illustrates introduction of the device 800 in a multiport configuration in which a scope 861 is inserted through a separate port or trocar.

Figure 227:
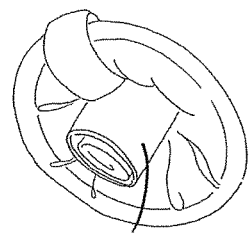
Figure 228:
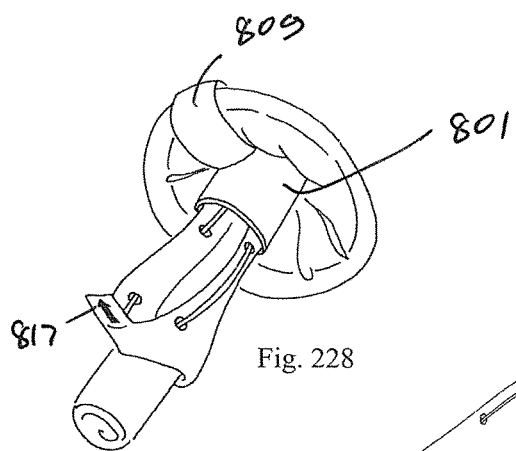

Referring to FIGS. 227 and 228 it will be apparent that the bag device 800 opens automatically as it is ejected from the introducer 801.

Figure 229:
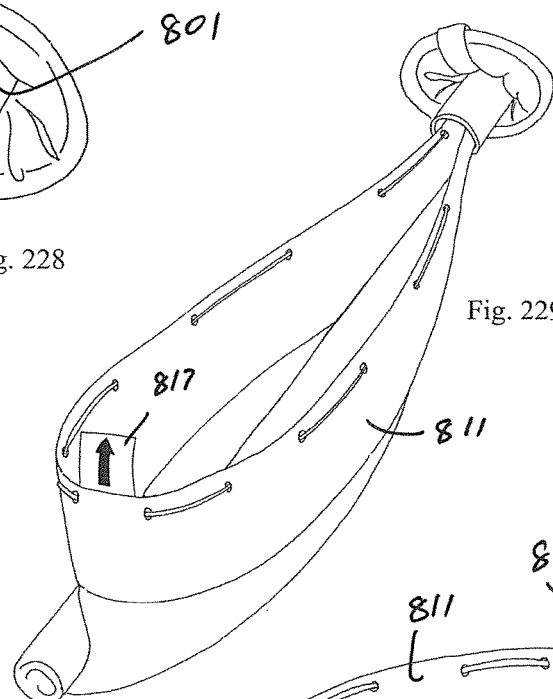
Figure 230:
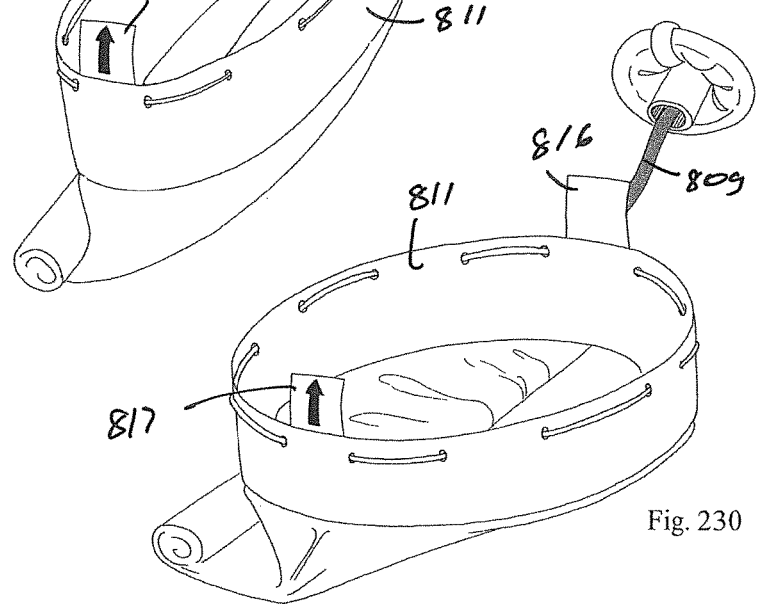

FIGS. 228 to 230 illustrate that as the bag device 800 is ejected from the introducer 801, the distal tab 817 pops up with an arrow printed on both sides to aid the surgeon with orientation—i.e. prevents the bag device being accidentally deployed upside down.

Figure 231:
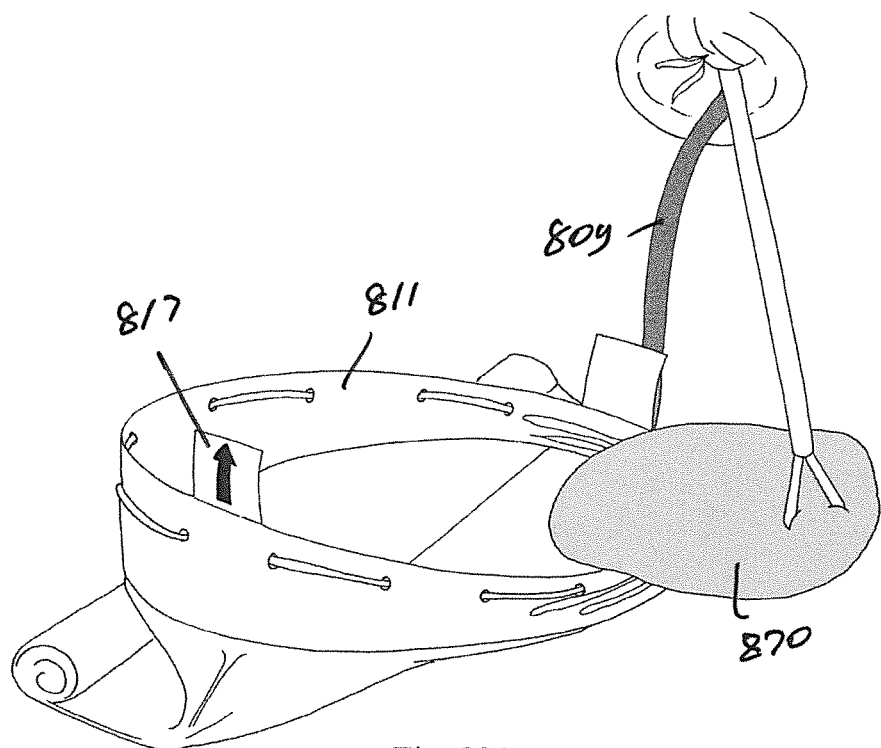
Figure 232:
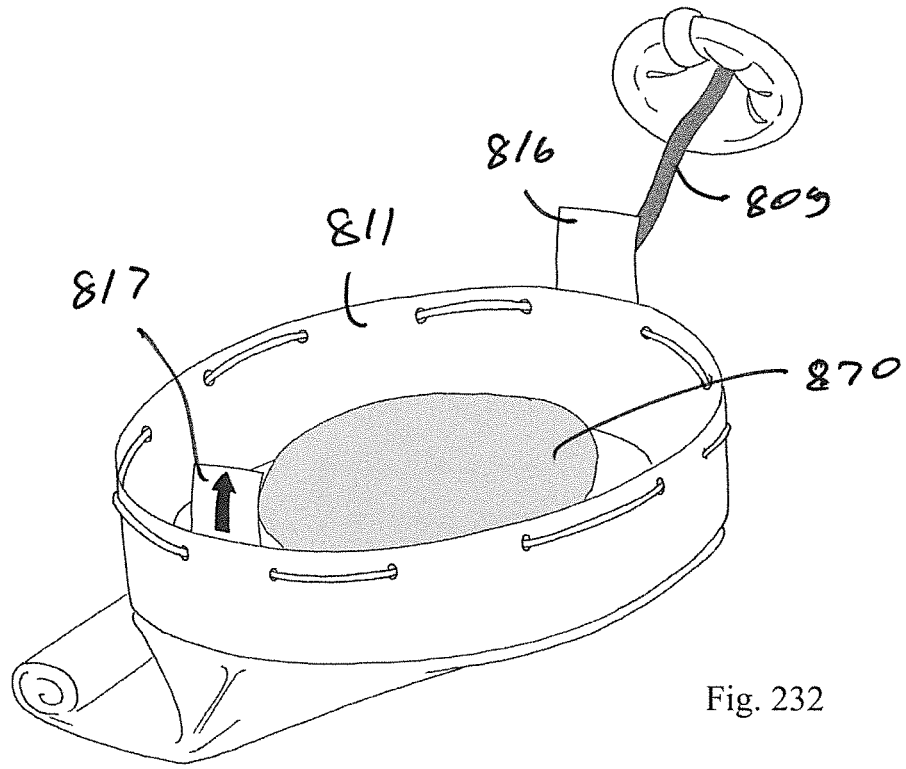

FIGS. 231 and 232 illustrate tissue 870 being manipulated into the opening of the device, in some cases using a flipping or a rolling action.

FIG. 233 shows a surgeon pulling the tether 809 until the opening ring is partially pulled through a large instrument valve 875.

FIGS. 234 and 235 illustrates that the device closes automatically as it is pulled up against the wound retractor 880.

Figure 236:
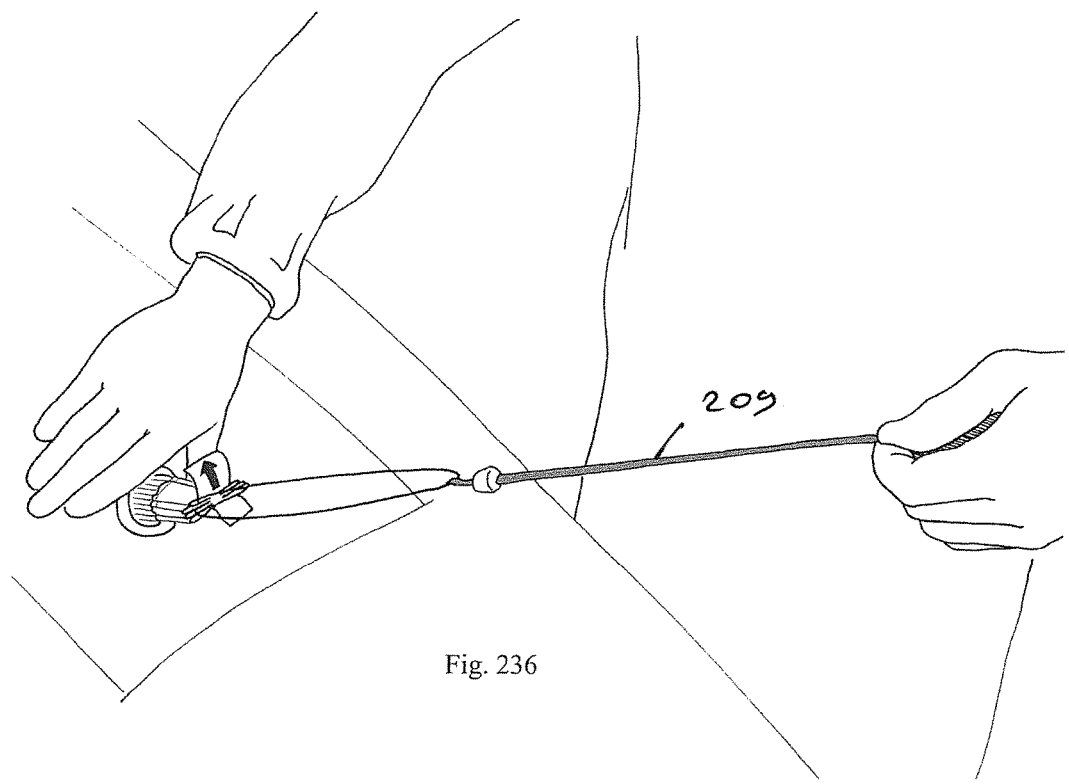
Figure 237:
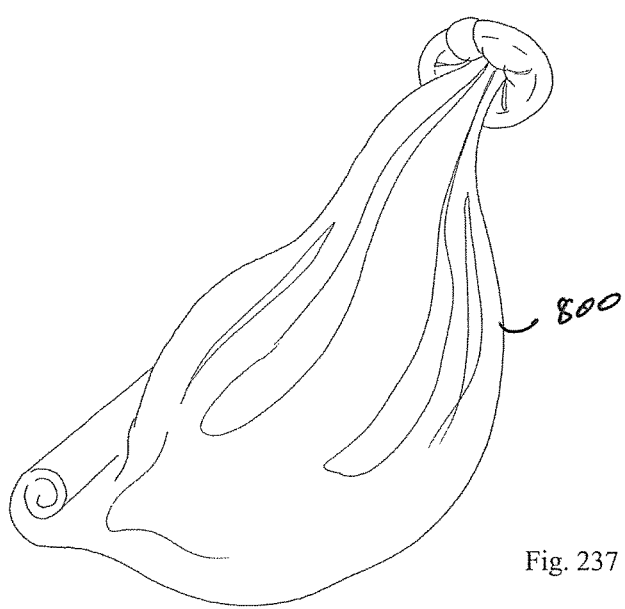

FIGS. 236 and 237 illustrate removal of the port and the surgeon continuing to pull the tether 209 until the device collar is exposed which is indicated by a line.

Figure 238:
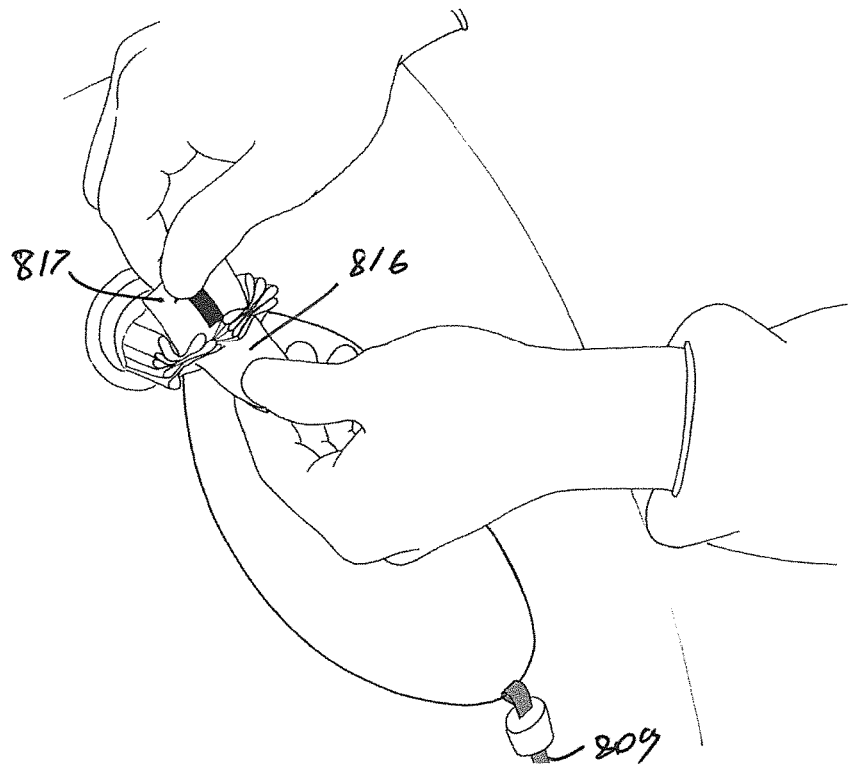
Figure 239:
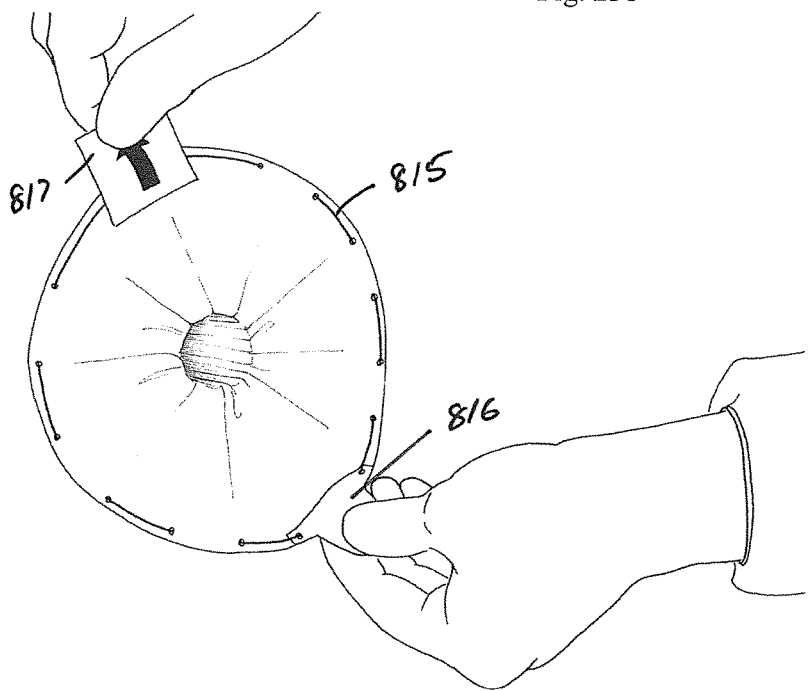

Referring to FIGS. 238 and 239 the surgeon then pulls the tabs 816, 817 apart to open the device.

FIGS. 240 and 241 are internal views of the bag device 200 before inflation. All gas is expelled from the abdomen before the access port 860 is reattached.

The reattachment of the port 860 is illustrated in FIG. 242.

Figure 243:
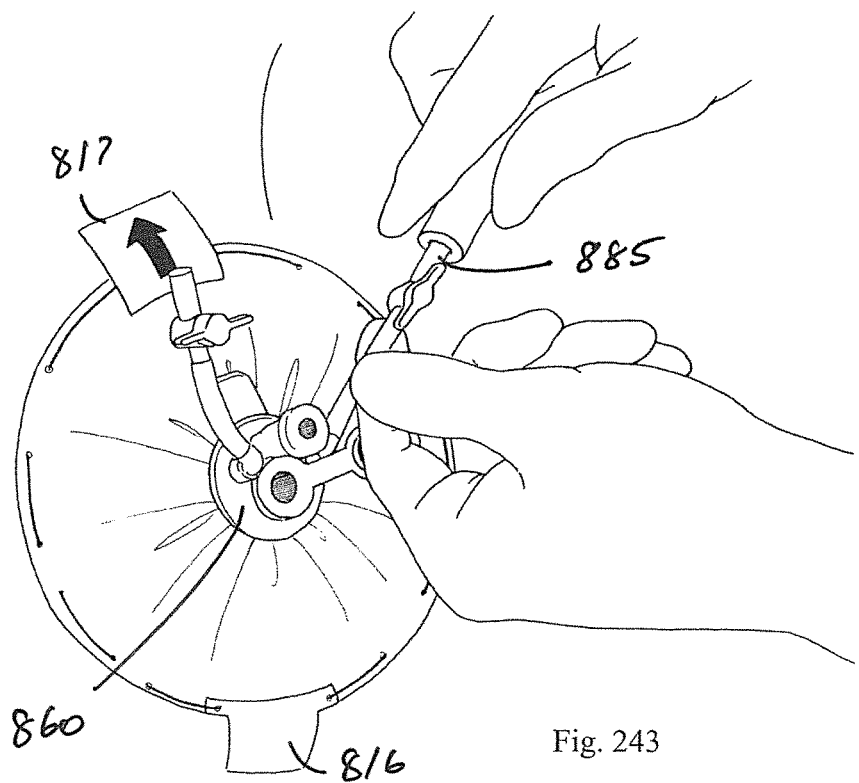
Figure 244:

Referring to FIGS. 243 and 244 an insufflation supply line 885 is connected to the access port 860 and the bag device 800 is inflated.

Figure 245:
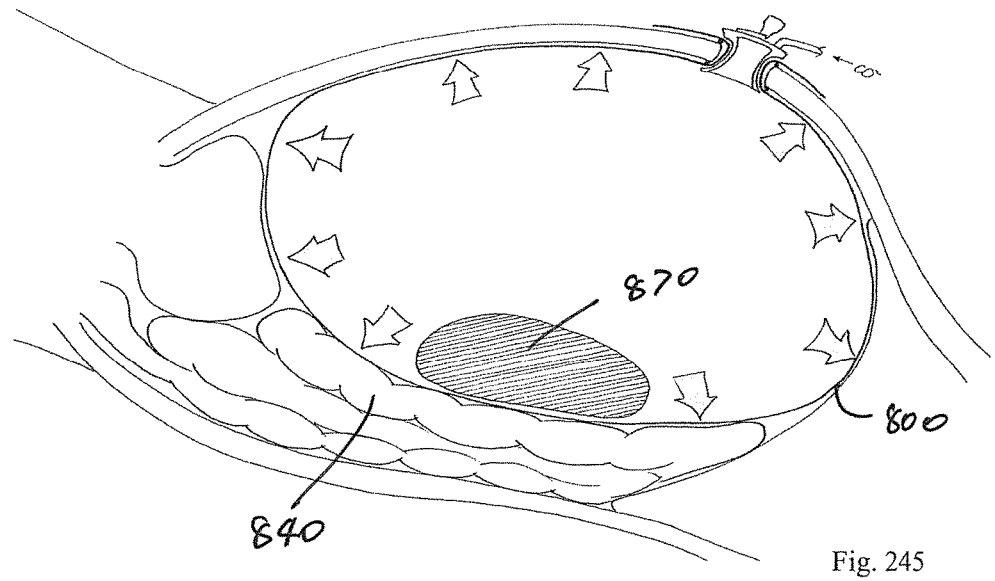

Referring to FIG. 245 it will be noted that the viscera 840 is retracted and the bag device 800 lines the abdominal wall when it is inflated.

Figure 246:
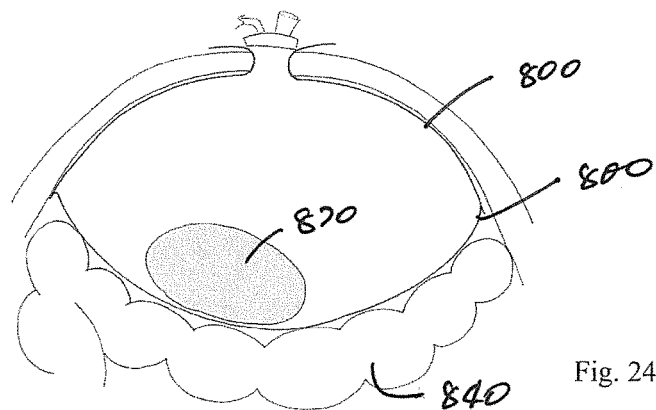
Figure 247:
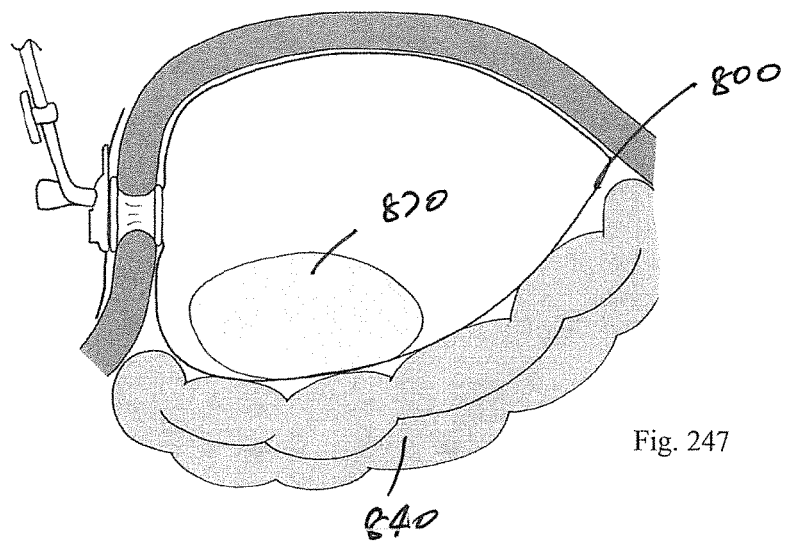

Referring to FIGS. 246 and 247 it will be noted that the bag device 800 prevents bowel 840 from creeping up over the device.

Figure 248:
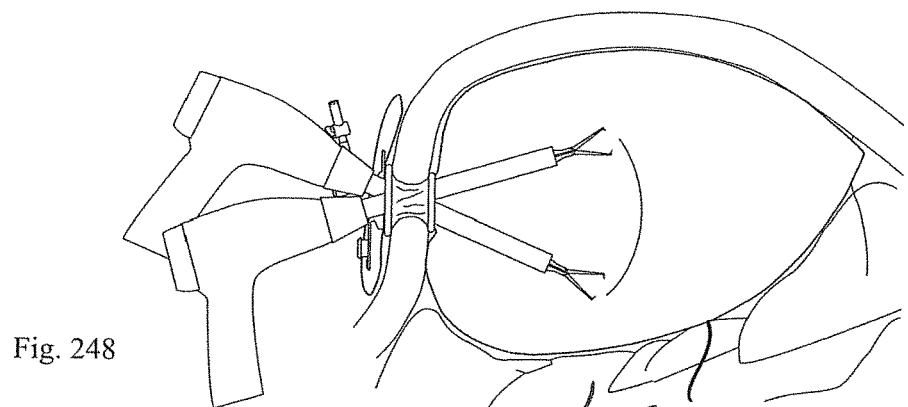
Figure 249:
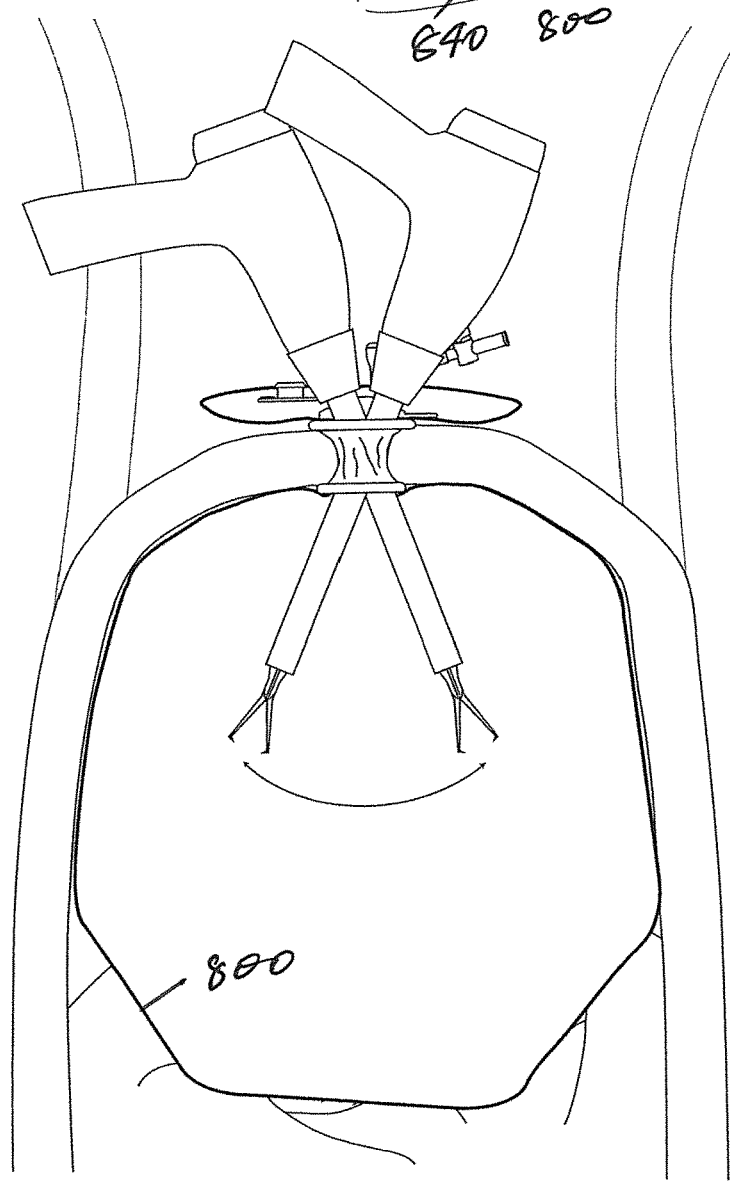

Referring to FIGS. 248 and 249 it will be apparent that the bag device 800 retracts bowel 840 to a safe distance avoiding accidental connection with the morcellator or its tenaculum under vision significantly.

Figure 250:
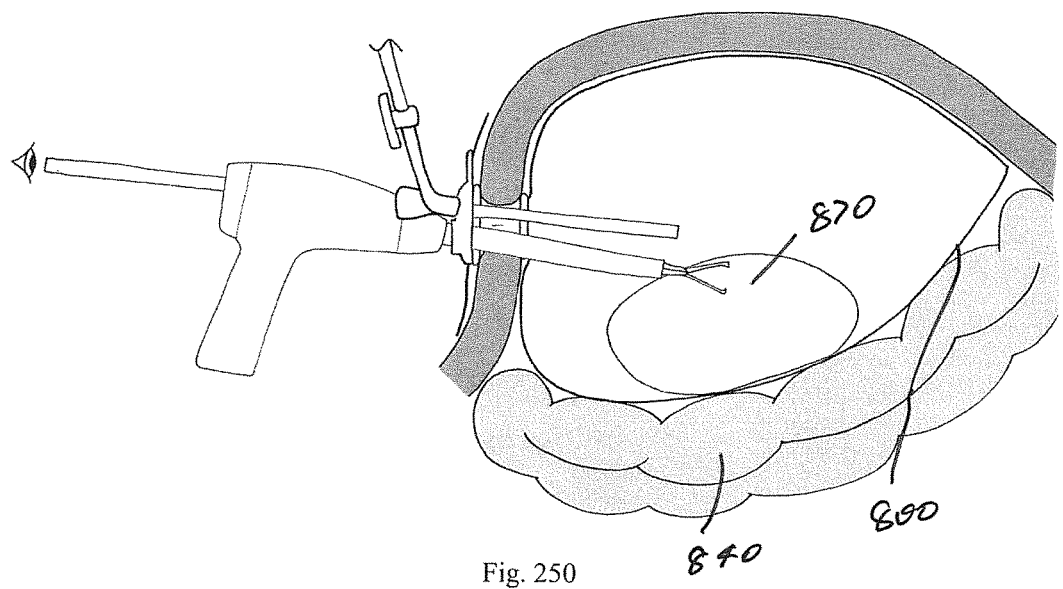
Figure 251:
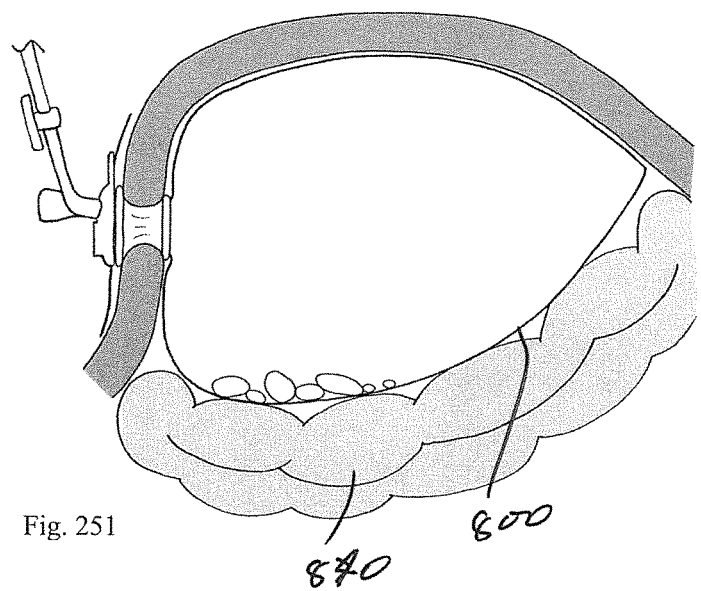

FIGS. 250 and 251 illustrate that under vision, the surgeon morcellates the tissue until no large chunks remain.

The bag device, according to an aspect of the disclosure, provides an artificial pneumoperitoneum in which procedures can be carried out on tissue isolated in the bag.

Figure 252:
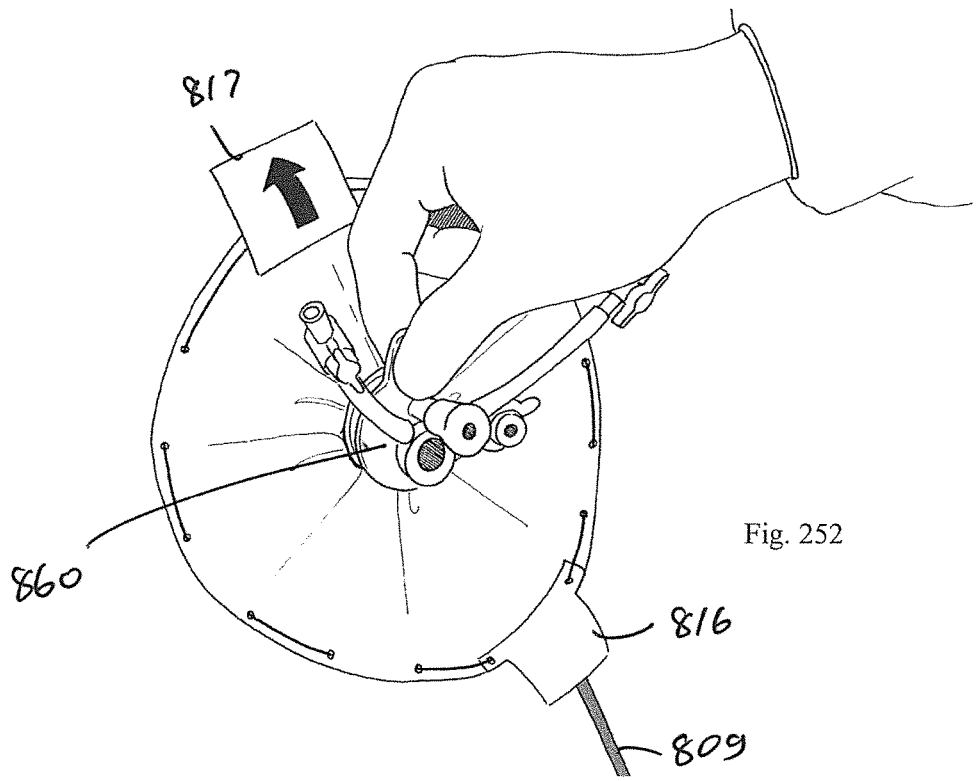
Figure 253:
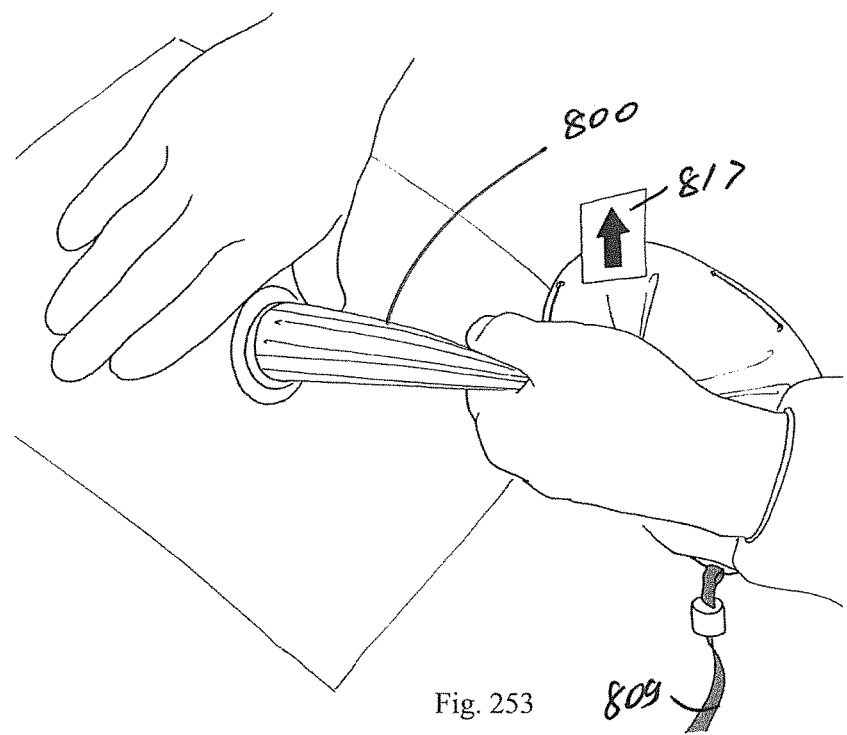

Referring to FIGS. 252 and 253 illustrate removal of the access port and, once deflated, the bag device 800 can be pulled out, bringing with it all the debris from the morcellation.

Figure 254:
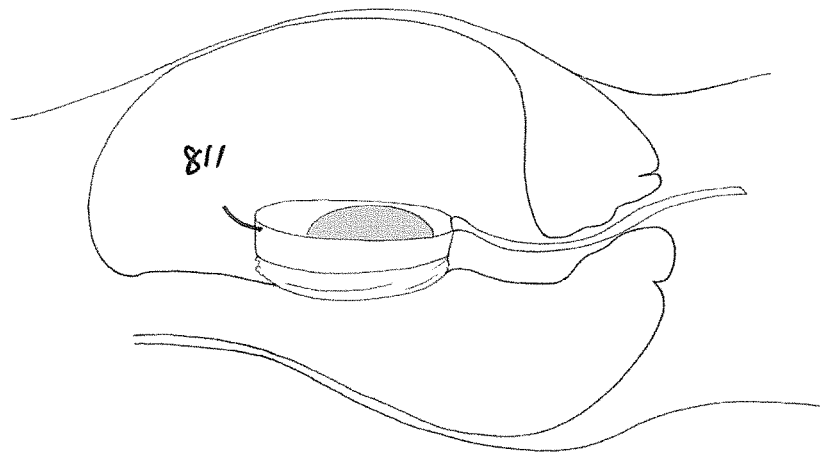
FIGS. 254 to 256 illustrate the device according to an aspect of the disclosure used trans-vaginally.
Figure 255:
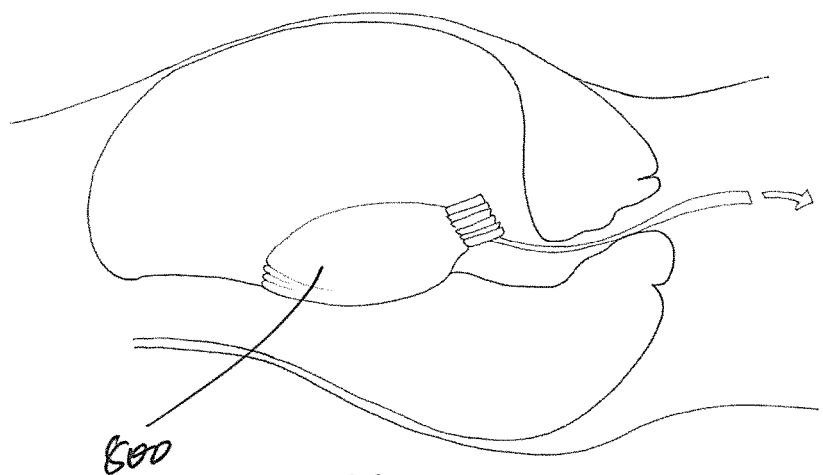
Figure 256:
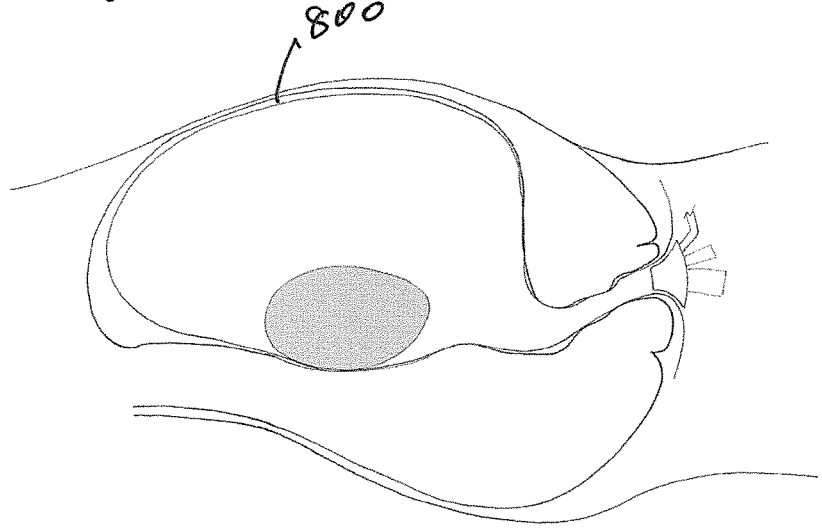

The device, according to an aspect of the disclosure, can also be used in trans-vaginal procedures in which the device is introduced into the vagina as illustrated in FIGS. 254 to 256.

Figure 257:
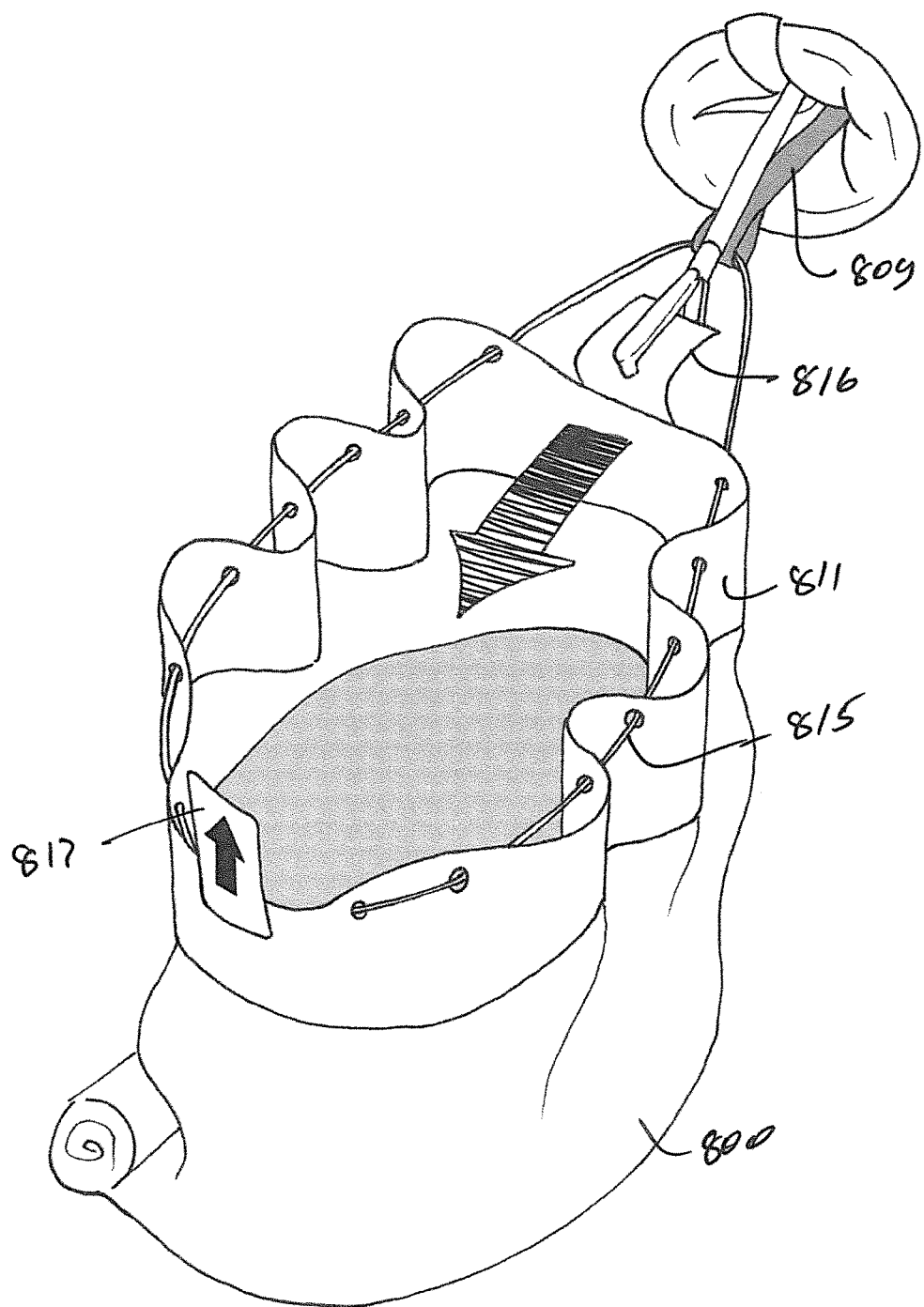
FIG. 257 illustrates the closing of the device within the pneumoperitoneum.

In some cases the bag device 800 may be closed within the insufflated abdomen as illustrated in FIG. 257.

Figure 258:
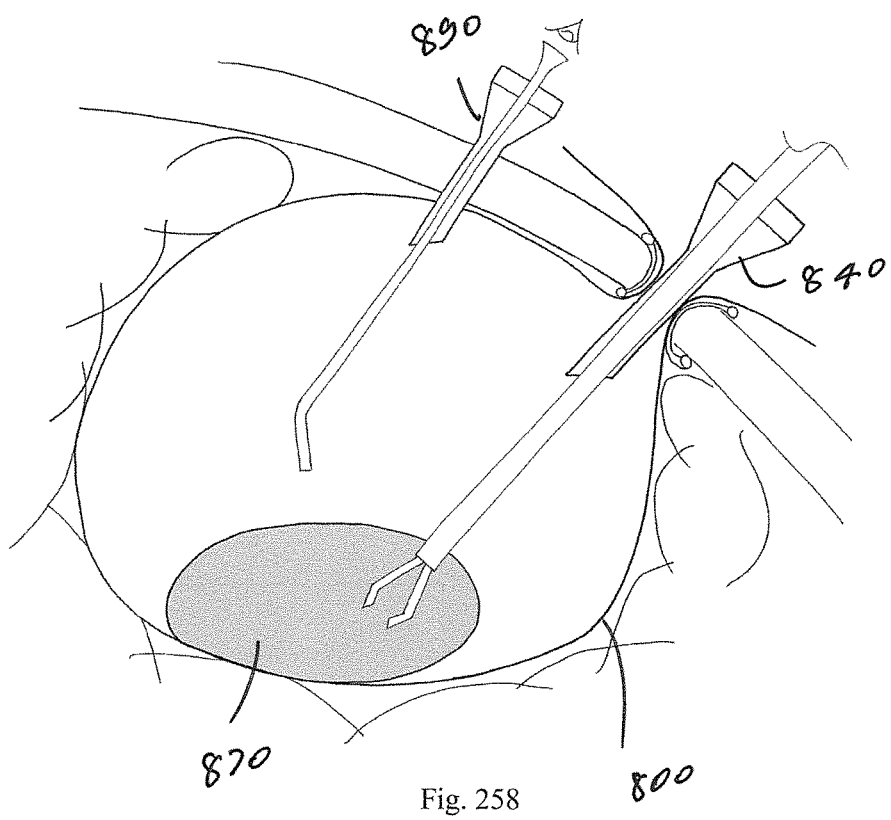
FIG. 258 illustrates the use of the device in a procedure which involves the uses of an additional port.

Referring to FIG. 258 in some cases an additional port 890 may be used to pass through the bag device 800 to provide access for an instrument or a laparoscope.

Figure 259:
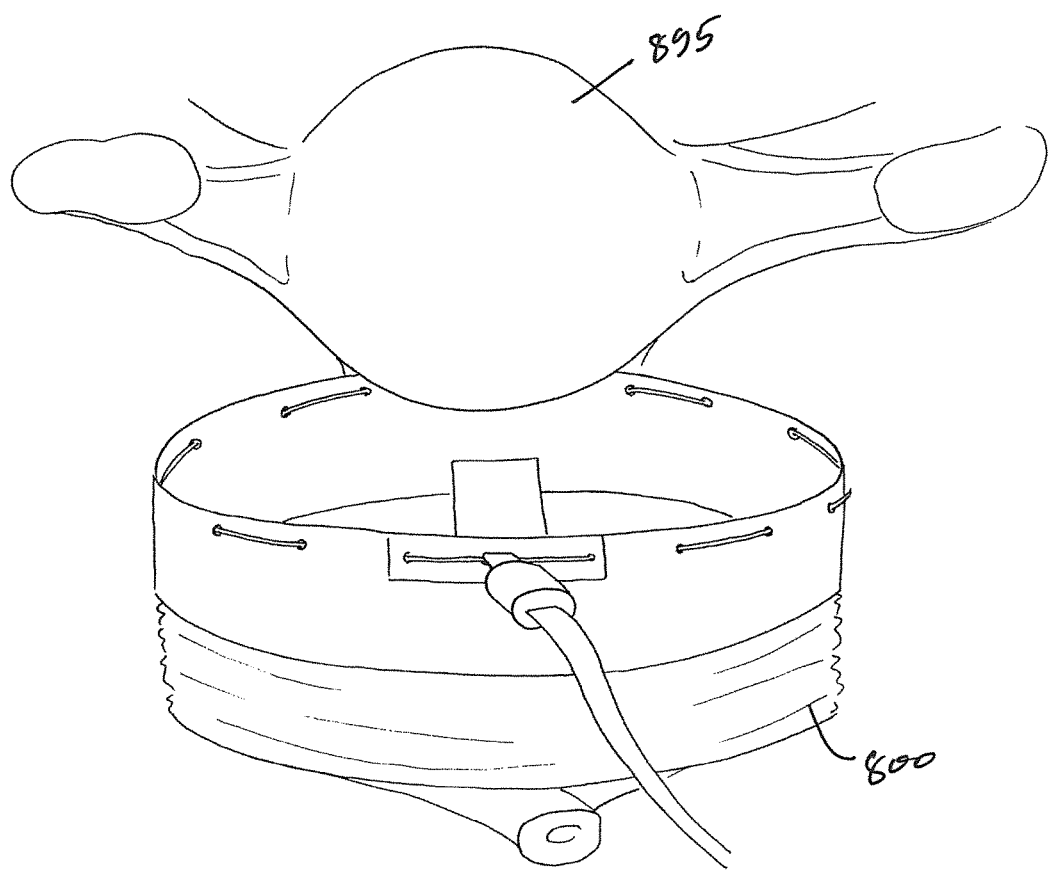
FIGS. 259 and 260 illustrate an artificial pneumoperitoneum device according to an aspect of the disclosure being used in different ways.

Referring to FIG. 259 illustrates that the key device 800 can be deployed before the tissue has been resected. The device can be placed under the uterus 895 during dissection to catch any droplets of blood or tissue.

Figure 260:
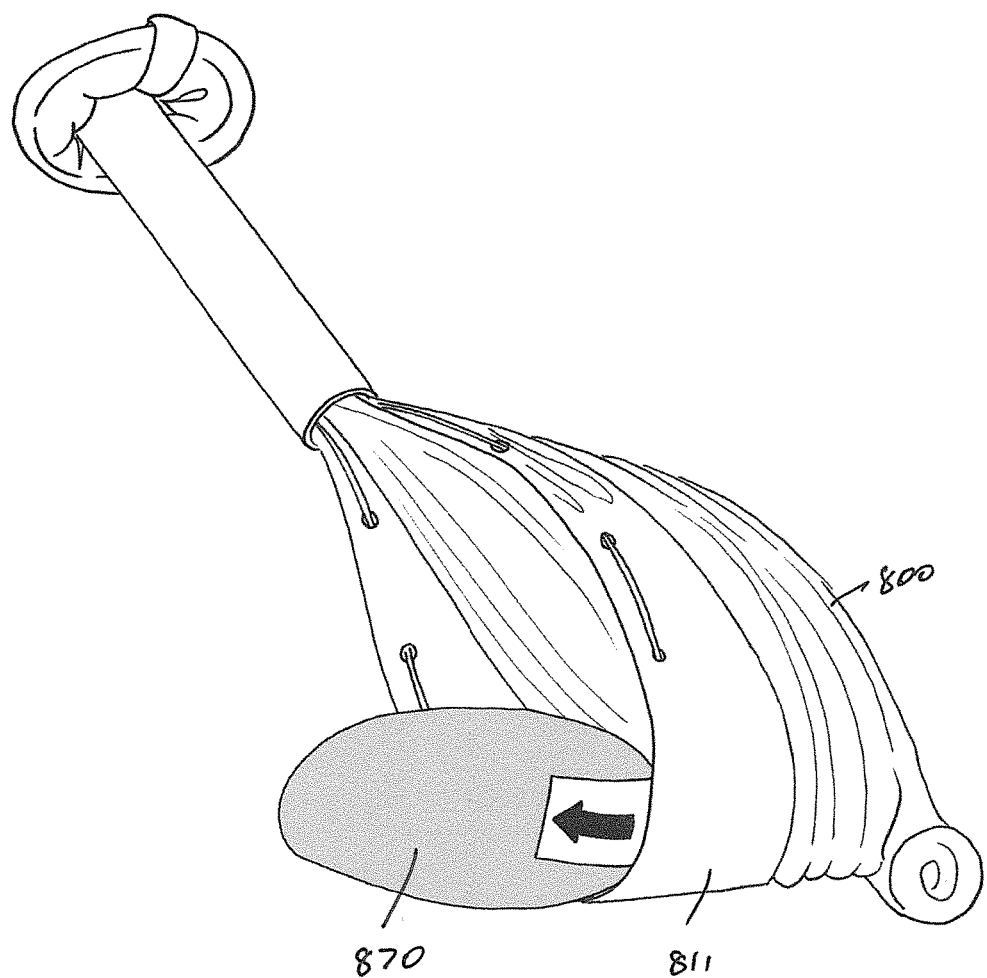

FIG. 260 illustrated that whilst partially deployed, the device can scoop up tissue. This is facilitated by the relatively stiff collar 811.

Referring to FIGS. 261 and 262 in this case the device is made with excess material in the top area which can be grabbed with a grasper to be pulled through a trocar.

Referring to FIGS. 263 to 266 illustrates a supplementary or second skin 900 on the device. Through a trocar incision 902, a grab tab 901 on the excess material 900 is pulled up through the wound. A hole is cut into the excess material 900 and the trocar is reinserted insider the extra material—this material then protects the wound from any insemination. The trocar then punctures into the main chamber of the device. This ensures that the insertion of the trocar does not cause material to egress through the hole created by the trocar.

Figure 267:
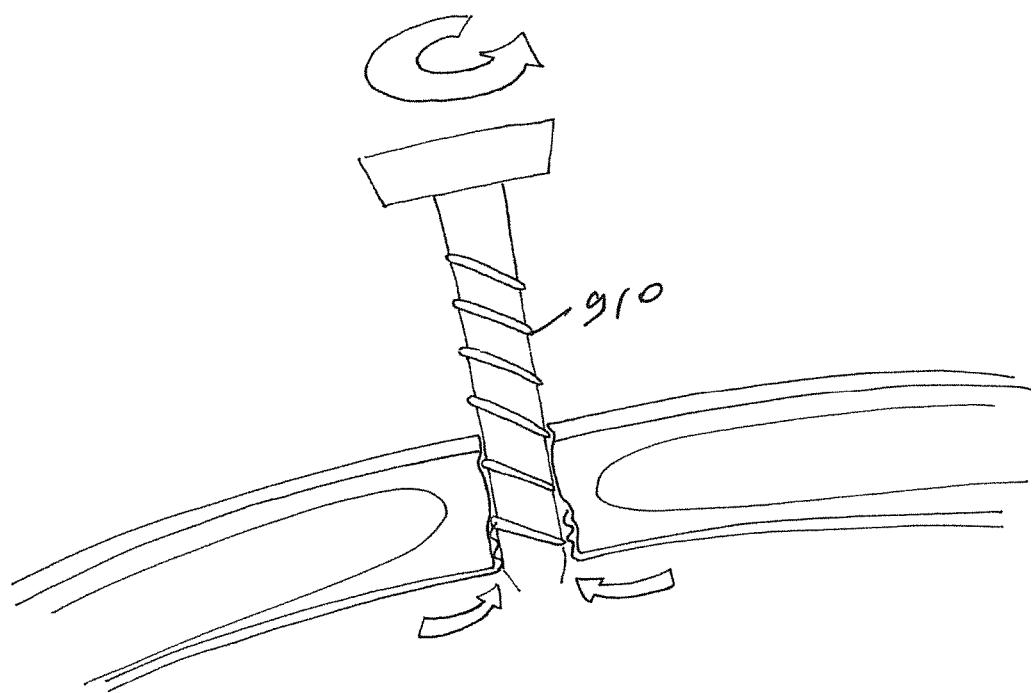
FIG. 267 illustrates the use of the device with a threaded trocar.

FIG. 267 illustrates the puncturing of the device with a threaded trocar 910 twisting the trocar will pull excess material in the device up through the wound, therefore protecting it from dissemination.

Figures 268, 269, 270:
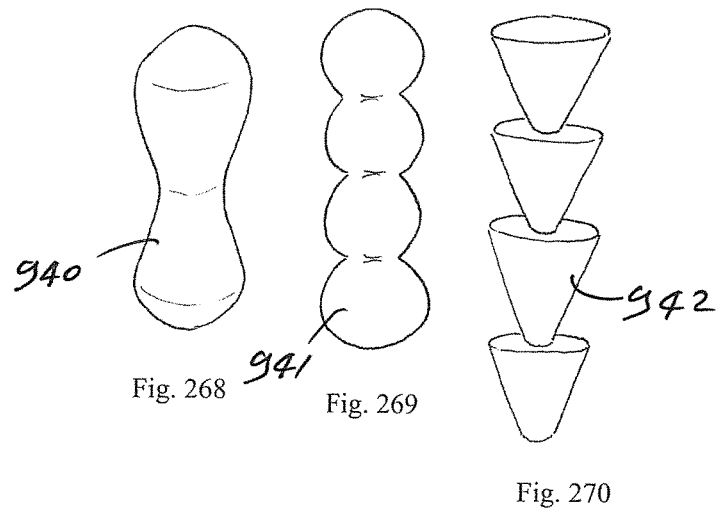
FIGS. 268 to 276 illustrate various bungs for use with the trocar.

FIGS. 268 to 270 illustrate various bungs 940, 941, 942 which may be of closed cell foam in several shapes—this is pushed down through the trocar once the surgery is complete and before the insufflation is removed.

Figures 271, 272, 273:
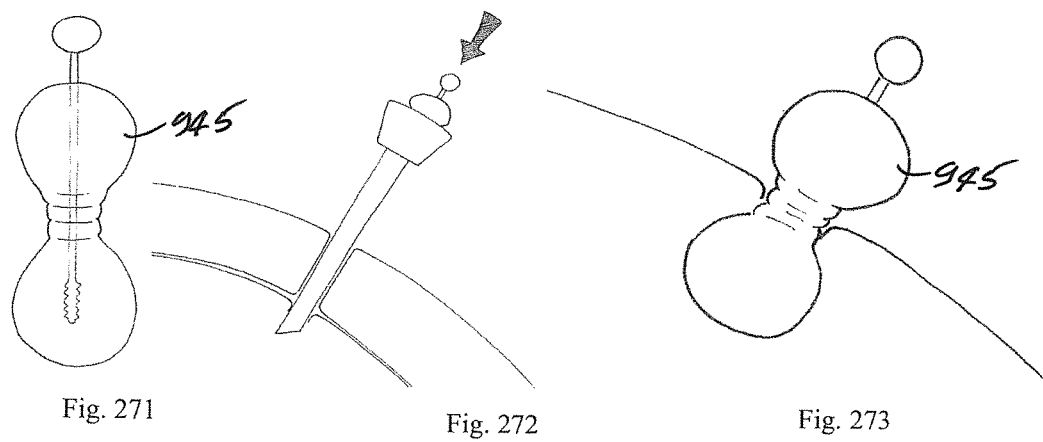

FIGS. 271 to 273 illustrate that a bung 945 may have a rigid core to aide pushing the bung through the trocar.

Figures 274, 275, 276:
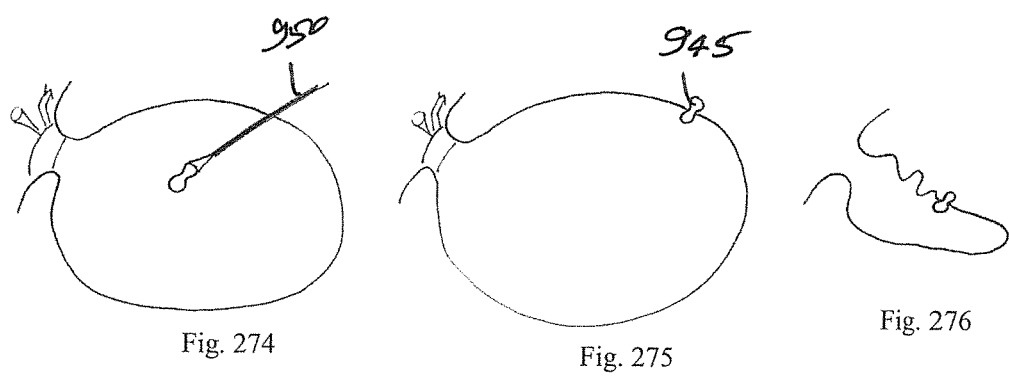
Figure 277:
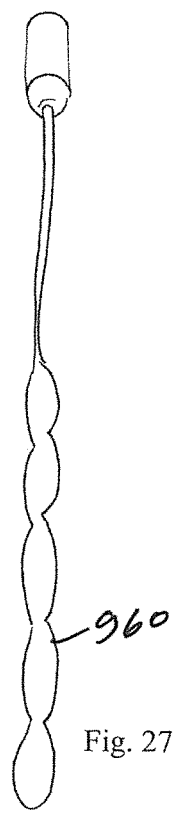
FIGS. 277 to 280 illustrate an inflatable bung and its use.
Figure 278:
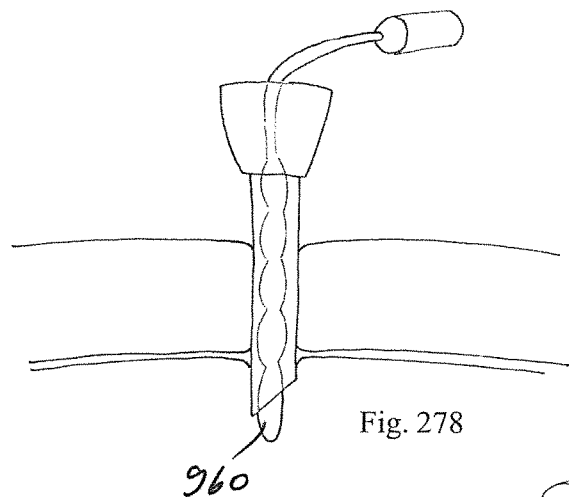
Figure 279:
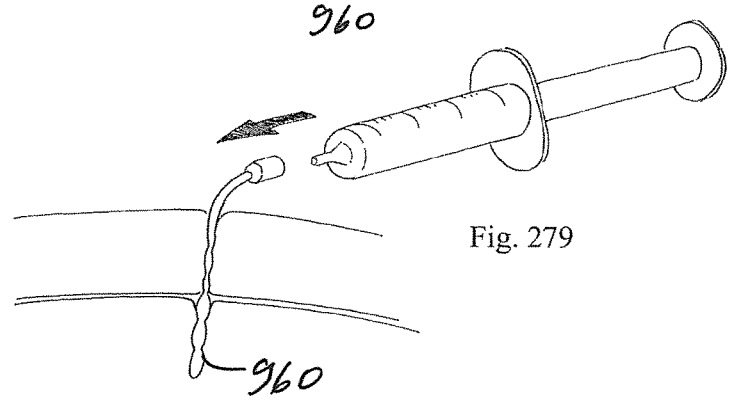
Figure 280:
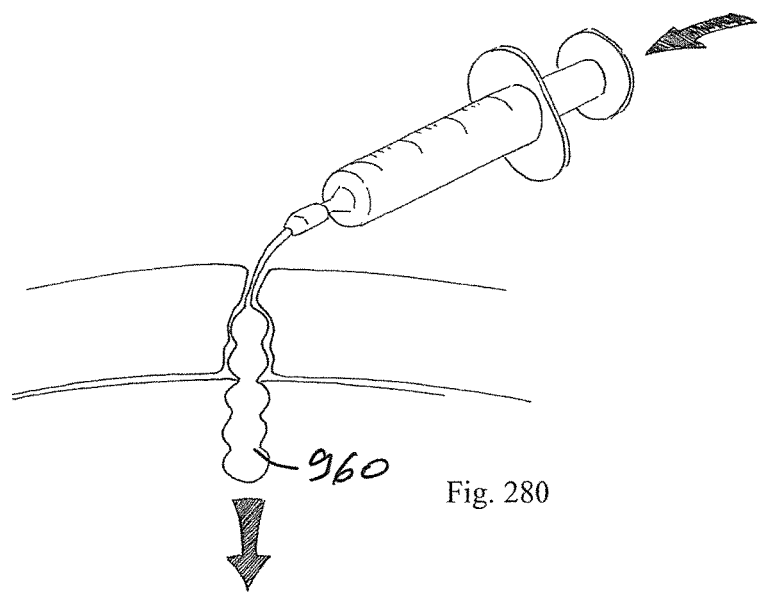

FIGS. 274 to 276 a bung 945 may be placed inside the inflated device. A grasper introduced via a second trocar 950 grabs the bung and pulls it up to the trocar. The trocar is pulled back and the bung is pulled into the puncture hold to seal it.

Referring to FIGS. 277 to 280 illustrate an inflatable bung 960. Deflated—the bung 960 is passed through the trocar. Once in place, the bung 960 is inflated using a large syringe. The bung may contain a one way valve.

FIGS. 281A, 281B, 282A, 282B, and 283 to 285 illustrate a cover 970 for a trocar 971 that can be inflated to block the hole in the device once the trocar 971 has been removed. FIGS. 281A and 281B show the cover 970 uninflated. FIGS. 282A and 282B shows the cover 970 inflated.

Figure 286A:
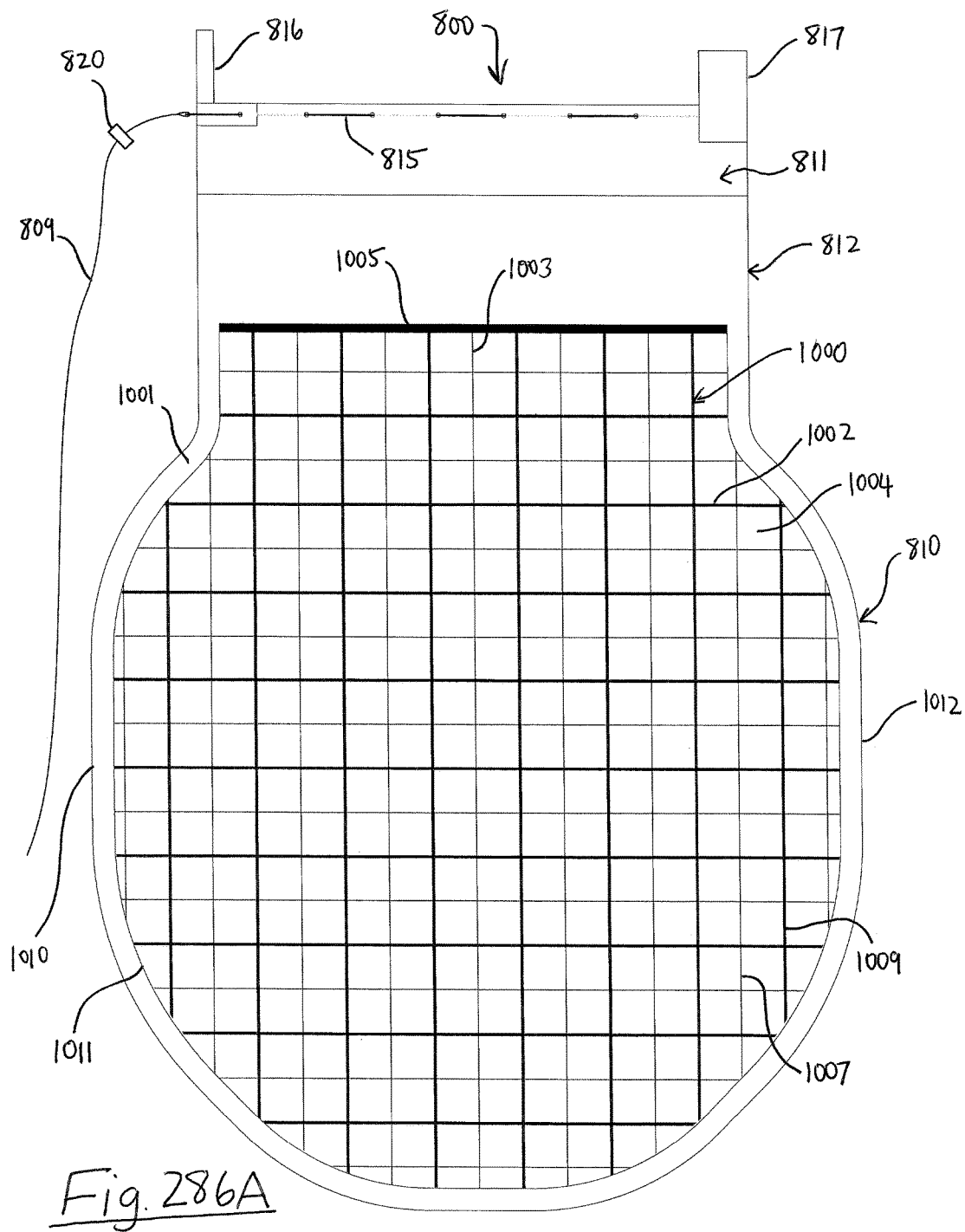
FIGS. 286A to 286C are views illustrating the device having an indicator.

FIG. 286A illustrates bag device 800 with one or more indicators 1000. The bag device 800 may include any of the features disclosed above. Indicator 1000 may be visible to surgeons or any other users. Indicator 1000 may include a dye or other visible material applied onto an outer surface of bag device 800, onto an inner surface of bag device 800, and/or within a wall of bag device 800 (hereinafter referred to as "on" the bag device 800). Indicator 1000 may be anywhere on the bag device 800, including, for example, on a first side of the bag device 800, a second side of the bag device 800 opposite the first side, and/or on a bottom of the bag device 800 at the closed end of the bag device 800.

Figure 286B:
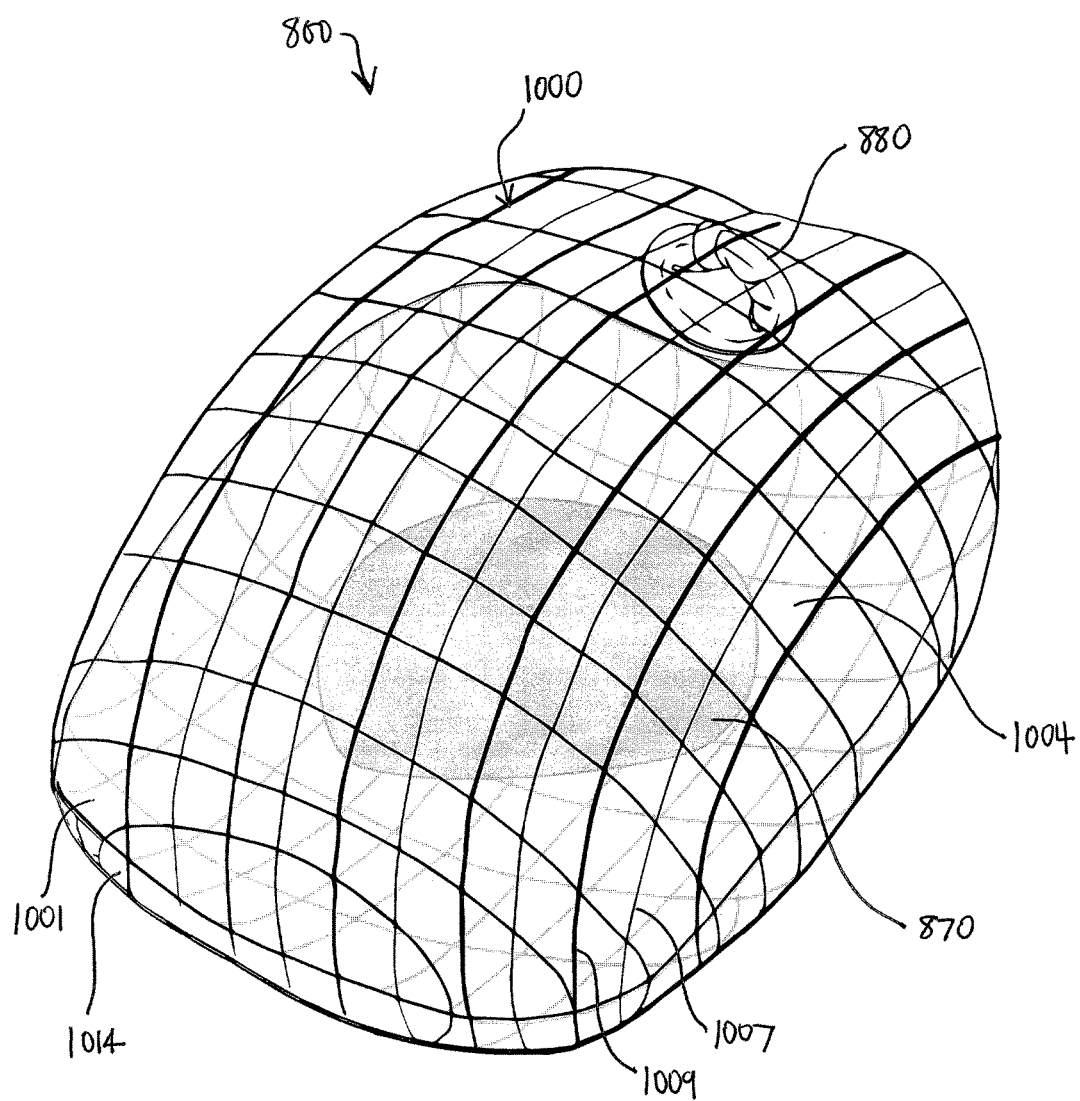

According to one aspect, the bag device 800 may include material formed with an open end, a closed end, and a wall between the open and closed ends that defines an enclosed volume. For example, the bag device 800 may include a membrane having the shape of a sack or pouch. Alternatively, the bag device 800 may include a first sheet 1001 joined at its edges. Alternatively, bag device 800 may include the first sheet 1001 and a second sheet 1014 (FIG. 286B). The second sheet may be joined at its edges to first sheet 1001 to form bag device 800.

Indicator 1000 may be on one or more portions of bag device 800 including, for example, main body region 810, neck/shoulder region 812, and/or collar region 811. Collar region 811 may be formed of a double-layer of material including an inner layer (not shown) and an outer layer. Indicator 1000 may be provided on only one of those inner and outer layers. Alternatively, indicator 1000 may be provided on both the inner layer and the outer layer.

Indicator 1000 may be on only one side of bag device 800. For example, the side of the bag device 800 having indicator 1000 may be a posterior side configured to face away from the abdominal wall when the bag device 800 fills the peritoneal cavity. Alternatively, the side of the bag device 800 having indicator 1000 may be an anterior side configured to face the abdominal wall when the bag device fills the peritoneal cavity. It is also contemplated that the anterior and posterior sides may include indicator 1000.

Indicator 1000 may be in the form of a pattern. The pattern may be continuous and may repeat over at least a portion of bag device 800. For example, indicator 1000 may include straight lines 1002 forming a grid. Grid lines 1002 may intersect with one another. Some grid lines 1002 may extend lengthwise along bag device 800, while other grid lines 1002 may extend widthwise along bag device 800. For example, first grid lines 1002 may extend in a direction along a central longitudinal axis of bag device 800, perpendicular to an edge 1006 that defines an opening (not shown) in bag device 800, in a direction parallel to one or more of edges 1010 and 1012 of bag device 800, and/or parallel to one another. Second grid lines 1002 may extend in a direction parallel to edge 1006, in a direction perpendicular to one or more of edges 1010 and 1012, in a direction perpendicular to first grid lines 1002, and/or parallel to one another. Alternatively, grid lines 1002 may extend in a direction that is neither perpendicular nor parallel relative to edges 1006, 1010, and/or 1012. For example, grid lines 1002 may be angled relative to edges 1006, 1010, and/or 1012. Grid lines 1002 may also be angled relative to each other. Alternatively, grid lines 1002 may include one or more longitudinal lines similar to markings on a ruler. Alternatively, grid lines 1002 may be wavy (e.g., sinusoidal) or otherwise curved. For example, grid lines 1002 may be circular, forming a series of concentric rings, while other grid lines 1002 may extend radially outward from a center point, intersecting the concentric rings. Indicator 1000 may include any combination of the above-described grid lines 1002. All portions of bag device 800 may have the same type of grid lines 1002. Alternatively, different portions of bag device 800 may have different types of grid lines 1002.

Grid lines 1002 may alternate between lines 1007 having a lesser thickness, and lines 1009 having a greater thickness. A grid line 1005 may be thicker than the other grid lines 1002. Grid line 1005 may be closest in proximity to the proximal end of bag device 800. The proximal end of bag device 800 may be pulled out of the peritoneal cavity by the surgeon or other user (see, e.g., FIGS. 236 and 237) until grid line 1005 is visible outside of the patient. Thus, grid line 1005 may act as a reference line by which the surgeon or other user can visually confirm that a sufficient amount of bag device 800 has been exposed from within the patient to allow the proximal end of the bag to be sufficiently opened. The degree of opening of the proximal end of the bag may be that in which Nitinol loop 815 may reach a fully expanded state. Thus, when the surgeon or other user sees grid line 1005, the surgeon or user may stop pulling bag device 800. Other grid lines 1002 may only be present in regions of bag device 800 distal to grid line 1005.

Grid lines 1002 may include a contour line 1011 extending along a periphery of bag device 800, from one end of grid line 1005 to the other. The other grid lines 1002 may terminate at contour line 1011, leaving a gap between contour line 1011 and the periphery of bag device 800.

A plurality of cells 1004 may be formed between grid lines 1002. Cells 1004 may have a quadrilateral (e.g., square or rectangular) shape. Alternatively, cells 1004 may have another shape. For example, grid lines 1002 may form cells 1004 that are triangular, pentagonal, hexagonal, and/or any other type of polygonal shape. Additionally or alternatively, cells 1004 may have an irregular shape. Bag device 800 may include any combination of the above-described cells 1004.

Indicator 1000 may have characteristics to help enhance its visibility. For example, the thickness of grid lines 1002 may be selected so that they are visible to a surgeon viewing bag device 800 using a visualization system (not shown), such as a scope-mounted camera (not shown). It is also contemplated that some of grid lines 1002 may have one thickness, while other grid lines may have a different thickness. For example, grid lines 1002 may include alternating thick and thin lines.

According to another exemplary aspect, grid lines 1002 may be tinted and/or colored lines. Their tinting and/or coloration may allow grid lines 1002 to contrast with body structures, tissue (e.g., viscera), and/or bodily fluids, to increase the visibility of grid lines 1002. Additionally or alternatively, grid lines 1002 may be luminescent. Additionally or alternatively, grid lines 1002 may be radiopaque, allowing visualization from outside of the patient's body.

Indicator 1000 may be arranged to convey particular size information. For example, the space between grid lines 1002 or the sides of the cells 1004 may be predetermined or otherwise known to the surgeon, making them useful for estimating dimensions. For example, the cells 1004 may be 25.4 mm by 25.4 mm, or 1 mm by 1 mm. According to one aspect, each cell 1004 may be 20 mm by 20 mm. Additionally or alternatively, indicator 1000 may include one or more characters, such as letters, numbers, and/or symbols. For example, each of grid lines 1002 and/or cells 1004 may have at least one identifying character on or adjacent to the grid line or cell. Each identifying character may correspond to a distance value, allowing bag device 800 to act as a ruler. In another example, identifying characters may allow grid lines 1002 and/or cells 1004 to act as a Cartesian coordinate system, with specific areas of bag device 800 being associated with points or coordinates defined by grid lines 1002 and/or cells 1004. Grid lines 1002 may be concentric circles with sizes known or provided on the bag device 800, or a longitudinal ruler with known gradations provided on bag device 800. It is also contemplated that the grid lines 1002 may have thereon strings of identifying characters.

The characteristics of indicator 1000 of bag device 800 may be selected to assist a surgeon with performing a certain type of procedure, treating a certain type of patient, and/or using a certain type of instrument. One or more of those characteristics may be different for bag devices used during performance of another type of procedure, used on another type of patient, and/or used with another type of instrument. Thus, different models of bag devices may be provided separately or in a kit, with each model being advantageous for a particular environment of use.

Figure 286C:
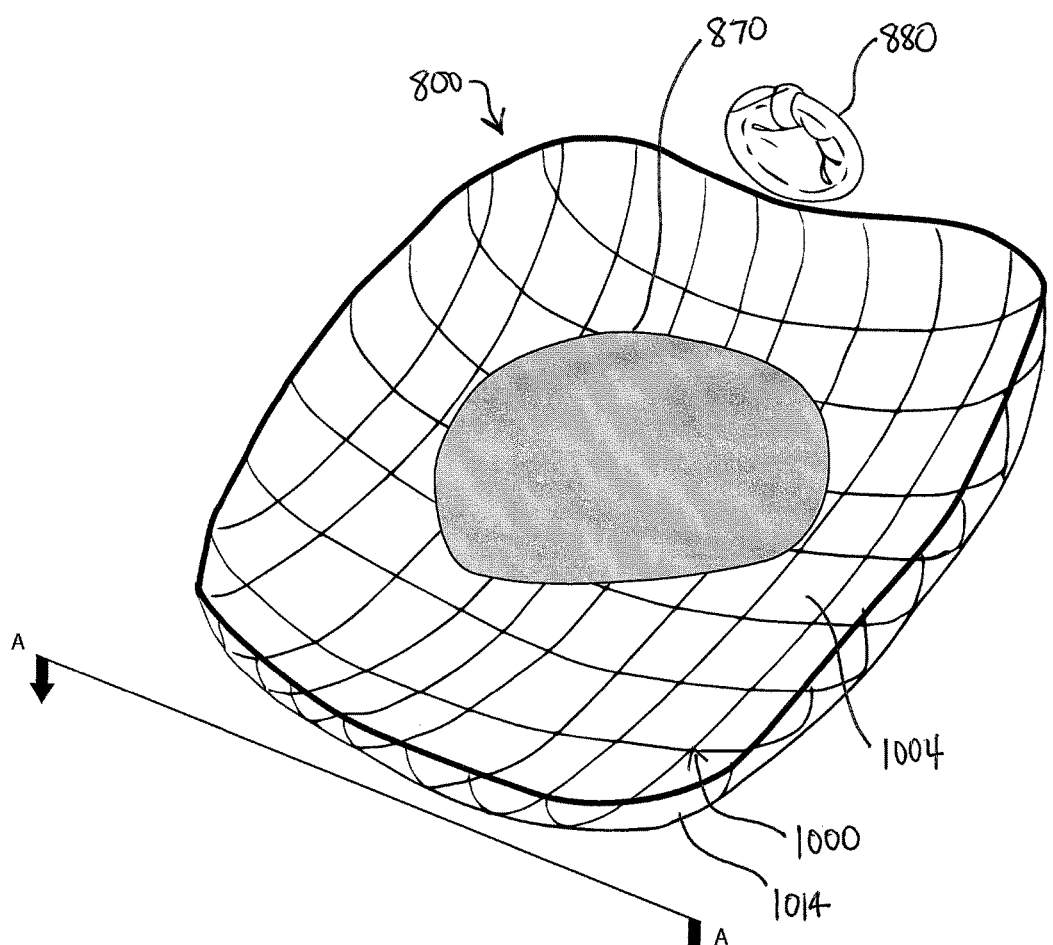

FIG. 286B is an isometric view illustrating bag device 800 in an inflated state and containing tissue 870. FIG. 286C is a cross-sectional isometric view of bag device 800 along a plane A-A, showing a lower half of bag device 800, in an inflated state, with tissue 870 resting thereon. The portion of bag device 800 shown in FIG. 286C may correspond to portions of the second sheet 1014.

Indicator 1000 may provide the surgeon with the ability to measure material near or in contact with bag device 800. For example, the surgeon may position tissue (e.g., an organ) within a portion of bag device 800. The surgeon may be able to determine one or more dimensions of the tissue (e.g., length, width, and/or height) by positioning the tissue against the wall of bag device 800, and using indicator 1000 as a scale or ruler. This may include determining how many grid lines 1002 the tissue crosses and/or how many cells 1004 the organ covers. This determination may be performed with bag device 800 either partially or fully unrolled, and/or inflated or deflated. After morcellating the tissue, the surgeon may be able to determine dimensions of morcellated pieces of tissue using the indicator 1000 on the wall of bag device 800. The surgeon may be able to determine dimensions of other bodily structures, such as anatomical structures on or forming a part of the abdominal wall, anatomical structures surrounding bag device 800, and/or other material in or forming the peritoneal cavity, using similar steps.

Indicator 1000 may also provide the surgeon with a way to determine how much of bag device 800 remains rolled up after bag device 800 has been inflated. For example, the surgeon may compare the amount of indicator 1000 visible in the inflated portion, to the known amount of indicator 1000 on bag device 800, and associate the length of bag device 800 that remains rolled with the difference between the two amounts. Indicator 1000 may also provide the surgeon with improved depth perception by giving the surgeon a frame of reference to view as the surgeon performs a procedure. Indicator 1000 may also provide the surgeon with a visual representation of a contour of the patient's abdomen and internal anatomical structures, as bag device 800 and indicator 1000 thereon conform to the shape of the abdomen and anatomical structures. For example, grid lines 1002 may follow the contour of the abdomen and anatomical structures, acting as visually identifiable contour lines.

Indicator 1000 may also provide the surgeon with an indication of when a crease, pleat, or fold has formed in bag device 800. After bag device 800 has been inflated, a portion of bag device 800 may form into a crease, pleat, or fold. The crease, pleat, or fold may create a bend, reversal of direction, visual discontinuity, and/or other irregularity along one or more of grid lines 1002. The bend, reversal of direction, visual discontinuity, and/or other irregularity may be visible to the surgeon, indicating the presence of the pleat or fold. The surgeon may maneuver, inflate, or otherwise adjust the configuration of bag device 800 to reduce the size or get rid of the crease, pleat, or fold. Additionally or alternatively, the surgeon may avoid contacting the region of bag device 800 having the crease, pleat, or fold with any surgical instruments, such as morcellator 78 (FIGS. 34 and 35), to avoid damaging the bag material with morcellator 78.

Indicator 1000 may also provide the surgeon with a signal of whether bag device 800 is properly situated in the peritoneal cavity. According to an aspect of this disclosure, indicator 1000 may include a reference feature that, when bag device 800 is properly situated, aligns with one or more body structures near bag device 800. For example, a central longitudinal grid line 1003 may be referenced with a central longitudinal axis of the patient when bag device 800 is properly situated.

Indicator 1000 may also be useful for guiding a surgeon's movements. For example, by viewing the location of tissue (inside or outside of bag device 800) relative to indicator 1000, the surgeon may determine how far, and in what direction, to move an instrument to engage or disengage the instrument from the tissue. Additionally or alternatively, the surgeon may use indicator 1000 as a coordinate system to help guide an instrument to a location defined by a point or coordinate, or between locations defined by points or coordinates. Identifying locations with points or coordinates may allow the surgeon to reach those locations easily, consistently, and accurately.

Furthermore, after bag device 800 has been inflated, the surgeon may view instruments against indicator 1000, and based on thereon, may visually establish a working zone within bag device 800 through which instruments can be moved without coming into contact with or damaging bag device 800. It is also contemplated that indicator 1000 may help the surgeon identify different portions of bag device 800, such as reinforced bottom portion 690 (FIG. 188). Indicator 1000 may also help a surgical team performing a procedure to communicate more efficiently with one another by providing a common set of reference points or coordinates the surgical team can use to describe locations and desired instrument movements to one another.

FIG. 287 illustrates bag device 800 introduced into the patient after bag device 800 has been folded, rolled, and scrunched in the manner shown in FIGS. 206 to 209, loaded into an introducer (not shown) such as introducer 801 in FIGS. 228 to 230, and ejected from the introducer into the peritoneal cavity. With respect to the folding, rolling, and scrunching, side portions 1110 of bag device 800 may be folded to have a constant width less than or equal to a width of ring 850 when ring 850 is in a compressed state. The compressed state of ring 850 may correspond to its state just prior to, during, or after being inserted into the introducer. The side portions 1110 of bag device 800 provide bag device 800 with a larger width to depth ratio without having to enlarge collar 811 and/or other proximal portions of bag device 800. Thus, the amount of material forming collar 811 and/or other proximal portions of bag device 800 may be reduced, creating more room for instruments in the body portion 810 and less of an obstruction to sight lines into the peritoneal cavity.

As shown in FIG. 287, collar 811 may be positioned over the portion 1100 of bag device 800 that was scrunched. Scrunched portion 1100 may remain scrunched after bag device 800 has been ejected. Scrunched portion 1000 of bag device 800 may be positioned over the portion 1102 of bag device 800 that was rolled. Rolled portion 1102 may remain rolled after bag device 800 has been ejected. Rolled portion 1102 may be positioned on an interior surface of the peritoneal cavity. A central longitudinal axis 1104 of rolled portion 1102 may lie alongside or within a median or sagittal plane of the peritoneal cavity. Additionally or alternatively, central longitudinal axis 1104 may lie within a median or sagittal plane of the patient.

In FIG. 288, tissue 870 is being manipulated into the opening of bag device 800. As illustrated in FIG. 289, tissue 870 may be positioned within collar 811 of bag device 800. Tether 809 may extend out of the patient through wound retractor 880. Tether 809 may be gripped by the surgeon.

By pulling tether 809 in a proximal direction, the surgeon may begin to pull ring 850 out of the peritoneal cavity through wound retractor 880. FIG. 290 shows ring 850 partially pulled through wound retractor 880. The pulling may extend scrunched portion 1100, causing scrunched portion 1100 to straighten out, allowing collar 811 to be lifted over tissue 870. The extension movement is identified with a straight arrow in FIG. 290. The extension of scrunched portion 1100 may further facilitate complete encapsulation of tissue 870. For example, the pulling may cause a tensile force to develop in a distal portion 1106 of bag device 800. Rolled portion 1102 may begin to rotate. For example, central longitudinal axis 1104 of rolled portion 1102 may rotate out of the median or sagittal plane (represented by a line 1108). The rotational movement is identified with a curved arrow in FIG. 290.

As illustrated in FIG. 291, with continued pulling of ring 850 through wound retractor 880, bag device 800 may close automatically as it is pulled toward and against wound retractor 880. Rolled portion 1102 may continue to rotate, with its rotational movement identified by two curved arrows. Curtaining of collar 811 around ring 850 may facilitate closing of bag device 800, maintain slack at a proximal portion or end of bag device 800, and/or maintain tension at distal portion 1106 of bag device 800, to guide rotation of rolled portion 1102 further out of median or sagittal plane 1108.

The surgeon may continue to pull tether 809 until ring 850 and collar 811 are outside of the patient. Once collar 811 is outside of the patient, tissue 870 may be fully encapsulated within bag device 800. Rolled portion 1102 may be positioned to encourage inflation of bag device 800 in a desired direction. For example, central longitudinal axis 1104 of rolled portion 1102 may be perpendicular to median or sagittal plane 1108. When bag device 800 is inflated, rolled portion 1102 may unroll in the direction of median or sagittal plane 1108.

Bag device 800 may have dimensions that, when bag device 800 is fully inflated, make bag device 800 larger than most patient cavities in which bag device 800 may be used. For example the fully-inflated bag device 800 may have a larger volume than most abdominal cavities. This may help ensure that all available space in the peritoneal cavity can be taken up by the inflated bag device 800. Further, the shape of bag device 800, the way bag device 800 is loaded into and ejected from the introducer, and/or the way bag device 800 is positioned within the peritoneal cavity, minimizes the likelihood of creases, pleats, or folds developing in the material forming the inflated bag device 800. This may provide the surgeon with a smoothly-lined peritoneal cavity.

One factor that helps minimize creasing, pleating, or folding is the shape of bag device 800. For example, the round corners of bag device 800 may allow bag device 800 to conform to the shape of the peritoneal cavity. Another factor is the ability of bag device 800 to self-vary or self-limit its degree of expansion. As illustrated in FIGS. 216 and 293 to 295, when bag device 800 is inflated, it only unrolls as much material as needed to fill the available space in the peritoneal cavity, leaving excess material (if any) neatly rolled on the outside.

Figure 294:
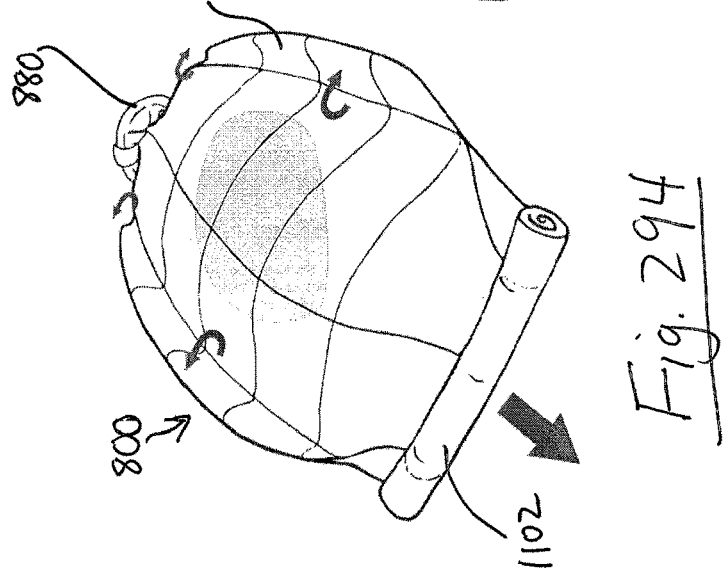
Figure 293:
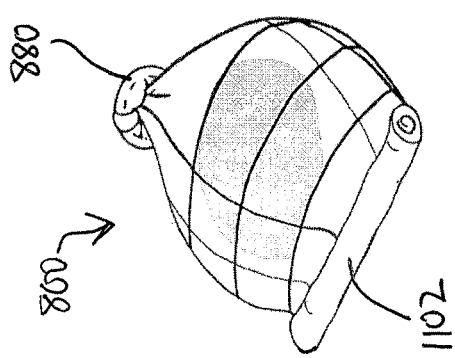

FIGS. 293 to 295 show bag device 800 when inflated in patient cavities having different volumes. FIG. 293 shows bag device 800 when inflated in a peritoneal cavity having a small volume. The entire length of folded lateral portions 1110 of the bag device 800 of FIG. 293 (folded, for example, in the manner shown in FIG. 207) may remain rolled when bag device 800 has filled the peritoneal cavity. Even if only the proximal ends or portions of folded lateral portions 1110 are unrolled by inflation of bag device 800, with the rest of folded lateral portions 1110 remaining rolled, the proximal ends or portions may remain flat against or adjacent to an outer surface of bag device 800. This may help limit the expansion of bag device 800, thereby reducing creasing, pleating, or folding caused by overexpansion.

FIG. 294 shows bag device 800 when inflated in a peritoneal cavity having a medium volume. More of rolled portion 1102 has unrolled in the medium volume cavity than in the small volume cavity (FIG. 293). As more of rolled portion 1102 unrolls, incrementally more of folded lateral portions 1110 are exposed. The exposed portions of the folded lateral portions 1110 may unfold and expand outward in lateral directions. The exposed portions may follow an arced path into contact with viscera, thus aiding in retracting the viscera. Additionally or alternatively, the movement of the exposed folded lateral portions 1110 along the arced path may help align bag device 800 in the peritoneal cavity. For example, the unfolding folded lateral portions 1110 may have a tendency to be guided toward lateral portions of the peritoneal cavity by the shape of the peritoneal cavity. The rest of folded lateral portions 1110 may remain rolled, helping to limit the expansion of bag device 800 and thereby reduce creasing, pleating, or folding. It is contemplated that each folded lateral portion 1110 may start unfolding when at least half of its length has been unrolled.

FIG. 295 shows bag device 800 when inflated in a peritoneal cavity having a large volume. All of rolled portion 1102 has unrolled, exposing the entire length of folded lateral portions 1110, and the entire length of bag device 800. The unrolling and inflating of the distal portions of folded lateral portions 1110 may aid in retracting viscera, making final adjustments to the alignment of bag device 800 in the peritoneal cavity, and/or allow more complete lateral expansion of folded lateral portions 1110. In FIGS. 293-295, several contour lines have been added to the figures to show contours of the outer surface of bag device 800. Those contour lines are not necessarily visible on the surface of bag device 800. It should be understood, however, that the contour lines may be grid lines 1002 of indicator 1000 (FIG. 286A).

Various features, according to aspects of the disclosure, are described and illustrated. It will be appreciated that at least some of the features described in relation to one aspect may be used not only in or with the aspect specifically described but also in or with other aspects. As used herein, the term "approximately" or "about" is understood to mean close in value or amount, but not precise. To the extent that such a definition for "approximate" or "about" is not considered sufficiently definite, approximate is understood to mean plus or minus 5% of the relevant parameter.

Aspects of this disclosure are not limited to the aspects hereinbefore described, with reference to the accompanying drawings, which may be varied in construction and detail.

The invention claimed is:

1. An artificial pneumoperitoneum device, comprising:
   a bag, including:
   a membrane,
   an open end,
   a closed end,
   a body between the open end and the closed end, wherein the membrane at least partially defines the open end, the closed end, and the body, and
   dye formed on or in the membrane and arranged in a series of lines, wherein the series of lines includes a first set of lines and a second set of lines, the first set of lines extending across the second set of lines.

2. The artificial pneumoperitoneum device of claim 1, wherein the lines of the first set are perpendicular to the lines of the second set.

3. The artificial pneumoperitoneum device of claim 1, wherein the lines of the first set have the same thickness as the lines of the second set.

4. The artificial pneumoperitoneum device of claim 1, wherein each of the lines of the first set has a first thickness, each of the lines of the second set has a second thickness, and the first thickness is different than the second thickness.

5. The artificial pneumoperitoneum device of claim 1, wherein the lines of the first set run parallel to each other.

6. The artificial pneumoperitoneum device of claim 5, wherein the first set of lines includes a first subset of lines and a second subset of lines, lines of the first subset have a first thickness, lines of the second subset have a second thickness, and the first thickness is different than the second thickness.

7. The artificial pneumoperitoneum device of claim 6, wherein the lines of the first subset alternate with the lines of the second subset.

8. The artificial pneumoperitoneum device of claim 1, wherein the bag further includes a central longitudinal axis, and the lines of the first set extend longitudinally.

9. An artificial pneumoperitoneum device, comprising:
   a bag, including:
   a membrane,
   an open end,
   a closed end,
   a body between the open end and the closed end, wherein the membrane at least partially defines the open end, the closed end, and the body, and
   dye formed on or in the membrane and arranged in a series of intersecting lines.

10. The artificial pneumoperitoneum device of claim 9, wherein the intersecting lines include a first set of lines and a second set of lines, and the lines of the first set are perpendicular to the lines of the second set.

11. The artificial pneumoperitoneum device of claim 9, wherein the intersecting lines include a first set of lines running perpendicular to the open end.

12. The artificial pneumoperitoneum device of claim 9, wherein the intersecting lines include a first set of lines and a second set of lines, and the lines of the first set have the same thickness as the lines of the second set.

13. The artificial pneumoperitoneum device of claim 9, wherein the intersecting lines include a first set of lines and a second set of lines, the lines of the first set have a first thickness, the lines of the second set have a second thickness, and the first thickness is different than the second thickness.

14. The artificial pneumoperitoneum device of claim 9, wherein the intersecting lines include a first plurality of parallel lines, and a second plurality of parallel lines, with parallel lines of the first plurality intersecting parallel lines of the second plurality.

15. An artificial pneumoperitoneum device, comprising:
   a bag, including:
   a membrane,
   an open end,
   a closed end,
   a body between the open end and the closed end, wherein the membrane at least partially defines the open end, the closed end, and the body, and
   dye formed on or in the membrane and arranged in a grid on or in the membrane.

16. The artificial pneumoperitoneum device of claim 15, wherein the grid includes lines surrounding four-sided cells.

17. The artificial pneumoperitoneum device of claim 15, wherein the grid includes a first set of lines extending lengthwise along the bag, and a second set of lines extending widthwise along the bag.

18. The artificial pneumoperitoneum device of claim 17, wherein lines of the first set are perpendicular to lines of the second set.

19. The artificial pneumoperitoneum device of claim 15, wherein a first portion of the grid is on or in an anterior wall of the membrane, and a second portion of the grid is on or in a posterior wall of the membrane.

20. The artificial pneumoperitoneum device of claim 15, wherein the grid includes a first set of lines and a second set of lines, and the lines of the first set have a different thickness than lines of the second set.

* * * * *